United States Patent
Ibebunjo et al.

(10) Patent No.: US 11,180,546 B2
(45) Date of Patent: Nov. 23, 2021

(54) TGFBETA 2 ANTIBODIES

(71) Applicant: Novartis AG, Basel (CH)

(72) Inventors: Chikwendu Ibebunjo, Newton, MA (US); Carsten Jacobi, Muttenz (CH); Angelika Meyer, Basel (CH); Eveline Schaadt, Oberhaching (DE); Anne-Ulrike Trendelenburg, Cambridge, MA (US); Olga Vladimirovna Mitina, Munich (DE)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/999,368

(22) PCT Filed: Feb. 17, 2017

(86) PCT No.: PCT/IB2017/050917
§ 371 (c)(1),
(2) Date: Aug. 17, 2018

(87) PCT Pub. No.: WO2017/141208
PCT Pub. Date: Aug. 24, 2017

(65) Prior Publication Data
US 2019/0092846 A1    Mar. 28, 2019

Related U.S. Application Data

(60) Provisional application No. 62/296,282, filed on Feb. 17, 2016.

(51) Int. Cl.
*C07K 16/22* (2006.01)
*A61K 39/00* (2006.01)

(52) U.S. Cl.
CPC ........ *C07K 16/22* (2013.01); *A61K 2039/505* (2013.01); *C07K 2317/14* (2013.01); *C07K 2317/33* (2013.01); *C07K 2317/34* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,571,714 | A | 11/1996 | Dasch et al. |
| 7,368,111 | B2 | 5/2008 | Thompson et al. |
| 2013/0011397 | A1 | 1/2013 | Pasricha |

FOREIGN PATENT DOCUMENTS

| EP | 1245676 A1 | 10/2002 |
| EP | 0646012 B1 | 1/2003 |
| WO | 1997013844 | 4/1997 |
| WO | 2006/116002 | 11/2006 |

OTHER PUBLICATIONS

Database Biosis [Online] BioSciences Information Service, Philadelphia, PA, US; 1993, Pasquale Louis R et al: "Immunolocalization of TGF-beta-1, TGF-beta-w, and TGF-beta-3 in the anterior segment of the human eye", XP002768926, Database accession No. PREV199395091674 abstract.
Pasquale Louis R et al: "Immunolocalization of TGF-beta-1, TGF-beta-2, and TGF-beta-3 in the anterior segment of he human eye", Investigative Ophthalmology and Visual Science, vol. 34, No. 1, 1993, pp. 23-30, XP002769673, ISSN: 0146-0404, p. 24, left-hand column, paragraph 3—p. 25, left-hand column, paragraph 1.
Database Medline [Online] US National Library of Medicine (NLM), Bethesda, MD, US; Sep. 2001 (Sep. 2001), Hill C et al: "Transforming growth factor-beta2 antibody attenuates fibrosis in the experimental diabetic rat kidney.", XP002768927 Database accession No. NLM11524245 abstract.
Hill C et al: "Transforming growth factor-beta2 antibody attenuates fibrosis in the experimental diabetic rat kidneys.", The Journal of Endocrinology Sep. 2001, vol. 170, No. 3, Sep. 2001 (Sep. 2001), pp. 647-651, XP002769674, ISSN: 0022-0795 abstract.
International Search Report, PCT/IB2017/050917, completed Apr. 28, 2017; dated May 12, 2017.
Dasch, J.R., et al., Monoclonal Antibodies Recognizing Transforming Growth Factor, The Journal of Immunology Transforming Growth Factor.
Thompson J. E. et al., "A fully human antibody neutralising biologically active human TGFbeta2 for use in therapy," Journal of Immunological Methods, vol. 227 (1999), pp. 17-29.
Koniski A. et al., "Axolotl (Ambystoma mexicanum) lymphocytes produce and are growth-inhibited by transforming growth factor-beta," Developmental and Comparative Immunology, vol. 22 No. 1 (1998), pp. 91-102.

*Primary Examiner* — Gary B Nickol
*Assistant Examiner* — Jegatheesan Seharaseyon
(74) *Attorney, Agent, or Firm* — Seth E. Cockrum

(57) ABSTRACT

This invention is in the field of anti-transforming growth factor beta 2 (TGF-β2) antibodies. In particular, the invention provides human monoclonal antibodies that bind the human TGF-β2 isoform preferentially over the human TGF-β1 or TGF-β3 isoforms.

13 Claims, 14 Drawing Sheets
Specification includes a Sequence Listing.

Figure 1: *Kd determination by SET measurement (MOR13436)*

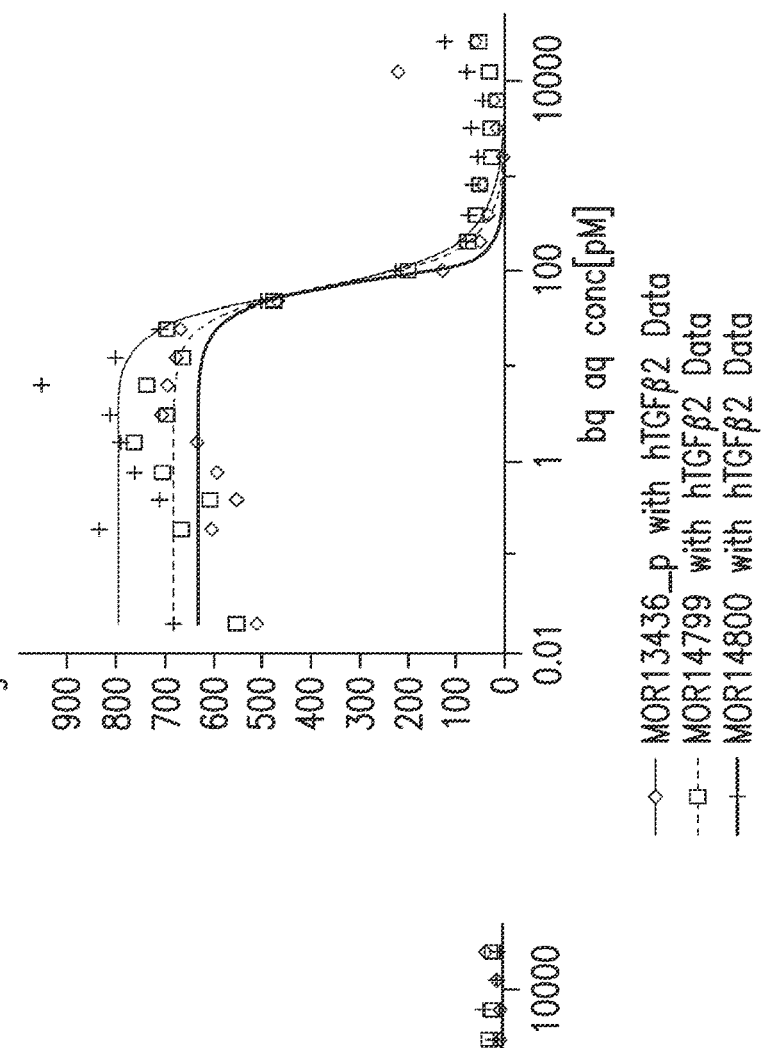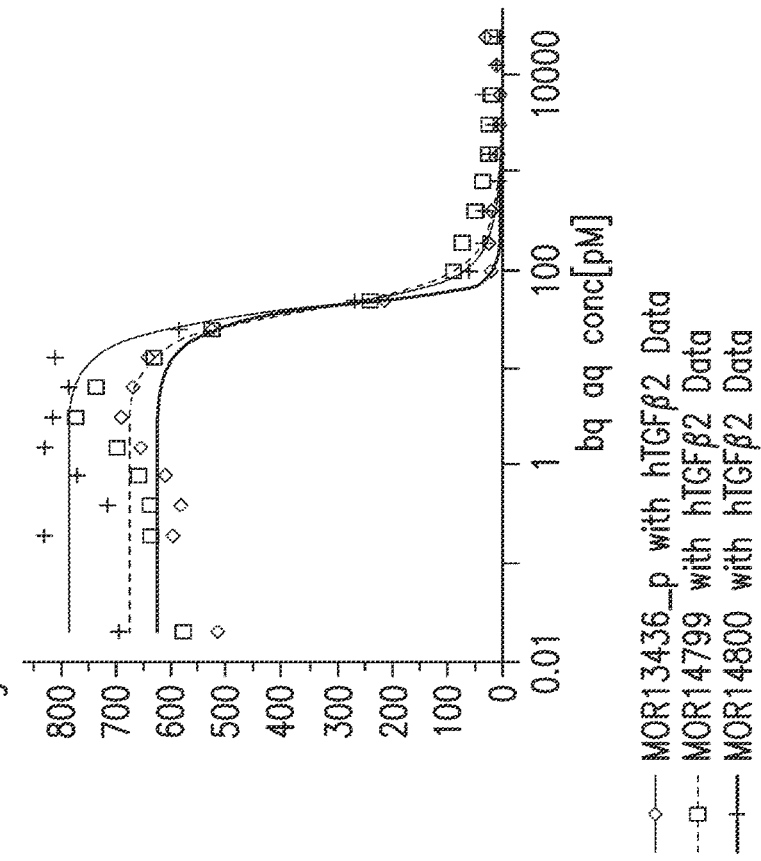
FIG. 2

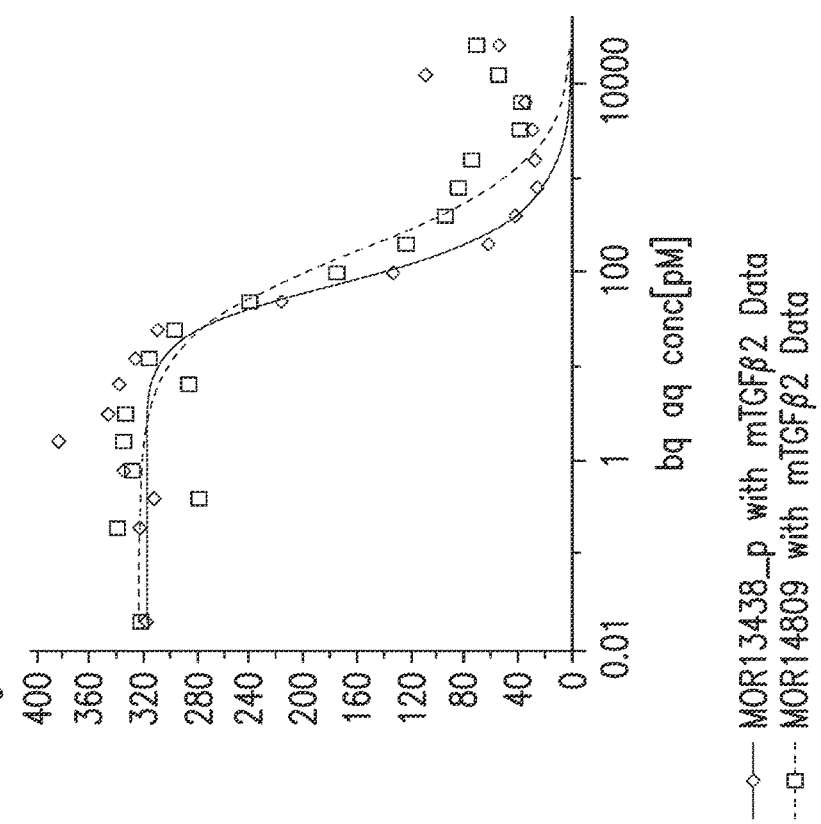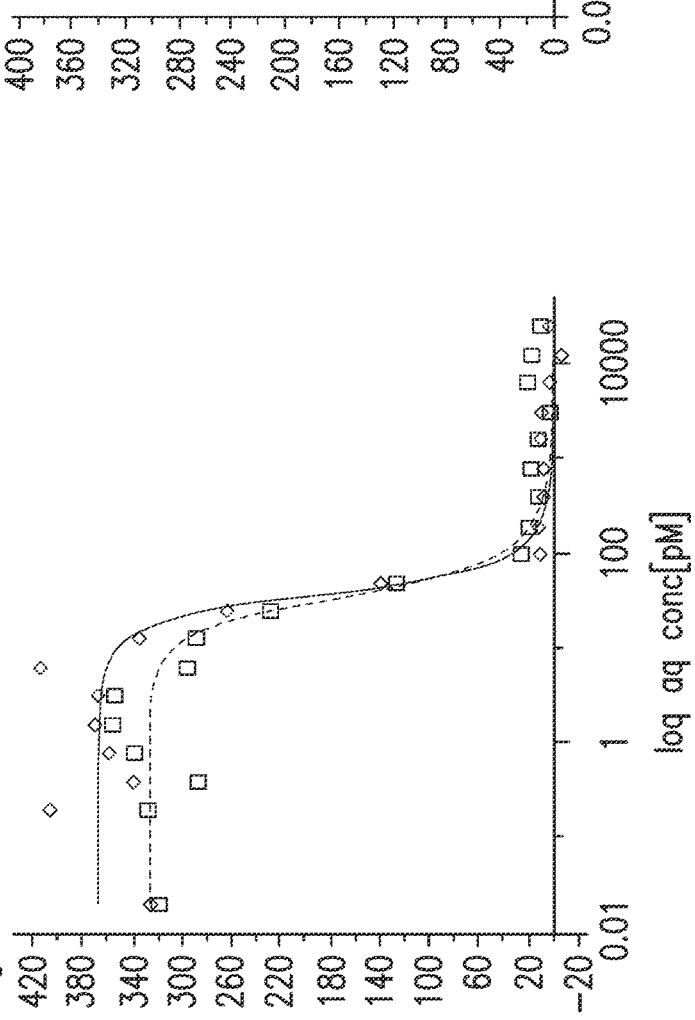
FIG. 2 (Continued)

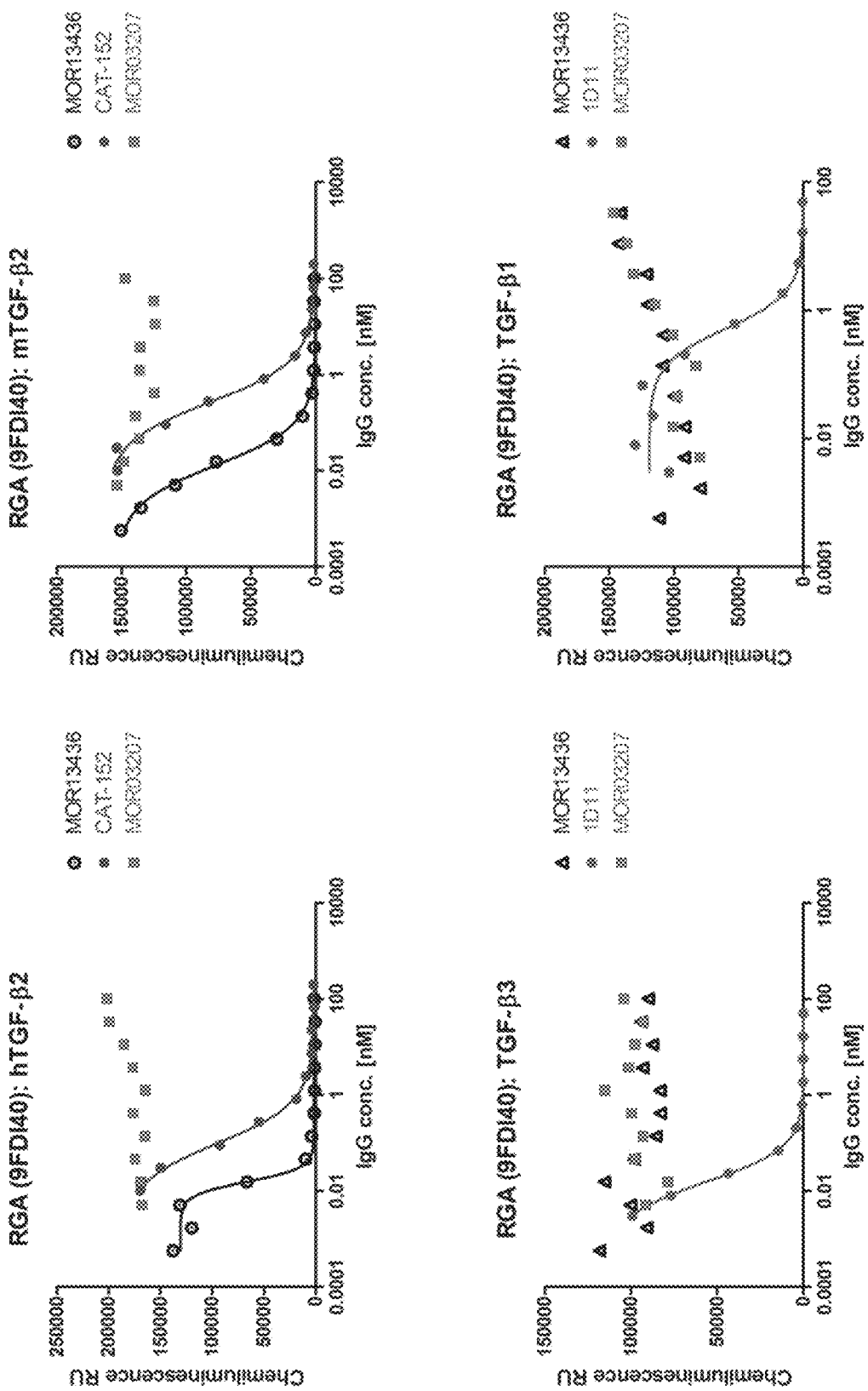
Figure 3: Biologic activity and isoform-specificity by RGA activity (MOR13436)

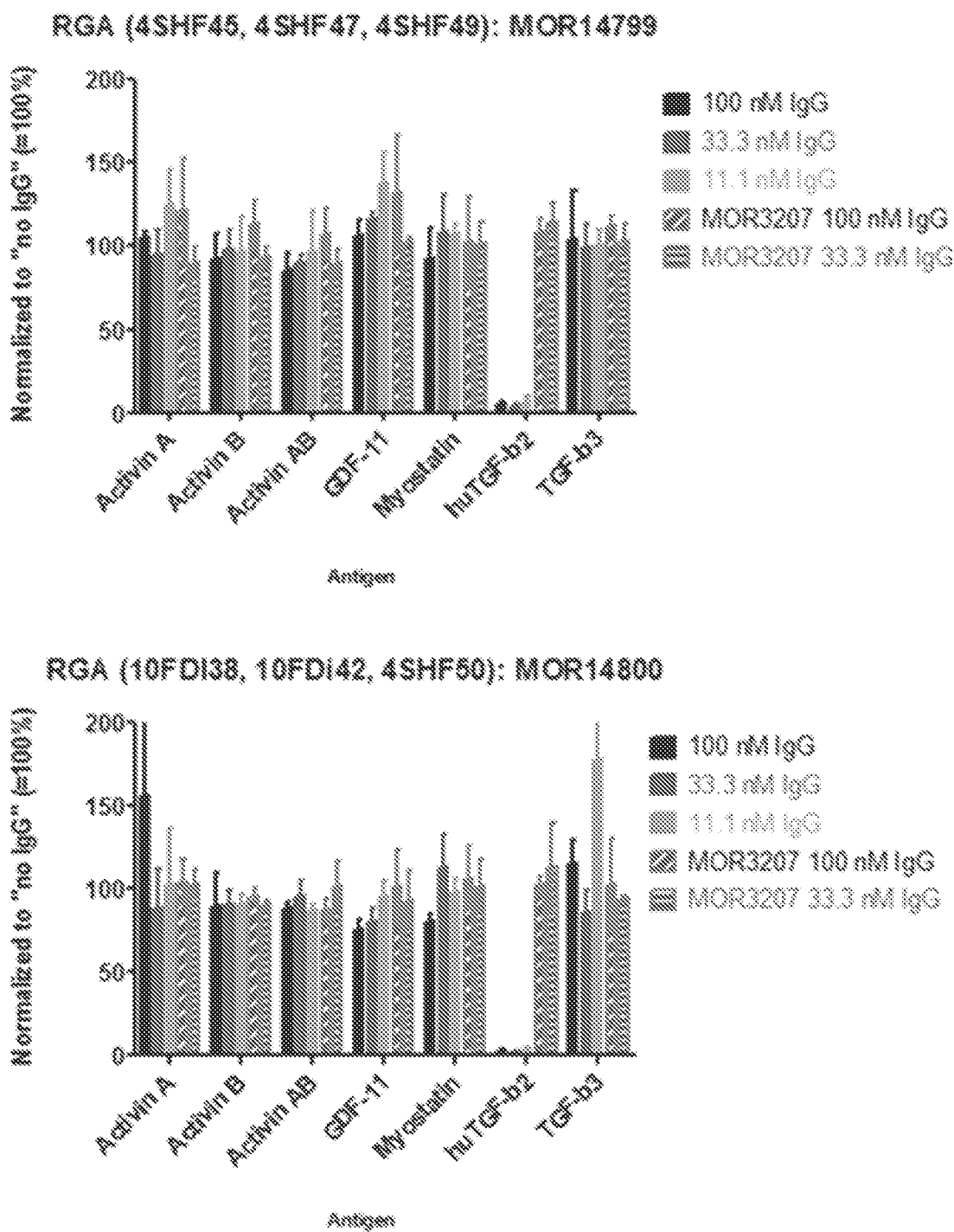
Figure 4: Biologic activity and specificity by RGA activity (germlined/PTM removed)

Fig. 4 (continued)
Figure 4: *Biologic activity and specificity by RGA activity (germlined/PTM removed)*
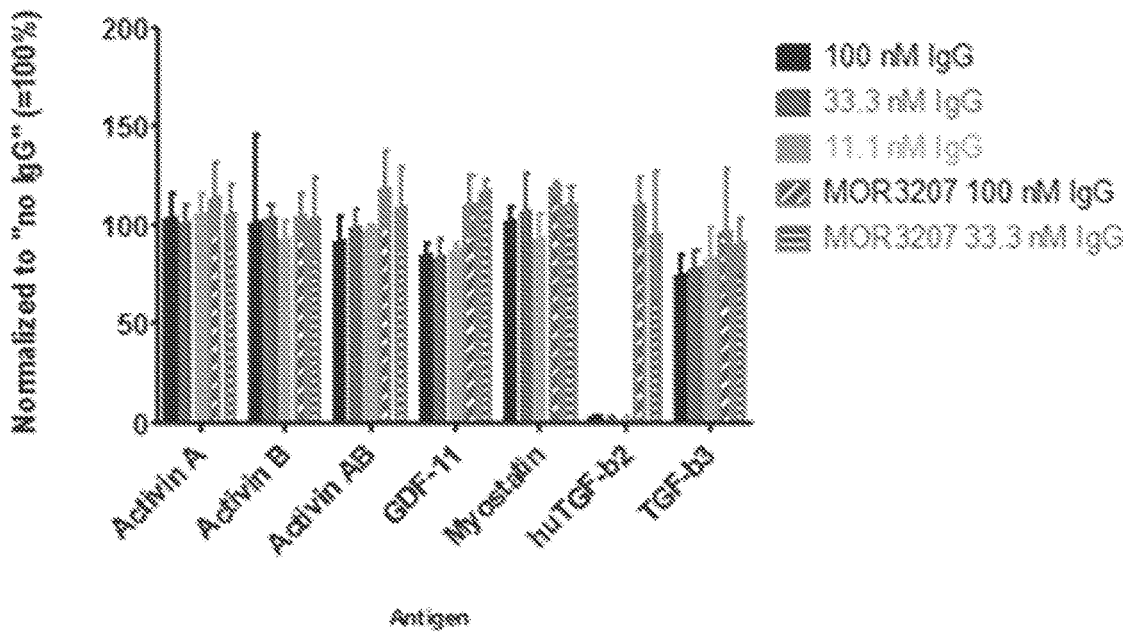
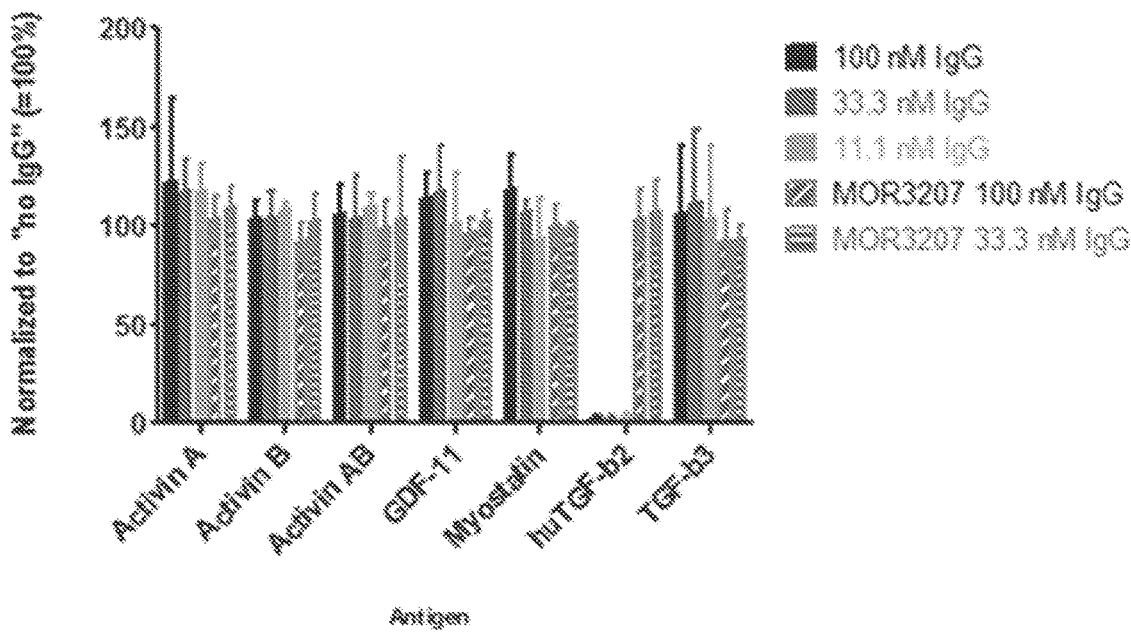

Figure 5: *Biologic activity and selectivity by counteracting skMC differentiation*
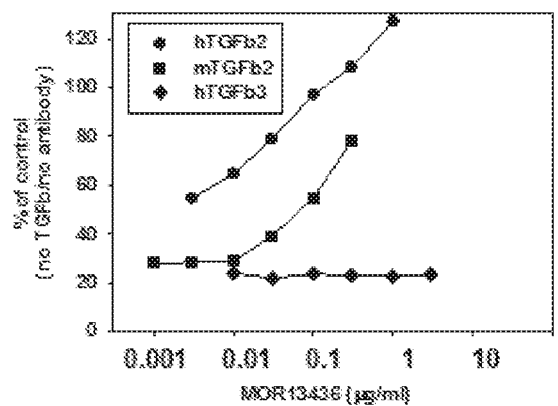

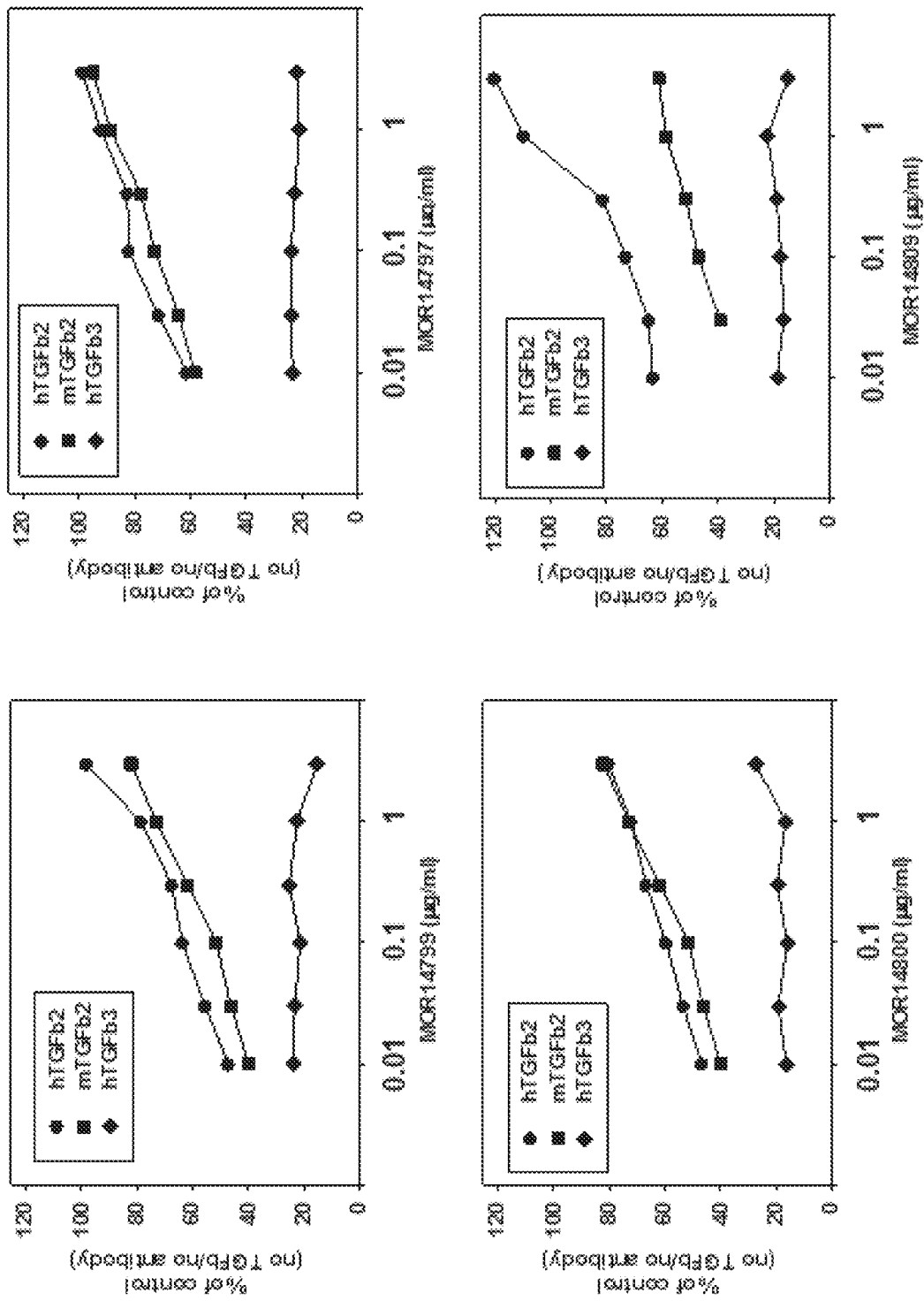
Figure 6: Biologic activity and selectivity by counteracting skMC differentiation Figure 7: *Biologic activity in Dupuytren patient cultures on collagen 1 protein*
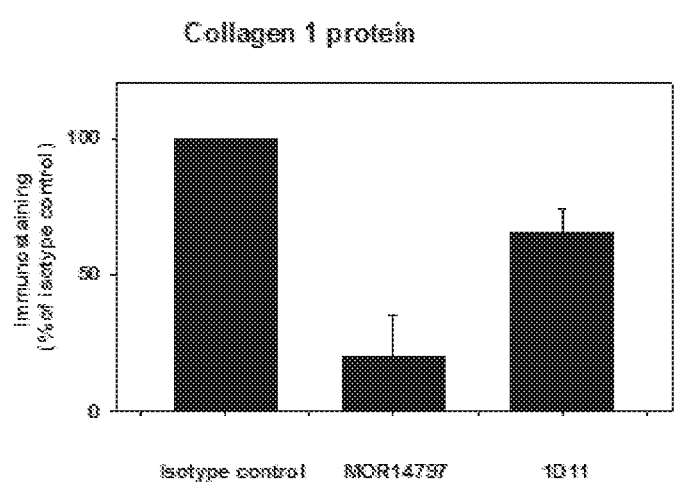

Figure 8: *Biologic activity in Dupuytren patient cultures on collagen 1 protein*
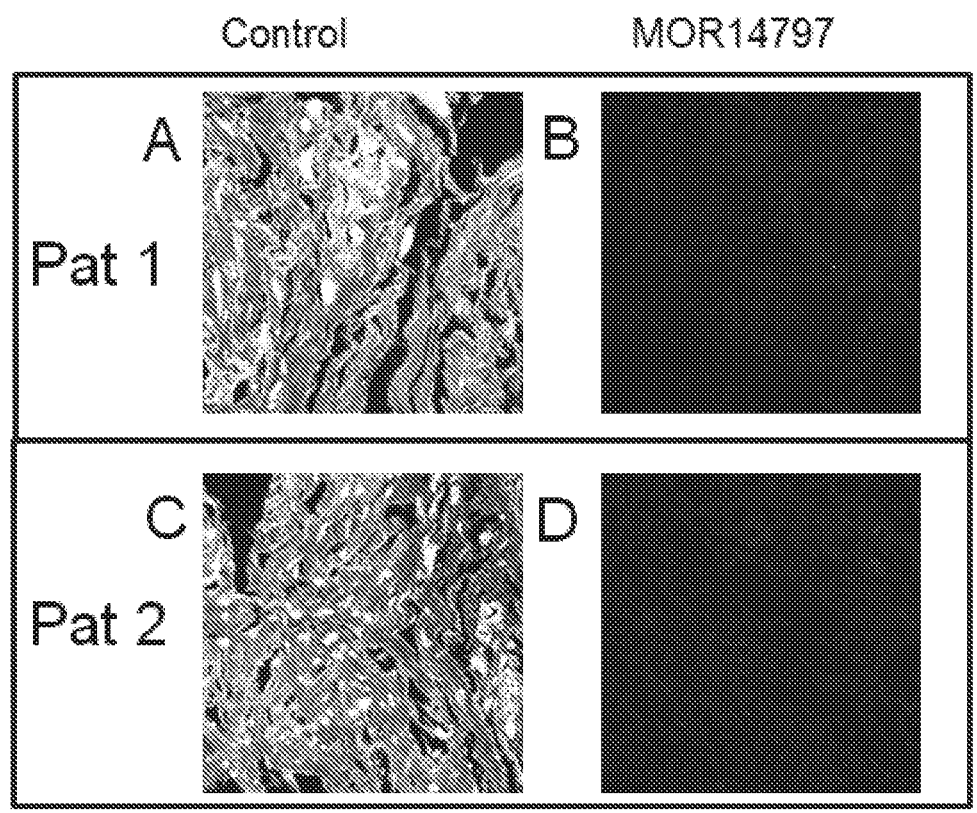

Figure 9: *Biologic activity in unilateral ureteral obstruction (UUO)*
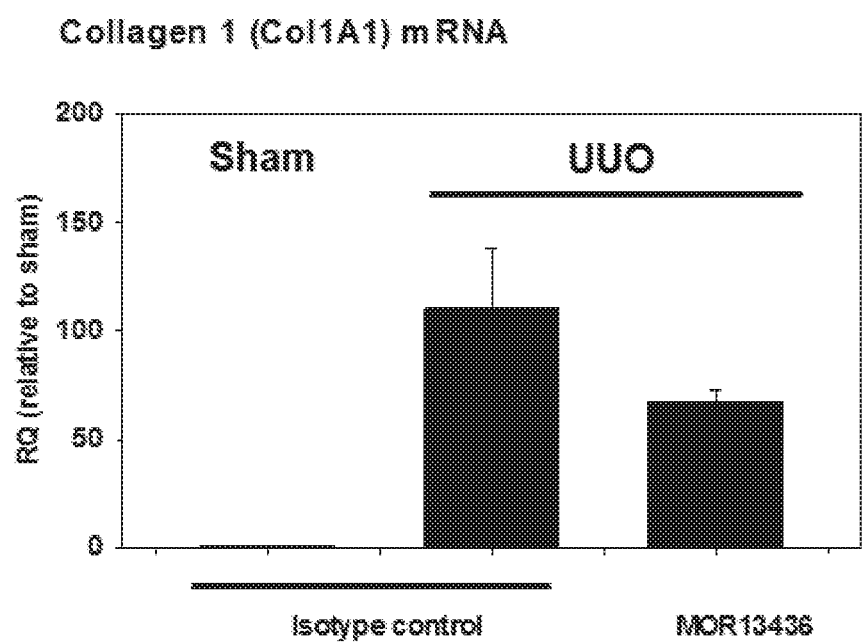

Figure 11: Paratope of MOR14797 binding to TGFβ-2.
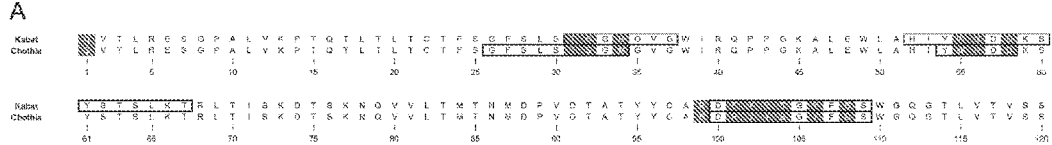
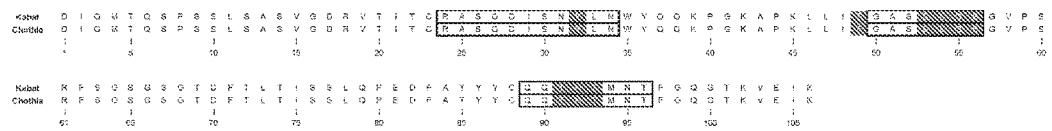

SEQUENCE LISTING

<160> NUMBER OF SEQ ID NOS: 204

<210> SEQ ID NO 1
<211> LENGTH: 5
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 1

Arg Tyr Tyr Val Ala
1               5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Trp Ile Asp Pro Gly Gln Ser Asn Thr Arg Tyr Ser Pro Ser Phe Gln
1               5                   10                  15

Gly

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Met Leu Ala Trp Gly Trp Phe Asp Tyr
1               5

<210> SEQ ID NO 4
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Tyr Ser Phe Thr Arg Tyr
1               5

<210> SEQ ID NO 5
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Asp Pro Gly Gln Ser Asn
1               5

<210> SEQ ID NO 6
<211> LENGTH: 9
<212> TYPE: PRT
<213> ORGANISM: Artificial Sequence
<220> FEATURE:
<221> NAME/KEY: source
```

<223> OTHER INFORMATION: /note="Description of Artificial Sequence:
    Synthetic peptide"

<400> SEQUENCE: 6

Met Leu Ala Trp Gly Trp Phe Asp Tyr
1               5

<210> SEQ ID NO 7
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 7

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Tyr
            20                  25                  30

Tyr Val Ala Trp Val Arg Gln Met Pro Gly Lys Gly Leu Glu Trp Met
        35                  40                  45

Gly Trp Ile Asp Pro Gly Gln Ser Asn Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Leu Ala Trp Gly Trp Phe Asp Tyr Trp Gly Gln Gly Thr
            100                 105                 110

Leu Val Thr Val Ser Ser
        115

<210> SEQ ID NO 8
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 8
caggtgcagc tggtgcagtc aggcgccgaa gtgaagaagc ccggcgagtc actgaagatt      60
agctgtaaag gctcaggcta tagcttcact aggtactacg tggcctgggt gagacagatg     120
cccggcaagg gcctggagtg gatgggctgg atcgaccccg gccagtctaa cactagatat     180
agccctagct ttcagggcca ggtgacaatt agcgccgata gtctattag caccgcctac      240 ctgcagtggt ctagcctgaa ggctagtgac accgctatgt actactgcgc tagaatgctg     300
gcctggggct ggttcgacta ctggggccag ggcaccctgg tgacagtgtc tagc           354

<210> SEQ ID NO 9
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 9

-continued

```
Gln Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Arg Tyr
            20                  25                  30

Tyr Val Ala Trp Val Arg Gln Met Pro Gly Lys Gly Leu Glu Trp Met
        35                  40                  45

Gly Trp Ile Asp Pro Gly Gln Ser Asn Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Leu Ala Trp Gly Trp Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 10
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10

```
caggtgcagc tggtgcagtc aggcgccgaa gtgaagaagc ccggcgagtc actgaagatt     60
agctgtaaag gctcaggcta tagcttcact aggtactacg tggcctgggt gagacagatg    120
cccggcaagg gcctggagtg gatgggctgg atcgaccccg ccagtctaa cactagatat     180
agccctagct ttcagggcca ggtgacaatt agcgccgata gtctattag caccgcctac     240
ctgcagtggt ctagcctgaa ggctagtgac accgctatgt actactgcgc tagaatgctg    300
gcctggggct ggttcgacta ctggggccag ggcaccctgg tgacagtgtc tagcgctagc    360
accaagggcc caagtgtgtt tcccctggcc cccagcagca gtctacttc ggcggaact     420
gctgccctgg gttgcctggt gaaggactac ttccccgagc ccgtgacagt gtcctggaac    480
tctgggctc tgacttccgg cgtgcacacc ttccccgccg tgctgcagag cagcggcctg    540
tacagcctga gcagcgtggt gacagtgccc tccagctctc tgggaaccca gacctatatc    600
tgcaacgtga accacaagcc cagcaacacc aaggtggaca gagagtgga gcccaagagc    660
tgcgacaaga cccacacctg cccccccctgc ccagctccag aactgctggg agggccttcc    720
gtgttcctgt tccccccaa gcccaaggac accctgatga tcagcaggac cccgaggtg    780
acctgcgtg tggtggacgt gtcccacgag gacccagagg tgaagttcaa ctggtacgtg    840
gacggcgtgg aggtgcacaa cgccaagacc aagcccagag aggagcagta caacagcacc    900
tacagggtgg tgtccgtgct gaccgtgctg caccaggact ggctgaacgg caaagaatac    960
aagtgcaaag tctccaacaa ggccctgcca gccccaatcg aaaagacaat cagcaaggcc   1020
aagggccagc cacgggagcc ccaggtgtac accctgcccc ccagccggga ggagatgacc   1080
aagaaccagg tgtccctgac ctgtctggtg aagggcttct accccagcga tatcgccgtg   1140
gagtgggaga gcaacggcca gcccgagaac aactacaaga ccaccccccc agtgctggac   1200
agcgacggca gcttcttcct gtacagcaag ctgaccgtgg acaagtccag gtggcagcag   1260
ggcaacgtgt tcagctgcag cgtgatgcac gaggccctgc acaaccacta cacccagaag   1320
tccctgagcc tgagccccgg caag                                          1344
```

<210> SEQ ID NO 11
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 11

```
Ser Gly Asp Asn Leu Gly Gly Tyr Tyr Ala His
1               5                   10
```

```
<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Lys Ser Asp Arg Pro Ser
1               5

<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ala Ser Tyr Asp Ser Ser Leu Met Met Val
1               5                   10

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asp Asn Leu Gly Gly Tyr Tyr
1               5

<210> SEQ ID NO 15
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Asp Lys Ser
1

<210> SEQ ID NO 16
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Tyr Asp Ser Ser Leu Met Met
1               5

<210> SEQ ID NO 17
<211> LENGTH: 107
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Leu Gly Gly Tyr Tyr Ala
            20                  25                  30

His Trp Tyr Gln Gln Lys Pro Gly Gln Ala Pro Val Leu Val Ile Tyr
        35                  40                  45

Asp Lys Ser Asp Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Ala Ser Tyr Asp Ser Ser Leu Met Met
                85                  90                  95

Val Phe Gly Gly Gly Thr Lys Leu Thr Val Leu
            100                 105

<210> SEQ ID NO 18
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
agctacgagc tgactcagcc cctgtcagtg tcagtggccc tgggccagac cgctagaatc      60
acctgtagcg gcgataacct gggcggctac tacgctcact ggtatcagca gaagcccggc    120
caggcccccg tgctggtgat ctacgataag tcagatagac ctagcggaat ccccgagcgg    180
tttagcggct ctaatagcgg caacaccgct accctgacta tctctagggc tcaggccggc    240
gacgaggcca actactactg cgctagttac gactctagcc tgatgatggt gttcggcgga    300
ggcactaagc tgaccgtgct g                                              321

<210> SEQ ID NO 19
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Leu Gly Gly Tyr Tyr Ala
            20                  25                  30

His Trp Tyr Gln Gln Lys Pro Gly Gln Ala Pro Val Leu Val Ile Tyr
        35                  40                  45

Asp Lys Ser Asp Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80
```

```
Asp Glu Ala Asp Tyr Tyr Cys Ala Ser Tyr Asp Ser Ser Leu Met Met
                85                  90                  95
Val Phe Gly Gly Gly Thr Lys Leu Thr Val Leu Gly Gln Pro Lys Ala
            100                 105                 110
Ala Pro Ser Val Thr Leu Phe Pro Pro Ser Ser Glu Glu Leu Gln Ala
        115                 120                 125
Asn Lys Ala Thr Leu Val Cys Leu Ile Ser Asp Phe Tyr Pro Gly Ala
    130                 135                 140
Val Thr Val Ala Trp Lys Ala Asp Ser Ser Pro Val Lys Ala Gly Val
145                 150                 155                 160
Glu Thr Thr Thr Pro Ser Lys Gln Ser Asn Asn Lys Tyr Ala Ala Ser
                165                 170                 175
Ser Tyr Leu Ser Leu Thr Pro Glu Gln Trp Lys Ser His Arg Ser Tyr
            180                 185                 190
Ser Cys Gln Val Thr His Glu Gly Ser Thr Val Glu Lys Thr Val Ala
        195                 200                 205
Pro Thr Glu Cys Ser
    210
```

<210> SEQ ID NO 20
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20

```
agctacgagc tgactcagcc cctgtcagtg tcagtggccc tgggccagac cgctagaatc      60
acctgtagcg gcgataacct gggcggctac tacgctcact ggtatcagca gaagcccggc     120
caggcccccg tgctggtgat ctacgataag tcagatagac ctagcggaat ccccgagcgg     180
tttagcggct ctaatagcgg caacaccgct accctgacta tctctagggc tcaggccggc     240
gacgaggccg actactactg cgctagttac gactctagcc tgatgatggt gttcggcgga     300
ggcactaagc tgaccgtgct gggccagcct aaggctgccc cagcgtgac cctgttcccc       360
cccagcagcg aggagctgca ggccaacaag gccaccctgg tgtgcctgat cagcgacttc     420
tacccaggcg ccgtgaccgt ggcctggaag gccgacagca gccccgtgaa ggccggcgtg     480
gagaccacca cccccagcaa gcagagcaac aacaagtacg ccgccagcag ctacctgagc     540
ctgacccccg agcagtggaa gagccacagg tcctacagct gccaggtgac ccacgagggc     600
agcaccgtgg aaaagaccgt ggccccaacc gagtgcagc                            639
```

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 21

```
Arg Tyr Tyr Val Ala
1               5
```

<210> SEQ ID NO 22

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Trp Ile Asp Pro Gly Gln Ser Asn Thr Arg Tyr Ser Pro Ser Phe Gln
1               5                   10                  15

Gly

<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Met Leu Ala Trp Gly Trp Phe Asp Tyr
1               5

<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Tyr Ser Phe Thr Arg Tyr
1               5

<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asp Pro Gly Gln Ser Asn
1               5

<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Met Leu Ala Trp Gly Trp Phe Asp Tyr
1               5

<210> SEQ ID NO 27
<211> LENGTH: 118
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Tyr
            20                  25                  30

Tyr Val Ala Trp Val Arg Gln Met Pro Gly Lys Gly Leu Glu Trp Met
        35                  40                  45

Gly Trp Ile Asp Pro Gly Gln Ser Asn Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Leu Ala Trp Gly Trp Phe Asp Tyr Trp Gly Gln Gly Thr
            100                 105                 110

Leu Val Thr Val Ser Ser
        115
```

<210> SEQ ID NO 28
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

```
caggtgcagc tggtgcagtc aggcgccgaa gtgaagaagc ccggcgagtc actgaagatt      60
agctgtaaag gctcaggcta tagcttcact aggtactacg tggcctgggt gagacagatg     120
cccggcaagg gcctggagtg gatgggctgg atcgaccccg gccagtctaa cactagatat     180
agccctagct ttcagggcca ggtgacaatt agcgccgata agtctattag caccgcctac     240
ctgcagtggt ctagcctgaa ggctagtgac accgctatgt actactgcgc tagaatgctg     300
gcctggggct ggttcgacta ctggggccag ggcacccctg gtgacagtgtc tagc          354
```

<210> SEQ ID NO 29
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Tyr
            20                  25                  30

Tyr Val Ala Trp Val Arg Gln Met Pro Gly Lys Gly Leu Glu Trp Met
        35                  40                  45

Gly Trp Ile Asp Pro Gly Gln Ser Asn Thr Arg Tyr Ser Pro Ser Phe
    50                  55                  60
```

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg Met Leu Ala Trp Gly Trp Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 30
<211> LENGTH: 1344
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 30

```
caggtgcagc tggtgcagtc aggcgccgaa gtgaagaagc ccggcgagtc actgaagatt    60
agctgtaaag gctcaggcta tagcttcact aggtactacg tggcctgggt gagacagatg   120
cccggcaagg gcctggagtg gatgggctgg atcgacccccg gccagtctaa cactagatat   180
agccctagct ttcagggcca ggtgacaatt agcgccgata agtctattag caccgcctac   240
ctgcagtggt ctagcctgaa ggctagtgac accgctatgt actactgcgc tagaatgctg   300
gcctggggct ggttcgacta ctggggccag ggcacccctgg tgacagtgtc tagcgctagc   360
accaagggcc caagtgtgtt tcccctggcc ccagcagca agtctacttc cggcggaact    420
gctgccctgg gttgcctggt gaaggactac ttccccgagc ccgtgacagt gtcctggaac   480
tctgggctc tgacttccgg cgtgcacacc ttccccgccg tgctgcagag cagcggcctg   540
tacagcctga gcagcgtggt gacagtgccc tccagctctc tgggaaccca gacctatatc   600
tgcaacgtga accacaagcc cagcaacacc aaggtggaca gagagtgga gcccaagagc   660
tgcgacaaga cccacacctg cccccccctgc ccagctccag aactgctggg agggccttcc   720
gtgttcctgt tccccccaa gcccaaggac accctgatga tcagcaggac ccccgaggtg   780
acctgcgtgg tggtggacgt gtcccacgag gacccagagg tgaagttcaa ctggtacgtg   840
gacggcgtgg aggtgcacaa cgccaagacc aagcccagag aggagcagta caacagcacc   900
tacagggtgg tgtccgtgct gaccgtgctg caccaggact ggctgaacgg caaagaatac   960
aagtgcaaag tctccaacaa ggccctgcca gccccaatcg aaaagacaat cagcaaggcc  1020
aagggccagc cacgggagcc ccaggtgtac accctgcccc ccagccggga ggagatgacc  1080
aagaaccagg tgtccctgac ctgtctggtg aagggcttct accccagcga tatcgccgtg  1140
gagtgggaga gcaacggcca gcccgagaac aactacaaga ccaccccccc agtgctggac  1200
agcgacggca gcttcttcct gtacagcaag ctgaccgtgg acaagtccag gtggcagcag  1260
ggcaacgtgt tcagctgcag cgtgatgcac gaggccctgc acaaccacta cacccagaag  1320
tccctgagcc tgagccccgg caag                                          1344
```

<210> SEQ ID NO 31
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 31

Ser Gly Asp Asn Leu Gly Gly Tyr Tyr Ala His
1               5                   10

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

Asp Thr Ser Asp Arg Pro Ser
1               5

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ala Ser Tyr Asp Ser Ser Leu Met Met Val
1               5                   10

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Asp Asn Leu Gly Gly Tyr Tyr
1               5

<210> SEQ ID NO 35
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Asp Thr Ser
1

<210> SEQ ID NO 36
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Tyr Asp Ser Ser Leu Met Met
1               5

<210> SEQ ID NO 37
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Leu Gly Gly Tyr Tyr Ala

```
                20                  25                  30

His Trp Tyr Gln Gln Lys Pro Gly Gln Ala Pro Val Leu Val Ile Tyr
            35                  40                  45

Asp Thr Ser Asp Arg Pro Ser Gly Ile Pro Glu Arg Phe Ser Gly Ser
        50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Ala Ser Tyr Asp Ser Ser Leu Met Met
                85                  90                  95

Val Phe Gly Gly Gly Thr Lys Leu Thr Val Leu
            100                 105

<210> SEQ ID NO 38
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38
agctacgagc tgactcagcc cctgtcagtg tcagtggccc tgggccagac cgctagaatc      60
acctgtagcg gcgataacct gggcggctac tacgctcact ggtatcagca gaagcccggc     120 caggccccg tgctggtgat ctacgacact agcgatagac ctagcggaat ccccgagcgg      180
tttagcggct ctaatagcgg caacaccgct accctgacta tctctagggc tcaggccggc    240
gacgaggccg actactactg cgctagttac gactctagcc tgatgatggt gttcggcgga    300
ggcactaagc tgaccgtgct g                                               321

<210> SEQ ID NO 39
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Ser Tyr Glu Leu Thr Gln Pro Leu Ser Val Ser Val Ala Leu Gly Gln
 1               5                  10                  15

Thr Ala Arg Ile Thr Cys Ser Gly Asp Asn Leu Gly Gly Tyr Tyr Ala
            20                  25                  30

His Trp Tyr Gln Gln Lys Pro Gly Gln Ala Pro Val Leu Val Ile Tyr
        35                  40                  45

Asp Thr Ser Asp Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Ala Ser Tyr Asp Ser Ser Leu Met Met
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140
```

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 40
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
agctacgagc tgactcagcc cctgtcagtg tcagtggccc tgggccagac cgctagaatc      60
acctgtagcg gcgataacct gggcggctac tacgctcact ggtatcagca gaagcccggc     120
caggcccccg tgctggtgat ctacgacact agcgatagac tagcggaat ccccgagcgg      180 tttagcggct ctaatagcgg caacaccgct accctgacta tctctagggc tcaggccggc     240
gacgaggccg actactactg cgctagttac gactctagcc tgatgatggt gttcggcgga     300
ggcactaagc tgaccgtgct gggccagcct aaggctgccc ccagcgtgac cctgttcccc     360
cccagcagca ggagctgca ggccaacaag gccaccctgg tgtgcctgat cagcgacttc      420
tacccaggcg ccgtgaccgt ggcctggaag gccgacagca gccccgtgaa ggccggcgtg     480
gagaccacca ccccccagcaa gcagagcaac aacaagtacg ccgccagcag ctacctgagc    540
ctgacccccg agcagtggaa gagccacagg tcctacagct gccaggtgac ccacgagggc    600
agcaccgtgg aaaagaccgt ggcccccaacc gagtgcagc                           639

<210> SEQ ID NO 41
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Arg Tyr Trp Ile Ala
1               5

<210> SEQ ID NO 42
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ile Ile Asp Pro Gly Thr Ser Asp Thr Arg Tyr Ser Pro Ser Phe Gln
1               5                   10                  15

Gly

<210> SEQ ID NO 43
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ile Asp Lys Ser Leu Ile Leu His Ser Ala Phe Asp Tyr
1               5                   10

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Tyr Ser Phe Thr Arg Tyr
1               5

<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Asp Pro Gly Thr Ser Asp
1               5

<210> SEQ ID NO 46
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ile Asp Lys Ser Leu Ile Leu His Ser Ala Phe Asp Tyr
1               5                   10

<210> SEQ ID NO 47
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Tyr

```
            20                  25                  30
Trp Ile Ala Trp Val Arg Gln Met Pro Gly Lys Gly Leu Glu Trp Met
        35                  40                  45

Gly Ile Ile Asp Pro Gly Thr Ser Asp Thr Arg Tyr Ser Pro Ser Phe
    50                  55                  60

Gln Gly Gln Val Thr Ile Ser Ala Asp Lys Ser Ile Ser Thr Ala Tyr
 65                 70                  75                  80

Leu Gln Trp Ser Ser Leu Lys Ala Ser Asp Thr Ala Met Tyr Tyr Cys
                85                  90                  95

Ala Arg Ile Asp Lys Ser Leu Ile Leu His Ser Ala Phe Asp Tyr Trp
            100                 105                 110

Gly Gln Gly Thr Leu Val Thr Val Ser Ser
            115                 120
```

<210> SEQ ID NO 48
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 48

```
caggtgcagc tggtgcagtc aggcgccgaa gtgaagaagc ccggcgagtc actgaagatt    60
agctgtaaag gctcaggcta tagcttcact agatactgga tcgcctgggt gagacagatg   120
cccggcaagg gctggagtg atgggaatt atcgacccg gcactagcga cactagatat   180
agccctagct ttcagggcca ggtgacaatt agcgccgata agtctattag caccgcctac   240
ctgcagtggt ctagcctgaa ggctagtgac accgctatgt actactgcgc tagaatcgat   300
aagtcactga tcctgcactc agccttcgac tactggggcc agggcaccct ggtgacagtg   360
tctagc                                                              366
```

<210> SEQ ID NO 49
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Arg Tyr
            20                  25                  30

Trp Ile Ala Trp Val Arg Gln Met Pro Gly Lys Gly Leu Glu Trp Met
        35                  40                  45

Gly Ile Ile Asp Pro Gly Thr Ser Asp Thr Arg Tyr Ser Pro Ser Phe
    50                  55                  60

Gln Gly Gln Val Thr Ile Ser Ala Asp Lys Ser Ile Ser Thr Ala Tyr
 65                 70                  75                  80

Leu Gln Trp Ser Ser Leu Lys Ala Ser Asp Thr Ala Met Tyr Tyr Cys
                85                  90                  95

Ala Arg Ile Asp Lys Ser Leu Ile Leu His Ser Ala Phe Asp Tyr Trp
            100                 105                 110
```

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
450

<210> SEQ ID NO 50
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50
caggtgcagc tggtgcagtc aggcgccgaa gtgaagaagc ccggcgagtc actgaagatt    60

-continued

```
agctgtaaag gctcaggcta tagcttcact agatactgga tcgcctgggt gagacagatg    120
cccggcaagg gcctggagtg gatgggaatt atcgaccccg gcactagcga cactagatat    180
agccctagct ttcagggcca ggtgacaatt agcgccgata agtctattag caccgcctac    240
ctgcagtggt ctagcctgaa ggctagtgac accgctatgt actactgcgc tagaatcgat    300
aagtcactga tcctgcactc agccttcgac tactggggcc agggcaccct ggtgacagtg    360
tctagcgcta gcaccaaggg cccaagtgtg tttcccctgg cccccagcag caagtctact    420
tccggcggaa ctgctgccct gggttgcctg gtgaaggact acttccccga gcccgtgaca    480
gtgtcctgga actctggggc tctgacttcc ggcgtgcaca ccttccccgc cgtgctgcag    540
agcagcggcc tgtacagcct gagcagcgtg gtgacagtgc cctccagctc tctgggaacc    600
cagacctata tctgcaacgt gaaccacaag cccagcaaca ccaaggtgga caagagagtg    660
gagcccaaga gctgcgacaa gacccacacc tgcccccccct gcccagctcc agaactgctg    720
ggagggcctt ccgtgttcct gttcccccccc aagcccaagg acaccctgat gatcagcagg    780
acccccgagg tgacctgcgt ggtggtggac gtgtcccacg aggacccaga ggtgaagttc    840
aactggtacg tggacggcgt ggaggtgcac aacgccaaga ccaagcccag agaggagcag    900
tacaacagca cctacagggt ggtgtccgtg ctgaccgtgc tgcaccagga ctggctgaac    960
ggcaaagaat acaagtgcaa agtctccaac aaggccctgc cagccccaat cgaaaagaca   1020
atcagcaagg ccaagggcca gccacgggag ccccaggtgt acaccctgcc ccccagccgg   1080
gaggagatga ccaagaacca ggtgtccctg acctgtctgg tgaagggctt ctaccccagc   1140
gatatcgccg tggagtggga gagcaacggc cagcccgaga caactacaa gaccacccc    1200 ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga gtccctgag cctgagcccc ggcaag                              1356
```

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ser Gly Asp Asn Leu Gly Gly Tyr Tyr Ala Tyr
1               5                   10

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Glu Thr Asn Asn Arg Pro Ser
1               5

<210> SEQ ID NO 53
<211> LENGTH: 11
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ala Ser Thr Thr Gln Asp Tyr Leu Val Phe Val
1               5                   10

<210> SEQ ID NO 54
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Asp Asn Leu Gly Gly Tyr Tyr
1               5

<210> SEQ ID NO 55
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Glu Thr Asn
1

<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Thr Thr Gln Asp Tyr Leu Val Phe
1               5

<210> SEQ ID NO 57
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Leu Gly Gly Tyr Tyr Ala
            20                  25                  30

Tyr Trp Tyr Gln Gln Lys Pro Gly Gln Ala Pro Val Leu Val Ile Tyr
        35                  40                  45

Glu Thr Asn Asn Arg Pro Ser Gly Ile Pro Glu Arg Phe Ser Gly Ser
    50                  55                  60
```

Asn Ser Gly Asn Thr Ala Thr Leu Thr Ile Ser Arg Ala Gln Ala Gly
65                  70                  75                  80

Asp Glu Ala Asp Tyr Tyr Cys Ala Ser Thr Thr Gln Asp Tyr Leu Val
                85                  90                  95

Phe Val Phe Gly Gly Gly Thr Lys Leu Thr Val Leu
            100                 105

<210> SEQ ID NO 58
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58
agctacgagc tgactcagcc cctgtcagtg tcagtggccc tgggccagac cgctagaatc      60
acctgtagcg gcgataacct gggcggctac tacgcctact ggtatcagca gaagcccggc     120
caggcccccg tgctggtgat ctacgagact aacaatagac ctagcggaat ccccgagcgg     180
tttagcggct ctaatagcgg caacaccgct accctgacta tctctagggc tcaggccggc     240
gacgaggccg actactactg cgctagtact actcaggact acctggtgtt cgtgttcggc     300
ggaggcacta agctgaccgt gctg                                            324

<210> SEQ ID NO 59
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Leu Gly Gly Tyr Tyr Ala
            20                  25                  30

Tyr Trp Tyr Gln Gln Lys Pro Gly Gln Ala Pro Val Leu Val Ile Tyr
        35                  40                  45

Glu Thr Asn Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Ala Ser Thr Thr Gln Asp Tyr Leu Val
                85                  90                  95

Phe Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 60
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60

```
agctacgagc tgactcagcc cctgtcagtg tcagtggccc tgggccagac cgctagaatc    60
acctgtagcg gcgataacct gggcggctac tacgcctact ggtatcagca gaagcccggc   120
caggcccccg tgctggtgat ctacgagact aacaatagac ctagcggaat ccccgagcgg   180
tttagcggct ctaatagcgg caacaccgct accctgacta tctctagggc tcaggccggc   240
gacgaggccg actactactg cgctagtact actcaggact acctggtgtt cgtgttcggc   300
ggaggcacta agctgaccgt gctgggccag cctaaggctg cccccagcgt gaccctgttc   360 cccccagca gcgaggagct gcaggccaac aaggccaccc tggtgtgcct gatcagcgac   420
ttctacccag cgccgtgac cgtggcctgg aaggccgaca gcagcccgt gaaggccggc   480 gtggagacca ccacccccag caagcagagc aacaacaagt acgccgccag cagctacctg   540
agcctgaccc ccgagcagtg gaagagccac aggtcctaca gctgccaggt gacccacgag   600
ggcagcaccg tggaaaagac cgtggccca accgagtgca gc                      642
```

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Thr Ser Gly Met Gly Val Gly
1               5

<210> SEQ ID NO 62
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

His Ile Tyr Trp Asn Asp Asp Lys Ser Tyr Ser Thr Ser Leu Lys Thr
1               5                   10                  15

<210> SEQ ID NO 63
<211> LENGTH: 10
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic peptide"

<400> SEQUENCE: 63

Asp Phe Tyr Tyr Ser Gly Tyr Phe Asp Ser
1               5                   10

<210> SEQ ID NO 64
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Gly Phe Ser Leu Ser Thr Ser Gly Met
1               5

<210> SEQ ID NO 65
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Tyr Trp Asn Asp Asp
1               5

<210> SEQ ID NO 66
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Asp Phe Tyr Tyr Ser Gly Tyr Phe Asp Ser
1               5                   10

<210> SEQ ID NO 67
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Tyr Trp Asn Asp Asp Lys Ser Tyr Ser Thr Ser
    50                  55                  60

Leu Lys Thr Arg Leu Thr Ile Ser Lys Asp Thr Ser Lys Asn Gln Val

```
                65                  70                  75                  80
Val Leu Thr Met Thr Asn Met Asp Pro Val Asp Thr Ala Thr Tyr Tyr
                    85                  90                  95

Cys Ala Arg Asp Phe Tyr Tyr Ser Gly Tyr Phe Asp Ser Trp Gly Gln
                100                 105                 110

Gly Thr Leu Val Thr Val Ser Ser
            115                 120
```

<210> SEQ ID NO 68
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 68

```
caggtgacac tgagagagtc aggccctgcc ctggtgaaac ctactcagac cctgaccctg      60
acctgcacct ttagcggctt tagcctgagc actagcggaa tgggcgtggg ctggattaga     120
cagccccctg caaggccct ggagtggctg gctcacatct actggaacga cgataagtcc     180
tactctacta gcctgaaaac taggctgact atctctaagg acacctctaa gaatcaggtg     240
gtgctgacta tgactaatat ggaccccgtg gacaccgcta cctactactg cgctagagac     300
ttctactata gcggctactt cgatagctgg ggccagggca ccctggtgac agtgtctagc     360
```

<210> SEQ ID NO 69
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 69

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Gly Trp Ile Arg Gln Pro Pro Gly Lys Ala Leu Glu
            35                  40                  45

Trp Leu Ala His Ile Tyr Trp Asn Asp Asp Lys Ser Tyr Ser Thr Ser
        50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                    85                  90                  95

Cys Ala Arg Asp Phe Tyr Tyr Ser Gly Tyr Phe Asp Ser Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 70
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70
caggtgacac tgagagagtc aggccctgcc ctggtgaaac ctactcagac cctgaccctg      60
acctgcacct ttagcggctt tagcctgagc actagcggaa tgggcgtggg ctggattaga     120
cagccccctg gcaaggccct ggagtggctg gctcacatct actggaacga cgataagtcc     180
tactctacta gcctgaaaac taggctgact atctctaagg acacctctaa gaatcaggtg     240
gtgctgacta tgactaatat ggaccccgtg acaccgcta ctactactg cgctagagac       300 ttctactata gcggctactt cgatagctgg ggccagggca ccctggtgac agtgtctagc     360

```
gctagcacca agggcccaag tgtgtttccc ctggccccca gcagcaagtc tacttccggc    420
ggaactgctg ccctgggttg cctggtgaag gactacttcc ccgagcccgt gacagtgtcc    480
tggaactctg gggctctgac ttccggcgtg cacaccttcc ccgccgtgct gcagagcagc    540
ggcctgtaca gcctgagcag cgtggtgaca gtgccctcca gctctctggg aacccagacc    600
tatatctgca acgtgaacca caagcccagc aacaccaagg tggacaagag agtggagccc    660
aagagctgcg acaagaccca cacctgcccc cctgcccag ctccagaact gctgggaggg    720
ccttccgtgt tcctgttccc ccccaagccc aaggacaccc tgatgatcag caggaccccc    780
gaggtgacct gcgtggtggt ggacgtgtcc cacgaggacc cagaggtgaa gttcaactgg    840
tacgtggacg gcgtggaggt gcacaacgcc aagaccaagc ccagagagga gcagtacaac    900
agcacctaca gggtggtgtc cgtgctgacc gtgctgcacc aggactggct gaacggcaaa    960
gaatacaagt gcaaagtctc caacaaggcc ctgccagccc caatcgaaaa gacaatcagc   1020
aaggccaagg gccagccacg ggagccccag gtgtacaccc tgcccccag ccggaggag   1080
atgaccaaga accaggtgtc cctgacctgt ctggtgaagg gcttctaccc cagcgatatc   1140
gccgtggagt gggagagcaa cggccagccc gagaacaact acaagaccac ccccccagtg   1200
ctggacagcg acggcagctt cttcctgtac agcaagctga ccgtggacaa gtccaggtgg   1260
cagcagggca acgtgttcag ctgcagcgtg atgcacgagg ccctgcacaa ccactacacc   1320
cagaagtccc tgagcctgag ccccggcaag                                    1350
```

<210> SEQ ID NO 71
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Arg Ala Ser Gln Asp Ile Ser Asn Tyr Leu Asn
1               5                   10

<210> SEQ ID NO 72
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Gly Ala Ser Ser Leu Gln Ser
1               5

<210> SEQ ID NO 73
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gln Gln Thr Asn Thr Met Asn Thr
1               5

<210> SEQ ID NO 74
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Ser Gln Asp Ile Ser Asn Tyr
1               5

<210> SEQ ID NO 75
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Gly Ala Ser
1

<210> SEQ ID NO 76
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Thr Asn Thr Met Asn
1               5

<210> SEQ ID NO 77
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Phe Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Thr Met Asn Thr
                85                  90                  95

Phe Gly Gln Gly Thr Lys Val Glu Ile Lys
            100                 105

-continued

```
<210> SEQ ID NO 78
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
gatattcaga tgactcagtc acctagtagc ctgagcgcta gtgtgggcga tagagtgact      60
atcacctgta gagcctctca ggatatctct aactacctga actggtatca gcagaagccc     120
ggcaaggccc ctaagctgct gatcttcggc gcctctagcc tgcagtcagg cgtgccctct     180
aggtttagcg gctcaggctc aggcaccgac ttcaccctga ctattagtag cctgcagccc     240
gaggacttcg ctacctacta ctgtcagcag actaacacta tgaacacctt cggccagggc     300
actaaggtgg agattaag                                                   318

<210> SEQ ID NO 79
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Phe Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Thr Met Asn Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 80
```

-continued

<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80

```
gatattcaga tgactcagtc acctagtagc ctgagcgcta gtgtgggcga tagagtgact      60
atcacctgta gagcctctca ggatatctct aactacctga actggtatca gcagaagccc     120
ggcaaggccc ctaagctgct gatcttcggc gcctctagcc tgcagtcagg cgtgccctct     180
aggtttagcg gctcaggctc aggcaccgac ttcaccctga ctattagtag cctgcagccc     240
gaggacttcg ctacctacta ctgtcagcag actaacacta tgaacacctt cggccagggc     300
actaaggtgg agattaagcg tacggtggcc gctcccagcg tgttcatctt cccccccagc     360
gacgagcagc tgaagagcgg caccgccagc gtggtgtgcc tgctgaacaa cttctacccc     420
cgggaggcca aggtgcagtg gaaggtggac aacgccctgc agagcggcaa cagccaggag     480
agcgtcaccg agcaggacag caaggactcc acctacagcc tgagcagcac cctgaccctg     540
agcaaggcca ctacgagaa gcataaggtg tacgcctgcg aggtgaccca ccagggcctg      600
tccagccccg tgaccaagag cttcaacagg ggcgagtgc                            639
```

<210> SEQ ID NO 81
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Arg Tyr Tyr Val Ala
1               5

<210> SEQ ID NO 82
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Trp Ile Asp Pro Gly Thr Ser Asn Thr Arg Tyr Ser Pro Ser Phe Gln
1               5                   10                  15

Gly

<210> SEQ ID NO 83
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Met Leu Ala Trp Gly Trp Phe Asp Tyr
1               5

<210> SEQ ID NO 84
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 84

```
Gly Tyr Ser Phe Thr Arg Tyr
1               5
```

<210> SEQ ID NO 85
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 85

```
Asp Pro Gly Thr Ser Asn
1               5
```

<210> SEQ ID NO 86
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 86

```
Met Leu Ala Trp Gly Trp Phe Asp Tyr
1               5
```

<210> SEQ ID NO 87
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 87

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Tyr
            20                  25                  30

Tyr Val Ala Trp Val Arg Gln Met Pro Gly Lys Gly Leu Glu Trp Met
        35                  40                  45

Gly Trp Ile Asp Pro Gly Thr Ser Asn Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Leu Ala Trp Gly Trp Phe Asp Tyr Trp Gly Gln Gly Thr
            100                 105                 110

Leu Val Thr Val Ser Ser
```

<210> SEQ ID NO 88
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88

```
caggtgcagc tggtgcagtc aggcgccgaa gtgaagaagc ccggcgagtc actgaagatt      60
agctgtaaag gctcaggcta tagcttcact aggtactacg tggcctgggt gagacagatg     120
cccggcaagg gcctggagtg gatgggctgg atcgaccccg gcacctctaa cactagatat     180
agccctagct ttcagggcca ggtgacaatt agcgccgata agtctattag caccgcctac     240
ctgcagtggt ctagcctgaa ggctagtgac accgctatgt actactgcgc tagaatgctg     300
gcctggggct ggttcgacta ctggggccag ggcaccctgg tgacagtgtc tagc            354
```

<210> SEQ ID NO 89
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 89

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Tyr
            20                  25                  30

Tyr Val Ala Trp Val Arg Gln Met Pro Gly Lys Gly Leu Glu Trp Met
        35                  40                  45

Gly Trp Ile Asp Pro Gly Thr Ser Asn Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Met Leu Ala Trp Gly Trp Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220
```

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 90
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 90

```
caggtgcagc tggtgcagtc aggcgccgaa gtgaagaagc ccggcgagtc actgaagatt     60
agctgtaaag gctcaggcta tagcttcact aggtactacg tggcctgggt gagacagatg    120
cccggcaagg gcctggagtg gatgggctgg atcgaccccg gcacctctaa cactagatat    180
agccctagct ttcagggcca ggtgacaatt agcgccgata gtctattagc caccgcctac    240
ctgcagtggt ctagcctgaa ggctagtgac accgctatgt actactgcgc tagaatgctg    300
gcctggggct ggttcgacta ctggggccag ggcaccctgg tgacagtgtc tagcgctagc    360
accaagggcc caagtgtgtt tcccctggcc ccagcagca agtctacttc cggcggaact    420
gctgccctgg gttgcctggt gaaggactac ttccccgagc ccgtgacagt gtcctggaac    480 tctgggctc tgacttccgg cgtgcacacc ttccccgccg tgctgcagag cagcggcctg    540
tacagcctga gcagcgtggt gacagtgccc tccagctctc tgggaaccca gacctatatc    600
tgcaacgtga accacaagcc cagcaacacc aaggtggaca gagagtgga gcccaagagc    660 tgcgacaaga cccacacctg ccccccctgc ccagctccag aactgctggg agggccttcc    720
```

```
gtgttcctgt tcccccccaa gcccaaggac accctgatga tcagcaggac ccccgaggtg     780
acctgcgtgg tggtggacgt gtcccacgag gacccagagg tgaagttcaa ctggtacgtg     840
gacggcgtgg aggtgcacaa cgccaagacc aagcccagag aggagcagta caacagcacc     900
tacagggtgg tgtccgtgct gaccgtgctg caccaggact ggctgaacgg caaagaatac     960
aagtgcaaag tctccaacaa ggccctgcca gccccaatcg aaaagacaat cagcaaggcc    1020
aagggccagc cacgggagcc ccaggtgtac accctgcccc cagccgggga ggagatgacc    1080
aagaaccagg tgtccctgac ctgtctggtg aagggcttct accccagcga tatcgccgtg    1140
gagtgggaga gcaacggcca gcccgagaac aactacaaga ccaccccccc agtgctggac    1200
agcgacggca gcttcttcct gtacagcaag ctgaccgtgg acaagtccag gtggcagcag    1260
ggcaacgtgt tcagctgcag cgtgatgcac gaggccctgc acaaccacta cacccagaag    1320
tccctgagcc tgagccccgg caag                                            1344
```

<210> SEQ ID NO 91
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Ser Gly Asp Asn Leu Gly Gly Tyr Tyr Ala His
1               5                   10

<210> SEQ ID NO 92
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Asp Lys Ser Asp Arg Pro Ser
1               5

<210> SEQ ID NO 93
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Ala Ser Tyr Asp Ser Ser Leu Met Met Val
1               5                   10

<210> SEQ ID NO 94
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Asp Asn Leu Gly Gly Tyr Tyr
1               5

<210> SEQ ID NO 95
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Asp Lys Ser
1

<210> SEQ ID NO 96
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Tyr Asp Ser Ser Leu Met Met
1               5

<210> SEQ ID NO 97
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Leu Gly Gly Tyr Tyr Ala
            20                  25                  30

His Trp Tyr Gln Gln Lys Pro Gly Gln Ala Pro Val Leu Val Ile Tyr
        35                  40                  45

Asp Lys Ser Asp Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Ala Ser Tyr Asp Ser Ser Leu Met Met
                85                  90                  95

Val Phe Gly Gly Gly Thr Lys Leu Thr Val Leu
                100                 105

<210> SEQ ID NO 98
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98
agctacgagc tgactcagcc cctgtcagtg tcagtggccc tgggccagac cgctagaatc     60

```
acctgtagcg gcgataacct gggcggctac tacgctcact ggtatcagca gaagcccggc    120
caggcccccg tgctggtgat ctacgataag tcagatagac ctagcggaat ccccgagcgg    180
tttagcggct ctaatagcgg caacaccgct accctgacta tctctagggc tcaggccggc    240
gacgaggccg actactactg cgctagttac gactctagcc tgatgatggt gttcggcgga    300
ggcactaagc tgaccgtgct g                                              321
```

```
<210> SEQ ID NO 99
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99
```

| | | | | | | | | | | | | | | | |
|---|---|---|---|---|---|---|---|---|---|---|---|---|---|---|---|
| Ser | Tyr | Glu | Leu | Thr | Gln | Pro | Leu | Ser | Val | Ser | Val | Ala | Leu | Gly | Gln |
| 1 | | | | 5 | | | | | 10 | | | | | 15 | |
| Thr | Ala | Arg | Ile | Thr | Cys | Ser | Gly | Asp | Asn | Leu | Gly | Gly | Tyr | Tyr | Ala |
| | | | 20 | | | | | 25 | | | | | 30 | | |
| His | Trp | Tyr | Gln | Gln | Lys | Pro | Gly | Gln | Ala | Pro | Val | Leu | Val | Ile | Tyr |
| | | | 35 | | | | | 40 | | | | | 45 | | |
| Asp | Lys | Ser | Asp | Arg | Pro | Ser | Gly | Ile | Pro | Glu | Arg | Phe | Ser | Gly | Ser |
| 50 | | | | | 55 | | | | | 60 | | | | | |
| Asn | Ser | Gly | Asn | Thr | Ala | Thr | Leu | Thr | Ile | Ser | Arg | Ala | Gln | Ala | Gly |
| 65 | | | | | 70 | | | | | 75 | | | | | 80 |
| Asp | Glu | Ala | Asp | Tyr | Tyr | Cys | Ala | Ser | Tyr | Asp | Ser | Ser | Leu | Met | Met |
| | | | | 85 | | | | | 90 | | | | | 95 | |
| Val | Phe | Gly | Gly | Gly | Thr | Lys | Leu | Thr | Val | Leu | Gly | Gln | Pro | Lys | Ala |
| | | | | 100 | | | | | 105 | | | | | 110 | |
| Ala | Pro | Ser | Val | Thr | Leu | Phe | Pro | Pro | Ser | Ser | Glu | Glu | Leu | Gln | Ala |
| | | | 115 | | | | | 120 | | | | | 125 | | |
| Asn | Lys | Ala | Thr | Leu | Val | Cys | Leu | Ile | Ser | Asp | Phe | Tyr | Pro | Gly | Ala |
| | 130 | | | | | 135 | | | | | 140 | | | | |
| Val | Thr | Val | Ala | Trp | Lys | Ala | Asp | Ser | Ser | Pro | Val | Lys | Ala | Gly | Val |
| 145 | | | | | 150 | | | | | 155 | | | | | 160 |
| Glu | Thr | Thr | Thr | Pro | Ser | Lys | Gln | Ser | Asn | Asn | Lys | Tyr | Ala | Ala | Ser |
| | | | | 165 | | | | | 170 | | | | | 175 | |
| Ser | Tyr | Leu | Ser | Leu | Thr | Pro | Glu | Gln | Trp | Lys | Ser | His | Arg | Ser | Tyr |
| | | | 180 | | | | | 185 | | | | | 190 | | |
| Ser | Cys | Gln | Val | Thr | His | Glu | Gly | Ser | Thr | Val | Glu | Lys | Thr | Val | Ala |
| | | | 195 | | | | | 200 | | | | | 205 | | |
| Pro | Thr | Glu | Cys | Ser | | | | | | | | | | | |
| | | | 210 | | | | | | | | | | | | |

```
<210> SEQ ID NO 100
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100
agctacgagc tgactcagcc cctgtcagtg tcagtggccc tgggccagac cgctagaatc    60
```

```
acctgtagcg gcgataacct gggcggctac tacgctcact ggtatcagca gaagcccggc    120
caggcccccg tgctggtgat ctacgataag tcagatagac ctagcggaat ccccgagcgg    180
tttagcggct ctaatagcgg caacaccgct accctgacta tctctagggc tcaggccggc    240
gacgaggccg actactactg cgctagttac gactctagcc tgatgatggt gttcggcgga    300
ggcactaagc tgaccgtgct gggccagcct aaggctgccc ccagcgtgac cctgttcccc    360
cccagcagcg aggagctgca ggccaacaag gccaccctgg tgtgcctgat cagcgacttc    420
tacccaggcg ccgtgaccgt ggcctggaag gccgacagca gccccgtgaa ggccggcgtg    480
gagaccacca cccccagcaa gcagagcaac aacaagtacg ccgccagcag ctacctgagc    540
ctgacccccg agcagtggaa gagccacagg tcctacagct gccaggtgac ccacgagggc    600
agcaccgtgg aaaagaccgt ggccccaacc gagtgcagc                           639
```

```
<210> SEQ ID NO 101
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ser Tyr Ala Ile Ser
1               5

<210> SEQ ID NO 102
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Val Ile Val Pro Lys Trp Gly His Pro Gln Tyr Ala Gln Lys Phe Gln
1               5                   10                  15

Gly

<210> SEQ ID NO 103
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Glu Gly Asp Phe Val Val Leu Val Leu Thr Glu His Tyr Met Gly Gly
1               5                   10                  15

Phe Asp Val

<210> SEQ ID NO 104
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 104

Gly Gly Thr Phe Ser Ser Tyr
1               5

<210> SEQ ID NO 105
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Val Pro Lys Trp Gly His
1               5

<210> SEQ ID NO 106
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Glu Gly Asp Phe Val Val Leu Val Leu Thr Glu His Tyr Met Gly Gly
1               5                   10                  15

Phe Asp Val

<210> SEQ ID NO 107
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Val Pro Lys Trp Gly His Pro Gln Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Asp Phe Val Val Leu Val Leu Thr Glu His Tyr Met
            100                 105                 110

Gly Gly Phe Asp Val Trp Gly Gln Gly Thr Leu Val Thr Val Ser Ser
        115                 120                 125

<210> SEQ ID NO 108
<211> LENGTH: 384
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 108

```
caggtgcagc tggtgcagtc aggcgccgaa gtgaagaaac ccggctctag cgtgaaagtg      60
agctgtaaag ctagtggcgg caccttctct agctacgcta ttagctgggt gagacaggcc     120
ccaggccagg gcctggagtg gatgggcgtg atcgtgccta agtggggcca ccctcagtac     180
gctcagaaat tcagggcag agtgactatc accgccgacg agtctactag caccgcctat      240
atggaactgt ctagcctgag atcagaggac accgccgtgt actactgcgc tagagaaggc     300
gacttcgtgg tgctggtgct gaccgagcac tatatgggcg gcttcgacgt gtggggccag     360
ggcaccctgg tgacagtgtc tagc                                            384
```

<210> SEQ ID NO 109
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Val Pro Lys Trp Gly His Pro Gln Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Asp Phe Val Val Leu Val Leu Thr Glu His Tyr Met
            100                 105                 110

Gly Gly Phe Asp Val Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255
```

```
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
        275                 280                 285
Tyr Val Asp Gly Val Glu Val His Asn Ala Lys Thr Lys Pro Arg Glu
    290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
            340                 345                 350
Gln Pro Arg Glu Pro Gln Val Tyr Thr Leu Pro Pro Ser Arg Glu Glu
        355                 360                 365
Met Thr Lys Asn Gln Val Ser Leu Thr Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly Lys
    450                 455
```

<210> SEQ ID NO 110
<211> LENGTH: 1374
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 110

| | | | | |
|---|---|---|---|---|
| caggtgcagc tggtgcagtc aggcgccgaa gtgaagaaac ccggctctag cgtgaaagtg | 60 |
| agctgtaaag ctagtggcgg caccttctct agctacgcta ttagctgggt gagacaggcc | 120 |
| ccaggccagg gcctggagtg gatgggcgtg atcgtgccta gtggggccac ccctcagtac | 180 |
| gctcagaaat tcagggcag agtgactatc accgccgacg agtctactag caccgcctat | 240 |
| atggaactgt ctagcctgag atcagaggac accgccgtgt actactgcgc tagagaaggc | 300 |
| gacttcgtgg tgctggtgct gaccgagcac tatatgggcg gcttcgacgt gtggggccag | 360 |
| ggcacccctg tgacagtgtc tagcgctagc accaagggcc caagtgtgtt ccccctggcc | 420 |
| cccagcagca gtctactttc cggcggaact gctgccctgg gttgcctggt gaaggactac | 480 |
| ttccccgagc ccgtgacagt gcctggaac tctgggctc tgacttccgg cgtgcacacc | 540 |
| ttccccgccg tgctgcagag cagcggcct tacagcctga gcagcgtggt gacagtgccc | 600 |
| tccagctctc tgggaaccca gacctatatc tgcaacgtga accacaagcc cagcaacacc | 660 |
| aaggtggaca gagagtgga gcccaagagc tgcgacaaga cccacacctg cccccccctgc | 720 |
| ccagctccag aactgctggg agggcctccc gtgttcctgt tccccccaa gcccaaggac | 780 |
| accctgatga tcagcaggac ccccgaggtg acctgcgtgg tggtggacgt gtcccacgag | 840 |

```
gacccagagg tgaagttcaa ctggtacgtg gacggcgtgg aggtgcacaa cgccaagacc    900
aagcccagag aggagcagta caacagcacc tacagggtgg tgtccgtgct gaccgtgctg    960
caccaggact ggctgaacgg caaagaatac aagtgcaaag tctccaacaa ggccctgcca   1020
gccccaatcg aaaagacaat cagcaaggcc aagggccagc cacgggagcc ccaggtgtac   1080
accctgcccc ccagccggga ggagatgacc aagaaccagg tgtccctgac ctgtctggtg   1140
aagggcttct accccagcga tatcgccgtg gagtgggaga gcaacggcca gcccgagaac   1200
aactacaaga ccaccccccc agtgctggac agcgacggca gcttcttcct gtacagcaag   1260
ctgaccgtgg acaagtccag gtggcagcag ggcaacgtgt tcagctgcag cgtgatgcac   1320
gaggccctgc acaaccacta cacccagaag tccctgagcc tgagccccgg caag         1374
```

<210> SEQ ID NO 111
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Arg Ala Ser Gln Ser Ile Asp Glu Tyr Leu Asn
1               5                   10

<210> SEQ ID NO 112
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Ala Gly Ser Asn Leu Gln Ser
1               5

<210> SEQ ID NO 113
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Leu Gln Gly Tyr Ser Tyr Pro Arg Thr
1               5

<210> SEQ ID NO 114
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Ser Gln Ser Ile Asp Glu Tyr
1               5

<210> SEQ ID NO 115
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Ala Gly Ser
1

<210> SEQ ID NO 116
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Gly Tyr Ser Tyr Pro Arg
1               5

<210> SEQ ID NO 117
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Glu Tyr
            20                  25                  30

Leu Asn Trp Tyr Gln Gln Lys Pro Gly Lys Ala Pro Lys Leu Leu Ile
        35                  40                  45

Tyr Ala Gly Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Tyr Ser Tyr Pro Arg
                85                  90                  95

Thr Phe Gly Gln Gly Thr Lys Val Glu Ile Lys
            100                 105

<210> SEQ ID NO 118
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 118
gatattcaga tgactcagtc acctagtagc ctgagcgcta gtgtgggcga tagagtgact      60
atcacctgta gagcctctca gtctatcgac gagtacctga ctggtatca gcagaagccc     120

```
ggcaaggccc ctaagctgct gatctacgcc ggctctaacc tgcagtcagg cgtgccctct    180
aggtttagcg gctcaggctc aggcaccgac ttcaccctga ctatctctag cctgcagccc    240
gaggacttcg ctacctacta ctgtctgcag ggctatagct accctagaac cttcggccag    300
ggcactaagg tggagattaa g                                              321
```

<210> SEQ ID NO 119
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 119

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Glu Tyr
            20                  25                  30

Leu Asn Trp Tyr Gln Gln Lys Pro Gly Lys Ala Pro Lys Leu Leu Ile
        35                  40                  45

Tyr Ala Gly Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Tyr Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 120
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 120

```
gatattcaga tgactcagtc acctagtagc ctgagcgcta gtgtgggcga tagagtgact     60
atcacctgta gagcctctca gtctatcgac gagtacctga actggtatca gcagaagccc    120
ggcaaggccc ctaagctgct gatctacgcc ggctctaacc tgcagtcagg cgtgccctct    180
```

```
aggtttagcg gctcaggctc aggcaccgac ttcaccctga ctatctctag cctgcagccc    240
gaggacttcg ctacctacta ctgtctgcag ggctatagct accctagaac cttcggccag    300
ggcactaagg tggagattaa gcgtacggtg gccgctccca gcgtgttcat cttccccccc    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac agggggcgagt gc                     642
```

<210> SEQ ID NO 121
<211> LENGTH: 390
<212> TYPE: PRT
<213> ORGANISM: Homo sapiens

<400> SEQUENCE: 121

```
Met Pro Pro Ser Gly Leu Arg Leu Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285
```

```
Thr Glu Lys Asn Cys Cys Val Arg Gln Leu Tyr Ile Asp Phe Arg Lys
        290                 295                 300
Asp Leu Gly Trp Lys Trp Ile His Glu Pro Lys Gly Tyr His Ala Asn
305                 310                 315                 320
Phe Cys Leu Gly Pro Cys Pro Tyr Ile Trp Ser Leu Asp Thr Gln Tyr
                325                 330                 335
Ser Lys Val Leu Ala Leu Tyr Asn Gln His Asn Pro Gly Ala Ser Ala
            340                 345                 350
Ala Pro Cys Cys Val Pro Gln Ala Leu Glu Pro Leu Pro Ile Val Tyr
        355                 360                 365
Tyr Val Gly Arg Lys Pro Lys Val Glu Gln Leu Ser Asn Met Ile Val
370                 375                 380
Arg Ser Cys Lys Cys Ser
385                 390

<210> SEQ ID NO 122
<211> LENGTH: 414
<212> TYPE: PRT
<213> ORGANISM: Homo sapiens

<400> SEQUENCE: 122

Met His Tyr Cys Val Leu Ser Ala Phe Leu Ile Leu His Leu Val Thr
1               5                   10                  15
Val Ala Leu Ser Leu Ser Thr Cys Ser Thr Leu Asp Met Asp Gln Phe
            20                  25                  30
Met Arg Lys Arg Ile Glu Ala Ile Arg Gly Gln Ile Leu Ser Lys Leu
        35                  40                  45
Lys Leu Thr Ser Pro Pro Glu Asp Tyr Pro Glu Pro Glu Glu Val Pro
50                  55                  60
Pro Glu Val Ile Ser Ile Tyr Asn Ser Thr Arg Asp Leu Leu Gln Glu
65                  70                  75                  80
Lys Ala Ser Arg Arg Ala Ala Ala Cys Glu Arg Glu Arg Ser Asp Glu
                85                  90                  95
Glu Tyr Tyr Ala Lys Glu Val Tyr Lys Ile Asp Met Pro Pro Phe Phe
            100                 105                 110
Pro Ser Glu Asn Ala Ile Pro Pro Thr Phe Tyr Arg Pro Tyr Phe Arg
        115                 120                 125
Ile Val Arg Phe Asp Val Ser Ala Met Glu Lys Asn Ala Ser Asn Leu
130                 135                 140
Val Lys Ala Glu Phe Arg Val Phe Arg Leu Gln Asn Pro Lys Ala Arg
145                 150                 155                 160
Val Pro Glu Gln Arg Ile Glu Leu Tyr Gln Ile Leu Lys Ser Lys Asp
                165                 170                 175
Leu Thr Ser Pro Thr Gln Arg Tyr Ile Asp Ser Lys Val Val Lys Thr
            180                 185                 190
Arg Ala Glu Gly Glu Trp Leu Ser Phe Asp Val Thr Asp Ala Val His
        195                 200                 205
Glu Trp Leu His His Lys Asp Arg Asn Leu Gly Phe Lys Ile Ser Leu
210                 215                 220
His Cys Pro Cys Cys Thr Phe Val Pro Ser Asn Asn Tyr Ile Ile Pro
225                 230                 235                 240
Asn Lys Ser Glu Glu Leu Glu Ala Arg Phe Ala Gly Ile Asp Gly Thr
                245                 250                 255
Ser Thr Tyr Thr Ser Gly Asp Gln Lys Thr Ile Lys Ser Thr Arg Lys
            260                 265                 270
```

-continued

```
Lys Asn Ser Gly Lys Thr Pro His Leu Leu Met Leu Leu Pro Ser
            275                 280                 285

Tyr Arg Leu Glu Ser Gln Gln Thr Asn Arg Arg Lys Arg Ala Leu
    290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                325                 330                 335

Glu Pro Lys Gly Tyr Asn Ala Asn Phe Cys Ala Gly Ala Cys Pro Tyr
            340                 345                 350

Leu Trp Ser Ser Asp Thr Gln His Ser Arg Val Leu Ser Leu Tyr Asn
                355                 360                 365

Thr Ile Asn Pro Glu Ala Ser Ala Ser Pro Cys Cys Val Ser Gln Asp
    370                 375                 380

Leu Glu Pro Leu Thr Ile Leu Tyr Tyr Ile Gly Lys Thr Pro Lys Ile
385                 390                 395                 400

Glu Gln Leu Ser Asn Met Ile Val Lys Ser Cys Lys Cys Ser
                405                 410

<210> SEQ ID NO 123
<211> LENGTH: 412
<212> TYPE: PRT
<213> ORGANISM: Homo sapiens

<400> SEQUENCE: 123

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
                20                  25                  30

Gly His Ile Lys Lys Lys Arg Val Glu Ala Ile Arg Gly Gln Ile Leu
            35                  40                  45

Ser Lys Leu Arg Leu Thr Ser Pro Pro Glu Pro Thr Val Met Thr His
50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
            115                 120                 125

Ser Lys Val Phe Arg Phe Asn Val Ser Ser Val Glu Lys Asn Arg Thr
130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
```

```
                225                 230                 235                 240

Asn Ile His Glu Val Met Glu Ile Lys Phe Lys Gly Val Asp Asn Glu
                        245                 250                 255

Asp Asp His Gly Arg Gly Asp Leu Gly Arg Leu Lys Lys Gln Lys Asp
                        260                 265                 270

His His Asn Pro His Leu Ile Leu Met Met Ile Pro Pro His Arg Leu
                        275                 280                 285

Asp Asn Pro Gly Gln Gly Gln Arg Lys Arg Ala Leu Asp Thr
        290                 295                 300

Asn Tyr Cys Phe Arg Asn Leu Glu Glu Asn Cys Cys Val Arg Pro Leu
        305                 310                 315                 320

Tyr Ile Asp Phe Arg Gln Asp Leu Gly Trp Lys Trp Val His Glu Pro
                        325                 330                 335

Lys Gly Tyr Tyr Ala Asn Phe Cys Ser Gly Pro Cys Pro Tyr Leu Arg
                        340                 345                 350

Ser Ala Asp Thr Thr His Ser Thr Val Leu Gly Leu Tyr Asn Thr Leu
                        355                 360                 365

Asn Pro Glu Ala Ser Ala Ser Pro Cys Cys Val Pro Gln Asp Leu Glu
        370                 375                 380

Pro Leu Thr Ile Leu Tyr Tyr Val Gly Arg Thr Pro Lys Val Glu Gln
        385                 390                 395                 400

Leu Ser Asn Met Val Val Lys Ser Cys Lys Cys Ser
                        405                 410

<210> SEQ ID NO 124
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Gly Tyr Ser Phe Thr Arg Tyr Tyr Val Ala
1               5                   10

<210> SEQ ID NO 125
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gly Tyr Ser Phe Thr Arg Tyr Tyr Val Ala
1               5                   10

<210> SEQ ID NO 126
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Gly Tyr Ser Phe Thr Arg Tyr Trp Ile Ala
1               5                   10
```

```
<210> SEQ ID NO 127
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Gly Phe Ser Leu Ser Thr Ser Gly Met Gly Val Gly
1               5                   10

<210> SEQ ID NO 128
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Gly Tyr Ser Phe Thr Arg Tyr Tyr Val Ala
1               5                   10

<210> SEQ ID NO 129
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Gly Gly Thr Phe Ser Ser Tyr Ala Ile Ser
1               5                   10

<210> SEQ ID NO 130

<400> SEQUENCE: 130

000

<210> SEQ ID NO 131
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Asn Ser Gly Asn
1

<210> SEQ ID NO 132
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132
```

```
Gly Ser Gly Thr
1

<210> SEQ ID NO 133
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Thr Tyr Trp Met His
1               5

<210> SEQ ID NO 134
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Asn Ile Tyr Pro Gly Thr Gly Gly Ser Asn Phe Asp Glu Lys Phe Lys
1               5                   10                  15

Asn

<210> SEQ ID NO 135
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Trp Thr Thr Gly Thr Gly Ala Tyr
1               5

<210> SEQ ID NO 136
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Gly Tyr Thr Phe Thr Thr Tyr
1               5

<210> SEQ ID NO 137
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Tyr Pro Gly Thr Gly Gly
```

<210> SEQ ID NO 138
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Trp Thr Thr Gly Thr Gly Ala Tyr
1               5

<210> SEQ ID NO 139
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 140
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 140
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctaccccg gcaccggcgg ctctaacttc     180
gacgagaagt ttaagaatag agtgactatc accgccgata gtctactagc accgcctat     240 atggaactgt ctagcctgag atcagaggac accgccgtct actactgcac taggtggact     300
accggcacag gcgcctactg gggtcaaggc actaccgtga ccgtgtctag c              351

<210> SEQ ID NO 141

<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 141

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

```
Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly
                435                 440

<210> SEQ ID NO 142
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 142
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctaccccg gcaccggcgg ctctaacttc     180
gacgagaagt ttaagaatag agtgactatc accgccgata gtctactagc accgcctat      240 atggaactgt ctagcctgag atcagaggac accgccgtct actactgcac taggtggact     300
accggcacag gcgcctactg gggtcaaggc actaccgtga ccgtgtctag cgctagcact     360
aagggcccgt ccgtgttccc cctggcacct tgtagccgga gcactagcga atccaccgct     420
gccctcggct gcctggtcaa ggattacttc ccggagcccg tgaccgtgtc ctggaacagc     480
ggagccctga cctccggagt gcacaccttc cccgctgtgc tgcagagctc cgggctgtac     540
tcgctgtcgt cggtggtcac ggtgccttca tctagcctgg gtaccaagac ctacacttgc     600
aacgtggacc acaagccttc caacactaag gtgacaagc gcgtcgaatc gaagtacggc     660
ccaccgtgcc cgccttgtcc cgcgccggag ttcctcggcg gtccctcggt ctttctgttc     720
ccaccgaagc ccaaggacac tttgatgatt tcccgcaccc ctgaagtgac atgcgtggtc     780
gtggacgtgt cacaggaaga tccggaggtg cagttcaatt ggtacgtgga tggcgtcgag     840
gtgcacaacg ccaaaaccaa gccgagggag gagcagttca actccactta ccgcgtcgtg     900
tccgtgctga cggtgctgca tcaggactgg ctgaacggga aggagtacaa gtgcaaagtg     960
tccaacaagg gacttcctag ctcaatcgaa aagaccatct cgaaagccaa gggacagccc    1020
cgggaacccc aagtgtatac cctgccaccg agccaggaag aaatgactaa gaaccaagtc    1080
tcattgactt gccttgtgaa gggcttctac ccatcggata tcgccgtgga atgggagtcc    1140
aacggccagc cggaaaacaa ctacaagacc acccctccgg tgctggactc agacggatcc    1200
ttcttcctct actcgcggct gaccgtggat aagagcagat ggcaggaggg aaatgtgttc    1260
agctgttctg tgatgcatga agccctgcac aaccactaca ctcagaagtc cctgtccctc    1320
tccctggga                                                           1329

<210> SEQ ID NO 143
<211> LENGTH: 17
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 143

Lys Ser Ser Gln Ser Leu Leu Asp Ser Gly Asn Gln Lys Asn Phe Leu
1               5                   10                  15

Thr

<210> SEQ ID NO 144
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Trp Ala Ser Thr Arg Glu Ser
1               5

<210> SEQ ID NO 145
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Gln Asn Asp Tyr Ser Tyr Pro Tyr Thr
1               5

<210> SEQ ID NO 146
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Ser Gln Ser Leu Leu Asp Ser Gly Asn Gln Lys Asn Phe
1               5                   10

<210> SEQ ID NO 147
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Trp Ala Ser
1

<210> SEQ ID NO 148
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 148

Asp Tyr Ser Tyr Pro Tyr
1               5

<210> SEQ ID NO 149
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 150
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 150
gagatcgtcc tgactcagtc acccgctacc ctgagcctga gccctggcga gcgggctaca      60
ctgagctgta aatctagtca gtcactgctg atagcggta atcagaagaa cttcctgacc      120
tggtatcagc agaagcccgg taaagcccct aagctgctga tctactgggc ctctactaga     180
gaatcaggcg tgccctctag gtttagcggt agcggtagtg gcaccgactt cacccttcact     240 atctctagcc tgcagcccga ggatatcgct acctactact gtcagaacga ctatagctac      300
ccctacacct tcggtcaagg cactaaggtc gagattaag                              339

<210> SEQ ID NO 151
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 151

Glu Ile Val Leu Thr Gln Ser Pro Ala Thr Leu Ser Leu Ser Pro Gly

```
  1               5                   10                  15
Glu Arg Ala Thr Leu Ser Cys Lys Ser Ser Gln Ser Leu Leu Asp Ser
                20                  25                  30

Gly Asn Gln Lys Asn Phe Leu Thr Trp Tyr Gln Gln Lys Pro Gly Lys
            35                  40                  45

Ala Pro Lys Leu Leu Ile Tyr Trp Ala Ser Thr Arg Glu Ser Gly Val
     50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 152
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 152

```
gagatcgtcc tgactcagtc acccgctacc ctgagcctga gccctggcga gcgggctaca   60
ctgagctgta aatctagtca gtcactgctg gatagcggta atcagaagaa cttcctgacc  120
tggtatcagc agaagcccgg taaagcccct aagctgctga tctactgggc ctctactaga  180
gaatcaggcg tgccctctag gtttagcggt agcggtagtg gcaccgactt caccttcact  240
atctctagcc tgcagcccga ggatatcgct acctactact gtcagaacga ctatagctac  300
ccctacacct tcggtcaagg cactaaggtc gagattaagc gtacggtggc cgctcccagc  360
gtgttcatct tcccccccag cgacgagcag ctgaagagcg gcaccgccag cgtggtgtgc  420
ctgctgaaca acttctaccc ccgggaggcc aaggtgcagt ggaaggtgga caacgccctg  480
cagagcggca acagccagga gagcgtcacc gagcaggaca gcaaggactc cacctacagc  540
ctgagcagca ccctgaccct gagcaaggcc gactacgaga agcataaggt gtacgcctgc  600
gaggtgaccc accagggcct gtccagcccc gtgaccaaga gcttcaacag gggcgagtgc  660
```

<210> SEQ ID NO 153
<211> LENGTH: 5
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Thr Tyr Trp Met His
1               5

<210> SEQ ID NO 154
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Asn Ile Tyr Pro Gly Thr Gly Gly Ser Asn Phe Asp Glu Lys Phe Lys
1               5                   10                  15

Asn

<210> SEQ ID NO 155
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Trp Thr Thr Gly Thr Gly Ala Tyr
1               5

<210> SEQ ID NO 156
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Gly Tyr Thr Phe Thr Thr Tyr
1               5

<210> SEQ ID NO 157
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Tyr Pro Gly Thr Gly Gly
1               5

<210> SEQ ID NO 158
<211> LENGTH: 8
<212> TYPE: PRT
<213> ORGANISM: Artificial Sequence
<220> FEATURE:
```

<221> NAME/KEY: source
<223> OTHER INFORMATION: /note="Description of Artificial Sequence:
     Synthetic peptide"

<400> SEQUENCE: 158

Trp Thr Thr Gly Thr Gly Ala Tyr
1               5

<210> SEQ ID NO 159
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 159

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 160
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 160
gaggtgcagc tggtgcagtc aggcgccgaa gtgaagaagc ccggcgagtc actgagaatt     60
agctgtaaag gttcaggcta caccttcact acctactgga tgcactgggt ccgccaggct    120
accggtcaag gcctcgagtg gatgggtaat atctaccccg gcaccggcgg ctctaacttc    180
gacgagaagt ttaagaatag agtgactatc accgccgata agtctactag caccgcctat    240
atggaactgt ctagcctgag atcagaggac accgccgtct actactgcac taggtggact    300
accggcacag gcgcctactg gggtcaaggc actaccgtga ccgtgtctag c              351

<210> SEQ ID NO 161
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

-continued

```
<400> SEQUENCE: 161

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415
```

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 162
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 162

```
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctaccccg gcaccggcgg ctctaacttc     180
gacgagaagt ttaagaatag agtgactatc accgccgata agtctactag caccgcctat     240
atggaactgt ctagcctgag atcagaggac accgccgtct actactgcac taggtggact     300
accggcacag gcgcctactg gggtcaaggc actaccgtga ccgtgtctag cgctagcact     360
aagggcccgt ccgtgttccc cctggcacct tgtagccgga gcactagcga atccaccgct     420
gccctcggct gcctggtcaa ggattacttc ccggagcccg tgaccgtgtc ctggaacagc     480
ggagccctga cctccggagt gcacaccttc ccgctgtgc tgcagagctc cgggctgtac     540
tcgctgtcgt cggtggtcac ggtgccttca tctagcctgg gtaccaagac ctacacttgc     600
aacgtggacc acaagccttc caacactaag gtggacaagc gcgtcgaatc gaagtacggc     660
ccaccgtgcc cgccttgtcc cgcgccggag ttcctcggcg gtccctcggt ctttctgttc     720
ccaccgaagc ccaaggacac tttgatgatt cccgcaccc ctgaagtgac atgcgtggtc     780
gtggacgtgt cacaggaaga tccggaggtg cagttcaatt ggtacgtgga tggcgtcgag     840
gtgcacaacg ccaaaaccaa gccgagggag gagcagttca actccactta ccgcgtcgtg     900
tccgtgctga cggtgctgca tcaggactgg ctgaacggga aggagtacaa gtgcaaagtg     960
tccaacaagg gacttcctag ctcaatcgaa aagaccatct cgaaagccaa gggacagccc    1020
cgggaacccc aagtgtatac cctgccaccg agccaggaag aaatgactaa gaaccaagtc    1080
tcattgactt gccttgtgaa gggcttctac ccatcggata tcgccgtgga atgggagtcc    1140
aacggccagc cggaaaacaa ctacaagacc accctccgg tgctggactc agacggatcc    1200
ttcttcctct actcgcggct gaccgtggat aagagcagat ggcaggaggg aaatgtgttc    1260
agctgttctg tgatgcatga agccctgcac aaccactaca ctcagaagtc cctgtccctc    1320
tccctggga                                                             1329
```

<210> SEQ ID NO 163
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Lys Ser Ser Gln Ser Leu Leu Asp Ser Gly Asn Gln Lys Asn Phe Leu
1               5                   10                  15

Thr

<210> SEQ ID NO 164
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Trp Ala Ser Thr Arg Glu Ser
1               5

<210> SEQ ID NO 165
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Gln Asn Asp Tyr Ser Tyr Pro Tyr Thr
1               5

<210> SEQ ID NO 166
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Ser Gln Ser Leu Leu Asp Ser Gly Asn Gln Lys Asn Phe
1               5                   10

<210> SEQ ID NO 167
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Trp Ala Ser
1

<210> SEQ ID NO 168
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Asp Tyr Ser Tyr Pro Tyr
1               5

<210> SEQ ID NO 169
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 169

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 170
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 170
gagatcgtcc tgactcagtc acccgctacc ctgagcctga gccctggcga gcgggctaca    60
ctgagctgta atctagtca gtcactgctg gatagcggta atcagaagaa cttcctgacc   120
tggtatcagc agaagcccgg tcaagcccct agactgctga tctactgggc tctactaga   180 gaatcaggcg tgccctctag gtttagcggt agcggtagtg gcaccgactt caccttcact   240
atctctagcc tggaagccga ggacgccgct acctactact gtcagaacga ctatagctac   300
ccctacacct tcggtcaagg cactaaggtc gagattaag                          339

<210> SEQ ID NO 171
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 171

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Phe Thr
 65                  70                  75                  80

Ile Ser Ser Leu Glu Ala Glu Asp Ala Ala Thr Tyr Tyr Cys Gln Asn
                 85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 172
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 172
gagatcgtcc tgactcagtc acccgctacc ctgagcctga gcctggcga gcgggctaca      60 ctgagctgta atctagtca gtcactgctg gatagcggta atcagaagaa cttcctgacc     120
tggtatcagc agaagcccgg tcaagcccct agactgctga tctactgggc ctctactaga    180
gaatcaggcg tgccctctag gtttagcggt agcggtagtg gcaccgactt caccttcact    240
atctctagcc tggaagccga ggacgccgct acctactact gtcagaacga ctatagctac    300
ccctacacct tcggtcaagg cactaaggtc gagattaagc gtacggtggc cgctcccagc    360
gtgttcatct cccccccag cgacgagcag ctgaagagcg gcaccgccag cgtggtgtgc    420
ctgctgaaca acttctaccc ccgggaggcc aaggtgcagt ggaaggtgga caacgccctg    480
cagagcggca cagccagga gagcgtcacc gagcaggaca gcaaggactc cacctacagc    540
ctgagcagca ccctgaccct gagcaaggcc gactacgaga gcataaggt gtacgcctgc    600 gaggtgaccc accagggcct gtccagcccc gtgaccaaga gcttcaacag gggcgagtgc    660

<210> SEQ ID NO 173
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
acctactgga tgcac                                              15

<210> SEQ ID NO 174
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
aatatctacc ccggcaccgg cggctctaac ttcgacgaga agtttaagaa t        51

<210> SEQ ID NO 175
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
tggactaccg gcacaggcgc ctac                                    24

<210> SEQ ID NO 176
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
ggctacacct tcactaccta c                                       21

<210> SEQ ID NO 177
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
taccccggca ccggcggc                                           18

<210> SEQ ID NO 178
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
tggactaccg gcacaggcgc ctac                                    24

<210> SEQ ID NO 179
<211> LENGTH: 51
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 179
aaatctagtc agtcactgct ggatagcggt aatcagaaga acttcctgac c         51

<210> SEQ ID NO 180
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
tgggcctcta ctagagaatc a                                          21

<210> SEQ ID NO 181
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
cagaacgact atagctaccc ctacacc                                    27

<210> SEQ ID NO 182
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
agtcagtcac tgctggatag cggtaatcag aagaacttc                       39

<210> SEQ ID NO 183
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183 tgggcctct                                                        9

<210> SEQ ID NO 184
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
gactatagct acccctac                                              18

<210> SEQ ID NO 185
```

```
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
acctactgga tgcac                                                        15

<210> SEQ ID NO 186
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
aatatctacc ccggcaccgg cggctctaac ttcgacgaga agtttaagaa t                 51

<210> SEQ ID NO 187
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
tggactaccg gcacaggcgc ctac                                              24

<210> SEQ ID NO 188
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
ggctacacct tcactaccta c                                                 21

<210> SEQ ID NO 189
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
taccccggca ccggcggc                                                     18

<210> SEQ ID NO 190
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
```

```
tggactaccg gcacaggcgc ctac                                            24

<210> SEQ ID NO 191
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
aaatctagtc agtcactgct ggatagcggt aatcagaaga acttcctgac c              51

<210> SEQ ID NO 192
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
tgggcctcta ctagagaatc a                                               21

<210> SEQ ID NO 193
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
cagaacgact atagctaccc ctacacc                                         27

<210> SEQ ID NO 194
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
agtcagtcac tgctggatag cggtaatcag aagaacttc                            39

<210> SEQ ID NO 195
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195 tgggcctct                                                              9

<210> SEQ ID NO 196
<211> LENGTH: 18
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 196
gactatagct acccctac                                                        18

<210> SEQ ID NO 197
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197
```

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

-continued

```
Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 198
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 198

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 199
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 199

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
```

```
                355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445

<210> SEQ ID NO 200
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 200

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
            20                  25                  30
Gly Tyr Ser Tyr Leu His Trp Tyr Gln Gln Lys Pro Gly Gln Ala Pro
        35                  40                  45
Arg Leu Leu Ile Tyr Leu Ala Ser Tyr Leu Glu Ser Gly Val Pro Ala
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln His Ser Arg
                85                  90                  95
Asp Leu Pro Leu Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 201
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 201

| | | | | | | | | | | | | | | | |
|---|---|---|---|---|---|---|---|---|---|---|---|---|---|---|---|
| Gln | Val | Gln | Leu | Val | Gln | Ser | Gly | Ser | Glu | Leu | Lys | Lys | Pro | Gly | Ala |
| 1 | | | | 5 | | | | | 10 | | | | | 15 | |
| Ser | Val | Lys | Ile | Ser | Cys | Lys | Ala | Ser | Gly | Tyr | Thr | Phe | Thr | Asn | Tyr |
| | | | 20 | | | | | 25 | | | | | 30 | | |
| Gly | Met | Asn | Trp | Val | Arg | Gln | Ala | Pro | Gly | Gln | Gly | Leu | Gln | Trp | Met |
| | | 35 | | | | | 40 | | | | | 45 | | | |
| Gly | Trp | Ile | Asn | Thr | Asp | Ser | Gly | Glu | Ser | Thr | Tyr | Ala | Glu | Glu | Phe |
| | 50 | | | | | 55 | | | | | 60 | | | | |
| Lys | Gly | Arg | Phe | Val | Phe | Ser | Leu | Asp | Thr | Ser | Val | Asn | Thr | Ala | Tyr |
| 65 | | | | | 70 | | | | | 75 | | | | | 80 |
| Leu | Gln | Ile | Thr | Ser | Leu | Thr | Ala | Glu | Asp | Thr | Gly | Met | Tyr | Phe | Cys |
| | | | | 85 | | | | | 90 | | | | | 95 | |
| Val | Arg | Val | Gly | Tyr | Asp | Ala | Leu | Asp | Tyr | Trp | Gly | Gln | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| | 130 | | | | | 135 | | | | | 140 | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Arg | Val | Glu | Pro | Lys | Ser | Cys | Asp | Lys | Thr | His |
| | 210 | | | | | 215 | | | | | 220 | | | | |
| Thr | Cys | Pro | Pro | Cys | Pro | Ala | Pro | Glu | Leu | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Pro | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Glu | Glu | Met | Thr | Lys | Asn | Gln | Val | Ser | Leu | Thr | Cys | Leu |
| | | 355 | | | | | 360 | | | | | 365 | | | |
| Val | Lys | Gly | Phe | Tyr | Pro | Ser | Asp | Ile | Ala | Val | Glu | Trp | Glu | Ser | Asn |
| | 370 | | | | | 375 | | | | | 380 | | | | |
| Gly | Gln | Pro | Glu | Asn | Asn | Tyr | Lys | Thr | Thr | Pro | Pro | Val | Leu | Asp | Ser |
| 385 | | | | | 390 | | | | | 395 | | | | | 400 |

-continued

```
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 202
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Glu Ile Val Leu Thr Gln Ser Pro Ser Ser Leu Ser Ala Ser Val Gly
1               5                   10                  15
Asp Arg Val Thr Ile Thr Cys Ser Ala Arg Ser Ser Val Ser Tyr Met
            20                  25                  30
His Trp Phe Gln Gln Lys Pro Gly Lys Ala Pro Lys Leu Trp Ile Tyr
        35                  40                  45
Arg Thr Ser Asn Leu Ala Ser Gly Val Pro Ser Arg Phe Ser Gly Ser
    50                  55                  60
Gly Ser Gly Thr Ser Tyr Cys Leu Thr Ile Asn Ser Leu Gln Pro Glu
65                  70                  75                  80
Asp Phe Ala Thr Tyr Tyr Cys Gln Gln Arg Ser Ser Phe Pro Leu Thr
                85                  90                  95
Phe Gly Gly Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 203
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Gly Tyr Thr Phe Thr Thr Tyr Trp Met His
1               5                   10
```

```
<210> SEQ ID NO 204
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 204

His His His His His His
1               5
```

TGFBETA 2 ANTIBODIES

SEQUENCE LISTING

The instant application contains a Sequence Listing which has been submitted electronically in ASCII format and is hereby incorporated by reference in its entirety. Said ASCII copy, created on Feb. 13, 2017, is named PAT057206-WO-PCT_SL.TXT and is 162,071 bytes in size.

FIELD OF THE INVENTION

The present invention relates to anti-transforming growth factor beta 2 (TGF-β2) antibodies. In particular, the invention provides human monoclonal antibodies that bind the human TGF-β2 isoform preferentially over the human TGF-β1 or TGF-β3 isoforms.

BACKGROUND OF THE INVENTION

Members of the transforming growth factor beta (TGF-β) superfamily are cytokines which are associated with a variety of pathological conditions such as fibrosis, scarring, cancer (Growth Factors. 2011 August; 29(4):140-52), specific conditions like Marfan-associated condition (U.S. Pat. No. 8,597,646) and Epidermolysis bullosa. U.S. Pat. No. 5,571,714 discloses the use of anti TGF beta antibodies in treating malignancies and metastatic cancer. Anti-TGFbeta antibodies have been used in the treatment of numerous diseases like: lung fibrosis (S. N. Giri et al. Thorax 48, 959-966, 1993); neural scarring (A. Logan et al. Eur. J. Neurosci. 6, 355-363, 1994); arterial injury (Y. G. Wolf, L. M. Rasmussen & E. Ruoslahti J. Clin. Invest. 93, 1172-1178, 1994); glomerulonephritis (W. A Border et al. Nature 346, 371-374, 1990); rheumatoid arthritis (Wahl et al J. Exp. Medicine 177, 225-230, 1993) and dermal scarring (M. Shah et al. Lancet 339, 213-214 1992; M. Shah et al. J. Cell Science 107, 1137-1157, 1994; M. Shah et al. 108, 985-1002, 1995). Therefore, targeting TGF-β activity is an active area of research using different approaches comprising antisense oligonucleotides (Curr Pharm Biotechnol. 2011 December; 12(12):2203-13.)), small molecule inhibitors of the TGF-β receptor kinases (e.g. LY2109761 targeting TGF-β receptor type I and II (Mol Cancer Ther 2008 7; 829)), soluble receptor ectodomains capturing their natural ligands, and monoclonal antibodies (reviewed in Growth Factors. 2011 August; 29(4):140-52; WO9713844).

Transforming growth factor beta 2 (TGF-β2) is one member of >30 members of the TGF-β protein family. It is closely related to the TGF-β1/3 isoforms. All TGF-β precursor proteins consist of a N-terminal signal peptide, a large propeptide-segment and a C-terminal polypeptide. The latter dimerize to form the active, mature TGF-β2 proteins which are referred to as TGF-β2. Homology between mature TGF-β1, TGF-β2 and TGF-β3 is relatively high (71-79%), whereas the propeptide-segments are remarkably unconserved (43-54% homology). Moreover, homology of TGF-β2 to other TGF-β family proteins is only <33%, whereas very high homology is observed between TGF-β2 from various species including human, cynomolgus monkey and mouse (95-100%).

The most widely described TGF-β signaling pathway is through TGF-β type II receptor, ALK5 and Smad2/3, but many other pathways, including ALK- and Smad-independent pathways, have been established. The majority of commercially-available TGF-β antibodies are either polyclonal antibodies derived from non-human species or mouse monoclonal antibodies such as such as the TGF-β1-specific MAB240 (by R&D Systems™) for use in Western blot analyses (J Immunol Methods. 1999 May 27; 225(1-2):87-93). Antibodies for use in clinical studies in humans have to meet different requirements than tool antibodies. A critical requirement is the reduction of potential immunogenicity by use of chimeric, humanised, or fully human antibodies. There are a number of TGF-β isoform antibodies in clinical development that meet these requirements comprising:
1. the fully-human monoclonal antibody GC1008 (Fresolimumab) that neutralizes the TGF-β isoforms 1, 2 and 3,
2. the antibody LY2382770 that neutralizes TGF-β1,
3. the antibody CAT-192 (Metelimumab) that neutralizes TGF-β1, and
4. the antibody CAT-152 (Lerdelimumab, also known as 6B1) has a high affinity for TGF-β2 and cross-reactivity with TGF-β3 (all above reviewed in Growth Factors. 2011 August; 29(4):140-52).

CAT-152: CAT-152 is a fully human IgG4 antibody that has affinity for TGF-β2 (Biacore® system dissociation constant of 0.89 nM) and 9% cross-reactivity with TGF-β3 (Biacore® system dissociation constant of 10 nM) whilst showing no detectable binding to TGF-β1 (J Immunol Methods. 1999 Jul. 30; 227(1-2):17-29; Drugs R&D 2002; 3 (2):106-108; WO9713844). CAT-152 was developed as an adjunct to glaucoma drainage surgery also known as trabeculectomy (Drugs R&D 2002; 3 (2):106-108). However, CAT-152 failed to prevent the progression of fibrosis in certain glaucoma patients after first-time trabeculectomy in a phase III trial (Ophthalmology. 2007 October; 114(10): 1822-30.).

CAT-192: The TGF-β1 specific recombinant human antibody CAT-192 failed to show evidence of efficacy in a Phase I/II trial investigating the treatment of early-stage diffuse cutaneous systemic sclerosis (Arthritis Rheum. 2007 January; 56(1):323-33). Moreover, more adverse events were observed in patients receiving CAT-192 than in patients receiving placebo in that trial. These findings are furthermore supported by results obtained in a mutant mouse model, showing that decreased levels of active TGF-β1 are associated with multiorgan inflammation, lack of Langerhans cells in the epidermis and development of tumors (Proc Natl Acad Sci USA. 2008 Dec. 2; 105(48)).

The presence of the three closely related TGF-β1/2/3 isoforms creates the need for compounds that allow a specific detection and neutralisation of those proteins in humans to avoid any interference with other pathways which may be associated with adverse or unwanted events. More specifically, this creates the strong medical need for isoform specific anti-TGF-β2 therapeutic antibodies which effectively neutralise TGF-β2 and exhibit preferential binding and neutralisation of TGF-β2 over TGF-β1 or TGF-β3. Ideally, the specificity of the TGF-β2 antibodies is combined with high binding affinities, because high binding affinities are associated with increased potency and lower dosing requirements, contributing to enhanced efficacy, safety and lower costs (MAbs. 2012 May-June; 4(3):341-8). Often monoclonal antibodies may require very low (e.g. picomolar) dissociation constants to disrupt very tight protein:protein interactions in a disease mechanism (MAbs. 2012 May-June; 4(3):341-8). This creates the strong medical need for isoform specific TGF-β2 therapeutic antibodies exhibiting very low picomolar dissociation constants which is also solved by the present invention.

SUMMARY OF THE INVENTION

Certain embodiments of the disclosure are described in the following aspects:

1. A human monoclonal anti-TGF-β2 antibody or a functional fragment thereof that neutralizes the human TGF-β isoform TGF-β2 and does not neutralize human isoform TGF-β3.

2. An antibody or a functional fragment thereof according to aspect 1, which neutralizes the human TGF-β isoform TGF-β2 and does not neutralize human isoforms TGF-β3 and TGF-β1.

3. A human monoclonal anti-TGF-β2 antibody or a functional fragment thereof according to aspects 1 or 2, wherein neutralization is determined by a Smad dependent reporter gene assay.

4. An antibody or a functional fragment thereof according to any preceding aspect, which neutralises human TGF-β2 with an half maximal inhibitory concentration (IC50) of less than 250 pM and which neutralises human TGF-β1 and/or TGF-β3 with an half maximal inhibitory concentration (IC50) of greater than 100 nM as determined by a Smad dependent reporter gene assay.

5. A human monoclonal anti-TGF-β2 antibody or a functional fragment thereof that binds the human TGF-β isoform TGF-β2 preferentially over the human isoforms TGF-β1 and TGF-β3 with a dissociation constant that is at least 70-fold lower than its dissociation constant for TGF-β1 or TGF-β3, wherein the antibody neutralises human TGF-β2.

6. An antibody or a functional fragment thereof according to any of the preceding aspects, which binds to human TGF-β2 with a $K_D$ of 1 pM or less.

7. The antibody or functional fragment according to any of aspects 1-6, wherein said antibody or functional fragment thereof comprises a heavy chain variable CDR1 region comprising an amino acid sequence having at least 95% sequence identity to a sequence selected from the group consisting of SEQ ID NOs: 1, 21, 41, 61, 81, 101 or 4, 24, 44, 64, 84, 104 or 124-129; a heavy chain variable CDR2 region comprising an amino acid sequence having at least 95% sequence identity to a sequence selected from the group consisting of SEQ ID NOs: 2, 22, 42, 62, 82, 102 or 5, 25, 45, 65, 85, 105; a heavy chain variable CDR3 region comprising an amino acid sequence having at least 95% sequence identity to a sequence selected from the group consisting of SEQ ID NOs: 3, 23, 43, 63, 83, 103 or 6, 26, 46, 66, 86, 106; a light chain variable CDR1 region comprising an amino acid sequence having at least 95% sequence identity to a sequence selected from the group consisting of SEQ ID NOs: 11, 31, 51, 71, 91, 111 or 14, 34, 54, 74, 94, 114; a light chain variable CDR2 region comprising an amino acid sequence having at least 95% sequence identity to a sequence selected from the group consisting of SEQ ID NOs: 12, 32, 52, 72, 92, 112 or 15, 35, 55, 75, 95, 115; and a light chain variable CDR3 region comprising an amino acid sequence having at least 95% sequence identity to a sequence selected from the group consisting of SEQ ID NOs: 13, 33, 53, 73, 93, 113 or 16, 36, 56, 76, 96, 116.

8. The antibody or functional fragment according to any of aspects 1-7, wherein said antibody or functional fragment thereof comprises a heavy chain variable region polypeptide sequence having at least 95% sequence identity to at least one of SEQ ID NOs: 7, 27, 47, 67, 87, or 107.

9. The antibody or functional fragment according to any of aspects 1-8, wherein said antibody or functional fragment thereof comprises a light chain variable region polypeptide sequence having at least 95% sequence identity to at least one of SEQ ID NOs: 17, 37, 57, 77, 97, or 117.

10. The antibody or functional fragment according to any of aspects 1-9, wherein said antibody or functional fragment thereof comprises a heavy chain variable region polypeptide sequence having at least 95% sequence identity to at least one of SEQ ID NOs: 7, 27, 47, 67, 87, or 107 and a light chain variable region polypeptide sequence having at least 95% sequence identity to at least one of SEQ ID NOs: 17, 37, 57, 77, 97, or 117.

11. The antibody or functional fragment according to any of aspects 1-10, wherein said antibody or functional fragment thereof comprises a heavy chain variable region CDR1 comprising an amino acid sequence selected from the group consisting of SEQ ID NOs: 1, 21, 41, 61, 81, 101 or 4, 24, 44, 64, 84, 104 or 124-129; a heavy chain variable region CDR2 comprising an amino acid sequence selected from the group consisting of SEQ ID NOs: 2, 22, 42, 62, 82, 102 or 5, 25, 45, 65, 85, 105; a heavy chain variable region CDR3 comprising an amino acid sequence selected from the group consisting of SEQ ID NOs: 3, 23, 43, 63, 83, 103 or 6, 26, 46, 66, 86, 106; a light chain variable region CDR1 comprising an amino acid sequence selected from the group consisting of SEQ ID NOs: 11, 31, 51, 71, 91, 111 or 14, 34, 54, 74, 94, 114; a light chain variable region CDR2 comprising an amino acid sequence selected from the group consisting of SEQ ID NOs: 12, 32, 52, 72, 92, 112 or 15, 35, 55, 75, 95, 115; a light chain variable region CDR3 comprising an amino acid sequence selected from the group consisting of SEQ ID NOs: 13, 33, 53, 73, 93, 113 or 16, 36, 56, 76, 96, 116.

12. A human monoclonal anti-TGF-β2 antibody or functional fragment according to any one of aspects 1-11 comprising:
(a) a heavy chain variable region CDR1 of SEQ ID NO: 1; a heavy chain variable region CDR2 of SEQ ID NO: 2; a heavy chain variable region CDR3 of SEQ ID NO: 3; a light chain variable region CDR1 of SEQ ID NO: 11; a light chain variable region CDR2 of SEQ ID NO: 12; and a light chain variable region CDR3 of SEQ ID NO: 13,
(b) a heavy chain variable region CDR1 of SEQ ID NO: 21 a heavy chain variable region CDR2 of SEQ ID NO: 22; a heavy chain variable region CDR3 of SEQ ID NO: 23; a light chain variable region CDR1 of SEQ ID NO: 31; a light chain variable region CDR2 of SEQ ID NO: 32; and a light chain variable region CDR3 of SEQ ID NO: 33,
(c) a heavy chain variable region CDR1 of SEQ ID NO: 41; a heavy chain variable region CDR2 of SEQ ID NO: 42; a heavy chain variable region CDR3 of SEQ ID NO: 43; a light chain variable region CDR1 of SEQ ID NO: 51; a light chain variable region CDR2 of SEQ ID NO: 52; and a light chain variable region CDR3 of SEQ ID NO: 53,
(d) a heavy chain variable region CDR1 of SEQ ID NO: 61; a heavy chain variable region CDR2 of SEQ ID NO: 62; a heavy chain variable region CDR3 of SEQ ID NO: 63; a light chain variable region CDR1 of SEQ ID NO: 71; a light chain variable region CDR2 of SEQ ID NO: 72; and a light chain variable region CDR3 of SEQ ID NO: 73,
(e) a heavy chain variable region CDR1 of SEQ ID NO: 81; a heavy chain variable region CDR2 of SEQ ID NO: 82; a heavy chain variable region CDR3 of SEQ ID NO: 83; a light chain variable region CDR1 of SEQ ID NO: 91; a light chain variable region CDR2 of SEQ ID NO: 92; and a light chain variable region CDR3 of SEQ ID NO: 93, or
(f) a heavy chain variable region CDR1 of SEQ ID NO: 101; a heavy chain variable region CDR2 of SEQ ID NO: 102; a heavy chain variable region CDR3 of SEQ ID NO: 103; a light chain variable region CDR1 of SEQ ID NO: 111; a light chain variable region CDR2 of SEQ ID NO: 112; and a light chain variable region CDR3 of SEQ ID NO: 113.

13. The antibody or functional fragment according to any of aspects 1-12, wherein said antibody or functional fragment thereof comprises a full length heavy chain amino acid sequence having at least 95% sequence identity to at least one sequence selected from the group consisting of SEQ ID NOs: 9, 29, 49, 69, 89, 109.

14. The antibody or functional fragment according to any of aspects 1-13, wherein said antibody or functional fragment thereof comprises a full length light chain amino acid sequence having at least 95% sequence identity to at least one sequence selected from the group consisting of SEQ ID NOs: 19, 39, 59, 79, 99, 119.

15. The antibody or functional fragment according to any of aspects 1-14, wherein said antibody or functional fragment thereof comprises a full length heavy chain amino acid sequence having at least 95% sequence identity to at least one sequence selected from the group consisting of SEQ ID NOs: 9, 29, 49, 69, 89, 109 and a full length light chain amino acid sequence having at least 95% sequence identity to at least one sequence selected from the group consisting of SEQ ID NOs: 19, 39, 59, 79, 99, 119.

16. A human monoclonal anti-TGF-β2 antibody comprising:
(a) the variable heavy chain sequence of SEQ ID NO: 7 and variable light chain sequence of SEQ ID NO: 17;
(b) the variable heavy chain sequence of SEQ ID NO: 27 and variable light chain sequence of SEQ ID NO: 37;
(c) the variable heavy chain sequence of SEQ ID NO: 47 and variable light chain sequence of SEQ ID NO: 57;
(d) the variable heavy chain sequence of SEQ ID NO: 67 and variable light chain sequence of SEQ ID NO: 77;
(e) the variable heavy chain sequence of SEQ ID NO: 87 and variable light chain sequence of SEQ ID NO: 97; or
(f) the variable heavy chain sequence of SEQ ID NO: 107 and variable light chain sequence of SEQ ID NO: 117.

17. A human monoclonal anti-TGF-β2 antibody comprising:
(a) the heavy chain sequence of SEQ ID NO: 9 and light chain sequence of SEQ ID NO: 19;
(b) the heavy chain sequence of SEQ ID NO: 29 and light chain sequence of SEQ ID NO: 39;
(c) the heavy chain sequence of SEQ ID NO: 49 and light chain sequence of SEQ ID NO: 59;
(d) the heavy chain sequence of SEQ ID NO: 69 and light chain sequence of SEQ ID NO: 79;
(e) the heavy chain sequence of SEQ ID NO: 89 and light chain sequence of SEQ ID NO: 99; or
(f) the heavy chain sequence of SEQ ID NO: 109 and light chain sequence of SEQ ID NO: 119.

18. An anti-TGF-β2 antibody according to any previous aspect, wherein said antibody is of the IgG1 isotype.

19. A human monoclonal anti-TGF-β2 antibody according to any previous aspect, which has altered effector function through mutation of the Fc region.

20. An isolated polynucleotide sequence encoding an antibody or functional fragment according to any previous aspect.

21. An isolated polynucleotide sequence according to aspect 20, comprising one or more of SEQ ID NOs: 8, 10, 18, 20, 28, 30, 38, 40, 48, 50, 58, 60, 68, 70, 78, 80, 88, 90, 98, 100, 108, 110, 118, or 120.

22. A cloning or expression vector comprising one or more isolated polynucleotide sequences according to aspect 20 or aspect 21.

23. A vector according to aspect 22, wherein said vector comprises one or more of SEQ ID NOs: 8, 10, 18, 20, 28, 30, 38, 40, 48, 50, 58, 60, 68, 70, 78, 80, 88, 90, 98, 100, 108, 110, 118, or 120, or fragment thereof encoding at least one CDR region.

24. A host cell comprising one or more vectors according to aspect 22 or aspect 23.

25. A process for the production of an antibody or functional fragment thereof of any one of aspects 1-19, comprising culturing the host cell of aspect 24 and isolating said antibody or functional fragment.

26. A pharmaceutical composition comprising an antibody or functional fragment thereof according to any one of the aspects 1-19.

27. A pharmaceutical composition comprising an antibody or functional fragment thereof of any of the aspects 12, 15, 16, 17 or 26 for use in therapy.

28. A pharmaceutical composition comprising an antibody or functional fragment thereof of any of the aspects 12, 15, 16, 17 or 26 for use as a medicament.

29. A pharmaceutical composition according to aspect 26 to 28, further comprising a pharmaceutically acceptable diluent or carrier.

30. A pharmaceutical composition according to aspect 26 to 29, further comprising one or more additional active agents.

31. The pharmaceutical composition of aspect 26 to 30 for use in the treatment of Dupuytren's disease.

32. The pharmaceutical composition of aspect 26 to 30 for use in the treatment of Loeys-Dietz-Syndrome.

33. The pharmaceutical composition of aspect 26 to 30 for use in the treatment of Marfan-associated conditions or Marfan's disease.

34. The pharmaceutical composition of aspect 26 to 30 for use in the treatment of Epidermolysis bullosa.

35. The pharmaceutical composition of aspect 26 to 30 for use in the treatment of Trabeculectomy.

36. The pharmaceutical composition of aspect 26 to 30 for use in the treatment of cutaneous systemic sclerosis.

37. The pharmaceutical composition of aspect 26 to 30 for use in the treatment of musculoskeletal disease or disorder.

38. The pharmaceutical composition of aspect 37, wherein said musculoskeletal disease or disorder is muscle atrophy, for example caused by a myopathy, such as myotonia, a congenital myopathy, including nemalene myopathy, multi/minicore myopathy and myotubular (centronuclear) myopathy, mitochondrial myopathy, familial periodic paralysis, inflammatory myopathy, metabolic myopathy, such as caused by a glycogen or lipid storage disease, dermatomyositis, polymyositis, inclusion body myositis, myositis ossificans, rhabdomyolysis and myoglobinurias; a muscular dystrophy, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy; osteoporosis; a bone fracture; short stature; dwarfism; prolonged bed rest; voluntary inactivity; or involuntary inactivity.

39. A method of treating a patient suffering from a Dupuytren's disease, comprising administering an effective dose of a pharmaceutical composition according to any one of aspects 26-30 to said patient.

40. A method of treating a patient suffering from a Marfan-associated condition or Marfan's disease, comprising administering an effective dose of a pharmaceutical composition according to any one of aspects 26-30 to said patient.

41. A method of treating a patient suffering from Epidermolysis bullosa, comprising administering an effective dose of a pharmaceutical composition according to any one of aspects 26-30 to said patient.

42. A method of treating a patient suffering from Trabeculectomy, comprising administering an effective dose of a pharmaceutical composition according to any one of aspects 26-30 to said patient.

43. A method of treating a patient suffering from cutaneous systemic sclerosis, comprising administering an effective dose of a pharmaceutical composition according to any one of aspects 26-30 to said patient.

44. A method of treating a patient suffering from Loeys-Dietz-Syndrome, comprising administering an effective dose of a pharmaceutical composition according to any one of aspects 26-30 to said patient.

45. A method of treating a patient suffering from musculoskeletal disease or disorder, comprising administering an effective dose of a pharmaceutical composition according to any one of aspects 26-30 to said patient.

46. A method according to aspect 45, wherein said musculoskeletal disease or disorder is muscle atrophy, for example caused by a myopathy, such as myotonia, a congenital myopathy, including nemaline myopathy, multi/minicore myopathy and myotubular (centronuclear) myopathy, mitochondrial myopathy, familial periodic paralysis, inflammatory myopathy, metabolic myopathy, such as caused by a glycogen or lipid storage disease, dermatomyositis, polymyositis, inclusion body myositis, myositis ossificans, rhabdomyolysis and myoglobinurias; a muscular dystrophy, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy; osteoporosis; a bone fracture; short stature; dwarfism; prolonged bed rest; voluntary inactivity; or involuntary inactivity.

47. Use of an antibody or functional fragment according to any one of aspects 1-19, the polynucleotide sequence according to aspect 20 or 21, or the pharmaceutical composition according to any one of aspects 26-30 in the manufacture of a medicament for the treatment of a Dupuytren's disease, a Marfan-associated conditions or Marfan's disease, Epidermolysis bullosa, Trabeculectomy, Loeys-Dietz-Syndrome, cutaneous systemic sclerosis or a musculoskeletal disease or disorder.

48. The use of aspect 47, wherein said musculoskeletal disease or disorder is muscle atrophy, for example caused by a myopathy, such as myotonia, a congenital myopathy, including nemaline myopathy, multi/minicore myopathy and myotubular (centronuclear) myopathy, mitochondrial myopathy, familial periodic paralysis, inflammatory myopathy, metabolic myopathy, such as caused by a glycogen or lipid storage disease, dermatomyositis, polymyositis, inclusion body myositis, myositis ossificans, rhabdomyolysis and myoglobinurias; a dystrophy, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy; osteoporosis; a bone fracture; short stature; dwarfism; prolonged bed rest; voluntary inactivity; or involuntary inactivity.

49. An antibody or functional fragment thereof which cross-blocks or is cross blocked by at least one antibody of aspect 17 from binding to TGFbeta-2.

BRIEF DESCRIPTION OF THE DRAWINGS

FIG. 3: is showing biologic "neutralizing" activity of the TGF-β2-specific AB MOR13436. Shown are concentration-response curves of the Antibody against the effects of recombinant human TGF-β2, mouse TGF-β2, human TGF-β3 and human TGF-β1 in HEK293T/17 CAGA-12 (HEK293T-RGA), a luciferase reporter assay specific for phosphorylated Smad-2 and Smad-3. Recombinant TGF-βs induce Smad-2 and Smad-3 phosphorylation which bind to the CAGA-12 reporter and causes luciferase gene expression. MOR13436 neutralizes recombinant human and mouse TGF-β2, but not human TGF-β1 and TGF-β3. The IgG Antibody MOR03207 served as negative control. MOR03207 recognizes an enzyme that is part of human innate immune system.

FIG. 4: is showing biologic "neutralizing" activity of the TGF-β2-specific ABs MOR14799, MOR14800, MOR14797 and MOR14809. Shown are concentration-response curves of the ABs against the effects of various recombinant human TGF-β family proteins: Activin A, Activin B, Activin AB, GDF-11, myostatin, TGF-b2 and TGF-b3 in HEK293T/17 CAGA-12 (HEK293T-RGA), a luciferase reporter assay specific for phosphorylated Smad-2 and Smad-3. Recombinant TGF-βs induced Smad-2 and Smad-3 phosphorylation which bind to the CAGA-12 reporter and causes luciferase gene expression. All ABs neutralize recombinant human TGF-β2, but not any other TGF-β protein family members. The IgG Antibody MOR03207 (assessed at 100 nM and 33.3 nM) served as negative control. MOR03207 recognizes an enzyme that is part of human innate immune system.

FIG. 5: is showing biologic "neutralizing" activity of the TGF-β2-specific AB MOR13436. Shown is a concentration-response curve of the AB counteracting inhibition of human skeletal muscle cells (skMC) differentiation by recombinant human TGF-β2 (●), mouse TGF-β2 (■) and human TGF-β3 (♦). Cells were differentiated up to 120 hours and creatine kinase (CK) activity, a well-established skeletal muscle cell differentiation marker, was measured. All TGF-βs inhibit CK activity and the Ab counteracts TGF-β2, but not TGF-β3 responses.

FIG. 6: is showing biologic "neutralizing" activity of the TGF-β2-specific ABs (A) MOR14799, (B) MOR14800, (C) MOR14797 and (D) MOR14809. Shown are concentration-response curves of the ABs counteracting inhibition of human skeletal muscle cells (skMC) differentiation by recombinant human TGF-β2 (●), mouse TGF-β2 (■) and human TGF-β3 (♦). Cells were differentiated up to 120 hours and creatine kinase (CK) activity, a well-established skeletal muscle cell differentiation marker, was measured. All TGF-βs inhibit CK activity and the Abs counteracts TGF-β2, but not TGF-β3 responses.

FIG. 7: is showing bar graphs quantifying immunostaining for collagen I protein in a Dupuytren patient sample cultured for seven days with the TGF-β2-specific AB MOR14797 or the pan-TGF-β antibody 1D11. Patient tissue was sliced, cultured for 7 days in the presence of Ab and then immunostained for collagen I.

FIG. 8: is showing immunostainings for collagen I protein in two different Dupuytren patient samples cultured for seven days with the TGF-β2-specific AB MOR14797 (B/D) compare to isotype controls (A/C). Results from patient 1 are shown in A/B and from patient 2 in C/D. Patient tissue was sliced, cultured for 7 days in the presence of Ab and then immunostained for collagen I.

FIG. 9: is showing bar graphs quantifying mRNA expression for collagen I protein in mouse kidneys from a unilateral urethral obstruction model (UUO) treated with the TGF-β2-specific AB MOR13436. Sham- or UUO-operated animals were treated for 14 days with the Ab, kidneys removed, mRNA isolated and analysed by qPCR.

FIG. 11: Paratope of MOR14797 binding to TGFβ-2: Sequence of MOR14797 VH (A) (SEQ ID NOS 67 and 67, respectively, in order of appearance) and VL (B) (SEQ ID NOS 77 and 77, respectively, in order of appearance) are listed. CDR loops (both Kabat and Chothia definitions) are boxed. Residues of MOR14797 within 5 Å distance to TGFβ-2 dimer are shaded in grey.

GENERAL DEFINITIONS

Figure 1:
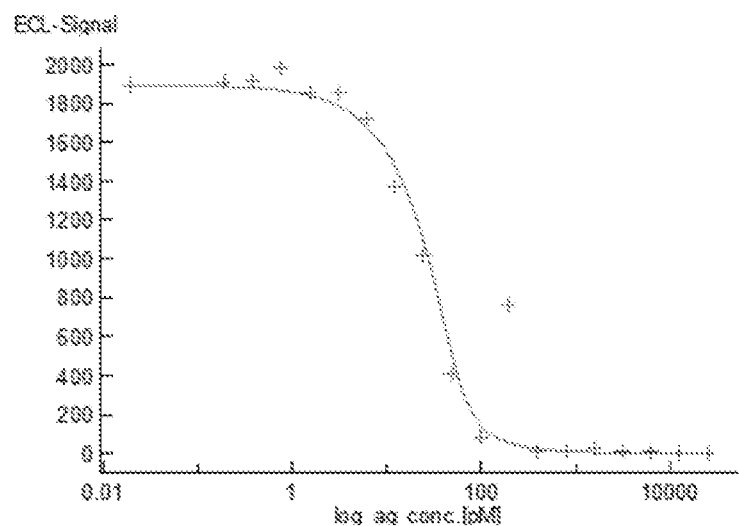
FIG. 1: is showing a concentrations-response curve of TGF-β2-specific AB MOR13436 binding on human recombinant TGF-β2 obtained using Solution Equilibrium Titration (SET) Method (Sector Imager 6000 (MSD). $K_D$ affinity determination was performed as described in the literature (Friquet et al., J Immnunol Meth 77, 305-319. 1985). In order to improve the sensitivity and accuracy of the SET method, it was transferred from classical ELISA to ECL based technology (Haenel et al., Anal Biochem 339, 182-184. 2005).
Figure 2:
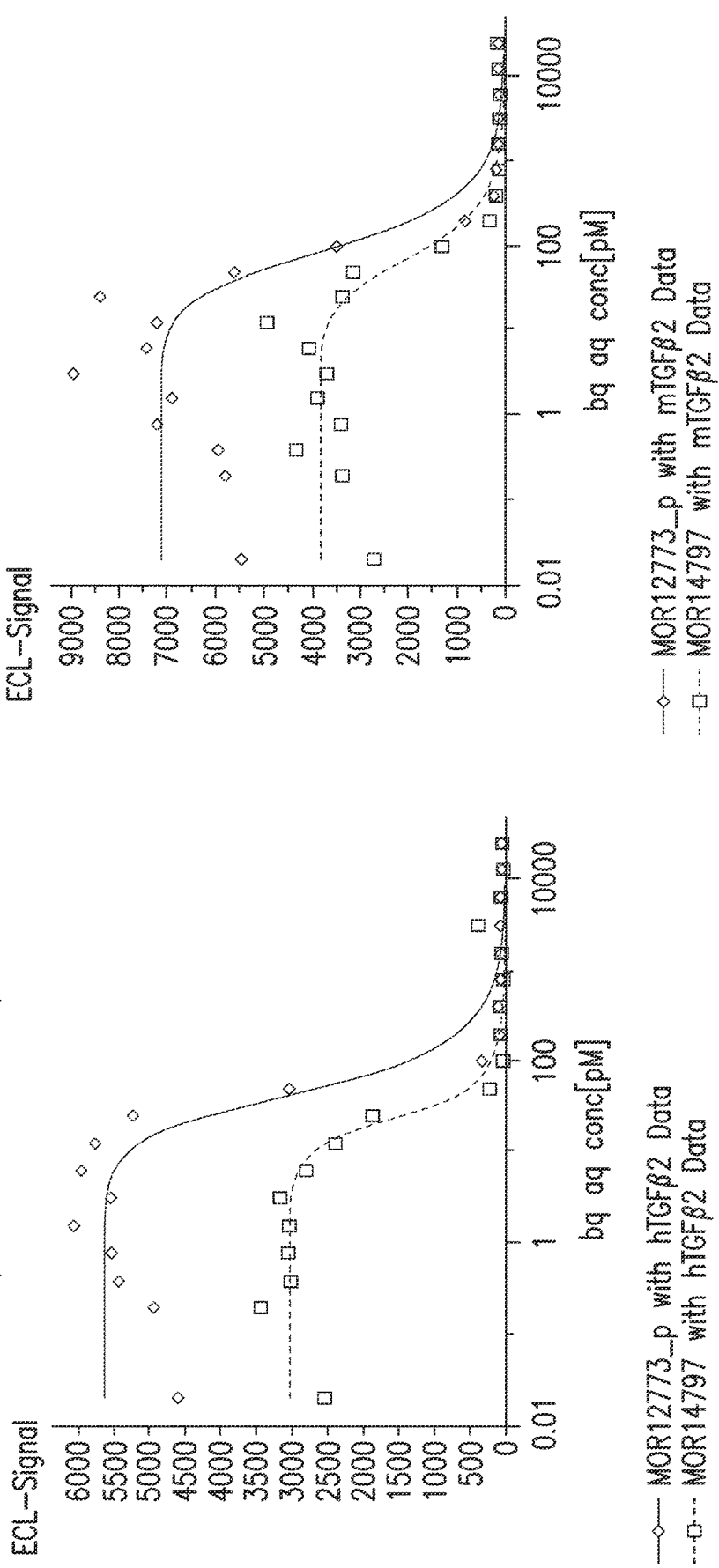
FIG. 2: is showing concentrations-response curve of TGF-β2-specific ABs (A) MOR14799, (B) MOR14800, (C) MOR14797 and (D) MOR14809 on human recombinant TGF-β2 and mouse recombinant TGF-β2 obtained using Solution Equilibrium Titration (SET) Method (Sector Imager 6000 (MSD). $K_d$ affinity determination was performed as described in the literature (Friquet et al., J Immnunol Meth 77, 305-319. 1985). In order to improve the sensitivity and accuracy of the SET method, it was transferred from classical ELISA to ECL based technology (Haenel et al., Anal Biochem 339, 182-184. 2005).
Figure 10A:
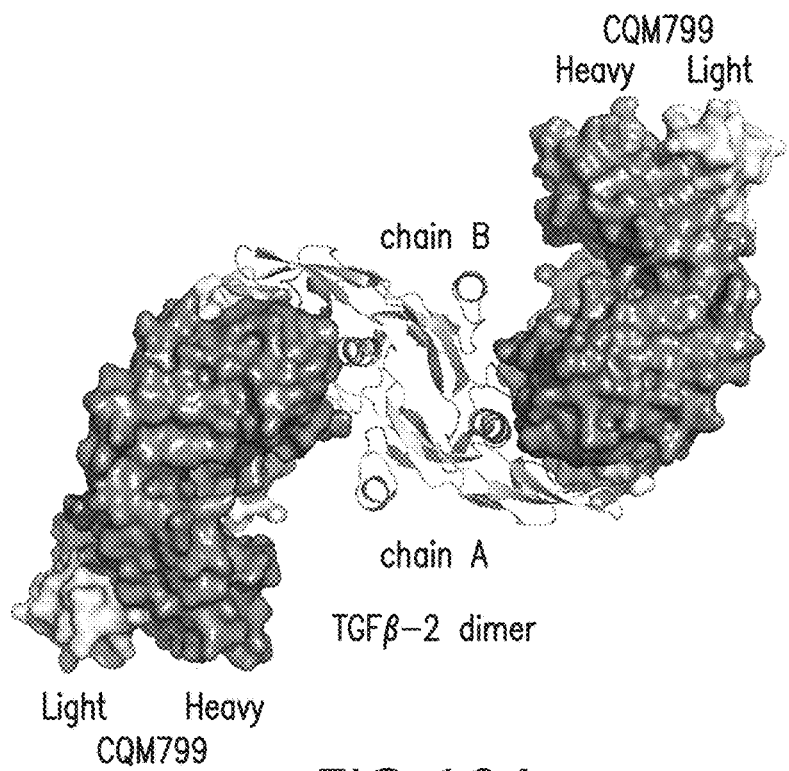
FIG. 10: Epitope of MOR14797 binding to TGFβ-2: (A) Overall structure of two MOR14797 Fabs binding to TGFβ-2 dimer. MOR14797 is shown as surface, TGFβ-2 as ribbon. (B) Residues of TGFβ-2 dimer within 5 Å distance to MOR14797 are shown as sticks.
Figure 10B:
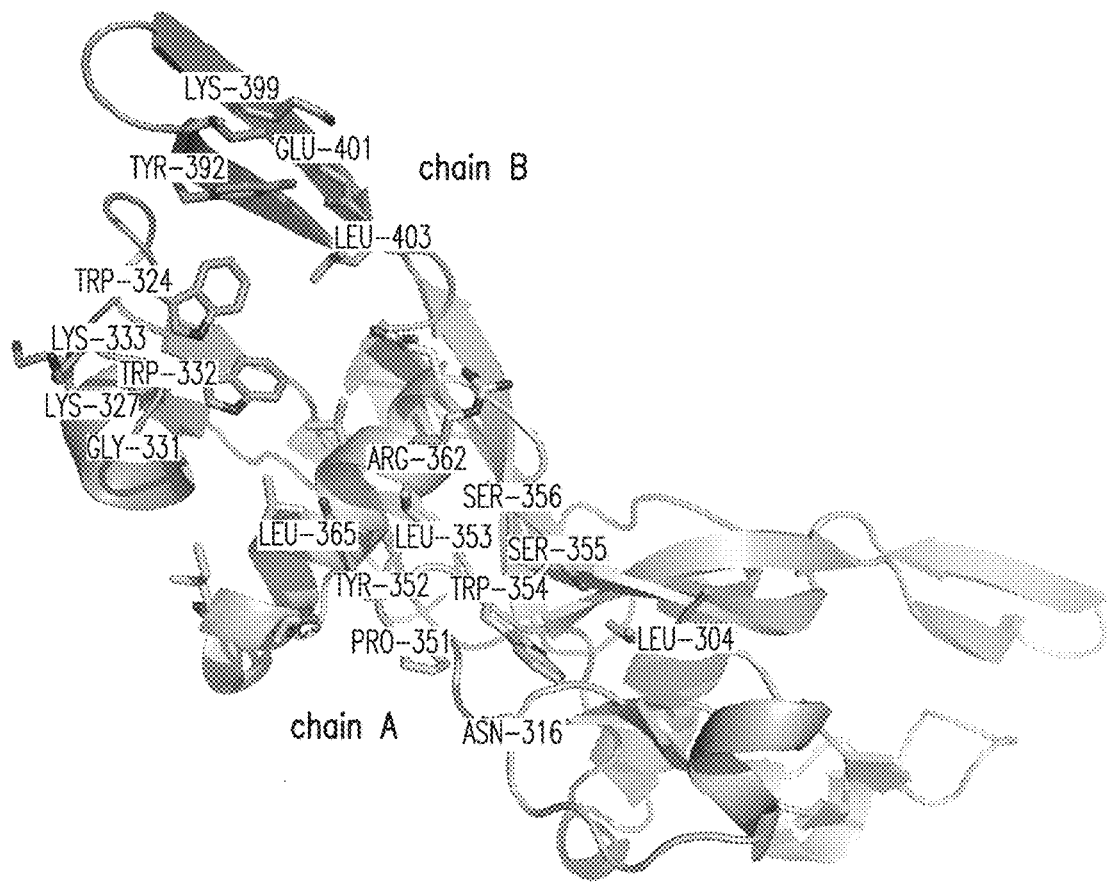

In order that the present invention may be more readily understood, certain terms are first defined. Additional definitions are set forth throughout the detailed description.

Comprising: the term "comprising" means "including" e.g. a composition "comprising" X may consist exclusively of X or may include something additional e.g. X+Y.

The term "human TGF-β isoform" is used to describe members of the transforming growth factor beta (TGF-β) superfamily, namely the human TGF-β isoforms TGF-β1, TGF-β2 and TGF-β3, respectively. The terms "human TGF-β isoform TGF-β2", "TGF-β2 isoform", "TGFβ2" and "TGF-β2" and TGFbeta-2 are used synonymously throughout the instant disclosure.

The term "antibody" as referred to herein includes whole antibodies and any antigen binding fragment (i.e. "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

An "isolated antibody", as used herein, refers to an antibody that is substantially free of other antibodies having different antigenic specificities (e.g. an isolated antibody that specifically binds antigen-binding portion is substantially free of antibodies that specifically bind antigens other than TGFbeta-2).

The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well-established in the art. A method for determining the $K_D$ of an antibody is surface plasmon resonance, such as the biosensor system of Biacore®, or Solution Equilibrium Titration (SET) (see Friguet B et al. (1985) J. Immunol Methods; 77(2): 305-319, and Hanel C et al. (2005) Anal Biochem; 339(1): 182-184). The term "$K_{assoc}$" or "$K_a$" is intended to refer to the association rate of a particular antibody-antigen interaction, whereas the term "$K_{dis}$" or "$K_d$", as used herein, is intended to refer to the dissociation rate of a particular antibody-antigen interaction.

Throughout the specification different scientific notations to writing powers to 10 are used. The scientific E notation (e.g. 1.1E-15) is used as an alternative to writing powers of 10. For example, 0.000000001 Mole can be written as 3.0×10-9 Mole or as 3.0E-9 Mole.

As used herein, the term "ADCC" or "antibody dependent cellular cytotoxicity" activity refers to human B cell depleting activity. ADCC activity can be measured by the human B cell depleting assays known in the art.

The term "human antibody", as used herein, is intended to include antibodies having variable regions in which both the framework and CDR regions are derived from sequences of human origin. Furthermore, if the antibody contains a constant region, the constant region also is derived from such human sequences, e.g. human germline sequences, or mutated versions of human germline sequences or antibody containing consensus framework sequences derived from human framework sequences analysis, for example, as described in Knappik, et al. (2000. J Mol Biol 296, 57-86). The human antibodies of the invention may include amino acid residues not encoded by human sequences (e.g. mutations introduced by random or site-specific mutagenesis in vitro or by somatic mutation in vivo; or humanized antibodies).

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g. a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g. a mouse) that is transgenic or transchromosomal for human immunoglobulin genes or a hybridoma prepared therefrom, antibodies isolated from a host cell transformed to express the human antibody, e.g. from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g. IgM, IgE, IgG such as IgG1 or IgG2) that is provided by the heavy chain constant region genes.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions. Examples of solid tumors include malignancies, e.g., sarcomas, and carcinomas (including adenocarcinomas and squamous cell carcinomas), of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies, e.g., in the lung, esophagus, skin, head and neck region, oral cavity, anus, and cervix. In one embodiment, the cancer is a melanoma, e.g., an advanced stage melanoma. Metastatic lesions of the aforementioned cancers can also be treated or prevented using the methods and compositions of the invention. Exemplary cancers whose growth can be inhibited using the antibodies molecules disclosed herein include cancers typically responsive to immunotherapy. Non-limiting examples of preferred cancers for treatment include melanoma (e.g., metastatic malignant melanoma), renal cancer (e.g., clear cell carcinoma), prostate cancer (e.g., hormone refractory prostate adenocarcinoma), breast cancer, colon cancer and lung cancer (e.g., non-small cell lung cancer). Additionally, refractory or recurrent malignancies can be treated using the antibody molecules described herein.

Examples of other cancers that can be treated include bone cancer, pancreatic cancer, skin cancer, cancer of the head or neck, cutaneous or intraocular malignant melanoma, uterine cancer, ovarian cancer, rectal cancer, anal cancer, gastro-esophageal, stomach cancer, liposarcoma, testicular cancer, uterine cancer, carcinoma of the fallopian tubes, carcinoma of the endometrium, carcinoma of the cervix, carcinoma of the vagina, carcinoma of the vulva, Merkel cell cancer, Hodgkin lymphoma, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, multiple myeloma, myelodisplastic syndromes, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos (e.g., mesothelioma), and combinations of said cancers. In certain embodiments, the cancer is a skin cancer, e.g., a Merkel cell carcinoma or a melanoma. In one embodiment, the cancer is a Merkel cell carcinoma. In other embodiments, the cancer is a melanoma. In other embodiments, the cancer is a breast cancer, e.g., a triple negative breast cancer (TNBC) or a HER2-negative breast cancer. In other embodiments, the cancer is kidney cancer, e.g., a renal cell carcinoma (e.g., clear cell renal cell carcinoma (CCRCC) or a non-clear cell renal cell carcinoma (nccRCC)). In other embodiments, the cancer is a thyroid cancer, e.g., an anaplastic thyroid carcinoma (ATC). In other embodiments, the cancer is a neuroendocrine tumor (NET), e.g., an atypical pulmonary carcinoid tumor or an NET in pancreas, gastrointestinal (GI) tract, or lung. In certain embodiments, the cancer is a lung cancer, e.g., a non-small cell lung cancer (NSCLC) (e.g., a squamous NSCLC or a non-squamous NSCLC).

As used herein, the term "Programmed Death 1" or "PD-1" relates to the CD28/CTLA-4 family member expressed, e.g., on activated CD4+ and CD8+ T cells, Tregs, and B cells. It negatively regulates effector T cell signaling and function. PD-1 is induced on tumor-infiltrating T cells, and can result in functional exhaustion or dysfunction (Keir et al. (2008) Annu. Rev. Immunol. 26:677-704; Pardoll et al. (2012) Nat Rev Cancer 12(4):252-64). PD-1 delivers a coinhibitory signal upon binding to either of its two ligands, Programmed Death-Ligand 1 (PD-L1) or Programmed Death-Ligand 2 (PD-L2). PD-L1 is expressed on a number of cell types, including T cells, natural killer (NK) cells, macrophages, dendritic cells (DCs), B cells, epithelial cells, vascular endothelial cells, as well as many types of tumors. High expression of PD-L1 on murine and human tumors has been linked to poor clinical outcomes in a variety of cancers (Keir et al. (2008) Annu. Rev. Immunol. 26:677-704; Pardoll et al. (2012) Nat Rev Cancer 12(4):252-64). PD-L2 is expressed on dendritic cells, macrophages, and some tumors. Blockade of the PD-1 pathway has been pre-clinically and clinically validated for cancer immunotherapy. Both preclinical and clinical studies have demonstrated that anti-PD-1 blockade can restore activity of effector T cells and results in robust anti-tumor response. For example, blockade of PD-1 pathway can restore exhausted/dysfunctional effector T cell function (e.g., proliferation, IFN-γ secretion, or cytolytic function) and/or inhibit Treg cell function (Keir et al. (2008) Annu. Rev. Immunol. 26:677-704; Pardoll et al. (2012) Nat Rev Cancer 12(4):252-64). Blockade of the PD-1 pathway can be effected with an antibody, an antigen binding fragment thereof, an immunoadhesin, a fusion protein, or oligopeptide of PD-1, PD-L1 and/or PD-L2. The amino acid sequence of PD-1, e.g., human PD-1, is known in the art, e.g., Shinohara T et al. (1994) Genomics 23(3):704-6; Finger L R, et al. Gene (1997) 197(1-2):177-87.

Various definitions and aspects of the invention are provided/described in further detail in the following subsections.

DETAILED DESCRIPTION OF THE INVENTION

The specific neutralization of one of several highly homologous targets that are associated with distinct functions with human monoclonal antibodies remains a major challenge. This challenge is more evident in a therapeutic context when cross-reactivity with other homologous targets may be associated with adverse or unwanted events. These problems may arise when targeting TGF-β2 with human monoclonal antibodies due to the presence of the homologous isoforms TGF-β1 and TGF-β3. These TGF-β isoforms are associated with distinct functions according to experimental data from knockout mice. In addition, the inhibition of TGF-β1 is known to be associated with a high risk of adverse events. Furthermore, the inventors herein disclose the unrecognized problem that the simultaneous inhibition of TGF-β3 and TGF-β2 is associated with valvulopathy, a serious disorder of the valves of the heart, in animal models. This creates the so far unresolved need for providing monoclonal therapeutic antibodies that specifically neutralize TGF-β2 but do not neutralize TGF-β3 or TGF-β3 and TGF-β1. More specifically, there is a need for neutralizing anti-TGF-β2 antibodies exhibiting very low picomolar dissociation constants to be effective in a clinical setting. In addition, neutralizing anti-TGF-β2 antibodies with high binding affinities are associated with an enhanced efficacy and safety as they need to be administered in lower doses which are less likely to cause interference with other pathways that may be associated with adverse events. Furthermore, the administration of lower doses of monoclonal anti-TGF-β2 antibodies is also associated with lower costs. These problems are solved by the present invention.

Neutralisation of TGF-beta1/2/3 isoforms is determined in a Smad dependent reporter gene assay. The terms "neutralizing antibody" and "antagonistic antibody" are used synonymously and are intended to refer to an antibody that inhibits TGFBeta-1, -2 and/or -3 induced signaling activity in the Smad dependent reporter gene assay with an IC50 of less than or equal to 100 nM. The phrase "a human monoclonal anti-TGF-β2 antibody or a functional fragment thereof that neutralizes the human TGF-β isoform TGF-β2 and does not neutralize human isoform TGF-133" or "specifically neutralize TGF-β2 but does not neutralize TGF-β3 or TGF-β1 (or both TGF-β3 and TGF-β1)" as used in the context of this invention refers to human monoclonal antibodies that specifically neutralize TGF-β2 with a half maximal inhibitory concentration (IC50) of less than 150 pM but do not neutralize human TGF-β1 and/or TGF-β3 determined by the Smad dependent reporter gene assay (e.g. having an IC 50 for human TGF-β1 and/or TGF-β3 of greater than 100 nM). Consequently, a human TGF-β2 neutralizing antibody of the present disclosure neutralizes human TGF-β2 with an half maximal inhibitory concentration (IC50) of less than e.g. 107 pM and neutralizes human TGF-β1 and/or TGF-β3 with an half maximal inhibitory concentration (IC50) of greater than 100 nM as determined by a Smad dependent reporter gene assay. In one embodiment the human TGF-β2 neutralizing antibody of the present disclosure neutralizes human TGF-β2 with an half maximal inhibitory concentration (IC50) of less than e.g. 107 pM and does not neutralize human TGF-β1 and/or TGF-β3 because said antibody exhibits essentially undetectable binding against these proteins in a Smad dependent reporter gene assay.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

An antibody that "cross-reacts" refers to an antibody that binds more than one antigen, wherein said binding can, but must not necessarily result in the manipulation (neutralization, reduction or activation) of the activity of said antigen(s). Cross reactivity can be determined using Smad dependent reporter gene assays and by determining the $K_D$ which may be determined using a surface plasmon resonance biosensor system, such as a Biacore® system, or Solution Equilibrium Titration.

"A human monoclonal anti-TGF-β2 antibody or a functional fragment thereof that binds the human TGF-β isoform TGF-β2 and does not bind (cross react) with the human isoform TGF-β3 or TGF-β1 or TGF-β3 and TGF-β1" is intended to also refer to an antibody that binds to TGF-β2 with a $K_D$ of about 1 pM or less and to TGF-β1 or TGF-β3 with a $K_D$ of about $2\times10^{-9}$ M, or about $5\times10^{-9}$ M or about $10\times10^{-9}$ M or higher. In certain embodiments, such antibodies that do not cross-react with the TGF-β3 and TGF-β1 antigen actually exhibit essentially undetectable binding against these proteins in standard binding assays.

Standard assays to evaluate the binding ability of the antibodies toward TGF-β2 of various species are known in the art, including for example, ELISAs, western blots and Radioimmunoassays (RIAs). Suitable assays are described in detail in the example section. The binding affinity of the antibodies also can be assessed by standard assays known in the art, such as surface plasmon resonance (e.g. Biacore® system analysis) or Solution Equilibrium Titration. Surface plasmon resonance based techniques such as Biacore® system can determine the binding kinetics which allows the calculation of the binding affinity. Assays to evaluate the effects of the antibodies on functional properties of TGF-β2 are described in further detail in the example section.

The present invention provides human monoclonal anti-TGF-β2 antibodies or functional fragments thereof. More particularly, it provides human monoclonal anti-TGF-β2 antibodies or functional fragments thereof that neutralize the human TGF-β isoform TGF-β2 (SEQ ID NO: 122) (UniProt ID: P61812-TGFB_2_HUMAN (http://www.uniprot.org/); gene symbol approved by the HUGO Gene Nomenclature Committee (HGNC)=TGFB2; HGNC ID=HGNC:11768) and do not neutralize the human isoform TGF-β3 (SEQ ID NO: 123) (UniProt ID: P10600-TGFB3_HUMAN; gene symbol HGNC=TGFB3; HGNC ID=HGNC:11769). In particular, the present invention provides human monoclonal anti-TGF-β2 antibodies or functional fragments thereof that neutralize the human TGF-β isoform TGF-β2 and do not neutralize human isoforms TGF-β3 and TGF-β1 (SEQ ID NO: 121) ((UniProt ID: P01137-TGFB1_HUMAN; gene symbol HGNC=TGFB1; HGNC ID=HGNC:11766). TGF-β1, TGF-β2, or TGF-β3 neutralization by the antibodies or functional fragments thereof is determined by the Smad dependent report gene assay as described in the example section. Preferably, the antibodies or a functional fragments thereof which are provided by the present invention neutralise human TGF-β2 with an half maximal inhibitory concentration (IC50) of less than 150 pM, or less than 107 pM, or less than 100 pM, or less than 95 pM or less than 80 pM, or less than 30 pM, or less than 20 pM, or less than 10 pM, and does not neutralise human TGF-β1 or TGF-β3 (having an IC50 greater than 100 nM) as determined by the Smad dependent reporter gene assay. In another embodiment of the disclosure, the antibodies or a functional fragments thereof neutralise human TGF-β2 with an half maximal inhibitory concentration (IC50) between about 1 pM and about 150 pM, or between about 1 pM and about 107 pM, or between about 1 pM and about 95 pM or between about 1 pM and about 80 pM and does not neutralise human TGF-β1 or TGF-β3 (having an IC50 greater than 100 nM) as determined by the Smad dependent reporter gene assay.

The present invention also provides human monoclonal anti-TGF-β2 antibodies or functional fragments thereof that bind the human TGF-β isoform TGF-β2 preferentially over the human isoforms TGF-β1 and/or TGF-β3. In particular, the provided human monoclonal anti-TGF-β2 antibodies or a functional fragment thereof bind the human TGF-β isoform TGF-β2 with a dissociation constant that is at least about 70-fold, about 1000-fold, about 2000-fold, about 10000-fold, about 20000-fold, about 200000-fold, about 300000-fold about 1000000-fold, or about 6000000-fold lower than its dissociation constant for TGF-β3, wherein the antibody or the functional fragment thereof neutralises human TGF-β2 but not TGF-β3.

In one embodiment, the dissociation constant of the provided antibodies for human TGF-β2 is about 2000-fold to about 1000000-fold lower than its dissociation constant for TGF-β1 or TGF-β3. In a another embodiment, the human monoclonal anti-TGF-β2 antibodies or a functional fragments thereof bind the human TGF-β isoform TGF-β2 with a dissociation constant that is at least 2000-fold or at least 1000000-fold lower than its dissociation constant for TGF-β3, wherein the antibody neutralises human TGF-β2 but not TGF-β3. The binding affinity of the antibodies also can be assessed by standard assays disclosed herein, such as surface plasmon resonance (e.g. Biacore® system analysis) or Solution Equilibrium Titration. The human monoclonal anti-TGF-β2 antibodies or functional fragments thereof that bind human TGF-β2 preferentially over the human isoforms TGF-β1 and TGF-β3, binds to TGF-β2 with a dissociation constant ($K_D$) of about 1 pM or less, or about 100 fM or less, or about 50 fM or less. In another embodiment, the disclosed antibodies or functional fragments bind to the human TGF-β isoform TGF-β2 with a dissociation constant ($K_D$) of 1 pM or less or about 1 pM to about 10 fM.

In another embodiment, the human monoclonal anti-TGF-β2 antibodies or functional fragments thereof bind human TGF-β isoform TGF-β2 preferentially over human TGF-β isoform TGF-β3 with a dissociation constant that is at least 70-fold lower than its dissociation constant for human TGF-β isoform TGF-β3, wherein the antibodies neutralise human TGF-β isoform TGF-β2 but do not neutralise human TGF-β isoform TGF-β3, and bind human TGF-β isoform TGF-β2 with a dissociation constant ($K_D$) of 1 pM or less.

In a preferred embodiment, the human monoclonal anti-TGF-β2 antibodies or functional fragments thereof bind human TGF-β2 preferentially over human TGF-β1 and TGF-β3 with a dissociation constant that is at least 70-fold lower than its dissociation constant for TGF-β1 and TGF-β3, wherein the antibodies neutralise human TGF-β2 but does not neutralise TGF-β3 and TGF-β1, and binds human TGF-β2 with a dissociation constant ($K_D$) of 1 pM or less. The anti-TGF-β2 antibodies, or antigen binding fragments thereof, as described herein can be single chain antibodies, Fab fragments, Fv fragments, F(ab')2 fragments, or scFv fragments, and/or IgG isotypes.

None of the prior art antibodies matches the antibodies disclosed herein, in particular the antibodies MOR14799, MOR14800, MOR14809, MOR14797, MOR14805 or MOR14787, in terms of specificity and selectivity. Antibodies of the invention include the human recombinant antibodies, isolated and structurally characterized, as described in the examples. The $V_H$ amino acid sequences of isolated antibodies of the invention are shown in SEQ ID NOs: 7, 27, 47, 67, 87 and 107, respectively. The $V_L$ amino acid sequences of isolated antibodies of the invention are shown in SEQ ID NOs: 17, 37, 57, 77, 97 and 117, respectively. Examples of preferred full length heavy chain amino acid sequences of antibodies of the invention are shown in SEQ ID NOs: 9, 29, 49, 69, 89 and 109, respectively. Examples of preferred full length light chain amino acid sequences of antibodies of the invention are shown in SEQ ID NOs: 19, 39, 59, 79, 99 and 119, respectively. Other antibodies of the invention include antibodies that have been mutated by amino acid deletion, insertion or substitution, yet have at least 80, 90, 95, 97 or 99 percent identity to the full length heavy chain amino acid sequences depicted in the sequences described above. Further, variable heavy chain nucleotide sequences are shown in SEQ ID NOs: 8, 28, 48, 68, 88 and 108, respectively. Variable light chain nucleotide sequences are shown in SEQ ID NOs: 18, 38, 58, 78, 98 and 118, respectively. Full length light chain nucleotide sequences are shown in SEQ ID NOs: 20, 40, 60, 80, 100 and 120, respectively. Full length heavy chain nucleotide sequences are shown in SEQ ID NOs: 10, 30, 50, 70, 90 and 110. Other antibodies of the invention include amino acids or nucleic acids that have been mutated, yet have at least 90 or more (i.e. 91, 92, 93, 94, 95, 97, 99 or more) percent identity to the sequences described above. Some embodiments include mutant amino acid sequences wherein no more than 1, 2, 3, 4 or 5 amino acids have been mutated by amino acid deletion, insertion or substitution in the variable regions when compared with the variable regions depicted in the sequence described above. Since each of these antibodies binds the same target, the $V_H$, $V_L$, full length light chain, and full length heavy chain sequences (nucleotide sequences and amino acid sequences) can be "mixed and matched" to create other anti-TGF-β2 antibodies of the invention. TGF-β2 binding of such "mixed and matched" antibodies can be tested using the binding assays described above and in the examples (e.g. ELISAs). When these chains are mixed and matched, a $V_H$ sequence from a particular $V_H/V_L$ pairing should be replaced with a structurally similar $V_H$ sequence. Likewise a full length heavy chain sequence from a particular full length heavy chain/full length light chain pairing should be replaced with a structurally similar full length heavy chain sequence. Likewise, a $V_L$ sequence from a particular $V_H/V_L$ pairing should be replaced with a structurally similar $V_L$ sequence. Likewise a full length light chain sequence from a particular full length heavy chain/full length light chain pairing should be replaced with a structurally similar full length light chain sequence. Accordingly, in one aspect, the invention provides an isolated recombinant anti-TGF-β2 antibody or antigen binding region thereof having: a heavy chain variable region comprising an amino acid sequence selected from the group consisting of SEQ ID NOs: 7, 27, 47, 67, 87 and 107; and a light chain variable region comprising an amino acid sequence selected from the group consisting of SEQ ID NOs: 17, 37, 57, 77, 97 and 117.

The terms "complementarity determining region," and "CDR," as used herein refer to the sequences of amino acids within antibody variable regions which contributes to the antigen specificity and binding affinity. In general, there are three CDRs in each heavy chain variable region (HCDR1, HCDR2, HCDR3) and three CDRs in each light chain variable region (LCDR1, LCDR2, LCDR3). The amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme). An alternative method of determining CDR regions uses the method devised by Chothia (Chothia et al. 1989, Nature, 342:877-883). The Chothia definition is based on the location of the structural loop regions. Other systems for defining CDRs exist and are known to the skilled person (see e.g. http://www.bioinf.org.uk/abs/). CDRs are assumed to account for the antigen recognition and binding and thus to contain antigen binding regions. In the context of this disclosure CDRs have been defined using the Kabat and the Chothia numbering system. CDRs defined using the Kabat system are designated "Kabat CDRs". CDRs defined using the Chothia system are designated "Chothia CDRs". CDRs predicted using the Kabat and Chothia system mostly overlap but are not necessarily identical. Hence, an antibody binding region can also be defined by merging the CDR amino acid sequences predicted by the Kabat and Chothia system ("Kabat/Chothia CDR"). It is known that some amino acid residues that actually bind the antigen fall outside the CDRs and, consequently, X-ray crystallography and X-ray diffraction data can also be used to define additional antibody binding regions/amino acids or paratope regions.

The terms "antibody binding regions", "antibody combining sites" and "paratope region" are used synonymously throughout this document and refer to those parts of the variable regions of both the light and heavy chains of an antibody that interact with the specific antigen. The paratope consists of stretches of amino acids or single amino acids comprised in the variable regions of antibodies that bind to an antigen by the establishment of chemical interactions (e.g. polar-, non-polar-, hydrogen-bonds/-contacts or salt bridges). The CDRs (e.g. predicted on the basis of the Kabat/Chothia system) are collectively referred to as the Kabat/Chothia paratope of an antibody. In the context of this disclosure a paratope consists of those amino acid residues of an antibody that are involved in the antibody/antigen binding/combining, wherein amino acids being within 5 Å distance to the antigen are considered to be involved in the antibody/antigen binding. The paratope may comprise CDR amino acids defined according to Kabat/Chothia as well as amino acids comprised in the framework region of the variable light and/or heavy chain regions of a given antibody that are involved in the antibody/antigen binding/combining. Beside the paratope prediction based on the Kabat/Chothia, the complete paratope of a given antibody can be identified using X-ray crystallography/X-ray diffraction data.

The phrase "functional fragments thereof" when used in the context of an antibody refers to a protein fragment of a full-length antibody comprising the antigen-binding regions (single chain antibodies, Fab fragments, Fv fragments, F(ab')2 fragments, and/or scFv fragments), wherein (i) said fragment retains the ability to specifically bind the antigen or (ii) upon transfer/fusion of said functional fragment to another antibody (sequence replacements) or antibody like structure the ability to specifically bind to an antigen (e.g. a portion of TGFbeta-2) is retained. Examples of "functional fragments" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g. Bird et al., 1988 Science 242:423-426; and Huston et al., 1988 Proc. Natl. Acad. Sci. 85:5879-5883). Such single chain antibodies are also intended to be encompassed within the term "functional fragment" of an antibody. These antibody fragments are obtained using conventional techniques known to those of skill in the art, and the fragments are screened for utility in the same manner as are intact antibodies.

In one aspect the human monoclonal anti-TGF-β2 antibodies of the present disclosure or functional fragments thereof comprise the following complementarity determining regions (CDR) defined by Kabat or Cothia or by Kabat and Cothia (i) the Kabat CDRs recited in SEQ ID NOs: 1-3, 11-13, 21-23, 31-33, 41-43, 51-53, 61-63, 71-73, 81-83, 91-93, 101-103, or 111-113, or (ii) the Chothia CDRs recited in SEQ ID NOs: 4-6, 14-16, 24-26, 34-36, 44-46, 54-56, 64-66, 74-76, 84-86, 94-96, 104-106, or 114-116, or (iii) the Kabat/Chothia CDRs recited on SEQ ID NOs: 124-129.

The human monoclonal anti-TGF-β2 antibodies of the present disclosure or functional fragments thereof comprise a heavy chain variable region CDR1 comprising an amino acid sequence having at least 80%, 90%, 95% or 100% sequence identity to a sequence selected from the group consisting of SEQ ID NOs: 1, 21, 41, 61, 81, 101 or 4, 24, 44, 64, 84, 104 or 124-129; a heavy chain variable region CDR2 comprising an amino acid sequence having at least 70%, 80%, 90, 95% or 100% sequence identity to a sequence selected from the group consisting of SEQ ID NOs: 2, 22, 42, 62, 82, 102 or 5, 25, 45, 65, 85, 105; a heavy chain variable region CDR3 comprising an amino acid sequence having at least 70%, 80%, 90 95% or 100% sequence identity to a sequence selected from the group consisting of SEQ ID NOs: 3, 23, 43, 63, 83, 103 or 6, 26, 46, 66, 86, 106; a light chain variable region CDR1 comprising an amino acid sequence having at least 70%, 80%, 90, 95% or 100% sequence identity to a sequence selected from the group consisting of SEQ ID NOs: 11, 31, 51, 71, 91, 111 or 14, 34, 54, 74, 94, 114; a light chain variable region CDR2 comprising an amino acid sequence having at least 80%, 90, 95% or 100% sequence identity to a sequence selected from the group consisting of SEQ ID NOs: 12, 32, 52, 72, 92, 112 or 15, 35, 55, 75, 95, 115; a light chain variable region CDR3 comprising an amino acid sequence having at least 70%, 80%, 90, 95% or 100% sequence identity to a sequence selected from the group consisting of SEQ ID NOs: 13, 33, 53, 73, 93, 113 or 16, 36, 56, 76, 96, 116.

The human monoclonal anti-TGF-β2 antibodies of the present disclosure or functional fragments thereof comprise a VH polypeptide sequence having at least 95%, 96%, 97%, 98%, or 99% sequence identity to at least one of SEQ ID NOs: 7, 27, 47, 67, 87, or 107.

The human monoclonal anti-TGF-β2 antibodies of the present disclosure or functional fragments thereof comprise a VL polypeptide sequence having at least 95%, 96%, 97%, 98%, 99% or 100% sequence identity to at least one of SEQ ID NOs: 17, 37, 57, 77, 97, or 117.

The human monoclonal anti-TGF-β2 antibodies of the present disclosure or functional fragments thereof comprise a VH polypeptide sequence having at least 95%, 96%, 97%, 98%, 99% or 100% sequence identity to at least one of SEQ ID NOs: 7, 27, 47, 67, 87, or 107 and a VL polypeptide sequence having at least 95%, 96%, 97%, 98%, or 99% sequence identity to at least one of SEQ ID NOs: 17, 37, 57, 77, 97, or 117.

The skilled person is aware of methods that can be used to assess identity of two DNA or protein sequences. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4. The nucleic acid and protein sequences described herein can be used as a "query sequence" to perform a search against public databases. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to a nucleic acid (SEQ ID NO: 1) molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. See http://www.ncbi.nlm.nih.gov.

The human monoclonal anti-TGF-β2 antibodies of the present disclosure or functional fragments thereof comprise a heavy chain variable region CDR1 comprising an amino acid sequence selected from the group consisting of SEQ ID NOs: 1, 21, 41, 61, 81, 101 or 4, 24, 44, 64, 84, 104 or 124-129; a heavy chain variable region CDR2 comprising an amino acid sequence selected from the group consisting of SEQ ID NOs: 2, 22, 42, 62, 82, 102 or 5, 25, 45, 65, 85, 105; a heavy chain variable region CDR3 comprising an amino acid sequence selected from the group consisting of SEQ ID NOs: 3, 23, 43, 63, 83, 103 or 6, 26, 46, 66, 86, 106; a light chain variable region CDR1 comprising an amino acid sequence selected from the group consisting of SEQ ID NOs: 11, 31, 51, 71, 91, 111 or 14, 34, 54, 74, 94, 114; a light chain variable region CDR2 comprising an amino acid sequence selected from the group consisting of SEQ ID NOs: 12, 32, 52, 72, 92, 112 or 15, 35, 55, 75, 95, 115; a light chain variable region CDR3 comprising an amino acid sequence selected from the group consisting of SEQ ID NOs: 13, 33, 53, 73, 93, 113 or 16, 36, 56, 76, 96, 116.

Because each of these antibodies can bind to TGF-β2, the $V_H$ CDR1, 2 and 3 sequences and $V_L$ CDR1, 2 and 3 sequences can be "mixed and matched". TGF-β2 binding of such "mixed and matched" antibodies can be tested using the binding assays described above and in the Examples (e.g. ELISAs). When $V_H$ CDR sequences are mixed and matched, the CDR1, CDR2 and/or CDR3 sequence from a particular $V_H$ sequence should be replaced with a structurally similar CDR sequence(s). Likewise, when $V_L$ CDR sequences are mixed and matched, the CDR1, CDR2 and/or CDR3 sequence from a particular $V_L$ sequence should be replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences shown herein for monoclonal antibodies of the present invention.

The human monoclonal anti-TGF-β2 antibody of the present invention or a functional fragment thereof comprises: (A) a heavy chain variable region CDR1 of SEQ ID NO: 1; a heavy chain variable region CDR2 of SEQ ID NO: 2; a heavy chain variable region CDR3 of SEQ ID NO: 3; a light chain variable region CDR1 of SEQ ID NO: 11; a light chain variable region CDR2 of SEQ ID NO: 12; and a light chain variable region CDR3 of SEQ ID NO: 13.

In another embodiment, the antibody of (A) described above comprises a heavy chain variable region CDR1 of SEQ ID NO: 124.

The human monoclonal anti-TGF-β2 antibody of the present invention or a functional fragment thereof comprises: (B) a heavy chain variable region CDR1 of SEQ ID NO: 4; a heavy chain variable region CDR2 of SEQ ID NO: 5; a heavy chain variable region CDR3 of SEQ ID NO: 6; a light chain variable region CDR1 of SEQ ID NO: 14; a light chain variable region CDR2 of SEQ ID NO: 15; and a light chain variable region CDR3 of SEQ ID NO: 16.

In another embodiment, the antibody of (B) described above comprises a heavy chain variable region CDR1 of SEQ ID NO: 124.

In one embodiment the human monoclonal anti-TGF-β2 antibody of the present invention consist of (C): a variable heavy chain comprising the CDRs of SEQ ID NOs: 1, 2 and 3 and a variable light chain comprising the CDRs of SEQ ID NOs: 11, 12 and 13, wherein the variable heavy chain and the variable light chain framework regions of said antibody having at least 95%, 96%, 97%, 98%, or 99% sequence identity to the framework regions of the variable heavy chain (VH) sequence of SEQ ID NO: 7 and framework regions of the variable light chain (VL) sequence of SEQ ID NO: 17, respectively.

In one embodiment the human monoclonal anti-TGF-β2 antibody of the present invention consist of (D): a variable heavy chain comprising the CDRs of SEQ ID NOs: 4, 5 and 6 and a variable light chain comprising the CDRs of SEQ ID NOs: 14, 15 and 16, wherein the variable heavy chain and the variable light chain framework regions of said antibody having at least 95%, 96%, 97%, 98%, or 99% sequence identity to the framework regions of the variable heavy chain (VH) sequence of SEQ ID NO: 7 and framework regions of the variable light chain (VL) sequence of SEQ ID NO: 17, respectively.

In one embodiment the human monoclonal anti-TGF-β2 antibody of the present invention consist of (E): a variable heavy chain comprising the CDRs of SEQ ID NOs: 61, 62 and 63 and a variable light chain comprising the CDRs of SEQ ID NOs: 71, 72 and 73, wherein the variable heavy chain and the variable light chain framework regions of said antibody having at least 95%, 96%, 97%, 98%, or 99% sequence identity to the framework regions of the heavy chain sequence (VH) of SEQ ID NO: 67 and the framework regions of the light chain sequence (VL) of SEQ ID NO: 77, respectively.

In one embodiment the human monoclonal anti-TGF-β2 antibody of the present invention or a functional fragment thereof comprises: (F) a heavy chain variable region CDR1 of SEQ ID NO: 61; a heavy chain variable region CDR2 of SEQ ID NO: 62; a heavy chain variable region CDR3 of SEQ ID NO: 63; a light chain variable region CDR1 of SEQ ID NO: 71; a light chain variable region CDR2 of SEQ ID NO: 72; and a light chain variable region CDR3 of SEQ ID NO: 73. In another embodiment, the antibody (F) described above comprises a heavy chain variable region CDR1 of SEQ ID NO: 127.

In one embodiment the human monoclonal anti-TGF-β2 antibody of the present invention or a functional fragment thereof comprises: (F2) a heavy chain variable domain CDR1 of SEQ ID NO: 61; a heavy chain variable domain CDR2 of SEQ ID NO: 62; a heavy chain variable domain CDR3 of SEQ ID NO: 63; a light chain variable domain CDR1 of SEQ ID NO: 71; a light chain variable domain CDR2 of SEQ ID NO: 72; and a light chain variable domain CDR3 of SEQ ID NO: 73, wherein the heavy chain variable domain and the light chain variable domain framework regions of said antibody have at least 95% sequence identity to the framework regions of the heavy chain variable domain (VH) of SEQ ID NO: 67 and the light chain variable domain (VL) of SEQ ID NO: 77, respectively. In another embodiment, the antibody (F2) described above comprises a heavy chain variable domain CDR1 of SEQ ID NO: 127.

In one embodiment the human monoclonal anti-TGF-β2 antibody of the present invention or a functional fragment thereof comprises: (G): a heavy chain variable domain comprising (i) the CDRs of SEQ ID NOs: 61, 62 and 63 and (ii) the amino acid Q at position 1 and the amino acid R at position 99; and a light chain variable domain comprising (iii) the CDRs of SEQ ID NOs: 71, 72 and 73, and (iv) the amino acid F at position 49, wherein the heavy chain variable domain and the light chain variable domain framework regions of said antibody have at least 95% sequence identity to the framework regions of the heavy chain variable domain sequence (VH) of SEQ ID NO: 67 and the light chain variable domain sequence (VL) of SEQ ID NO: 77, respectively, wherein the position of the amino acids mentioned in (ii) and (iv) correspond to positions 1, 99 and 49 of SEQ ID NOs.: 67 and 77, respectively.

In one embodiment the human monoclonal anti-TGF-β2 antibody of the present invention or a functional fragment thereof comprise: (H) a heavy chain variable region CDR1 of SEQ ID NO: 64; a heavy chain variable region CDR2 of SEQ ID NO: 65; a heavy chain variable region CDR3 of SEQ ID NO: 66; a light chain variable region CDR1 of SEQ ID NO: 74; a light chain variable region CDR2 of SEQ ID NO: 75; and a light chain variable region CDR3 of SEQ ID NO: 76. In another embodiment, the antibody (H) described above comprises a heavy chain variable region CDR1 of SEQ ID NO: 127.

In one embodiment the human monoclonal anti-TGF-β2 antibody of the present invention or a functional fragment thereof comprises: (H1) a heavy chain variable domain CDR1 of SEQ ID NO: 64; a heavy chain variable domain CDR2 of SEQ ID NO: 65; a heavy chain variable domain CDR3 of SEQ ID NO: 66; a light chain variable domain CDR1 of SEQ ID NO: 74; a light chain variable domain CDR2 of SEQ ID NO: 75; and a light chain variable domain CDR3 of SEQ ID NO: 76, wherein the heavy chain variable domain and the light chain variable domain framework regions of said antibody have at least 95% sequence identity to the framework regions of the heavy chain variable domain (VH) of SEQ ID NO: 67 and the light chain variable domain (VL) of SEQ ID NO: 77, respectively. In another embodiment, the antibody (H1) described above comprises a heavy chain variable domain CDR1 of SEQ ID NO: 127.

In one embodiment the human monoclonal anti-TGF-β2 antibody of the present invention or a functional fragment thereof comprises (H2): a heavy chain variable domain comprising (i) the CDRs of SEQ ID NOs: 64, 65 and 66 and (ii) the amino acid Q at position 1 and the amino acid R at position 99; and a light chain variable domain comprising (iii) the CDRs of SEQ ID NOs: 74, 75 and 76, and (iv) the amino acid F at position 49, wherein the heavy chain variable domain and the light chain variable domain framework regions of said antibody have at least 95% sequence identity to the framework regions of the heavy chain variable domain (VH) of SEQ ID NO: 67 and the light chain variable domain (VL) of SEQ ID NO: 77, respectively, wherein the position of the amino acids mentioned in (ii) and (iv) correspond to positions 1, 99 and 49 of SEQ ID NO.: 67 and 77, respectively.

In one embodiment the human monoclonal anti-TGF-β2 antibody of the present invention or a functional fragment thereof comprises (I): a heavy chain variable domain comprising the following amino acids: (i) a Q at position 1, a T at position 31, a S at position 32, a M at position 34, a W at position 55, a N at position 56, a D at position 58, a R at position 99, a F at position 101, a Y at positions 102 and 103, a S at position 104, a Y at position 106 and a D at position 108 and a light chain variable domain comprising the following amino acids: (ii) a Y at position 32, a F at position 49, a S at position 53, a L at position 54, a Q at position 55, a S at position 56, a T at position 91, a N at position 92 and a T at position 93, wherein the heavy chain variable domain and the light chain variable domain framework regions of said antibody having at least 95% sequence identity to the framework regions of the heavy chain variable domain (VH) of SEQ ID NO: 67 and the light chain variable domain (VL)

of SEQ ID NO: 77, respectively, wherein the position of the amino acids mentioned in (i) and (ii) correspond to positions 1, 31, 32, 34, 55, 56, 58, 99, 101, 102, 103, 104, 106 and 108 of SEQ ID NO.: 67 and to positions 32, 49, 53, 54, 55, 56, 91, 92 and 93 of SEQ ID NO.: 77, respectively.

In one embodiment the human monoclonal anti-TGF-β2 antibody of the present invention or a functional fragment thereof comprises (I1): a heavy chain variable domain comprising (i) amino acids at positions 1, 31, 32, 34, 55, 56, 58, 99, 101-104, 106 and 108 being, when bound to the TGFbeta-2 dimer, within 5 Å distance to said antigen and a light chain variable domain comprising (ii) amino acids at positions 32, 49, 53-56 and 91-93, being, when bound to the TGFbeta-2 dimer, within 5 Å distance to the antigen, wherein the position of the amino acids mentioned in (i) and (ii) correspond to positions 1, 31, 32, 34, 55, 56, 58, 99, 101-104, 106 and 108 of SEQ ID NO.: 67 and to positions 32, 49, 53-56, 91, 92 and 93 of SEQ ID NO.: 77, respectively.

In another embodiment, the antibody (I2) or a functional fragment thereof described above comprises at the positions 1, 31, 32, 34, 55, 56, 58, 99, 101-104, 106 and 108 of the heavy chain variable domain the same amino acids as those being at the same position in the heavy chain variable domain protein of SEQ ID NO: 67 and comprises at the positions 32, 49, 53-56 and 91-93 of the light chain variable domain the same amino acids as those being at the same position in the light chain variable domain protein of SEQ ID NO: 77.

In another embodiment, the antibody (I3) or a functional fragment thereof described above comprises at the positions 1, 31, 32, 34, 55, 56, 58, 99, 101-104, 106 and 108 of the heavy chain variable domain amino acid having a similar side chain as those amino acids being at the same position in the heavy chain variable domain protein of SEQ ID NO: 67 and comprises at the positions 32, 49, 53-56 and 91-93 of the heavy chain variable domain amino acid having a similar side chain as those amino acids being at the same position in the heavy chain variable domain protein of SEQ ID NO: 77.

In one embodiment the human monoclonal anti-TGF-β2 antibody of the present invention or a functional fragment thereof comprises (I4): a heavy chain variable domain comprising the following amino acids: a Q at position 1, a T at position 31, a S at position 32, a M at position 34, a W at position 55, a N at position 56, a D at position 58, a R at position 99, a F at position 101, a Y at positions 102 and 103, a S at position 104, a Y at position 106 and a D at position 108, being, when bound to the TGFbeta-2 dimer, within 5 Å distance to the antigen and a light chain variable domain comprising the following amino acids: a Y at position 32, a F at position 49, a S at position 53, a L at position 54, a Q at position 55, a S at position 56, a T at position 91, a N at position 92 and a T at position 93, being, when bound to the TGFbeta-2 dimer, within 5 Å distance to the antigen, wherein the heavy chain variable domain and the light chain variable domain framework regions of said antibody having at least 95% sequence identity to the framework regions of the heavy chain variable domain (VH) of SEQ ID NO: 67 and the light chain variable domain (VL) of SEQ ID NO: 77, respectively.

In one embodiment the human monoclonal anti-TGF-β2 antibody of the present invention or a functional fragment thereof comprises: (J) a heavy chain variable region CDR1 of SEQ ID NO: 21 a heavy chain variable region CDR2 of SEQ ID NO: 22; a heavy chain variable region CDR3 of SEQ ID NO: 23; a light chain variable region CDR1 of SEQ ID NO: 31; a light chain variable region CDR2 of SEQ ID NO: 32; and a light chain variable region CDR3 of SEQ ID NO: 33. In another embodiment, the antibody (J) described above comprises a heavy chain variable region CDR1 of SEQ ID NO: 125.

In one embodiment the human monoclonal anti-TGF-β2 antibody of the present invention consist of (K): a variable heavy chain comprising the CDRs of SEQ ID NOs: 21, 22 and 23 and a variable light chain comprising the CDRs of SEQ ID NOs: 31, 32 and 33, wherein the variable heavy chain and the variable light chain framework regions of said antibody having at least 95%, 96%, 97%, 98%, or 99% sequence identity to the framework regions of the heavy chain sequence (VH) of SEQ ID NO: 29 and the framework regions of the light chain sequence (VL) of SEQ ID NO: 39, respectively.

In one embodiment the human monoclonal anti-TGF-β2 antibody of the present invention or a functional fragment thereof comprises: (L) a heavy chain variable region CDR1 of SEQ ID NO: 21 a heavy chain variable region CDR2 of SEQ ID NO: 22; a heavy chain variable region CDR3 of SEQ ID NO: 23; a light chain variable region CDR1 of SEQ ID NO: 31; a light chain variable region CDR2 of SEQ ID NO: 32; and a light chain variable region CDR3 of SEQ ID NO: 33; and the framework paratope regions of SEQ IDs NO:131 and 132. In another embodiment, the antibody (L) described above comprises a heavy chain variable region CDR1 of SEQ ID NO: 125.

In one embodiment the human monoclonal anti-TGF-β2 antibody of the present invention or a functional fragment thereof comprises: (M) a heavy chain variable region CDR1 of SEQ ID NO: 24 a heavy chain variable region CDR2 of SEQ ID NO: 25; a heavy chain variable region CDR3 of SEQ ID NO: 26; a light chain variable region CDR1 of SEQ ID NO: 34; a light chain variable region CDR2 of SEQ ID NO: 35; and a light chain variable region CDR3 of SEQ ID NO: 36. In another embodiment, the antibody (M) described above comprises a heavy chain variable region CDR1 of SEQ ID NO: 125.

In one embodiment the human monoclonal anti-TGF-β2 antibody of the present invention or a functional fragment thereof comprises: (N) a heavy chain variable region CDR1 of SEQ ID NO: 24 a heavy chain variable region CDR2 of SEQ ID NO: 25; a heavy chain variable region CDR3 of SEQ ID NO: 26; a light chain variable region CDR1 of SEQ ID NO: 34; a light chain variable region CDR2 of SEQ ID NO: 35; and a light chain variable region CDR3 of SEQ ID NO: 36; and a paratope region of SEQ IDs NO:131 and 132. In another embodiment, the antibody (N) described above comprises a heavy chain variable region CDR1 of SEQ ID NO: 125.

In one embodiment the human monoclonal anti-TGF-β2 antibody of the present invention or a functional fragment thereof comprises: (O) a heavy chain variable region CDR1 of SEQ ID NO: 41; a heavy chain variable region CDR2 of SEQ ID NO: 42; a heavy chain variable region CDR3 of SEQ ID NO: 43; a light chain variable region CDR1 of SEQ ID NO: 51; a light chain variable region CDR2 of SEQ ID NO: 52; and a light chain variable region CDR3 of SEQ ID NO: 53. In another embodiment, the antibody (O) described above comprises a heavy chain variable region CDR1 of SEQ ID NO: 126.

In one embodiment the human monoclonal anti-TGF-β2 antibody of the present invention consist of (P): a variable heavy chain comprising the CDRs of SEQ ID NOs: 41, 42 and 43 and a variable light chain comprising the CDRs of SEQ ID NOs: 51, 52 and 53, wherein the variable heavy chain and the variable light chain framework regions of said antibody having at least 95%, 96%, 97%, 98%, or 99% sequence identity to the framework regions of the heavy chain sequence (VH) of SEQ ID NO: 47 and the framework regions of the light chain sequence (VL) of SEQ ID NO: 57, respectively.

In one embodiment the human monoclonal anti-TGF-β2 antibody of the present invention or a functional fragment thereof comprises: (Q) a heavy chain variable region CDR1 of SEQ ID NO: 44; a heavy chain variable region CDR2 of SEQ ID NO: 45; a heavy chain variable region CDR3 of SEQ ID NO: 46; a light chain variable region CDR1 of SEQ ID NO: 54; a light chain variable region CDR2 of SEQ ID NO: 55; and a light chain variable region CDR3 of SEQ ID NO: 56. In another embodiment, the antibody (Q) described above comprises a heavy chain variable region CDR1 of SEQ ID NO: 126.

In one embodiment the human monoclonal anti-TGF-β2 antibody of the present invention or a functional fragment thereof comprise: (R) a heavy chain variable region CDR1 of SEQ ID NO: 81; a heavy chain variable region CDR2 of SEQ ID NO: 82; a heavy chain variable region CDR3 of SEQ ID NO: 83; a light chain variable region CDR1 of SEQ ID NO: 91; a light chain variable region CDR2 of SEQ ID NO: 92; and a light chain variable region CDR3 of SEQ ID NO: 93. In another embodiment, the antibody (R) described above comprises a heavy chain variable region CDR1 of SEQ ID NO: 128.

In one embodiment the human monoclonal anti-TGF-β2 antibody of the present invention consist of (S): a variable heavy chain comprising the CDRs of SEQ ID NOs: 81, 82 and 83 and a variable light chain comprising the CDRs of SEQ ID NOs: 91, 92 and 93, wherein the variable heavy chain and the variable light chain framework regions of said antibody having at least 95%, 96%, 97%, 98%, or 99% sequence identity to the framework regions of the heavy chain sequence (VH) of SEQ ID NO: 87 and the framework regions of the light chain sequence (VL) of SEQ ID NO: 97, respectively.

In one embodiment the human monoclonal anti-TGF-β2 antibody of the present invention or a functional fragment thereof comprises: (T) a heavy chain variable region CDR1 of SEQ ID NO: 84; a heavy chain variable region CDR2 of SEQ ID NO: 85; a heavy chain variable region CDR3 of SEQ ID NO: 86; a light chain variable region CDR1 of SEQ ID NO: 94; a light chain variable region CDR2 of SEQ ID NO: 95; and a light chain variable region CDR3 of SEQ ID NO: 96. In another embodiment, the antibody (T) described above comprises a heavy chain variable region CDR1 of SEQ ID NO: 128.

In one embodiment the human monoclonal anti-TGF-β2 antibody of the present invention or a functional fragment thereof comprises: U) a heavy chain variable region CDR1 of SEQ ID NO: 101; a heavy chain variable region CDR2 of SEQ ID NO: 102; a heavy chain variable region CDR3 of SEQ ID NO: 103; a light chain variable region CDR1 of SEQ ID NO: 111; a light chain variable region CDR2 of SEQ ID NO: 112; and a light chain variable region CDR3 of SEQ ID NO: 113. In another embodiment, the antibody (U) described above comprises a heavy chain variable region CDR1 of SEQ ID NO: 129.

In one embodiment the human monoclonal anti-TGF-β2 antibody of the present invention consist of (V): a variable heavy chain comprising the CDRs of SEQ ID NOs: 101, 102 and 103 and a variable light chain comprising the CDRs of SEQ ID NOs: 111, 112 and 113, wherein the variable heavy chain and the variable light chain framework regions of said antibody having at least 95%, 96%, 97%, 98%, or 99% sequence identity to the framework regions of the heavy chain sequence (VH) of SEQ ID NO: 107 and the framework regions of the light chain sequence (VL) of SEQ ID NO: 117, respectively.

In one embodiment the human monoclonal anti-TGF-β2 antibody of the present invention or a functional fragment thereof comprises: (W) a heavy chain variable region CDR1 of SEQ ID NO: 104; a heavy chain variable region CDR2 of SEQ ID NO: 105; a heavy chain variable region CDR3 of SEQ ID NO: 106; a light chain variable region CDR1 of SEQ ID NO: 114; a light chain variable region CDR2 of SEQ ID NO: 115; and a light chain variable region CDR3 of SEQ ID NO: 116. In another embodiment, the antibody (W) described above comprises a heavy chain variable region CDR1 of SEQ ID NO: 129.

In another preferred embodiment, the human monoclonal anti-TGF-β2 antibodies (A) to (W) described above or functional fragments thereof bind human TGF-β2 preferentially over human TGF-β1 and TGF-β3 with a dissociation constant that is at least 2,000-fold lower than its dissociation constant for TGF-β1 or TGF-β3, wherein the antibodies neutralise human TGF-β2 but do not neutralise TGF-β3, and bind human TGF-β2 with a dissociation constant ($K_D$) of 1 pM or less. In another embodiment the human monoclonal anti-TGF-β2 antibodies of the present disclosure comprise a full length heavy chain amino acid sequence having at least 95%, 96%, 97%, 98%, 99% or 100% sequence identity to at least one sequence selected from the group consisting of SEQ ID NOs: 9, 29, 49, 69, 89 and 109.

In one embodiment the human monoclonal anti-TGF-β2 antibodies of the present disclosure comprise a full length light chain amino acid sequence having at least 95%, 96%, 97%, 98%, 99% or 100% sequence identity to at least one sequence selected from the group consisting of SEQ ID NOs: 19, 39, 59, 79, 99 and 119.

In one embodiment the human monoclonal anti-TGF-β2 antibodies of the present disclosure comprise full length heavy chain amino acid sequence having at least 95%, 96%, 97%, 98%, 99% or 100% sequence identity to at least one sequence selected from the group consisting of SEQ ID NOs: 9, 29, 49, 69, 89 and 109 and a full length light chain amino acid sequence having at least 95%, 96%, 97%, 98%, 99% or 100% sequence identity to at least one sequence selected from the group consisting of SEQ ID NOs: 19, 39, 59, 79, 99 and 119.

In one aspect the invention further provides human monoclonal anti-TGF-β2 antibodies or functional fragments thereof comprising:
(a) the variable heavy chain sequence of SEQ ID NO: 7 and variable light chain sequence of SEQ ID NO: 17; (b) the variable heavy chain sequence of SEQ ID NO: 27 and variable light chain sequence of SEQ ID NO: 37; (c) the variable heavy chain sequence of SEQ ID NO: 47 and variable light chain sequence of SEQ ID NO: 57; (d) the variable heavy chain sequence of SEQ ID NO: 67 and variable light chain sequence of SEQ ID NO: 77; (e) the variable heavy chain sequence of SEQ ID NO: 87 and variable light chain sequence of SEQ ID NO: 97; or (f) the variable heavy chain sequence of SEQ ID NO: 107 and variable light chain sequence of SEQ ID NO: 117.

In another embodiment, the human monoclonal anti-TGF-β2 antibodies or functional fragments thereof bind human TGF-β2 preferentially over human TGF-β1 and TGF-β3 with a dissociation constant that is at least 2,000-fold lower than its dissociation constant for TGF-β1 or TGF-β3, wherein the antibodies neutralise human TGF-β2 but do not neutralise TGF-β3, and bind human TGF-β2 with a dissociation constant ($K_D$) of 1 pM or less, wherein the antibodies or functional fragments thereof comprise: (a) the variable heavy chain sequence of SEQ ID NO: 7 and variable light chain sequence of SEQ ID NO: 17; (b) the variable heavy chain sequence of SEQ ID NO: 27 and variable light chain sequence of SEQ ID NO: 37; (c) the variable heavy chain sequence of SEQ ID NO: 47 and variable light chain sequence of SEQ ID NO: 57; (d) the variable heavy chain sequence of SEQ ID NO: 67 and variable light chain sequence of SEQ ID NO: 77; (e) the variable heavy chain sequence of SEQ ID NO: 87 and variable light chain sequence of SEQ ID NO: 97; or (f) the variable heavy chain sequence of SEQ ID NO: 107 and variable light chain sequence of SEQ ID NO: 117.

The invention further provides human monoclonal anti-TGF-β2 antibodies comprising:
(a) the heavy chain sequence of SEQ ID NO: 9 and light chain sequence of SEQ ID NO: 19;
(b) the heavy chain sequence of SEQ ID NO: 29 and light chain sequence of SEQ ID NO: 39;
(c) the heavy chain sequence of SEQ ID NO: 49 and light chain sequence of SEQ ID NO: 59;
(d) the heavy chain sequence of SEQ ID NO: 69 and light chain sequence of SEQ ID NO: 79;
(e) the heavy chain sequence of SEQ ID NO: 89 and light chain sequence of SEQ ID NO: 99; or
(f) the heavy chain sequence of SEQ ID NO: 109 and light chain sequence of SEQ ID NO: 119.

MOR14799: The monoclonal antibody of the present disclosure herein referred to as MOR14799 comprises a heavy chain sequence of SEQ ID NO: 9 and a light chain sequence of SEQ ID NO: 19. MOR14799 comprises a variable heavy chain sequence of SEQ ID NO: 7 and a variable light chain sequence of SEQ ID NO: 17. MOR14799 comprises a heavy chain variable region CDR1 of SEQ ID NO: 1; a heavy chain variable region CDR2 of SEQ ID NO: 2; a heavy chain variable region CDR3 of SEQ ID NO: 3; a light chain variable region CDR1 of SEQ ID NO: 11; a light chain variable region CDR2 of SEQ ID NO: 12; and a light chain variable region CDR3 of SEQ ID NO: 13. In another embodiment, MOR14799 comprises a heavy chain variable region CDR1 of SEQ ID NO: 124. The heavy chain and the heavy chain variable region of MOR14799 are encoded by the polynucleotide sequences of SEQ IDs: 10 and 8, respectively. The light chain and the light chain variable region of MOR14799 are encoded by the polynucleotide sequences of SEQ IDs: 20 and 18, respectively. The $K_D$ value of the antibody MOR14799 for (i) hTGFbeta-2 is 1.08E-15 M, (ii) with no detectable binding to TGFbeta-1 and (iii) a $K_D$ value for hTGFbeta-3 of 1.99E-11 M (see Table 4). From this follows, that the $K_D$ value of MOR14799 for TGFβ2 is more than 18000-fold lower than for TGFbeta 3. Even when applying a more conservative interpretation of the $K_D$ value measurements of the MOR14799, to consider possible measurement inaccuracies resulting from the extremely low $K_D$ values close to the detection limit of such an assay, by agreeing on a $K_D$ value of not more than 100 fM, the $K_D$ value of MOR14799 for TGFβ2 would still be 200-fold lower than for TGFbeta 3. These data illustrate the surprising superiority of MOR14799 over the prior art antibodies, because based on the data published by Thompson et al (J Immunol Methods. 1999 Jul. 30; 227(1-2):17-29), the $K_D$ value of the prior art antibody CAT-152 for (i) hTGFbeta-2 is 0.89 nM and (ii) the $K_D$ value for hTGFbeta-3 is 10 nM. From this follows, that the $K_D$ value of CAT-152 for TGFβ2 is just 11-fold lower than for TGFbeta 3. Based on the experimental data provided herein, the $K_D$ value of CAT-152 for TGFβ2 is 7.3E-11M and the $K_D$ value for hTGFbeta-3 is 1.18E-09M, which results in a $K_D$ value of CAT-152 for TGFβ2 that is only 16-fold lower than for TGFbeta 3.

Based on the experimental data provided herein, the $K_D$ value of 1D11 for TGFβ2 is 1.17 E-10M and the KD value for hTGFbeta-3 is 2.0 E-11M, which results in a $K_D$ value of 1D11 for TGFβ2 that is only 17-fold lower than for TGFbeta 3.

MOR14800: The monoclonal antibody of the present disclosure herein referred to as MOR14800 comprises a heavy chain sequence of SEQ ID NO: 29 and a light chain sequence of SEQ ID NO: 39. MOR14800 comprises a variable heavy chain sequence of SEQ ID NO: 27 and a variable light chain sequence of SEQ ID NO: 37. MOR14800 comprises a heavy chain variable region CDR1 of SEQ ID NO: 21 a heavy chain variable region CDR2 of SEQ ID NO: 22; a heavy chain variable region CDR3 of SEQ ID NO: 23; a light chain variable region CDR1 of SEQ ID NO: 31; a light chain variable region CDR2 of SEQ ID NO: 32; and a light chain variable region CDR3 of SEQ ID NO: 33. In another embodiment, MOR14800 comprises a heavy chain variable region CDR1 of SEQ ID NO: 125. The heavy chain and the heavy chain variable region of MOR14800 are encoded by the polynucleotide sequences of SEQ IDs: 30 and 28, respectively. The light chain and the light chain variable region of MOR14800 are encoded by the polynucleotide sequences of SEQ IDs: 40 and 38, respectively. The $K_D$ value of the antibody MOR14800 for (i) hTGFbeta-2 is 4.34E-16 M (conservative estimation 100 fM), (ii) with no detectable binding to TGFbeta-1 and (iii) no detectable binding to TGFbeta-3 (Table 4). Hence, the antibody MOR14800 does not react in any way with TGFbeta 1 or TGFbeta 3. These data illustrate the surprising superiority of MOR14800 over the prior art antibodies. In another embodiment of the disclosure, the monoclonal antibody MOR14800 comprises a heavy chain variable region CDR1 of SEQ ID NO: 21 a heavy chain variable region CDR2 of SEQ ID NO: 22; a heavy chain variable region CDR3 of SEQ ID NO: 23; a light chain variable region CDR1 of SEQ ID NO: 31; a light chain variable region CDR2 of SEQ ID NO: 32; and a light chain variable region CDR3 of SEQ ID NO: 33; and the framework paratope regions of SEQ IDs NO:131 and 132. In another embodiment, the antibody MOR14800 described above comprises a heavy chain variable region CDR1 of SEQ ID NO: 125.

MOR14809: The monoclonal antibody of the present disclosure herein referred to as MOR14809 comprises a heavy chain sequence of SEQ ID NO: 49 and a light chain sequence of SEQ ID NO: 59. MOR14809 comprises a variable heavy chain sequence of SEQ ID NO: 47 and a variable light chain sequence of SEQ ID NO: 57. MOR14809 comprises a heavy chain variable region CDR1 of SEQ ID NO: 41; a heavy chain variable region CDR2 of SEQ ID NO: 42; a heavy chain variable region CDR3 of SEQ ID NO: 43; a light chain variable region CDR1 of SEQ ID NO: 51; a light chain variable region CDR2 of SEQ ID NO: 52; and a light chain variable region CDR3 of SEQ ID NO: 53. In another embodiment, the antibody MOR14809 comprises a heavy chain variable region CDR1 of SEQ ID NO: 126. The heavy chain and the heavy chain variable region of MOR14809 are encoded by the polynucleotide sequences of SEQ IDs: 50 and 48, respectively. The light chain and the light chain variable region of MOR14809 are encoded by the polynucleotide sequences of SEQ IDs: 60 and 58, respectively. The $K_D$ value of the antibody MOR14809 for (i) hTGFbeta-2 is 5.24E-14M (conservative estimation 100 fM), (ii) with no detectable binding to TGFbeta-1 and (iii) no detectable binding to TGFbeta-3 (see Table 4). Hence, the antibody MOR14809 does not react in any way with TGFbeta-1 or TGFbeta-3. These data illustrate the surprising superiority of MOR14809 over the prior art antibodies.

MOR14797: The monoclonal antibody of the present disclosure herein referred to as MOR14797 comprises a heavy chain sequence of SEQ ID NO: 69 and a light chain sequence of SEQ ID NO: 79. MOR14797 comprises a variable heavy chain sequence of SEQ ID NO: 67 and a variable light chain sequence of SEQ ID NO: 77. MOR14797 comprises a heavy chain variable region CDR1 of SEQ ID NO: 61; a heavy chain variable region CDR2 of SEQ ID NO: 62; a heavy chain variable region CDR3 of SEQ ID NO: 63; a light chain variable region CDR1 of SEQ ID NO: 71; a light chain variable region CDR2 of SEQ ID NO: 72; and a light chain variable region CDR3 of SEQ ID NO: 73. In another embodiment, the antibody MOR14797 comprises a heavy chain variable region CDR1 of SEQ ID NO: 127. The heavy chain and the heavy chain variable region of MOR14797 are encoded by the polynucleotide sequences of SEQ IDs: 70 and 68, respectively. The light chain and the light chain variable region of MOR14797 are encoded by the polynucleotide sequences of SEQ IDs: 80 and 78, respectively. The $K_D$ value of the antibody MOR14797 for (i) hTGFbeta-2 is 4.46E-15 M, (ii) with no detectable binding to TGFbeta-1 and (iii) a $K_D$ value for hTGFbeta-3 of 2.74E-08 M (Table 4). From this follows, that the $K_D$ value of MOR14797 for TGFbeta-2 is 6 million-fold lower than for TGFbeta-3. Even when applying a more conservative interpretation of the $K_D$ value measurements of the MOR14799, to consider possible measurement inaccuracies resulting from the extremely low $K_D$ values close to the detection limit of such an assay, by agreeing on a $K_D$ value of not more than 100 fM, the $K_D$ value of MOR14797 for TGFβ2 would still be 270000-fold lower than for TGFbeta-3. These data illustrate the surprising superiority of MOR14797 over the prior art antibodies.

In one embodiment the human monoclonal anti-TGF-β2 antibody of the present invention or a functional fragment thereof comprises: a heavy chain variable domain comprising (i) the CDRs of SEQ ID NOs: 61, 62 and 63 and (ii) the amino acid Q at position 1 and the amino acid R at position 99; and a light chain variable domain comprising (iii) the CDRs of SEQ ID NOs: 71, 72 and 73, and (iv) the amino acid F at position 49, wherein the heavy chain variable domain and the light chain variable domain framework regions of said antibody have at least 98% sequence identity to the framework regions of the heavy chain variable domain sequence (VH) of SEQ ID NO: 67 and the light chain variable domain sequence (VL) of SEQ ID NO: 77, respectively, wherein the position of the amino acids mentioned in (ii) and (iv) correspond to positions 1, 99 and 49 of SEQ ID NOs.: 67 and 77, respectively.

In one embodiment the human monoclonal anti-TGF-β2 antibody of the present invention or a functional fragment thereof comprises: a heavy chain variable domain comprising (i) the CDRs of SEQ ID NOs: 64, 65 and 66 and (ii) the amino acid Q at position 1 and the amino acid R at position 99; and a light chain variable domain comprising (iii) the CDRs of SEQ ID NOs: 74, 75 and 76, and (iv) the amino acid F at position 49, wherein the heavy chain variable domain and the light chain variable domain framework regions of said antibody have at least 98% sequence identity to the framework regions of the heavy chain variable domain sequence (VH) of SEQ ID NO: 67 and the light chain variable domain (VL) of SEQ ID NO: 77, respectively, wherein the position of the amino acids mentioned in (ii) and (iv) correspond to positions 1, 99 and 49 of SEQ ID NO.: 67 and 77, respectively.

MOR14805: The monoclonal antibody of the present disclosure herein referred to as MOR14805 comprises a heavy chain sequence of SEQ ID NO: 89 and light chain sequence of SEQ ID NO: 99. MOR14805 comprises a variable heavy chain sequence of SEQ ID NO: 87 and variable light chain sequence of SEQ ID NO: 97. MOR14805 comprises a heavy chain variable region CDR1 of SEQ ID NO: 81; a heavy chain variable region CDR2 of SEQ ID NO: 82; a heavy chain variable region CDR3 of SEQ ID NO: 83; a light chain variable region CDR1 of SEQ ID NO: 91; a light chain variable region CDR2 of SEQ ID NO: 92; and a light chain variable region CDR3 of SEQ ID NO: 93. In another embodiment, the antibody MOR14805 comprises a heavy chain variable region CDR1 of SEQ ID NO: 128. The heavy chain and the heavy chain variable region of MOR14805 are encoded by the polynucleotide sequences of SEQ IDs: 90 and 88, respectively. The light chain and the light chain variable region of MOR14805 are encoded by the polynucleotide sequences of SEQ IDs: 100 and 98, respectively. The $K_D$ value of the antibody MOR14805 for (i) hTGFbeta-2 is 9.70E-13M, (ii) with no detectable binding to TGFbeta-1 and (iii) a $K_D$ value for hTGFbeta-3 of 7.05E-11M (see Table 4). From this follows, that the $K_D$ value of MOR14805 for TGFbeta-2 is 73-fold lower than for TGFbeta-3. These data illustrate the surprising superiority of MOR14805 over the prior art antibodies.

MOR14787: The monoclonal antibody of the present disclosure herein referred to as MOR14787 comprises a heavy chain sequence of SEQ ID NO: 109 and light chain sequence of SEQ ID NO: 119. MOR14787 comprises a variable heavy chain sequence of SEQ ID NO: 107 and variable light chain sequence of SEQ ID NO: 117. MOR14787 comprises a heavy chain variable region CDR1 of SEQ ID NO: 101; a heavy chain variable region CDR2 of SEQ ID NO: 102; a heavy chain variable region CDR3 of SEQ ID NO: 103; a light chain variable region CDR1 of SEQ ID NO: 111; a light chain variable region CDR2 of SEQ ID NO: 112; and a light chain variable region CDR3 of SEQ ID NO: 113. In another embodiment, the antibody MOR14787 comprises a heavy chain variable region CDR1 of SEQ ID NO: 129. The heavy chain and the heavy chain variable region of MOR14787 are encoded by the polynucleotide sequences of SEQ IDs: 110 and 108, respectively. The light chain and the light chain variable region of MOR14787 are encoded by the polynucleotide sequences of SEQ IDs: 120 and 118, respectively. The $K_D$ value of the antibody MOR14787 for (i) hTGFbeta-2 is 7.38E-16 M, (ii) with no detectable binding to TGFbeta-1 and (iii) no detectable binding to TGFbeta-3 (see Table 4). Hence, the antibody MOR14787 does not react in any way with TGFbeta-1 or TGFbeta-3. These data illustrate the surprising superiority of MOR14787 over the prior art antibodies. Neutralizing anti-TGF-β2 antibodies with high binding affinities/selectivity are less likely to cause interference with other pathways that may be associated with adverse events. The antibodies of the invention do not bind and/or neutralize the TGFbeta isoforms 1 and 3. Furthermore, the antibodies of the invention do not bind other proteins being active in the same or related metabolic pathways. In particular, the antibodies of the invention do not bind to the human proteins GDF-11, GDF-8, Activin A, Activin B and Activin A/B ("counter-targets"). Accordingly, in one embodiment the invention relates to the herein disclosed antibodies MOR14799, MOR14800, MOR14809, MOR14797, MOR14805 or MOR14787, wherein said antibodies do not neutralize to the counter-targets GDF-11, GDF-8, Activin A, Activin B and Activin A/B up to 100 nM IgG antibodies.

In certain embodiments, an antibody of the invention has a heavy chain variable region comprising CDR1, CDR2, and CDR3 sequences and a light chain variable region comprising CDR1, CDR2, CDR3 sequences, wherein one or more of these sequences have specified amino acid sequences based on the antibodies described herein or conservative modifications thereof, and wherein the antibodies retain the desired functional properties of the anti-TGFbeta-2 antibodies of the invention. Accordingly, the invention provides an isolated recombinant anti-TGFbeta-2 antibody, or a functional fragment thereof, consisting of a heavy chain variable region comprising CDR1, CDR2, and CDR3 sequences and a light chain variable region comprising CDR1, CDR2, CDR3 (a) selected from the group consisting of SEQ ID NOs: 1-3, 11-13, 21-23, 31-33, 41-43, 51-53, 61-63, 71-73, 81-83, 91-93, 101-103, 111-113 and 124-129 or conservative modifications thereof, or b) selected from the group consisting of SEQ ID NOs: 4-6, 14-16, 24-26, 34-36, 44-46, 54-56, 64-66, 74-76, 84-86, 94-96, 104-106, 114-116 and 124-129 or conservative modifications thereof. Preferably such an antibody exhibits at least one of the following functional properties: (i) neutralising human TGF-β2 with an half maximal inhibitory concentration (IC50) of less than 150 pM, or less than 107 pM, or less than 100 pM, or less than 80 pM or less than 30 pM, or less than 20 pM, or less than 10 pM, and neutralising human TGF-β1 or TGF-β3 with an half maximal inhibitory concentration (IC50) of greater than 100 nM as determined by a Smad dependent reporter gene assay, or (ii) neutralising human TGF-β2 with an half maximal inhibitory concentration (IC50) between about 1 pM and about 150 pM, or between about 1 pM and about 107 pM, or between about 1 pM and about 80 pM and neutralising human TGF-β1 or TGF-β3 with an half maximal inhibitory concentration (IC50) of greater than 100 nM as determined by a Smad dependent reporter gene assay. Such antibodies can be, for example, human antibodies, humanized antibodies or chimeric antibodies.

In other embodiments, an antibody of the invention optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the anti-TGFbeta-2 antibodies of the invention. Accordingly, the invention provides an isolated monoclonal anti-TGFbeta-2 antibody optimized for expression in a mammalian cell consisting of a full length heavy chain sequence of SEQ ID NO: 9, 29, 49, 69, 89 and 109 and a full length light chain sequences of SEQ ID NO: 19, 39, 59, 79, 99, or 119, wherein conservative modifications have been introduced into said sequences. In various embodiments, the antibody may exhibit one or both of the functional properties listed above. Such antibodies can be, for example, human antibodies, humanized antibodies or chimeric antibodies.

The human monoclonal anti-TGF-β2 antibodies of the present invention or functional fragments thereof may be of an IgG1, IgG2, IgG3, IgG4, IgA, IgE, IgM or IgD isotype, particularly chosen from e.g. human heavy chain constant regions of IgG1, IgG2, IgG3 and IgG4 isotype. As used herein, "isotype" refers to the antibody class (e.g. IgM, IgE, IgG such as IgG1 or IgG2) that is provided by the heavy chain constant region genes.

The human monoclonal anti-TGF-β2 antibodies or functional fragments of the present invention may have an altered effector function through mutation of the Fc region. In a further embodiment, the antibodies of the invention are of the IgG1 isotype and have an altered effector function through mutation of the Fc region. In one embodiment, said altered effector function is reduced antibody-dependent cellular cytotoxicity (ADCC) and complement-dependent cytotoxicity (CDC) activity. In one embodiment, said altered effector function is silenced ADCC and CDC activity. Antibodies can also be converted into the silent IgG1LALA format in which leucines at positions 234 and 235 were mutated to alanines to abrogate FcRγ binding and attenuate effector functions. Methods for altering an antibody constant region are known in the art. Antibodies with altered function, e.g., altered affinity for an effector ligand, such as FcR on a cell, or the C1 component of complement can be produced by replacing at least one amino acid residue in the constant portion of the antibody with a different residue (see e.g., EP388151; U.S. Pat. No. 5,624,821). Similar type of alterations could be described which if applied to the murine, or other species immunoglobulin would reduce or eliminate these functions.

Antibodies that Bind to the Same Epitope as Anti-TGF-β2 Antibodies of the Invention In another embodiment, the invention provides antibodies that bind to the same epitope as the various specific anti-TGF-β2 antibodies of the invention described herein. Thus, the invention provides an antibody or a functional fragment thereof that binds to an epitope recognised by an antibody comprising the heavy chain variable domain of SEQ ID NO: 67, and the light chain variable domain of SEQ ID NO: 77. Thus, the invention provides an antibody or a functional fragment thereof that binds to an epitope recognised by the antibody MOR14797. Following the Crystallization and structure determination the binding regions of preferred antibodies of the invention have been more clearly defined. Thus, the invention provides an antibody that binds to an epitope of the human TGFβ-2 protein comprising the amino acids LEU 304, ASN 316, PRO 351, TYR 352, LEU 353, TRP 354, SER 355, SER 356, GLN 359, ARG 362, VAL 363, LEU 366, THR 369 and ILE 370 of chain A of the human TGFβ-2 protein and LYS 327, GLY 331, TRP 332, LYS 333, TRP 334, TYR 392, ILE 394, LYS 399, GLU 401 and LEU 403 of chain B of the human TGFβ-2 protein.

Thus, the invention provides an antibody or a functional fragment thereof that binds to an epitope recognised by an antibody comprising the heavy chain variable domain of SEQ ID NO: 27, and the light chain variable domain of SEQ ID NO: 37. Thus, the invention provides an antibody or a functional fragment thereof that binds to an epitope recognised by the antibody MOR14800. Thus, the invention provides an antibody that binds to an epitope of the human TGFβ-2 protein comprising the amino acids GLY 29, TRP 30, LYS 31, TRP 32, TYR 90, TYR 91, ILE 92, GLU 99, LEU 101 and MET 104 of chain A of the human TGFβ-2 protein and ALAI, LEU 2, ASP 3, ALA 5, TYR 6, ASN 10, ASN 14, PRO 49, TYR 50, LEU 51, TRP 52, SER 53, SER 54, ASP 55, GLN 57, ARG 60, VAL 61, LEU 64, GLN 81, LYS 110 of chain B of the human TGFβ-2 protein.

Engineered and Modified Antibodies

An antibody of the invention further can be prepared using an antibody having one or more of the $V_H$ and/or $V_L$ sequences shown herein as starting material to engineer a modified antibody, which modified antibody may have altered properties from the starting antibody. An antibody can be engineered by modifying one or more residues within one or both variable regions (i.e. $V_H$ and/or $V_L$), for example within one or more CDR regions and/or within one or more framework regions. Additionally or alternatively, an antibody can be engineered by modifying residues within the constant region(s), for example to alter the effector function(s) of the antibody. One type of variable region engineering that can be performed is antibody binding region/paratope or CDR grafting. Because paratope sequences are responsible for antibody-antigen interactions, it is possible to express recombinant antibodies that mimic the properties of specific naturally occurring antibodies by constructing expression vectors that include CDR/paratope sequences from the specific naturally occurring antibody grafted onto framework sequences from a different antibody with different properties (see, e.g. Riechmann, L. et al., 1998 Nature 332:323-327; Jones, P. et al., 1986 Nature 321:522-525; Queen, C. et al., 1989 Proc. Natl. Acad. Sci. U.S.A. 86:10029-10033; U.S. Pat. No. 5,225,539 to Winter, and U.S. Pat. Nos. 5,530,101; 5,585,089; 5,693,762 and 6,180,370 to Queen et al.).

Accordingly, another embodiment of the invention pertains to an isolated monoclonal anti-TGFbeta-2 antibody, or a functional fragment thereof, comprising a mixture of complementarity determining region sequences selected from the group of sequences recited in (a) SEQ ID NOs: 1-3, 11-13, 21-23, 31-33, 41-43, 51-53, 61-63, 71-73, 81-83, 91-93, 101-103, 111-113 and 124-129 or b) SEQ ID NOs: 4-6, 14-16, 24-26, 34-36, 44-46, 54-56, 64-66, 74-76, 84-86, 94-96, 104-106, 114-116 and 124-129. Thus, such antibodies contain the $V_H$ and $V_L$ CDR sequences of the disclosed antibodies, yet may contain different framework sequences from these antibodies. Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., [supra]; Tomlinson, I. M., et al., 1992 J. fol. Biol. 227:776-798; and Cox, J. P. L. et al., 1994 Eur. J Immunol. 24:827-836. An example of framework sequences for use in the antibodies of the invention are those that are structurally similar to the framework sequences used by selected antibodies of the invention, e.g. consensus sequences and/or framework sequences used by monoclonal antibodies of the invention. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g. U.S. Pat. Nos. 5,530,101; 5,585,089; 5,693,762 and 6,180,370). Another type of variable region modification is to mutate amino acid residues within the $V_H$ and/or $V_L$ CDR1, CDR2 and/or CDR3 regions to thereby improve one or more binding properties (e.g. affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the examples. Conservative modifications (as discussed herein) can be introduced. The mutations may be amino acid substitutions, additions or deletions. Moreover, typically no more than one, two, three, four or five residues within a CDR region are altered.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to TGFbeta-2. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

Camelid Antibodies

Antibody proteins obtained from members of the camel and dromedary family (*Camelus bactrianus* and *Camelus dromaderius*) including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals (see WO94/04678). A region of the camelid antibody which is the small single variable domain identified as $V_{HH}$ can be obtained by genetic engineering to yield a small protein having high affinity for a target, resulting in a low molecular weight antibody-derived protein known as a "camelid nanobody" (see U.S. Pat. No. 5,759,808; Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520). Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e. the nanobody can be "humanized". Thus the natural low antigenicity of camelid antibodies to humans can be further reduced. The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e. camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitate drug transport across the blood brain barrier (see US2004/0161738). These features combined with the low antigenicity to humans indicate great therapeutic potential. Further, these molecules can be fully expressed in prokaryotic cells such as *E. coli* and are expressed as fusion proteins with bacteriophage and are functional. Accordingly, a feature of the present invention is a camelid antibody obtained by grafting the CDRs sequences of the heavy or light chain of the human antibodies of the invention into nanobody or single domain antibody framework sequences, as described for example in WO94/04678.

Non-Antibody Scaffold

Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immuno-pharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany), protein epitope mimetics (Polyphor Ltd, Allschwil, Switzerland).

(i) Fibronectin Scaffold

The fibronectin scaffolds are based preferably on fibronectin type III domain (e.g. the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

Framework or Fc Engineering

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in US2003/0153043. In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g. one or more chemical moieties can be attached to the antibody) or be modified to alter its glycosylation, again to alter one or more functional properties of the antibody. In one embodiment, the hinge region of CH1 is modified such that the number of cysteine residues in the hinge region is altered, e.g. increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody. In another embodiment, the antibody is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022. In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al. In particular, residues 234 and 235 may be mutated. In particular, these mutations may be to alanine. Thus in one embodiment the antibody of the invention has a mutation in the Fc region at one or both of amino acids 234 and 235. In another embodiment, one or both of amino acids 234 and 235 may be substituted to alanine. Substitution of both amino acids 234 and 235 to alanine results in a reduced ADCC activity. In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in WO00/42072. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604). In still another embodiment, the glycosylation of an antibody is modified. For example, an aglycosylated antibody can be made (i.e. the antibody lacks glycosylation). Glycosylation can be altered to, for example, increase the affinity of the antibody for the antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. Therefore, in one embodiment, the antibodies of the invention are produced by recombinant expression in a cell line which exhibit hypofucosylation pattern, for example, a mammalian cell line with deficient expression of the FUT8 gene encoding fucosyltransferase. WO03/035835 describes a variant CHO cell line, Lecl3 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). WO99/54342 describes cell lines engineered to express glycoprotein-modifying glycosyl transferases (e.g. beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Alternatively, the antibodies of the invention can be produced in a yeast or a filamentous fungi engineered for mammalian-like glycosylation pattern, and capable of producing antibodies lacking fucose as glycosylation pattern (see for example EP1297172B1).

Nucleic Acid Molecules Encoding Antibodies of the Invention

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Another aspect of the invention pertains to nucleic acid molecules that encode the antibodies of the invention. Examples of full length light chain nucleotide sequences are shown in SEQ ID NOs: 20, 40, 60, 80, 100 or 120. Examples of full length heavy chain nucleotide sequences are shown in SEQ ID NOs: 10, 30, 50, 70, 90 or 110. The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g. other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector. Nucleic acids of the invention can be obtained using standard molecular biology techniques. For antibodies expressed by hybridomas (e.g. hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g. using phage display techniques), nucleic acid encoding the antibody can be recovered from various phage clones that are members of the library. Also included within the scope of the invention are variant nucleic acid sequences that comprise one or more deletions, additions or substitutions. In one embodiment, the invention comprises one or more of SEQ ID NOs: 8, 10, 18, 20, 28, 30, 38, 40, 48, 50, 58, 60, 68, 70, 78, 80, 88, 90, 98, 100, 108, 110, 118, or 120. Due to the degeneracy of the genetic code, an amino acid may be encoded by more than one codon. Thus, it is possible to amend the nucleotide sequence, while the translated amino acid sequence remains the same. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter. The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g. Kabat, E. A., et al. [supra]) and DNA fragments encompassing these regions can be obtained by standard PCR amplification. The heavy chain constant region can be an IgG1, IgG2, IgG3, IgG4, IgA, IgE, IgM or IgD constant region. In some embodiments, the heavy chain constant region is selected among IgG1 isotypes. For a Fab fragment heavy chain gene, the $V_H$-encoding DNA can be operatively linked to another DNA molecule encoding only the heavy chain CH1 constant region. The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g. Kabat, E. A., et al. [supra]) and DNA fragments encompassing these regions can be obtained by standard PCR amplification. The light chain constant region can be a kappa or a lambda constant region. To create an scFv gene, the $V_H$- and $V_L$-encoding DNA fragments are operatively linked to another fragment encoding a flexible linker, e.g. encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g. Bird et al., 1988 Science 242:423-426; Huston et al., 1988 Proc. Natl. Acad. Sci. USA 85:5879-5883; McCafferty et al., 1990 Nature 348:552-554).

Generation of Monoclonal Antibodies of the Invention

Monoclonal antibodies (mAbs) can be produced by a variety of techniques, including conventional monoclonal antibody methodology e.g. the standard somatic cell hybridization technique of Kohler and Milstein (1975 Nature 256: 495). Many techniques for producing monoclonal antibody can be employed e.g. viral or oncogenic transformation of B lymphocytes. An animal system for preparing hybridomas is the murine system. Hybridoma production in the mouse is a well-established procedure. Immunization protocols and techniques for isolation of immunized splenocytes for fusion are known in the art. Fusion partners (e.g. murine myeloma cells) and fusion procedures are also known.

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0:055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization. To purify human monoclonal antibodies, selected hybridomas can be grown in two-liter spinner-flasks for monoclonal antibody purification. Supernatants can be filtered and concentrated before affinity chromatography with protein A-sepharose (Pharmacia). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies

Antibodies of the invention also can be produced in a host cell transfectoma using, for example, a combination of recombinant DNA techniques and gene transfection methods as is well known in the art (e.g. Morrison, S. (1985) Science 229:1202). For example, to express the antibodies, or antibody fragments thereof, DNAs encoding partial or full-length light and heavy chains, can be obtained by standard molecular biology techniques (e.g. PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g. ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e. a signal peptide from a non-immunoglobulin protein). In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g. polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g. the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472). In addition to the antibody chain genes and regulatory sequences, the recombinant expression vectors of the invention may carry additional sequences, such as sequences that regulate replication of the vector in host cells (e.g. origins of replication) and selectable marker genes. The selectable marker gene facilitates selection of host cells into which the vector has been introduced (see, e.g. U.S. Pat. Nos. 4,399,216, 4,634,665 and 5,179, 017). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr– host cells with methotrexate selection/amplification) and the neo gene (for G418 selection). Accordingly, in another embodiment the invention relates to a cloning or expression vector as described above comprising one or more of SEQ ID NOs: 8, 10, 18, 20, 28, 30, 38, 40, 48, 50, 58, 60, 68, 70, 78, 80, 88, 90, 98, 100, 108, 110, 118, or 120, or fragments thereof encoding at least one CDR region. For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g. electroporation, calcium-phosphate precipitation, DEAE-dextran transfection and the like. It is theoretically possible to express the antibodies of the invention in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13). Mammalian host cells for expressing the recombinant antibodies of the invention include Chinese Hamster Ovary (CHO cells) (including dhfr– CHO cells, described Urlaub and Chasin, 1980 Proc. Natl. Acad. Sci. USA 77:4216-4220 used with a DH FR selectable marker, e.g. as described in R. J. Kaufman and P. A. Sharp, 1982 Mol. Biol. 159:601-621), NSO myeloma cells, COS cells and SP2 cells. In one embodiment the host cells are CHO K1PD cells. In particular, for use with NSO myeloma cells, another expression system is the GS gene expression system shown in WO87/04462, WO89/01036 and EP 338, 841. In one embodiment, mammalian host cells for expressing the recombinant antibodies of the invention include mammalian cell lines deficient for FUT8 gene expression, for example as described in U.S. Pat. No. 6,946,292B2. Accordingly in one aspect, the invention provides a host cell comprising one or more of the vectors described above or disclosed herein.

When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Accordingly, the invention provides a process for the production of an TGFbeta-2 antibody of the invention or a functional fragment thereof, comprising culturing a host cell as described above and isolating the antibody or functional fragment thereof.

Pharmaceutical Compositions

In another aspect, the present invention provides a composition, e.g. a pharmaceutical composition, containing the TGFbeta-2 antibodies of the disclosure or functional fragments thereof. In one embodiment the composition is formulated together with a pharmaceutically acceptable carrier. Pharmaceutical compositions of the invention also can be administered in combination therapy, i.e. combined with other agents. For example, the TGFbeta-2 antibodies or functional fragments thereof can be combined with at least one muscle mass/strength increasing agent, for example IGF-1 or variants of IGF-1, an anti-myostatin antibody, an anti-Activin antibody, a myostatin propeptide, a myostatin decoy protein that binds ActRIIB but does not activate it, a ActRIIB decoy receptor, a β2 agonist, a Ghrelin agonist, a SARM, GH agonists/mimetics or follistatin. Treatment with TGFbeta-2 antibodies of the invention or functional fragments thereof may be combined with corticosteroids, immune suppressive agents, anti-cytokine agents, anti-cancer drugs; growth factors such as erythropoietin, G-CSF, GM-CSF, or others; drugs used for the treatment of diabetes (including insulin and oral hypoglycemic agents), anti-tuberculosis drugs, and antibiotics. Combinations may include both small molecule and biomolecule agents.

The pharmaceutical compositions of the invention may be administered as the sole active agent or in conjunction with an ActRIIB antibody, ActRIIA antibody or an ActRIIA and ActRIIB pan specific antibody. For example, the drug of the invention may be used in combination with an ActRIIB antibody as disclosed in WO2010125003. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Pharmaceutically acceptable carrier include any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g. by injection or infusion). Depending on the route of administration, the active compound, i.e. antibody, immunoconjuage, or bispecific molecule, may be coated in a material to protect the compound from the action of acids and other natural conditions that may inactivate the compound. A pharmaceutical composition of the invention also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin. Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions. Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin. Sterile injectable solutions can be prepared by incorporating the active compound in the required amount in an appropriate solvent with one or a combination of agents enumerated above, as required, followed by sterilization microfiltration. Generally, dispersions are prepared by incorporating the active compound into a sterile vehicle that contains a basic dispersion medium and the required other agents from those enumerated above. In the case of sterile powders for the preparation of sterile injectable solutions, the methods of preparation are vacuum drying and freeze-drying (lyophilization) that yield a powder of the active agent plus any additional desired agent from a previously sterile-filtered solution thereof. Accordingly, the invention provided pharmaceutical composition comprising TGFbeta-2 antibodies of the disclosure or functional fragments thereof, further comprising a pharmaceutically acceptable diluent or carrier.

The amount of active agent which can be combined with a carrier material to produce a single dosage form will vary depending upon the subject being treated, and the particular mode of administration. The amount of active agent which can be combined with a carrier material to produce a single dosage form will generally be that amount of the composition which produces a therapeutic effect. Generally, out of one hundred percent, this amount will range from about 0.0001 percent to about 15 percent of active agent, from about 0.01 percent to about 10 percent, or from about 0.1 percent to about 5 percent of active agent in combination with a pharmaceutically acceptable carrier. Dosage regimens are adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. A therapeutically effective amount of TGFbeta-2 antibodies of the disclosure or functional fragments thereof or composition comprising said TGFbeta-2 antibodies or functional fragments thereof, ranges from about 0.001 to 150 mg/kg, or 0.01 to 30 mg/kg, and more usually 0.1 to 10 mg/kg of the host body weight. The skilled person knows to identify a suitable effective dose, which will vary depending on the route of administration (e.g. intravenously or subcutaneously). An exemplary treatment regime entails administration once per day, once every week, once every two weeks, once every three weeks, once every four weeks or once a month. Such administration may be carried out intravenously or subcutaneously. Dosage regimens for TGFbeta-2 antibodies of the disclosure or functional fragments thereof include 0.01 mg/kg body weight or 0.1 mg/kg body weight or 0.5 mg/kg body weight or 1 mg/kg body weight or 3 mg/kg body weight or 10 mg/kg body weight by intravenous administration. Alternatively, the composition can be a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime. Actual dosage levels of the active agents in the pharmaceutical compositions of the present invention may be varied so as to obtain an amount of the active agent which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. An exemplary treatment regime entails administration once per week, once every two weeks, once every three weeks, once every four weeks, once a month, once every 3 months or once every three to 6 months. Alternatively, the antibody may be administered about once a year or once only. Such administration may be carried out intravenously or subcutaneously. Dosage regimens for an anti-TGFbeta-2 antibody of the invention may include 0.1 mg/kg body weight or 1 mg/kg body weight or 3 mg/kg body weight by intravenous administration, with the antibody being given using one of the following exemplified dosing schedules: every four weeks for six dosages, then every three months; every three weeks; 3 mg/kg body weight once followed by 1 mg/kg body weight every three weeks. Administration of a therapeutically effective dose of TGFbeta-2 antibodies of the disclosure or functional fragments thereof comprised in the compositions of the invention can result in a decrease in severity of disease symptoms, an increase in frequency and duration of disease symptom-free periods, or a prevention of impairment or disability due to the disease affliction i.e. a reduction of strong fibrous tissue between the handpalm and fingers, permanently disrupting the fine movement ability in Dupuytren's disease patients. Patients will receive an effective amount of the polypeptide active ingredient i.e. an amount that is sufficient to detect, treat, ameliorate, or prevent the disease or disorder in question. Therapeutic effects may also include reduction in physical symptoms. The optimum effective amount and concentration of a therapeutic protein for any particular subject will depend upon various factors, including the patient's age size health and/or gender, the nature and extent of the condition, the activity of the particular therapeutic protein, the rate of its clearance by the body, and also on any possible further therapeutic(s) administered in combination with the therapeutic protein. The effective amount delivered for a given situation can be determined by routine experimentation and is within the judgment of a clinician. Dosage can be by a single dose schedule or a multiple dose schedule.

A composition of the present invention can be administered by one or more routes of administration using one or more of a variety of methods known in the art. As will be appreciated by the skilled artisan, the route and/or mode of administration will vary depending upon the desired results. Routes of administration for the therapeutic proteins of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion. In one embodiment the antibody comprising composition is administered intravenously. In another embodiment the antibody is administered subcutaneously. Alternatively, an TGFbeta-2 antibodies of the disclosure or functional fragments thereof comprised in the compositions of the invention can be administered by a non-parenteral route, such as a topical, epidermal or mucosal route of administration, for example, intranasally, orally, vaginally, rectally, sublingually or topically.

The active compounds can be prepared with carriers that will protect the compound against immediate release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. Sustained and Controlled Release Drug Delivery Systems, J. R. Robinson, ed., Marcel Dekker, Inc., New York, 1978. Therapeutic compositions can be administered with medical devices known in the art. For example, in one embodiment, a therapeutic composition of the invention can be administered with a needleless hypodermic injection device, such as the devices shown in U.S. Pat. Nos. 5,399,163; 5,383,851; 5,312,335; 5,064,413; 4,941,880; 4,790,824 or 4,596,556. Examples of well-known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. Many other such implants, delivery systems, and modules are known to those skilled in the art and include those made by MicroCHIPS™ (Bedford, Mass.).

In certain embodiments, compositions comprising the TGFbeta-2 antibodies of the disclosure or functional fragments thereof can be formulated to ensure proper distribution in vivo. For example, the blood-brain barrier (BBB) excludes many highly hydrophilic compounds. To ensure that the therapeutic compounds of the invention cross the BBB (if desired); they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery (see, e.g. V. V. Ranade, 1989 J. Clin Pharmacol. 29:685). Exemplary targeting moieties include folate or biotin (see, e.g. U.S. Pat. No. 5,416,016); mannosides (Umezawa et al., 1988 Biochem. Biophys. Res. Commun. 153:1038); antibodies (P. G. Bloeman et al., 1995 FEBS Lett. 357:140; M. Owais et al., 1995 Antimicrob. Agents Chernother. 39:180); surfactant protein A receptor (Briscoe et al., 1995 Am. J. Physiol. 1233:134); p 120 (Schreier et al., 1994 J. Biol. Chem. 269:9090); see also K. Keinanen; M. L. Laukkanen, 1994 FEBSLett. 346:123; J. J. Killion; I. J. Fidler, 1994 Immunomethods 4:273.

Patient Groups

Patients who can benefit from the proposed treatment include patients recovering from acute or critical illness requiring intensive care or prolonged hospitalization (more than 1 week); frail elderly patients with sarcopenia; young adults recovering from severe trauma, such as motor vehicle accidents, severe burns, combat injuries, and other traumatic injuries; patients with chronic diseases known to cause cachexia, as listed above; and patients with muscle diseases, as listed above. Since loss of muscle is a common complication of most illnesses that are either severe or prolonged, it is anticipated that reversal of muscle wasting will speed the recovery and return to function of patients who experience muscle loss regardless of the root cause of this loss. Furthermore patients with pathological conditions such as Dupuytren's disease (a benign fibroproliferative disease of the hand, characterized by the excessive production of extracellular matrix (ECM) proteins, which form a strong fibrous tissue between the handpalm and fingers, permanently disrupting the fine movement ability) fibrosis, scarring, cancer, specific conditions like Marfan-associated condition, Epidermolysis bullosa, in particular dystrophic Epidermolysis bullosa or junctional Epidermolysis bullosa.

Trabeculectomy and cutaneous systemic sclerosis may benefit from the proposed treatment. Additionally, patients with glaucoma, age-related macular degeneration, diabetic retinopathy and fuchs dystrophy may benefit from the proposed treatment. Furthermore, patients with hyperproliferative disorders like Morbus Ledderhose, Peyronies' disease, Knuckle pads, Frozen shoulder, Fibromatosis on back of the hand Carpal tunnel syndrome, Fasciitis nodularis, Aggressive fibromatosis, Vibration white finger Moving fingers (also known as hand-arm vibration syndrome (HAVS)), Plantar fibromatosis and Garrods' pad may benefit from the proposed treatment. Fibrosis can occur in many tissues within the body, typically as a result of inflammation or damage, and examples include: lungs, liver, heart, knee, shoulder, other joints. Hence, patients with degenerative and fibrotic diseases such as scleroderma, hypertrophic scaring and Keloids, idiopathic pulmonary fibrosis, cardiac fibrosis (also fibrotic myocarditis), atrial fibrosis, endomyocardial fibrosis, liver fibrosis (e.g. NASH), lung fibrosis, kidney fibrosis (e.g. Alport syndrome), cystic fibrosis, systemic sclerosis, primary myelofibrosis, arthrofibrosis, artherosclerosis and mediastinal fibrosis may benefit from the proposed treatment.

Uses and Methods of the Invention

The antibodies of the present invention have therapeutic utilities. For example, these molecules can be administered to a subject and may be used in the treatment of a disease, prophylaxis and for delaying the onset of disease symptoms. The invention provides a polypeptide, nucleic acid or pharmaceutical composition of the invention for use in therapy or as a medicament. The invention further provides a polypeptide, nucleic acid or pharmaceutical composition of the invention for use in the treatment of a pathological disorder. The invention further provides use of a polypeptide, nucleic acid or pharmaceutical composition of the invention in the manufacture of a medicament for the treatment of a pathological disorder. The invention further provides a method of treating a patient suffering from a pathological disorder comprising administering a therapeutically effective amount of a polypeptide, nucleic acid or pharmaceutical composition of the invention to said patient. The term "subject" as used herein can be a mammal, e.g., a primate, preferably a higher primate, e.g., a human (e.g., a patient having, or at risk of having, a disorder described herein). In one embodiment, the subject is a human subject, e.g., a human patient having a disorder or condition characterized by abnormal TGFbeta-2 functioning. The invention provides a method of treating a patient suffering from a pathological disorder comprising administering a therapeutically effective amount of a TGFbeta-2 antibody of the disclosure or functional fragments thereof. Accordingly, the invention provides a method of treating a patient suffering from a pathological disorder comprising administering a therapeutically effective amount the antibodies MOR14799, MOR14800, MOR14809, MOR14797, MOR14805 or MOR14787. The invention also provides TGFbeta-2 antibodies of the disclosure or functional fragments thereof for use in therapy. Accordingly, the invention provides the antibodies MOR14799, MOR14800, MOR14809, MOR14797, MOR14805 or MOR14787 for use in therapy. As used herein, a "pathological disorder" includes, but is not limited to, musculoskeletal diseases or disorders, muscle atrophy, muscular dystrophy, Dupuytren's disease, sarcopenia, traumatic injuries, chronic diseases known to cause cachexia (e.g. cancer), pathological conditions such as fibrosis, Marfan-associated condition, Epidermolysis bullosa, in particular dystrophic Epidermolysis bullosa or junctional Epidermolysis bullosa, Trabeculectomy, Loeys-Dietz-Syndrome, cutaneous systemic sclerosis, hyperproliferative disorders like Morbus Ledderhose, Peyronies' disease, Knuckle pads, Frozen shoulder, Fibromatosis on back of the hand Carpal tunnel syndrome, Fasciitis nodularis, Aggressive fibromatosis, Vibration white finger Moving fingers, Plantar fibromatosis and Garrods' pad can benefit from the proposed treatment and degenerative and fibrotic diseases such as scleroderma, hypertrophic scaring and Keloids, idiopathic pulmonary fibrosis, cardiac fibrosis (also fibrotic myocarditis), liver fibrosis (e.g. NASH), lung fibrosis, kidney fibrosis (e.g. Alport), cystic fibrosis, systemic sclerosis, primary myelofibrosis, atherosclerosis, glaucoma, age-related macular degeneration, diabetic retinopathy and fuchs dystrophy. Epidermolysis bullosa refers to any form of Epidermolysis Bullosa, but particularly to dystrophic Epidermolysis bullosa and junctional Epidermolysis bullosa.

There are many causes of muscle atrophy, including as a result of treatment with a glucocorticoid such as cortisol, dexamethasone, betamethasone, prednisone, methylprednisolone, or prednisolone. The muscle atrophy can also be a result of denervation due to nerve trauma or a result of degenerative, metabolic, or inflammatory neuropathy (e.g., Guillian-Barrë syndrome, peripheral neuropathy, or exposure to environmental toxins or drugs). In addition, the muscle atrophy can be a result of myopathy, such as myotonia; a congential myopathy, including nemalene myopathy, multi/minicore myopathy and myotubular (centronuclear) myopathy; mitochondrial myopathy; familial periodic paralysis; inflammatory myopathy; metabolic myopathy, such as caused by a glycogen or lipid storage disease; dermatomyositisis; polymyositis; inclusion body myositis; myositis ossificans; rhabdomyolysis and myoglobinurias. The myopathy may be caused by a muscular dystrophy syndrome, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy. In addition, the muscle atrophy can be a result of an adult motor neuron disease such as amyotrophic lateral sclerosis; infantile spinal muscular atrophy, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, metabolic stress or nutritional insufficiency, cancer, AIDS, fasting, a thyroid gland or adrenal gland or pituitary gland disorder, diabetes, benign congenital hypotonia, central core disease, liver diseases (examples such as fibrosis, cirrhosis), sepsis, renal failure, congestive heart failure, ageing, space travel or time spent in a zero gravity environment. In another embodiment of the disclosure, the pharmaceutical composition of the invention can be used for the treatment of pathological disorders listed above. Accordingly, the pharmaceutical composition of the invention can be used for the treatment of Dupuytren's disease, or be used for the treatment of muscle dystrophy or be used for the treatment of sarcopenia, or be used for the treatment of fibrotic conditions, or be used for the treatment of Marfan-associated condition, or be used for the treatment of Epidermolysis bullosa, in particular dystrophic Epidermolysis bullosa or junctional Epidermolysis bullosa, Loeys-Dietz-Syndrome or be used for the treatment of Trabeculectomy, or be used for the treatment of cutaneous systemic sclerosis. In one embodiment the invention provides the antibodies MOR14799, MOR14800, MOR14809, MOR14797, MOR14805 or MOR14787 for use in the treatment of Dupuytren's disease, or the treatment of muscle dystrophy or the treatment of sarcopenia, or the treatment of fibrotic conditions, or the treatment of Marfan-associated condition, or the treatment of Epidermolysis bullosa, in particular dystrophic Epidermolysis bullosa or junctional Epidermolysis bullosa, or the treatment of Trabeculectomy, or the treatment of cutaneous systemic sclerosis or the treatment of Loeys-Dietz-Syndrome. In a particular embodiment, the pharmaceutical composition of the invention, comprising an antibody selected from the group consisting of MOR14799, MOR14800, MOR14809, MOR14797, MOR14805 and MOR14787 can be used for the treatment of Dupuytren's disease or the treatment of Loeys-Dietz-Syndrome. In another particular embodiment of the disclosure the pharmaceutical composition of the invention comprising an antibody selected from the group consisting of MOR14799, MOR14800, MOR14809, MOR14797, MOR14805 and MOR14787 can be used for the treatment of muscle dystrophy. Further conditions include cachexia, cachexia associated with a rheumatoid arthritis and cachexia associated with cancer. In another embodiment the disclosure relates to a method of treating a muscle disorder, the method comprising administering a therapeutically effective amount, as described above, of the antibodies of the inventions of functional fragments thereof. Accordingly, the disclosure relates to a method of treating a muscle disorder, the method comprising administering a therapeutically effective amount of an antibody selected from the group consisting of MOR14799, MOR14800, MOR14809, MOR14797, MOR14805 and MOR14787. The need of treatment with the disclosed polypeptides or compositions comprising them to increase muscle mass can result from one of the above mentioned conditions, particularly as a consequence of a musculoskeletal disease or disorder, such as muscle atrophy wherein the muscle disorder is a muscle atrophy selected from the group consisting of obesity-associated sarcopenia, sarcopenia, and diabetes-associated muscle atrophy.

Furthermore, the invention relates to the use of the antibodies of the inventions or functional fragments thereof, in particular an antibody selected from the group consisting of MOR14799, MOR14800, MOR14809, MOR14797, MOR14805 and MOR14787, for the manufacture of a medicament for the treatment of Dupuytren's disease, a Marfan-associated conditions or Marfan's disease, Epidermolysis bullosa, Trabeculectomy, Loeys-Dietz-Syndrome, cutaneous systemic sclerosis or a musculoskeletal disease or disorder.

TGF-β belongs to a large family of structurally-related cytokines including, e.g., bone morphogenetic proteins (BMPs), growth and differentiation factors, activins and inhibins. Under normal conditions, TGF-β maintains homeostasis and limits the growth of epithelial, endothelial, neuronal and hematopoietic cell lineages, e.g., through the induction of anti-proliferative and apoptotic responses. Canonical and non-canonical signaling pathways are involved in cellular responses to TGF-β. Activation of the TGF-β/Smad canonical pathway can mediate the anti-proliferative effects of TGF-β. The non-canonical TGF-β pathway can activate additional intra-cellular pathways, e.g., mitogen-activated protein kinases (MAPK), phosphatidylinositol 3 kinase/Protein Kinase B, Rho-like GTPases (Tian et al. *Cell Signal.* 2011; 23(6):951-62; Blobe et al. *N Engl J Med.* 2000; 342(18):1350-8), thus modulating epithelial to mesenchymal transition (EMT) and/or cell motility.

Alterations of TGF-β signaling pathway are associated with human diseases, e.g., cancers, cardio-vascular diseases, fibrosis, reproductive disorders, and wound healing. Without wishing to be bound by theory, it is believed that the role of TGF-β in cancer is dependent on the disease setting (e.g., tumor stage and genetic alteration) and/or cellular context. For example, in late stages of cancer, TGF-β can modulate a cancer-related process, e.g., by promoting tumor growth (e.g., inducing EMT), blocking anti-tumor immune responses, increasing tumor-associated fibrosis, or enhancing angiogenesis (Wakefield and Hill *Nat Rev Cancer.* 2013; 13(5):328-41).

Preclinical evidence indicates that TGF-β plays an important role in immune regulation (Wojtowicz-Praga *Invest New Drugs.* 2003; 21(1):21-32; Yang et al. *Trends Immunol.* 2010; 31(6):220-7). TGF-β can down-regulate the host-immune response via several mechanisms, e.g., shift of the T-helper balance toward Th2 immune phenotype; inhibition of anti-tumoral Th1 type response and M1-type macrophages; suppression of cytotoxic CD8+ T lymphocytes (CTL), NK lymphocytes and dendritic cell functions, generation of CD4+CD25+ T-regulatory cells; or promotion of M2-type macrophages with pro-tumoral activity mediated by secretion of immunosuppressive cytokines (e.g., 11_10 or VEGF), pro-inflammatory cytokines (e.g., IL6, TNFα, or IL1) and generation of reactive oxygen species (ROS) with genotoxic activity (Yang et al. *Trends Immunol.* 2010; 31(6): 220-7; Truty and Urrutia *Pancreatology.* 2007; 7(5-6):423-35; Achyut et al *Gastroenterology.* 2011; 141(4): 1167-78).

Without wishing to be bound by theory, it is believed that resistance to PD-1 immunotherapy is associated with the presence of a transcriptional signature which includes, e.g., genes connected to TGF-β signaling and TGF-β-dependent processes, e.g., wound healing or angiogenesis (Hugo et al. *Cell.* 2016; 165(1):35-44). TGF-β blockade extends the therapeutic window of a therapy that inhibits the PD-1/PD-L1 axis. TGF-β inhibitors can affect the clinical benefits of PD-1 immunotherapy, e.g., by modulating tumor microenvironment, e.g., vasculogenesis, fibrosis, or factors that affect the recruitment of effector T cells (Yang et al. *Trends Immunol.* 2010; 31(6):220-7; Wakefield and Hill *Nat Rev Cancer.* 2013; 13(5):328-41; Truty and Urrutia *Pancreatology.* 2007; 7(5-6):423-35).

Without wishing to be bound by theory, it is also believed that a number of elements of the anti-tumor immunity cycle express both PD-1 and TGF-β receptors, and PD-1 and TGF-β receptors are likely to propagate non-redundant cellular signals. For example, in mouse models of autochthonous prostate cancer, the use of either a dominant-negative form of TGFBRII, or abrogation of TGF-β production in T cells delays tumor growth (Donkor et al. *Immunity.* 2011; 35(1):123-34; Diener et al. *Lab Invest.* 2009; 89(2):142-51). Studies in the transgenic adenocarcinoma of the mouse prostate (TRAMP) mice showed that blocking TGF-β signaling in adoptively transferred T cells increases their persistence and antitumor activity (Chou et al. *J Immunol.* 2012; 189(8):3936-46). The antitumor activity of the transferred T cells may decrease over time, partially due to PD-1 upregulation in tumor-infiltrating lymphocytes, supporting a combination of PD-1 and TGF-β inhibition as described herein. The use of neutralizing antibodies against either PD-1 or TGF-β can also affect regulatory T-cells (Tregs), given their high expression levels of PD-1 and their responsiveness to TGF-β stimulation (Riella et al. *Am J Transplant.* 2012; 12(10):2575-87), supporting a combination of PD-1 and TGF-β inhibition to treat cancer, e.g., by enhancing the modulation of Tregs differentiation and function.

Without wishing to be bound by theory, it is believed that cancers can use TGF-β to escape immune surveillance to facilitate tumor growth and metastatic progression. For example, in certain advanced cancers, high levels of TGF-β are associated with tumor aggressiveness and poor prognosis, and TGF-β pathway can promote one or more of cancer cell motility, invasion, EMT, or a stem cell phenotype. Immune regulation mediated by cancer cells and leukocyte populations (e.g., through a variety of cell-expressed or secreted molecules, e.g., IL-10 or TGF-β) may limit the response to checkpoint inhibitors as monotherapy in certain patients. In certain embodiments, a combined inhibition of TGF-β with a checkpoint inhibitor (e.g., an inhibitor of PD-1) is used to treat a cancer that does not respond, or responds poorly, to a checkpoint inhibitor (e.g., anti-PD-1) monotherapy, e.g., a pancreatic cancer or a colorectal cancer (e.g., a microsatellite stable colorectal cancer (MSS-CRC)). In other embodiments, a combined inhibition of TGF-β with a checkpoint inhibitor (e.g., an inhibitor of PD-1) is used to treat a cancer that shows a high level of effector T cell infiltration, e.g., a lung cancer (e.g., a non-small cell lung cancer), a breast cancer (e.g., a triple negative breast cancer), a liver cancer (e.g., a hepatocellular carcinoma), a prostate cancer, or a renal cancer (e.g., a clear cell renal cell carcinoma). In one embodiment the disclosure relates to a method of treating a cancer in a subject, comprising administering to the subject a combination of a TGF-β-2 antibody an inhibitor of PD-1 (e.g., an anti-PD-1 antibody). In one embodiment, the combination includes the TGF-β-2 antibodies disclosed herein or functional fragments thereof and an inhibitor of PD-1 (e.g., an anti-PD-1 antibody). In one embodiment, the TGF-β-2 antibodies disclosed herein or functional fragments thereof are administered at a dose between 0.1 mg/kg and 15 mg/kg (e.g., between 0.3 mg/kg and 12 mg/kg or between 1 mg/kg and 6 mg, e.g., about 0.1 mg/kg, 0.3 mg/kg, 1 mg/kg, 3 mg/kg, 6 mg/kg, 12 mg/kg, or 15 mg/kg), e.g., once every three weeks, e.g., intravenously, and an antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a dose between 50 mg and 500 mg (e.g., between 100 mg and 400 mg, e.g., at a dose of about 100 mg, 200 mg, 300 mg, or 400 mg), e.g., once every 3 weeks or once every 4 weeks, e.g, by intravenous infusion. In some embodiments, the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a dose between 100 mg and 300 mg (e.g., at a dose of about 100 mg, 200 mg, or 300 mg), e.g., once every 3 weeks, e.g., by intravenous infusion.

In some embodiments, the TGF-β-2 antibodies disclosed herein or functional fragments thereof are administered at a dose of about 0.1 mg/kg or 0.3 mg/kg, e.g., once every 3 weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a dose of about 100 mg, e.g., once every 3 weeks, e.g., by intravenous infusion. In some embodiments, the TGF-β-2 antibodies disclosed herein or functional fragments thereof are administered at a dose of about 0.3 mg/kg, e.g., once every 3 weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a dose of about 100 mg or 300 mg, e.g., once every 3 weeks, e.g., by intravenous infusion. In some embodiments, the TGF-β-2 antibodies disclosed herein or functional fragments thereof are administered at a dose of about 1 mg/kg, 3 mg/kg, 6 mg/kg, 12 mg/kg, or 15 mg/kg, e.g., once every 3 weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a dose of about 300 mg, e.g., once every 3 weeks, e.g., by intravenous infusion.

In some embodiments, the TGF-β-2 antibodies disclosed herein or functional fragments thereof are administered at a dose between 0.1 mg and 0.2 mg (e.g., about 0.1 mg/kg), e.g., once every three weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a dose between 50 mg and 200 mg (e.g., about 100 mg), e.g., once every three weeks, e.g., by intravenous infusion.

In some embodiments, the TGF-β-2 antibodies disclosed herein or functional fragments thereof are administered at a dose between 0.2 mg and 0.5 mg (e.g., about 0.3 mg/kg), e.g., once every three weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a dose between 50 mg and 200 mg (e.g., about 100 mg), e.g., once every three weeks, e.g., by intravenous infusion.

In some embodiments, the TGF-β-2 antibodies disclosed herein or functional fragments thereof are administered at a dose between 0.2 mg and 0.5 mg (e.g., about 0.3 mg/kg), e.g., once every three weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a between 200 mg and 400 mg (e.g., about 300 mg), e.g., once every three weeks, e.g., by intravenous infusion.

In some embodiments, the TGF-β-2 antibodies disclosed herein or functional fragments thereof are administered at a dose between 0.5 mg and 2 mg (e.g., about 1 mg/kg), e.g., once every three weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a between 200 mg and 400 mg (e.g., about 300 mg), e.g., once every three weeks, e.g., by intravenous infusion.

In some embodiments, the TGF-β-2 antibodies disclosed herein or functional fragments thereof are administered at a dose between 2 mg and 5 mg (e.g., about 3 mg/kg), e.g., once every three weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a between 200 mg and 400 mg (e.g., about 300 mg), e.g., once every three weeks, e.g., by intravenous infusion.

In some embodiments, the TGF-β-2 antibodies disclosed herein or functional fragments thereof are administered at a dose between 5 mg and 10 mg (e.g., about 6 mg/kg), e.g., once every three weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a between 200 mg and 400 mg (e.g., about 300 mg), e.g., once every three weeks, e.g., by intravenous infusion.

In some embodiments, the TGF-β-2 antibodies disclosed herein or functional fragments thereof are administered at a dose between 10 mg and 15 mg (e.g., about 12 mg/kg), e.g., once every three weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a between 200 mg and 400 mg (e.g., about 300 mg), e.g., once every three weeks, e.g., by intravenous infusion.

In some embodiments, the TGF-β-2 antibodies disclosed herein or functional fragments thereof are administered at a dose between 10 mg and 20 mg (e.g., about 15 mg/kg), e.g., once every three weeks, e.g., by intravenous infusion, and the antibody capable of binding to human Programmed Death-1 (PD-1) protein comprising a VH comprising the amino acid sequence of SEQ ID NO: 159 and a VL comprising the amino acid sequence of SEQ ID NO: 169 is administered at a between 200 mg and 400 mg (e.g., about 300 mg), e.g., once every three weeks, e.g., by intravenous infusion.

In some embodiments, the TGF-β-2 antibodies disclosed herein or functional fragments thereof are administered before the inhibitor of PD-1 (e.g., the antibody capable of binding to human Programmed Death-1 (PD-1) protein comprising a VH comprising the amino acid sequence of SEQ ID NO: 159 and a VL comprising the amino acid sequence of SEQ ID NO: 169 is administered. In other embodiments, the TGF-β-2 antibodies disclosed herein or functional fragments thereof are administered after the inhibitor of PD-1 (e.g., the antibody capable of binding to human Programmed Death-1 (PD-1) protein comprising a VH comprising the amino acid sequence of SEQ ID NO: 159 and a VL comprising the amino acid sequence of SEQ ID NO: 169 is administered. In certain embodiments, the TGF-β-2 antibodies disclosed herein or functional fragments thereof and the inhibitor of PD-1 (e.g., the antibody capable of binding to human Programmed Death-1 (PD-1) protein comprising a VH comprising the amino acid sequence of SEQ ID NO: 159 and a VL comprising the amino acid sequence of SEQ ID NO: 169, are administered separately with at least a 30-minute (e.g., at least 1, 1.5, or 2 hours) break between the two administrations.

In one embodiment, the TGF-β-2 antibodies disclosed herein or functional fragments thereof are administered in combination with the antibody capable of binding to human Programmed Death-1 (PD-1) protein comprising a VH comprising the amino acid sequence of SEQ ID NO: 159 and a VL comprising the amino acid sequence of SEQ ID NO: 169 to treat a pancreatic cancer, a colorectal cancer (e.g., a microsatellite stable colorectal cancer (MSS-CRC)), a lung cancer (e.g., a non-small cell lung cancer), a breast cancer (e.g., a triple negative breast cancer), a liver cancer (e.g., a hepatocellular carcinoma), a prostate cancer, or a renal cancer (e.g., a clear cell renal cell carcinoma).

In one embodiment the TGF-β-2 antibodies or functional fragments thereof administered in combination with the antibody capable of binding to human Programmed Death-1 (PD-1) protein comprising a VH comprising the amino acid sequence of SEQ ID NO: 159 and a VL comprising the amino acid sequence of SEQ ID NO: 169 are the antibodies MOR14799, MOR14800, MOR14809, MOR14797, MOR14805 or MOR14787. In one embodiment the TGF-β-2 antibody or functional fragment thereof administered in combination with the antibody capable of binding to human Programmed Death-1 (PD-1) protein comprising a VH comprising the amino acid sequence of SEQ ID NO: 159 and a VL comprising the amino acid sequence of SEQ ID NO: 169 is the antibody MOR14797.

The cancer can be, e.g., a cancer described herein, such as lung cancer (squamous), lung cancer (adenocarcinoma), head and neck cancer, cervical cancer (squamous), stomach cancer, thyroid cancer, skin cancer, melanoma, nasopharyngeal cancer (e.g., differentiated or undifferentiated metastatic or locally recurrent nasopharyngeal carcinoma), kidney cancer, neuroendocrine tumor (NET), ovarian cancer, fallopian tube cancer, colorectal cancer, or breast cancer. In certain embodiments, the cancer is a skin cancer, e.g., a Merkel cell carcinoma or a melanoma. In one embodiment, the cancer is a Merkel cell carcinoma. In other embodiments, the cancer is a melanoma. In other embodiments, the cancer is a breast cancer, e.g., a triple negative breast cancer (TNBC) or a HER2-negative breast cancer. In other embodiments, the cancer is kidney cancer, e.g., a renal cell carcinoma (e.g., clear cell renal cell carcinoma (CCRCC) or a non-clear cell renal cell carcinoma (nccRCC)). In other embodiments, the cancer is a thyroid cancer, e.g., an anaplastic thyroid carcinoma (ATC). In other embodiments, the cancer is a neuroendocrine tumor (NET), e.g., an atypical pulmonary carcinoid tumor, or an NET in pancreas, gastrointestinal (GI) tract, or lung. In certain embodiments, the cancer is a lung cancer, e.g., a non-small cell lung cancer (NSCLC) (e.g., a squamous NSCLC or a non-squamous NSCLC). In certain embodiments, the cancer is an ovarian cancer. In certain embodiments, the cancer is a fallopian tube cancer. In certain embodiments, the cancer is a colorectal cancer (CRC) (e.g., a microsatellite instability-high colorectal cancer (MSI-high CRC) or a microsatellite stable colorectal cancer (MSS CRC)).

In another aspect, a method of treating a subject, e.g., reducing or ameliorating, a hyperproliferative condition or disorder (e.g., a cancer), e.g., solid tumor, a hematological cancer, soft tissue tumor, or a metastatic lesion, in a subject is provided. The method includes administering to the subject one or more of the TGF-β-2 antibody/PD-1 inhibitor combinations disclosed herein.

Certain Embodiments of the Disclosure are Described in the Following Aspects:

50. A method of treating a cancer, comprising administering to a subject in need thereof a human monoclonal anti-TGF-β2 antibody comprising
(a) the variable heavy chain sequence of SEQ ID NO: 7 and variable light chain sequence of SEQ ID NO: 17;
(b) the variable heavy chain sequence of SEQ ID NO: 27 and variable light chain sequence of SEQ ID NO: 37;
(c) the variable heavy chain sequence of SEQ ID NO: 47 and variable light chain sequence of SEQ ID NO: 57;
(d) the variable heavy chain sequence of SEQ ID NO: 67 and variable light chain sequence of SEQ ID NO: 77;
(e) the variable heavy chain sequence of SEQ ID NO: 87 and variable light chain sequence of SEQ ID NO: 97; or
(f) the variable heavy chain sequence of SEQ ID NO: 107 and variable light chain sequence of SEQ ID NO: 117.
and an antibody molecule capable of binding to human Programmed Death-1 (PD-1) protein in an amount effective to treat the cancer, wherein the antibody molecule comprises a heavy chain variable region (VH) comprising a VHCDR1 amino acid sequence of SEQ ID NO: 153, a VHCDR2 amino acid sequence of SEQ ID NO: 154, and a VHCDR3 amino acid sequence of SEQ ID NO: 155; and a light chain variable region (VL) comprising a VLCDR1 amino acid sequence of SEQ ID NO: 163, a VLCDR2 amino acid sequence of SEQ ID NO: 164, and a VLCDR3 amino acid sequence of SEQ ID NO: 165.

51. The method of aspect 50, wherein the antibody capable of binding to human Programmed Death-1 (PD-1) protein comprises a VH comprising the amino acid sequence of SEQ ID NO: 159 and a VL comprising the amino acid sequence of SEQ ID NO: 169.

52. The method of aspect 50 or 51, wherein the antibody capable of binding to human Programmed Death-1 (PD-1) protein comprises a heavy chain comprising the amino acid sequence of SEQ ID NO: 161 and a light chain comprising the amino acid sequence of SEQ ID NO: 171.

53. The method of aspect 50, wherein the antibody capable of binding to human Programmed Death-1 (PD-1) protein comprises a VH comprising the amino acid sequence of SEQ ID NO: 159 and a VL comprising the amino acid sequence of SEQ ID NO: 149.

54. The method of aspect 50 or 53, wherein the antibody capable of binding to human Programmed Death-1 (PD-1) protein comprises a heavy chain comprising the amino acid sequence of SEQ ID NO: 161 and a light chain comprising the amino acid sequence of SEQ ID NO: 151.

Exemplary PD-1 Inhibitors

In one embodiment, the PD-1 inhibitor is an anti-PD-1 antibody molecule. In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety.

In one embodiment, the anti-PD-1 antibody molecule comprises at least one, two, three, four, five or six complementarity determining regions (CDRs) (or collectively all of the CDRs) from a heavy and light chain variable region comprising an amino acid sequence shown in the sequence table (e.g., from the heavy and light chain variable region sequences of BAP049-Clone-E or BAP049-Clone-B disclosed in the sequence table), or encoded by a nucleotide sequence shown in the sequence table. In some embodiments, the CDRs are according to the Kabat definition (e.g., as set out in the sequence table). In some embodiments, the CDRs are according to the Chothia definition (e.g., as set out in the sequence table). In some embodiments, the CDRs are according to the combined CDR definitions of both Kabat and Chothia (e.g., as set out in the sequence table). In one embodiment, the combination of Kabat and Chothia CDR of VH CDR1 comprises the amino acid sequence GYTFTTYWMH (SEQ ID NO: 203. In one embodiment, one or more of the CDRs (or collectively all of the CDRs) have one, two, three, four, five, six or more changes, e.g., amino acid substitutions (e.g., conservative amino acid substitutions) or deletions, relative to the amino acid sequence shown in the sequence table, or encoded by a nucleotide sequence shown in the sequence table.

In one embodiment, the anti-PD-1 antibody molecule comprises a heavy chain variable region (VH) comprising a VHCDR1 amino acid sequence of SEQ ID NO: 153; a VHCDR2 amino acid sequence of SEQ ID NO: 154; and a VHCDR3 amino acid sequence of SEQ ID NO: 155; and a light chain variable region (VL) comprising a VLCDR1 amino acid sequence of SEQ ID NO: 163, a VLCDR2 amino acid sequence of SEQ ID NO: 164, and a VLCDR3 amino acid sequence of SEQ ID NO: 165, each disclosed in the sequence table.

In one embodiment, the antibody molecule comprises a VH comprising a VHCDR1 encoded by the nucleotide sequence of SEQ ID NO: 173; a VHCDR2 encoded by the nucleotide sequence of SEQ ID NO: 174; and a VHCDR3 encoded by the nucleotide sequence of SEQ ID NO: 175; and a VL comprising a VLCDR1 encoded by the nucleotide sequence of SEQ ID NO: 179; a VLCDR2 encoded by the nucleotide sequence of SEQ ID NO: 180; and a VLCDR3 encoded by the nucleotide sequence of SEQ ID NO: 181, each disclosed in the sequence table.

In one embodiment, the anti-PD-1 antibody molecule comprises a VH comprising the amino acid sequence of SEQ ID NO: 139, or an amino acid sequence at least 85%, 90%, 95%, or 99% identical or higher to SEQ ID NO: 139. In one embodiment, the anti-PD-1 antibody molecule comprises a VL comprising the amino acid sequence of SEQ ID NO: 169, or an amino acid sequence at least 85%, 90%, 95%, or 99% identical or higher to SEQ ID NO: 169. In one embodiment, the anti-PD-1 antibody molecule comprises a VL comprising the amino acid sequence of SEQ ID NO: 149, or an amino acid sequence at least 85%, 90%, 95%, or 99% identical or higher to SEQ ID NO: 149. In one embodiment, the anti-PD-1 antibody molecule comprises a VH comprising the amino acid sequence of SEQ ID NO: 139 and a VL comprising the amino acid sequence of SEQ ID NO: 169. In one embodiment, the anti-PD-1 antibody molecule comprises a VH comprising the amino acid sequence of SEQ ID NO: 139 and a VL comprising the amino acid sequence of SEQ ID NO: 149.

In one embodiment, the antibody molecule comprises a VH encoded by the nucleotide sequence of SEQ ID NO: 140, or a nucleotide sequence at least 85%, 90%, 95%, or 99% identical or higher to SEQ ID NO: 140. In one embodiment, the antibody molecule comprises a VL encoded by the nucleotide sequence of SEQ ID NO: 170 or 150, or a nucleotide sequence at least 85%, 90%, 95%, or 99% identical or higher to SEQ ID NO: 170 or 150. In one embodiment, the antibody molecule comprises a VH encoded by the nucleotide sequence of SEQ ID NO: 140 and a VL encoded by the nucleotide sequence of SEQ ID NO: 170 or 150. In one embodiment, the anti-PD-1 antibody molecule comprises a heavy chain comprising the amino acid sequence of SEQ ID NO: 141, or an amino acid sequence at least 85%, 90%, 95%, or 99% identical or higher to SEQ ID NO: 141. In one embodiment, the anti-PD-1 antibody molecule comprises a light chain comprising the amino acid sequence of SEQ ID NO: 171, or an amino acid sequence at least 85%, 90%, 95%, or 99% identical or higher to SEQ ID NO: 171. In one embodiment, the anti-PD-1 antibody molecule comprises a light chain comprising the amino acid sequence of SEQ ID NO: 151, or an amino acid sequence at least 85%, 90%, 95%, or 99% identical or higher to SEQ ID NO: 151. In one embodiment, the anti-PD-1 antibody molecule comprises a heavy chain comprising the amino acid sequence of SEQ ID NO: 141 and a light chain comprising the amino acid sequence of SEQ ID NO: 171. In one embodiment, the anti-PD-1 antibody molecule comprises a heavy chain comprising the amino acid sequence of SEQ ID NO: 141 and a light chain comprising the amino acid sequence of SEQ ID NO: 151.

In one embodiment, the antibody molecule comprises a heavy chain encoded by the nucleotide sequence of SEQ ID NO: 162, or a nucleotide sequence at least 85%, 90%, 95%, or 99% identical or higher to SEQ ID NO: 162. In one embodiment, the antibody molecule comprises a light chain encoded by the nucleotide sequence of SEQ ID NO: 172 or 152, or a nucleotide sequence at least 85%, 90%, 95%, or 99% identical or higher to SEQ ID NO: 172 or 152. In one embodiment, the antibody molecule comprises a heavy chain encoded by the nucleotide sequence of SEQ ID NO: 142 and a light chain encoded by the nucleotide sequence of SEQ ID NO: 172 or 152.

Generally, unless specifically indicated, the anti-PD-1 antibody molecules can include any combination of one or more Kabat CDRs and/or Chothia CDRs, e.g., described in the sequence table enclosed herein. Under all definitions, each VH and VL typically includes three CDRs and four frameworks (FR), arranged from amino-terminus to carboxy-terminus in the following order: FR1, CDR1, FR2, CDR2, FR3, CDR3, FR4.

Other Exemplary PD-1 Inhibitors

In one embodiment, the anti-PD-1 antibody molecule is Nivolumab (Bristol-Myers Squibb), also known as MDX-1106, MDX-1106-04, ONO-4538, BMS-936558, or OPDIVO®. Nivolumab (clone 5C4) and other anti-PD-1 antibodies are disclosed in U.S. Pat. No. 8,008,449 and WO 2006/121168, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Nivolumab disclosed in the sequence table.

In one embodiment, the anti-PD-1 antibody molecule is Pembrolizumab (Merck & Co), also known as Lambrolizumab, MK-3475, MK03475, SCH-900475, or KEYTRUDA®. Pembrolizumab and other anti-PD-1 antibodies are disclosed in Hamid, O. et al. (2013) New England Journal of Medicine 369 (2): 134-44, U.S. Pat. No. 8,354,509, and WO 2009/114335, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pembrolizumab disclosed in the sequence table.

In one embodiment, the anti-PD-1 antibody molecule is Pidilizumab (CureTech), also known as CT-011. Pidilizumab and other anti-PD-1 antibodies are disclosed in Rosenblatt, J. et al. (2011) J Immunotherapy 34(5): 409-18, U.S. Pat. Nos. 7,695,715, 7,332,582, and 8,686,119, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pidilizumab disclosed in the sequence table.

In one embodiment, the anti-PD-1 antibody molecule is MED10680 (Medimmune), also known as AMP-514. MED10680 and other anti-PD-1 antibodies are disclosed in U.S. Pat. No. 9,205,148 and WO 2012/145493, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of MED10680.

In one embodiment, the anti-PD-1 antibody molecule is REGN2810 (Regeneron). In one embodiment, the anti-PD-1 antibody molecule comprises one or more of the CDR sequences (or collectively all of the CDR sequences), the heavy chain or light chain variable region sequence, or the heavy chain or light chain sequence of REGN2810.

In one embodiment, the anti-PD-1 antibody molecule is PF-06801591 (Pfizer). In one embodiment, the anti-PD-1 antibody molecule comprises one or more of the CDR sequences (or collectively all of the CDR sequences), the heavy chain or light chain variable region sequence, or the heavy chain or light chain sequence of PF-06801591.

In one embodiment, the anti-PD-1 antibody molecule is BGB-A317 or BGB-108 (Beigene). In one embodiment, the anti-PD-1 antibody molecule comprises one or more of the CDR sequences (or collectively all of the CDR sequences), the heavy chain or light chain variable region sequence, or the heavy chain or light chain sequence of BGB-A317 or BGB-108.

In one embodiment, the anti-PD-1 antibody molecule is INCSHR1210 (Incyte), also known as INCSHR01210 or SHR-1210. In one embodiment, the anti-PD-1 antibody molecule comprises one or more of the CDR sequences (or collectively all of the CDR sequences), the heavy chain or light chain variable region sequence, or the heavy chain or light chain sequence of INCSHR1210.

In one embodiment, the anti-PD-1 antibody molecule is TSR-042 (Tesaro), also known as ANB011. In one embodiment, the anti-PD-1 antibody molecule comprises one or more of the CDR sequences (or collectively all of the CDR sequences), the heavy chain or light chain variable region sequence, or the heavy chain or light chain sequence of TSR-042.

Further known anti-PD-1 antibodies include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety. In one embodiment, the anti-PD-1 antibody is an antibody that competes for binding with, and/or binds to the same epitope on PD-1 as, one of the anti-PD-1 antibodies described herein. In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entirety).

In accordance with the foregoing the present invention provides in a yet further aspect:

Where the antibodies of the invention are administered in conjunction with another active agent, dosages of the co-administered combination compound will of course vary depending on the type of co-drug employed, on the specific drug employed, on the condition being treated and so forth. Also within the scope of the invention are kits consisting of the compositions comprising human antibodies of the invention and instructions for use. The kit can further contain at least one additional reagent, or one or more additional antibodies of the invention. Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will response to an anti-TGFbeta-2 antibody treatment. Such kits may comprise an antibody of the invention in lyophilised form, a diluent and instructions for use. The invention having been fully described, it is further illustrated by the following examples and claims, which are illustrative and are not meant to be further limiting.

SEQUENCES/SEQUENCE TABLE

MOR14799

| | | |
|---|---|---|
| SEQ ID NO: 1 (Kabat) | HCDR1 | RYYVA |
| SEQ ID NO: 2 (Kabat) | HCDR2 | WIDPGQSNTRYSPSFQG |
| SEQ ID NO: 3 (Kabat) | HCDR3 | MLAWGWFDY |
| SEQ ID NO: 4 (Chothia) | HCDR1 | GYSFTRY |
| SEQ ID NO: 5 (Chothia) | HCDR2 | DPGQSN |
| SEQ ID NO: 6 (Chothia) | HCDR3 | MLAWGWFDY |
| SEQ ID NO: 7 | VH | QVQLVQSGAEVKKPGESLKISCKGSGYSFTRYYVAWVRQMPGKGLEWMGWIDPGQSNTR YSPSFQGQVTISADKSISTAYLQWSSLKASDTAMYYCARMLAWGWFDYWGQGTLVTVSS |
| SEQ ID NO: 8 | DNA VH | caggtgcagctggtgcagtcaggcgccgaagtgaagaagcccggcgagtcactgaagat tagctgtaaaggctcaggctatagcttcactaggtactacgtggcctgggtgagacaga tgcccggcaagggcctggagtggatgggctggatcgaccccggccagtctaacactaga tatagccctagctttcagggccaggtgacaattagcgccgataagtctattagcaccgc ctacctgcagtggtctagcctgaaggctagtgacaccgctatgtactactgcgctagaa tgctggcctggggctggttcgactactggggccagggcaccctggtgacagtgtctagc |
| SEQ ID NO: 9 | Heavy Chain | QVQLVQSGAEVKKPGESLKISCKGSGYSFTRYYVAWVRQMPGKGLEWMGWIDPGQSNTR YSPSFQGQVTISADKSISTAYLQWSSLKASDTAMYYCARMLAWGWFDYWGQGTLVTVSS ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKRVEPKSCDKTHTCPPCPAPELL GGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSFFLYSKLTV DKSRWQQGNVFSCSVMHEALHNHYTQKSLSLSPGK |
| SEQ ID NO: 10 | DNA Heavy Chain | caggtgcagctggtgcagtcaggcgccgaagtgaagaagcccggcgagtcactgaagat tagctgtaaaggctcaggctatagcttcactaggtactacgtggcctgggtgagacaga tgcccggcaagggcctggagtggatgggctggatcgaccccggccagtctaacactaga tatagccctagctttcagggccaggtgacaattagcgccgataagtctattagcaccgc ctacctgcagtggtctagcctgaaggctagtgacaccgctatgtactactgcgctagaa tgctggcctggggctggttcgactactggggccagggcaccctggtgacagtgtctagc gctagcaccaagggcccaagtgtgtttcccctggcccccagcagcaagtctacttccgg cggaactgctgccctgggttgcctggtgaaggactacttccccgagcccgtgacagtgt cctggaactctggggctctgacttccggcgtgcacaccttcccagccgtgctgcagagc agcggcctgtacagcctgagcagcgtggtgacagtgccctccagctctctgggaaccca gacctatatctgcaacgtgaaccacaagcccagcaacaccaaggtggacaagagagtgg agcccaagagctgcgacaagacccacacctgccccccctgcccagctccagaactgctg ggagggcctccgtgttcctgttccccccaagcccaaggacaccctgatgatcagcag gaccccgaggtgacctgcgtggtggtggacgtgtcccacgaggacccagaggtgaagt |

| | | SEQUENCES/SEQUENCE TABLE |
|---|---|---|
| | | tcaactggtacgtggacggcgtggaggtgcacaacgccaagaccaagcccagagaggag<br>cagtacaacagcacctacagggtggtgtccgtgctgaccgtgctgcaccaggactggct<br>gaacggcaaagaatacaagtgcaaagtctccaacaaggccctgccagccccaatcgaaa<br>agacaatcagcaaggccaagggccagccacgggagcccccaggtgtacaccctgccccc<br>agccgggaggagatgaccaagaaccaggtgtccctgacctgtctggtgaagggcttcta<br>ccccagcgatatcgccgtggagtgggagagcaacggccagcccgagaacaactacaaga<br>ccaccccccagtgctggacagcgacggcagcttcttcctgtacagcaagctgaccgtg<br>gacaagtccaggtggcagcagggcaacgtgttcagctgcagcgtgatgcacgaggccct<br>gcacaaccactacacccagaagtccctgagcctgagccccggcaag |
| SEQ ID NO: 11<br>(Kabat) | LCDR1 | SGDNLGGYYAH |
| SEQ ID NO: 12<br>(Kabat) | LCDR2 | DKSDRPS |
| SEQ ID NO: 13<br>(Kabat) | LCDR3 | ASYDSSLMMV |
| SEQ ID NO: 14<br>(Chothia) | LCDR1 | DNLGGYY |
| SEQ ID NO: 15<br>(Chothia) | LCDR2 | DKS |
| SEQ ID NO: 16<br>(Chothia) | LCDR3 | YDSSLMM |
| SEQ ID NO: 17 | VL | SYELTQPLSVSVALGQTARITCSGDNLGGYYAHWYQQKPGQAPVLVIYDKSDRPSGIPE<br>RFSGSNSGNTATLTISRAQAGDEADYYCASYDSSLMMVFGGGTKLTVL |
| SEQ ID NO: 18 | DNA VL | agctacgagctgactcagcccctgtcagtgtcagtggccctgggccagaccgctagaat<br>cacctgtagcggcgataacctgggcggctactacgctcactggtatcagcagaagcccg<br>gccaggcccccgtgctggtgatctacgataagtcagatagacctagcggaatccccgag<br>cggtttagcggctctaatagcggcaacaccgctaccctgactatctctagggctcaggc<br>cggcgacgaggccgactactactgcgctagttacgactctagcctgatgatggtgttcg<br>gcggaggcactaagctgaccgtgctg |
| SEQ ID NO: 19 | Light<br>Chain | SYELTQPLSVSVALGQTARITCSGDNLGGYYAHWYQQKPGQAPVLVIYDKSDRPSGIPE<br>RFSGSNSGNTATLTISRAQAGDEADYYCASYDSSLMMVFGGGTKLTVLGQPKAAPSVTL<br>FPPSSEELQANKATLVCLISDFYPGAVTVAWKADSSPVKAGVETTTPSKQSNNKYAASS<br>YLSLTPEQWKSHRSYSCQVTHEGSTVEKTVAPTECS |
| SEQ ID NO: 20 | DNA<br>Light<br>Chain | agctacgagctgactcagcccctgtcagtgtcagtggccctgggccagaccgctagaat<br>cacctgtagcggcgataacctgggcggctactacgctcactggtatcagcagaagcccg<br>gccaggcccccgtgctggtgatctacgataagtcagatagacctagcggaatccccgag<br>cggtttagcggctctaatagcggcaacaccgctaccctgactatctctagggctcaggc<br>cggcgacgaggccgactactactgcgctagttacgactctagcctgatgatggtgttcg<br>gcggaggcactaagctgaccgtgctgggccagcctaaggctgcccccagcgtgaccctg<br>ttccccccagcagcgaggagctgcaggccaacaaggccaccctggtgtgcctgatcag<br>cgacttctacccaggcgccgtgaccgtggcctggaaggccgacagcagccccgtgaagg<br>ccggcgtggagaccaccacccccagcaagcagagcaacaacaagtacgccgccagcagc<br>tacctgagcctgaccccgagcagtggaagagccacaggtcctacagctgccaggtgac<br>ccacgagggcagcaccgtggaaaagaccgtggcccccaaccgagtgcagc |

MOR14800

| SEQ ID NO: 21<br>(Kabat) | HCDR1 | RYYVA |
|---|---|---|
| SEQ ID NO: 22<br>(Kabat) | HCDR2 | WIDPGQSNTRYSPSFQG |
| SEQ ID NO: 23<br>(Kabat) | HCDR3 | MLAWGWFDY |
| SEQ ID NO: 24<br>(Chothia) | HCDR1 | GYSFTRY |
| SEQ ID NO: 25<br>(Chothia) | HCDR2 | DPGQSN |
| SEQ ID NO: 26<br>(Chothia) | HCDR3 | MLAWGWFDY |
| SEQ ID NO: 27 | VH | QVQLVQSGAEVKKPGESLKISCKGSGYSFTRYYVAWVRQMPGKGLEWMGWIDPGQSNTR<br>YSPSFQGQVTISADKSISTAYLQWSSLKASDTAMYYCARMLAWGWFDYWGQGTLVTVSS |
| SEQ ID NO: 28 | DNA VH | caggtgcagctggtgcagtcaggcgccgaagtgaagaagcccggcgagtcactgaagat<br>tagctgtaaaggctcaggctatagcttcactaggtactacgtggcctgggtgagacaga<br>tgcccggcaagggcctggagtggatgggctggatcgaccccggccagtctaacactaga<br>tatagccctagctttcaggggccaggtgacaattagcgccgataagtctattagcaccgc<br>ctacctgcagtggtctagcctgaaggctagtgacaccgctatgtactactgcgctagaa<br>tgctggcctggggctggttcgactactggggccagggcaccctggtgacagtgtctagc |
| SEQ ID NO: 29 | Heavy<br>Chain | QVQLVQSGAEVKKPGESLKISCKGSGYSFTRYYVAWVRQMPGKGLEWMGWIDPGQSNTR<br>YSPSFQGQVTISADKSISTAYLQWSSLKASDTAMYYCARMLAWGWFDYWGQGTLVTVSS<br>ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKRVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SREEMTKNQVSLTCLVKGFYPSDIAVEWESNGQPENNYKTTPPVLDSDGSFFLYSKLTV<br>DKSRWQQGNVFSCSVMHEALHNHYTQKSLSLSPGK |

-continued

| SEQUENCES/SEQUENCE TABLE | | |
|---|---|---|
| SEQ ID NO: 30 | DNA Heavy Chain | caggtgcagctggtgcagtcaggcgccgaagtgaagaagcccggcgagtcactgaagat tagctgtaaaggctcaggctatagcttcactaggtactacgtggcctgggtgagacaga tgcccggcaagggcctggagtggatgggctggatcgaccccggccagtctaacactaga tatagccctagctttcagggccaggtgacaattagcgccgataagtctattagcaccgc ctacctgcagtggtctagcctgaaggctagtgacaccgctatgtactactgcgctagaa tgctggcctggggctggttcgactactggggccagggcaccctggtgacagtgtctagc gctagcaccaagggcccaagtgtgtttcccctggcccccagcagcaagtctacttccgg cggaactgctgccctgggttgcctggtgaaggactacttccccgagcccgtgacagtgt cctggaactctggggctctgacttccggcgtgcacaccttccccgccgtgctgcagagc agcggcctgtacagcctgagcagcgtggtgacagtgccctccagctctctgggaaccca gacctatatctgcaacgtgaaccacaagcccagcaacaccaaggtggacaagagagtgg agcccaagagctgcgacaagacccacacctgcccccccctgcccagctccagaactgctg ggagggccttccgtgttcctgttccccccaagcccaaggacaccctgatgatcagcag gacccccgaggtgacctgcgtggtggtggacgtgtcccacgaggacccagaggtgaagt tcaactggtacgtggacggcgtggaggtgcacaacgccaagaccaagcccagagaggag cagtacaacagcacctacagggtggtgtccgtgctgaccgtgctgcaccaggactggct gaacggcaaagaatacaagtgcaaagtctccaacaaggccctgccagccccaatcgaaa agacaatcagcaaggccaagggccagccacgggagcccaggtgtacaccctgcccccc agccgggaggagatgaccaagaaccaggtgtccctgacctgtctggtgaaggcttcta cccagcgatatcgccgtggagtgggagagcaacggccagcccgagaacaactacaaga ccaccccccagtgctggacagcgacggcagcttcttcctgtacagcaagctgaccgtg gacaagtccaggtggcagcagggcaacgtgttcagctgcagcgtgatgcacgaggccct gcacaaccactacacccagaagtccctgagcctgagccccggcaag |
| SEQ ID NO: 31 (Kabat) | LCDR1 | SGDNLGGYYAH |
| SEQ ID NO: 32 (Kabat) | LCDR2 | DTSDRPS |
| SEQ ID NO: 33 (Kabat) | LCDR3 | ASYDSSLMMV |
| SEQ ID NO: 34 (Chothia) | LCDR1 | DNLGGYY |
| SEQ ID NO: 35 (Chothia) | LCDR2 | DTS |
| SEQ ID NO: 36 (Chothia) | LCDR3 | YDSSLMM |
| SEQ ID NO: 37 | VL | SYELTQPLSVSVALGQTARITCSGDNLGGYYAHWYQQKPGQAPVLVIYDTSDRPSGIPE RFSGSNSGNTATLTISRAQAGDEADYYCASYDSSLMMVFGGGTKLTVL |
| SEQ ID NO: 38 | DNA VL | agctacgagctgactcagcccctgtcagtgtcagtggccctgggccagaccgctagaat cacctgtagcggcgataacctgggcggctactacgctcactggtatcagcagaagcccg gccaggcccccgtgctggtgatctacgacactagcgatagacctagcggaatccccgag cggtttagcggctctaatagcggcaacaccgctacctgactatctctagggctcaggc cggcgacgaggccgactactactgcgctagttacgactctagcctgatgatggtgttcg gcggaggcactaagctgaccgtgctg |
| SEQ ID NO: 39 | Light Chain | SYELTQPLSVSVALGQTARITCSGDNLGGYYAHWYQQKPGQAPVLVIYDTSDRPSGIPE RFSGSNSGNTATLTISRAQAGDEADYYCASYDSSLMMVFGGGTKLTVLGQPKAAPSVTL FPPSSEELQANKATLVCLISDFYPGAVTVAWKADSSPVKAGVETTTPSKQSNNKYAASS YLSLTPEQWKSHRSYSCQVTHEGSTVEKTVAPTECS |
| SEQ ID NO: 40 | DNA Light Chain | agctacgagctgactcagcccctgtcagtgtcagtggccctgggccagaccgctagaat cacctgtagcggcgataacctgggcggctactacgctcactggtatcagcagaagcccg gccaggcccccgtgctggtgatctacgacactagcgatagacctagcggaatccccgag cggtttagcggctctaatagcggcaacaccgctacctgactatctctagggctcaggc cggcgacgaggccgactactactgcgctagttacgactctagcctgatgatggtgttcg gcggaggcactaagctgaccgtgctgggccagcctaaggctgcccccagcgtgaccctg ttccccccagcagcgaggagctgcaggccaacaaggccaccctggtgtgcctgatcag cgacttctacccaggcgccgtgaccgtggcctggaaggccgacagcagccccgtgaagg ccggcgtggagaccaccacccccagcaagcagagcaacaacaagtacgccgccagcagc tacctgagcctgacccccgagcagtggaagagccacaggtcctacagctgccaggtgac ccacgagggcagcaccgtggaaaagaccgtggcccccaaccgagtgcagc |

MOR14809

| SEQ ID NO: 41 (Kabat) | HCDR1 | RYWIA |
| SEQ ID NO: 42 (Kabat) | HCDR2 | IIDPGTSDTRYSPSFQG |
| SEQ ID NO: 43 (Kabat) | HCDR3 | IDKSLILHSAFDY |
| SEQ ID NO: 44 (Chothia) | HCDR1 | GYSFTRY |
| SEQ ID NO: 45 (Chothia) | HCDR2 | DPGTSD |
| SEQ ID NO: 46 (Chothia) | HCDR3 | IDKSLILHSAFDY |
| SEQ ID NO: 47 | VH | QVQLVQSGAEVKKPGESLKISCKGSGYSFTRYWIAWVRQMPGKGLEWMGIIDPGTSDTR YSPSFQGQVTISADKSISTAYLQWSSLKASDTAMYYCARIDKSLILHSAFDYWGQGTLV TVSS |

| SEQUENCES/SEQUENCE TABLE | | |
|---|---|---|
| SEQ ID NO: 48 | DNA VH | caggtgcagctggtgcagtcaggcgccgaagtgaagaagcccggcgagtcactgaagat<br>tagctgtaaaggctcaggctatagcttcactagatactggatcgcctgggtgagacaga<br>tgcccggcaagggcctggagtggatgggaattatcgaccccggcactagcgacactaga<br>tatagccctagctttcagggccaggtgacaattagcgccgataagtctattagcaccgc<br>ctacctgcagtggtctagcctgaaggctagtgacaccgctatgtactactgcgctagaa<br>tcgataagtcactgatcctgcactcagccttcgactactggggcagggcaccctggtg<br>acagtgtctagc |
| SEQ ID NO: 49 | Heavy<br>Chain | QVQLVQSGAEVKKPGESLKISCKGSGYSFTRYWIAWVRQMPGKGLEWMGIIDPGTSDTR<br>YSPSFQGQVTISADKSISTAYLQWSSLKASDTAMYYCARIDKSLILHSAFDYWGQGTLV<br>TVSSASTKGPSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKRVEPKSCDKTHTCPPCPA<br>PELLGGPSVFLFPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISKAKGQPREPQVY<br>TLPPSREEMTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| SEQ ID NO: 50 | DNA<br>Heavy<br>Chain | caggtgcagctggtgcagtcaggcgccgaagtgaagaagcccggcgagtcactgaagat<br>tagctgtaaaggctcaggctatagcttcactagatactggatcgcctgggtgagacaga<br>tgcccggcaagggcctggagtggatgggaattatcgaccccggcactagcgacactaga<br>tatagccctagctttcagggccaggtgacaattagcgccgataagtctattagcaccgc<br>ctacctgcagtggtctagcctgaaggctagtgacaccgctatgtactactgcgctagaa<br>tcgataagtcactgatcctgcactcagccttcgactactggggcagggcaccctggtg<br>acagtgtctagctagcaccaagggcccaagtgtgtttcccctggccccagcagcaa<br>gtctacttccgcggaactgctgcctggggttgcctggtgaaggactacttccccgagc<br>ccgtgacagtgtcctggaactctggggctctgacttccggcgtgcacaccttccccgcc<br>gtgctgcagagcagcggcctgtacagcctgagcagcgtggtgacagtgccctccagctc<br>tctgggaacccagacctatatctgcaacgtgaaccacaagcccagcaacaccaaggtgg<br>acaagagagtggagcccaagagctgcgacaagacccacacctgccccccctgcccagct<br>ccagaactgctgggagggccttccgtgttcctgttcccccccaagcccaaggacaccct<br>gatgatcagcaggaccccgaggtgacctgcgtggtggtggacgtgtcccacgaggacc<br>cagaggtgaagttcaactggtacgtggacggcgtggaggtgcacaacgccaagaccaag<br>cccagagaggagcagtacaacagcacctacagggtggtgtccgtgctgaccgtgctgca<br>ccaggactggctgaacggcaaagaataacagtgcaaagtctccaacaaggccctgccag<br>ccccaatcgaaaagacaatcagcaaggccaagggccagccacgggagccccaggtgtac<br>accctgccccccagccgggaggagatgaccaagaaccaggtgtccctgacctgtctggt<br>gaagggcttctaccccagcgatatcgccgtggagtgggagagcaacggccagcccgaga<br>acaactacaagaccaccccccagtgctggacagcgacggcagcttcttcctgtacagc<br>aagctgaccgtggacaagtccaggtggcagcagggcaacgtgttcagctgcagcgtgat<br>gcacgaggcccctgcacaaccactacacccagaagtccctgagcctgagccccggcaag |
| SEQ ID NO: 51<br>(Kabat) | LCDR1 | SGDNLGGYYAY |
| SEQ ID NO: 52<br>(Kabat) | LCDR2 | ETNNRPS |
| SEQ ID NO: 53<br>(Kabat) | LCDR3 | ASTTQDYLVFV |
| SEQ ID NO: 54<br>(Chothia) | LCDR1 | DNLGGYY |
| SEQ ID NO: 55<br>(Chothia) | LCDR2 | ETN |
| SEQ ID NO: 56<br>(Chothia) | LCDR3 | TTQDYLVF |
| SEQ ID NO: 57 | VL | SYELTQPLSVSVALGQTARITCSGDNLGGYYAYWYQQKPGQAPVLVIYETNNRPSGIPE<br>RFSGSNSGNTATLTISRAQAGDEADYYCASTTQDYLVFVFGGGTKLTVL |
| SEQ ID NO: 58 | DNA VL | agctacgagctgactcagcccctgtcagtgtcagtggcccagaccgctagaat<br>cacctgtagcggcgataacctgggcggctactacgcctactggtatcagcagaagcccg<br>gccaggcccccgtgctggtgatctacgagactaacaatagacctagcggaatccccgag<br>cggtttagcggctctaatagcggcaacaccgctaccctgactatctctagggctcaggc<br>cggcgacgaggccgactactactgcgctagtactactcaggactacctggtgttcgtgt<br>tcggcggaggcactaagctgaccgtgctg |
| SEQ ID NO: 59 | Light<br>Chain | SYELTQPLSVSVALGQTARITCSGDNLGGYYAYWYQQKPGQAPVLVIYETNNRPSGIPE<br>RFSGSNSGNTATLTISRAQAGDEADYYCASTTQDYLVFVFGGGTKLTVLGQPKAAPSVT<br>LFPPSSEELQANKATLVCLISDFYPGAVTVAWKADSSPVKAGVETTTPSKQSNNKYAAS<br>YLSLTPEQWKSHRSYSCQVTHEGSTVEKTVAPTECS |
| SEQ ID NO: 60 | DNA<br>Light<br>Chain | agctacgagctgactcagcccctgtcagtcagtggccctgggccagaccgctagaat<br>cacctgtagcggcgataacctgggcggctactacgcctactggtatcagcagaagcccg<br>gccaggcccccgtgctggtgatctacgagactaacaatagacctagcggaatccccgag<br>cggtttagcggctctaatagcggcaacaccgctaccctgactatctctagggctcaggc<br>cggcgacgaggccgactactactgcgctagtactactcaggactacctggtgttcgtgt<br>tcggcggaggcactaagctgaccgtgctgggccagcctaaggctgccccccagcgtgacc<br>ctgttcccccagcagcgaggagctgcaggccaacaaggccacactggtgtgcctgat<br>cagcgacttctacccaggcgccgtgaccgtggcctggaaggccgacagcagcccgtga<br>aggcggcgtggagaccaccaccccccagcaagcagagcaacaacaagtacgccgccagc<br>agctacctgagcctgacccccgagcagtggaagagccacaggtcctacagctgccaggt<br>gacccacgagggcagcaccgtggaaaagaccgtggcccccaaccgagtgcagc |

-continued

| SEQUENCES/SEQUENCE TABLE | | |
|---|---|---|
| MOR14797 | | |
| SEQ ID NO: 61 (Kabat) | HCDR1 | TSGMGVG |
| SEQ ID NO: 62 (Kabat) | HCDR2 | HIYWNDDKSYSTSLKT |
| SEQ ID NO: 63 (Kabat) | HCDR3 | DFYYSGYFDS |
| SEQ ID NO: 64 (Chothia) | HCDR1 | GFSLSTSGM |
| SEQ ID NO: 65 (Chothia) | HCDR2 | YWNDD |
| SEQ ID NO: 66 (Chothia) | HCDR3 | DFYYSGYFDS |
| SEQ ID NO: 67 | VH | QVTLRESGPALVKPTQTLTLTCTFSGFSLSTSGMGVGWIRQPPGKALEWLAHIYWNDDK SYSTSLKTRLTISKDTSKNQVVLTMTNMDPVDTATYYCARDFYYSGYFDSWGQGTLVTV SS |
| SEQ ID NO: 68 | DNA VH | caggtgacactgagagagtcaggccctgccctggtgaaacctactcagaccctgaccct gacctgcacctttagcggctttagcctgagcactagcggaatgggcgtgggctggatta gacagccccctggcaaggcccggagtggctggctcacatctactggaacgacgataag tcctactctactagcctgaaaactaggctgactatctctaaggacacctctaagaatca ggtggtgctgactatgactaatatggaccccgtggacaccgctacctactactgcgcta gagacttctactatagcggctacttcgatagctggggccagggcaccctggtgacagtg tctagc |
| SEQ ID NO: 69 | Heavy Chain | QVTLRESGPALVKPTQTLTLTCTFSGFSLSTSGMGVGWIRQPPGKALEWLAHIYWNDDK SYSTSLKTRLTISKDTSKNQVVLTMTNMDPVDTATYYCARDFYYSGYFDSWGQGTLVTV SSASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKRVEPKSCDKTHTCPPCPAPE LLGGPSVFLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSDGSFFLYSKL TVDKSRWQQGNVFSCSVMHEALHNHYTQKSLSLSPGK |
| SEQ ID NO: 70 | DNA Heavy Chain | caggtgacactgagagagtcaggccctgccctggtgaaacctactcagaccctgaccct gacctgcacctttagcggctttagcctgagcactagcggaatgggcgtgggctggatta gacagccccctggcaaggcccggagtggctggctcacatctactggaacgacgataag tcctactctactagcctgaaaactaggctgactatctctaaggacacctctaagaatca ggtggtgctgactatgactaatatggaccccgtggacaccgctacctactactgcgcta gagacttctactatagcggctacttcgatagctggggccagggcaccctggtgacagtg tctagcgctagcaccaagggcccaagtgtgtttcccctggcccccagcagcaagtctac ttccggcggaactgctgccctgggttgcctggtgaaggactacttccccgagcccgtga cagtgtcctggaactctggggctctgacttccggcgtgcacaccttcccgccgtgctg cagagcagcggcctgtacagcctgagcagcgtggtgacagtgccctccagctctctggg aacccagacctatatctgcaacgtgaaccacaagcccagcaacaccaaggtggacaaga gatgggagcccaagagctgcgacaagacacacctgcccccctgccagctccagaa ctgctgggagggccttccgtgttcctgttccccccaagcccaaggacaccctgatgat cagcaggaccccgaggtgacctgcgtggtggtggacgtgtcccacgaggacccagagg tgaagttcaactggtacgtggacggcgtggaggtgcacaacgccaagaccaagcccaga gaggagcagtacaacagcacctacagggtggtgtccgtgctgaccgtgctgcaccagga ctggctgaacggcaaagaataacaagtgcaaagtctccaacaaggccctgccagcccaa tcgaaaagacaatcagcaaggccaagggccagccacgggagccccaggtgtacaccctg cccccagccgggaggagatgaccaagaaccaggtgtccctgacctgtctggtgaaggg cttctacccagcgatatcgccgtggagtgggagagcaacggccagcccgagaacaact acaagaccaccccccagtgctggacagcgacggcagcttcttcctgtacagcaagctg accgtggacaagtccaggtggcagcagggcaacgtgttcagctgcagcgtgatgcacga ggccctgcacaaccactacacccagaagtccctgagcctgagccccggcaag |
| SEQ ID NO: 71 (Kabat) | LCDR1 | RASQDISNYLN |
| SEQ ID NO: 72 (Kabat) | LCDR2 | GASSLQS |
| SEQ ID NO: 73 (Kabat) | LCDR3 | QQTNTMNT |
| SEQ ID NO: 74 (Chothia) | LCDR1 | SQDISNY |
| SEQ ID NO: 75 (Chothia) | LCDR2 | GAS |
| SEQ ID NO: 76 (Chothia) | LCDR3 | TNTMN |
| SEQ ID NO: 77 | VL | DIQMTQSPSSLSASVGDRVTITCRASQDISNYLNWYQQKPGKAPKLLIFGASSLQSGVP SRFSGSGSGTDFTLTISSLQPEDFATYYCQQTNTMNTFGQGTKVEIK |
| SEQ ID NO: 78 | DNA VL | gatattcagatgactcagtcacctagtagcctgagcgctagtgtgggcgatagagtgac tatcacctgtagagcctctcaggatatctctaactacctgaactggtatcagcagaagc ccggcaaggcccctaagctgctgatcttcggcgcctctagcctgcagtcaggcgtgccc tctaggtttagcggctcaggctcaggcaccgacttcacccctgactattagtagcctgca gcccgaggacttcgctacctactactgtcagcagactaacactatgaacaccttcggcc agggcactaaggtggagattaag |

| SEQUENCES/SEQUENCE TABLE | | |
|---|---|---|
| SEQ ID NO: 79 | Light Chain | DIQMTQSPSSLSASVGDRVTITCRASQDISNYLNWYQQKPGKAPKLLIFGASSLQSGVP SRFSGSGSGTDFTLTISSLQPEDFATYYCQQTNTMNTFGQGTKVEIKRTVAAPSVFIFP PSDEQLKSGTASVVCLLNNFYPREAKVQWKVDNALQSGNSQESVTEQDSKDSTYSLSST LTLSKADYEKHKVYACEVTHQGLSSPVTKSFNRGEC |
| SEQ ID NO: 80 | DNA Light Chain | gatattcagatgactcagtcacctagtagcctgagcgctagtgtgggcgatagagtgac tatcacctgtagagcctctcaggatatctctaactacctgaactggtatcagcagaagc ccggcaaggcccctaagctgctgatcttcggcgcctctagcctgcagtcaggcgtgccc tctaggtttagcggctcaggctcaggcaccgacttcaccctgactattagtagcctgca gcccgaggacttcgctacctactactgtcagcagactaacactatgaacaccttcggcc agggcactaaggtggagattaagcgtacggtggccgctcccagcgtgttcatcttcccc cccagcgacgagcagctgaagagcggcaccgccagcgtggtgtgcctgctgaacaactt ctaccccccgggaggccaaggtgcagtggaaggtggacaacgccctgcagagcggcaaca gccaggagagcgtcaccgagcaggacagcaaggactccacctacagcctgagcagcacc ctgaccctgagcaaggccgactacgagaagcataaggtgtacgcctgcgaggtgaccca ccagggcctgtccagcccgtgaccaagagcttcaacaggggcgagtgc |
| MOR14805 | | |
| SEQ ID NO: 81 (Kabat) | HCDR1 | RYYVA |
| SEQ ID NO: 82 (Kabat) | HCDR2 | WIDPGTSNTRYSPSFQG |
| SEQ ID NO: 83 (Kabat) | HCDR3 | MLAWGWFDY |
| SEQ ID NO: 84 (Chothia) | HCDR1 | GYSFTRY |
| SEQ ID NO: 85 (Chothia) | HCDR2 | DPGTSN |
| SEQ ID NO: 86 (Chothia) | HCDR3 | MLAWGWFDY |
| SEQ ID NO: 87 | VH | QVQLVQSGAEVKKPGESLKISCKGSGYSFTRYYVAWVRQMPGKGLEWMGWIDPGTSNTR YSPSFQGQVTISADKSISTAYLQWSSLKASDTAMYYCARMLAWGWFDYWGQGTLVTVSS |
| SEQ ID NO: 88 | DNA VH | caggtgcagctggtgcagtcaggcgccgaagtgaagaagcccggcgagtcactgaagat tagctgtaaaggctcaggctatagcttcactaggtactacgtggcctgggtgagacaga tgcccggcaagggcctggagtggatgggctggatcgaccccggcacctctaacactaga tatagccctagctttcagggccaggtgacaattagcgccgataagtctattagcaccgc ctacctgcagtggtctagcctgaaggctagtgacaccgctatgtactactgcgctagaa tgctggcctggggctggttcgactactggggccagggcaccctggtgacagtgtctagc |
| SEQ ID NO: 89 | Heavy Chain | QVQLVQSGAEVKKPGESLKISCKGSGYSFTRYYVAWVRQMPGKGLEWMGWIDPGTSNTR YSPSFQGQVTISADKSISTAYLQWSSLKASDTAMYYCARMLAWGWFDYWGQGTLVTVSS ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKRVEPKSCDKTHTCPPCPAPELL GGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSFFLYSKLTV DKSRWQQGNVFSCSVMHEALHNHYTQKSLSLSPGK |
| SEQ ID NO: 90 | DNA Heavy Chain | caggtgcagctggtgcagtcaggcgccgaagtgaagaagcccggcgagtcactgaagat tagctgtaaaggctcaggctatagcttcactaggtactacgtggcctgggtgagacaga tgcccggcaagggcctggagtggatgggctggatcgaccccggcacctctaacactaga tatagccctagctttcagggccaggtgacaattagcgccgataagtctattagcaccgc ctacctgcagtggtctagcctgaaggctagtgacaccgctatgtactactgcgctagaa tgctggcctggggctggttcgactactggggccagggcaccctggtgacagtgtctagc gctagcaccaagggcccaagtgtgtttccctggccccccagcagcaagtctactctccgg cggaactgctgccctgggttgctggtgaaggactacttccccgagcccgtgacagtgt cctggaactctggggctctgacttccggcgtgcacacctttcccgccgtgctgcagagc agcggcctgtacagcctgagcagcgtggtgacagtgccctccagctctctgggaaccca gacctatatctgcaacgtgaaccacaagcccagcaacaccaaggtggacaagagagtgg agcccaagagctgcgacaagacccacacctgcccccctgccagctccagaactgctg ggagggcttccgtgttcctgttccccccaagcccaaggacaccctgatgatcagcag gaccccgaggtgacctgcgtggtggtggacgtgtcccacgaggacccagaggtgaagt tcaactggtacgtggacggcgtggaggtgcacaacgccaagaccaagcccagagaggag cagtacaacagcacctacagggtggtgtccgtgctgaccgtgctgcaccaggactggct gaacggcaaagaatacaagtgcaaagtctccaacaaggcctgccagccccaatcgaaa agacaatcagcaaggccaagggccagcacgggagccccaggtgtacaccctgcccccc agccggagagatgaccaagaaccaggtgtccctgacctgtctggtgaagggcttcta cccagcgatatcgccgtgagtgggagagcaacggccagcccgagaacaactacaaga ccacccccgtgctgctggacagcgacggcagcttcttcctgtacagcaagctgaccgtg gacaagtccaggtggcagcagggcaacgtgttcagctgcagcgtgatgcacgaggccct gcacaaccactacacccagaagtccctgagcctgagccccggcaag |
| SEQ ID NO: 91 (Kabat) | LCDR1 | SGDNLGGYYAH |
| SEQ ID NO: 92 (Kabat) | LCDR2 | DKSDRPS |
| SEQ ID NO: 93 (Kabat) | LCDR3 | ASYDSSLMMV |
| SEQ ID NO: 94 (Chothia) | LCDR1 | DNLGGYY |

| | | |
|---|---|---|
| SEQ ID NO: 95 (Chothia) | LCDR2 | DKS |
| SEQ ID NO: 96 (Chothia) | LCDR3 | YDSSLMM |
| SEQ ID NO: 97 | VL | SYELTQPLSVSVALGQTARITCSGDNLGGYYAHWYQQKPGQAPVLVIYDKSDRPSGIPE<br>RFSGSNSGNTATLTISRAQAGDEADYYCASYDSSLMMVFGGGTKLTVL |
| SEQ ID NO: 98 | DNA VL | agctacgagctgactcagcccctgtcagtgtcagtggccctgggccagaccgctagaat<br>cacctgtagcggcgataaccctgggcggctactacgctcactggtatcagcagaagcccg<br>gccaggcccccgtgctggtgatctacgataagtcagatagacctagcggaatccccgag<br>cggtttagcggctctaatagcggcaacaccgctaccctgactatctctagggctcaggc<br>cggcgacgaggccgactactactgcgctagttacgactctagcctgatgatggtgttcg<br>gcggaggcactaagctgaccgtgctg |
| SEQ ID NO: 99 | Light Chain | SYELTQPLSVSVALGQTARITCSGDNLGGYYAHWYQQKPGQAPVLVIYDKSDRPSGIPE<br>RFSGSNSGNTATLTISRAQAGDEADYYCASYDSSLMMVFGGGTKLTVLGQPKAAPSVTL<br>FPPSSEELQANKATLVCLISDFYPGAVTVAWKADSSPVKAGVETTTPSKQSNNKYAASS<br>YLSLTPEQWKSHRSYSCQVTHEGSTVEKTVAPTECS |
| SEQ ID NO: 100 | DNA Light Chain | agctacgagctgactcagcccctgtcagtgtcagtggccctgggccagaccgctagaat<br>cacctgtagcggcgataaccctgggcggctactacgctcactggtatcagcagaagcccg<br>gccaggcccccgtgctggtgatctacgataagtcagatagacctagcggaatccccgag<br>cggtttagcggctctaatagcggcaacaccgctaccctgactatctctagggctcaggc<br>cggcgacgaggccgactactactgcgctagttacgactctagcctgatgatggtgttcg<br>gcggaggcactaagctgaccgtgctgggccagcctaaggctgcccccagcgtgaccctg<br>ttccccccagcagcgaggagctgcaggccaacaaggccaccctggtgtgcctgatcag<br>cgacttctacccaggcgccgtgaccgtggcctggaaggccgacagcagccccgtgaagg<br>ccggcgtggagaccacccccagcaagcagagcaacaacaagtacgccgccagcagc<br>tacctgagcctgacccccgagcagtggaagagccacaggtcctacagctgccaggtgac<br>ccacgagggcagcaccgtggaaaagaccgtggcccccaaccgagtgcagc |

MOR14787

| | | |
|---|---|---|
| SEQ ID NO: 101 (Kabat) | HCDR1 | SYAIS |
| SEQ ID NO: 102 (Kabat) | HCDR2 | VIVPKWGHPQYAQKFQG |
| SEQ ID NO: 103 (Kabat) | HCDR3 | EGDFVVLVLTEHYMGGFDV |
| SEQ ID NO: 104 (Chothia) | HCDR1 | GGTFSSY |
| SEQ ID NO: 105 (Chothia) | HCDR2 | VPKWGH |
| SEQ ID NO: 106 (Chothia) | HCDR3 | EGDFVVLVLTEHYMGGFDV |
| SEQ ID NO: 107 | VH | QVQLVQSGAEVKKPGSSVKVSCKASGGTFSSYAISWVRQAPGQGLEWMGVIVPKWGHPQ<br>YAQKFQGRVTITADESTSTAYMELSSLRSEDTAVYYCAREGDFVVLVLTEHYMGGFDVW<br>GQGTLVTVSS |
| SEQ ID NO: 108 | DNA VH | caggtgcagctggtgcagtcaggcgccgaagtgaagaaacccggctctagcgtgaaagt<br>gagctgtaaagctagtggcggcaccttctctagctacgctattagctgggtgagacagg<br>ccccaggccagggcctggagtggatgggcgtgatcgtgcctaagtggggccaccctcag<br>tacgctcagaaatttcagggcagagtgactatcaccgccgacgagtctactagcaccgc<br>ctatatggaactgtctagcctgagatcagaggacaccgccgtgtactactgcgctagag<br>aaggcgacttcgtggtgctggtgctgaccgagcactatatgggcggcttcgacgtgtgg<br>ggccagggcaccctggtgacagtgtctagc |
| SEQ ID NO: 109 | Heavy Chain | QVQLVQSGAEVKKPGSSVKVSCKASGGTFSSYAISWVRQAPGQGLEWMGVIVPKWGHPQ<br>YAQKFQGRVTITADESTSTAYMELSSLRSEDTAVYYCAREGDFVVLVLTEHYMGGFDVW<br>GQGTLVTVSSASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKRVEPKSCDKTHT<br>CPPCPAPELLGGPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAPIEKTISKAKGQP<br>REPQVYTLPPSREEMTKNQVSLTCLVKGFYPSDIAVEWESNGQPENNYKTTPPVLDSDG<br>SFFLYSKLTVDKSRWQQGNVFSCSVMHEALHNHYTQKSLSLSPGK |
| SEQ ID NO: 110 | DNA Heavy Chain | caggtgcagctggtgcagtcaggcgccgaagtgaagaaacccggctctagcgtgaaagt<br>gagctgtaaagctagtggcggcaccttctctagctacgctattagctgggtgagacagg<br>ccccaggccagggcctggagtggatgggcgtgatcgtgcctaagtggggccaccctcag<br>tacgctcagaaatttcagggcagagtgactatcaccgccgacgagtctactagcaccgc<br>ctatatggaactgtctagcctgagatcagaggacaccgccgtgtactactgcgctagag<br>aaggcgacttcgtggtgctggtgctgaccgagcactatatgggcggcttcgacgtgtgg<br>ggccagggcaccctggtgacagtgtctagcgctagcaccaagggcccaagtgtgtttcc<br>cctggccccagcagcaagtactttccggcggaactgctgcccgggttgcctggtga<br>aggactacttccccgagcccgtgacagtgtcctgaactctggggctctgacttccggc<br>gtgcacaccttccccgccgtgctgcagagcagcggcctgtacagcctgagcagcgtggt<br>gacagtgccctccagctctctgggaacccagacctatatctgcaacgtgaaccacaagc<br>ccagcaacaccaaggtggacaagagagtggagcccaagagctgcgacaagacccacacc<br>tgccccccctgcccagctccagaactgctgggagggccttccgtgttcctgttccccc<br>caagcccaaggacaccctgatgatcagcaggacccccgaggtgacctgcgtggtggtgg<br>acgtgtcccacgaggacccagaggtgaagttcaactggtacgtggacggcgtggaggtg<br>cacaacgccaagaccaagcccagagaggagcagtacaacagcacctacagggtggtgtc<br>cgtgctgaccgtgctgcaccaggactggctgaacggcaaagaatacaagtgcaaagtct |

-continued

| | | SEQUENCES/SEQUENCE TABLE |
|---|---|---|
| | | ccaacaaggccctgccagccccaatcgaaaagacaatcagcaaggccaagggccagcca<br>cgggagcccaggtgtacaccctgccccccagccggaggagatgaccaagaaccaggt<br>gtccctgacctgtctggtgaagggcttctaccccagcgatatcgccgtggagtgggaga<br>gcaacggccagcccgagaacaactacaagaccacccccccagtgctggacagcgacggc<br>agcttcttcctgtacagcaagctgaccgtggacaagtccaggtggcagcagggcaacgt<br>gttcagctgcagcgtgatgcacgaggccctgcacaaccactacacccagaagtccctga<br>gcctgagccccggcaag |
| SEQ ID NO:<br>111 (Kabat) | LCDR1 | RASQSIDEYLN |
| SEQ ID NO:<br>112 (Kabat) | LCDR2 | AGSNLQS |
| SEQ ID NO:<br>113 (Kabat) | LCDR3 | LQGYSYPRT |
| SEQ ID NO:<br>114 (Chothia) | LCDR1 | SQSIDEY |
| SEQ ID NO:<br>115 (Chothia) | LCDR2 | AGS |
| SEQ ID NO:<br>116 (Chothia) | LCDR3 | GYSYPR |
| SEQ ID NO:<br>117 | VL | DIQMTQSPSSLSASVGDRVTITCRASQSIDEYLNWYQQKPGKAPKLLIYAGSNLQSGVP<br>SRFSGSGSGTDFTLTISSLQPEDFATYYCLQGYSYPRTFGQGTKVEIK |
| SEQ ID NO:<br>118 | DNA VL | gatattcagatgactcagtcacctagtagcctgagcgctagtgtgggcgatagagtgac<br>tatcacctgtagagcctctcagtctatcgacgagtacctgaactggtatcagcagaagc<br>ccggcaaggcccctaagctgctgatctacgccggctctaacctgcagtcaggcgtgccc<br>tctaggtttagcggctcaggctcaggcaccgacttcaccctgactatctctagcctgca<br>gcccgaggacttcgctacctactactgtctgcagggctatagctacccctagaaccttcg<br>gccagggcactaaggtggagattaag |
| SEQ ID NO:<br>119 | Light<br>Chain | DIQMTQSPSSLSASVGDRVTITCRASQSIDEYLNWYQQKPGKAPKLLIYAGSNLQSGVP<br>SRFSGSGSGTDFTLTISSLQPEDFATYYCLQGYSYPRTFGQGTKVEIKRTVAAPSVFIF<br>PPSDEQLKSGTASVVCLLNNFYPREAKVQWKVDNALQSGNSQESVTEQDSKDSTYSLSS<br>TLTLSKADYEKHKVYACEVTHQGLSSPVTKSFNRGEC |
| SEQ ID NO:<br>120 | DNA<br>Light<br>Chain | gatattcagatgactcagtcacctagtagcctgagcgctagtgtgggcgatagagtgac<br>tatcacctgtagagcctctcagtctatcgacgagtacctgaactggtatcagcagaagc<br>ccggcaaggcccctaagctgctgatctacgccggctctaacctgcagtcaggcgtgccc<br>tctaggtttagcggctcaggctcaggcaccgacttcaccctgactatctctagcctgca<br>gcccgaggacttcgctacctactactgtctgcagggctatagctacccctagaaccttcg<br>gccagggcactaaggtggagattaagcgtacggtggccgctcccagcgtgttcatcttc<br>ccccccagcgacgagcagcagctgaagagcggcaccgccagcgtggtgtgcctgctgaacaa<br>cttctaccccggggaggccaaggtgcagtggaaggtggacaacgccctgcagagcggca<br>acagccaggagagcgtcaccgagcaggacagcaaggactccacctacagcctgagcagc<br>accctgaccctgagcaaggccgactacgagaagcataaggtgtacgcctgcgaggtgac<br>ccacggggcctgtccagcccgtgaccaagagcttcaacaggggcgagtgc |
| SEQ ID NO:<br>121 | Protein<br>TGFbeta<br>1<br>UniProt<br>ID:<br>P01137 | MPPSGLRLLLLLLPLLWLLVLTPGRPAAGLSTCKTIDMELVKRKRIEAIRGQILSKLRL<br>ASPPSQGEVPPGPLPEAVLALYNSTRDRVAGESAEPEPEPEADYYAKEVTRVLMVETHN<br>EIYDKFKQSTHSIYMFFNTSELREAVPEPVLLSRAELRLLRLKLKVEQHVELYQKYSNN<br>SWRYLSNRLLAPSDSPEWLSFDVTGVVRQWLSRGGEIEGFRLSAHCSCDSRDNTLQVDI<br>NGFTTGRRGDLATIHGMNRPFLLLMATPLERAQHLQSSRHRRALDTNYCFSSTEKNCCV<br>RQLYIDFRKDLGWKWIHEPKGYHANFCLGPCPYIWSLDTQYSKVLALYNQHNPGASAAP<br>CCVPQALEPLPIVYYVGRKPKVEQLSNMIVRSCKCS |
| SEQ ID NO:<br>122 | Protein<br>TGFp2<br>UniProt<br>ID:<br>P61812 | MHYCVLSAFLILHLVTVALSLSTCSTLDMDQFMRKRIEAIRGQILSKLKLTSPPEDYPE<br>PEEVPPEVISIYNSTRDLLQEKASRRAAACERERSDEEYYAKEVYKIDMPPFFPSENAI<br>PPTFYRPYFRIVRFDVSAMEKNASNLVKAEFRVLRQNPKARVPEQRIELYQILKSKDL<br>TSPTQRYIDSKVVKTRAEGEWLSFDVTDAVHEWLHHKDRNLGFKISLHCPCCTFVPSNN<br>YIIPNKSEELEARFAGIDGTSTYTSGDQKTIKSTRKKNSGKTPHLLLMLLPSYRLESQQ<br>TNRRKKRALDAAYCFRNVQDNCCLRPLYIDFKRDLGWKWIHEPKGYNANFCAGACPYLW<br>SSDTQHSRVLSLYNTINPEASASPCCVSQDLEPLTILYYIGKTPKIEQLSNMIVKSCKC<br>S |
| SEQ ID NO:<br>123 | Protein<br>TGFbeta<br>3<br>UniProt<br>ID:<br>P10600 | MKMHLQRALVVLALLNFATVSLSLSTCTTLDFGHIKKKRVEAIRGQILSKLRLTSPPEP<br>TVMTHVPYQVLALYNSTRELLEEMHGEREEGCTQENTESEYYAKEIHKFDMIQGLAEHN<br>ELAVCPKGITSKVFRFNVSSVEKNRTNLFRAEFRVLRVPNPSSKRNEQRIELFQILRPD<br>EHIAKQRYIGGKNLPTRGTAEWLSFDVTDTVREWLLRRESNLGLEISIHCPCHTFQPNG<br>DILENIHEVMEIKFKGVDNEDDHGRGDLGRLKKQKDHHNPHLILMMIPPHRLDNPGQGG<br>QRKKRALDTNYCFRNEENCCVRPLYIDFRQDLGWKWVHEPKGYYANFCSGPCPYLRSA<br>DTTHSTVLGLYNTLNPEASASPCCVPQDLEPLTILYYVGRTPKVEQLSNMVVKSCKCS |
| SEQ ID NO: 124<br>(Kabat SEQ ID<br>NO: 1/Chothia<br>SEQ ID NO: 4) | HCDR1 | GYSFTRYYVA |
| SEQ ID NO: 125<br>(Kabat SEQ ID<br>NO: 21/Chothia<br>SEQ ID NO:<br>24) | HCDR1 | GYSFTRYYVA |

| SEQUENCES/SEQUENCE TABLE | | |
|---|---|---|
| SEQ ID NO: 126 (Kabat SEQ ID NO: 41/ Chothia SEQ ID NO: 44) | HCDR1 | GYSFTRYWIA |
| SEQ ID NO: 127 (Kabat SEQ ID NO: 61/ Chothia SEQ ID NO: 64) | HCDR1 | GFSLSTSGMGVG |
| SEQ ID NO: 128 (Kabat SEQ ID NO: 81/ Chothia SEQ ID NO: 84) | HCDR1 | GYSFTRYYVA |
| SEQ ID NO: 129 (Kabat SEQ ID NO: 101/ Chothia SEQ ID NO: 104) | HCDR1 | GGTFSSYAIS |
| SEQ ID NO: 131 paratope sequence MOR14800 | VL | NSGN |
| SEQ ID NO: 132 paratope sequence MOR14800 | VL | GSGT |
| BAP049-Clone-B HC | | |
| SEQ ID NO: 133 (Kabat) | HCDR1 | TYWMH |
| SEQ ID NO: 134 (Kabat) | HCDR2 | NIYPGTGGSNFDEKFKN |
| SEQ ID NO: 135 (Kabat) | HCDR3 | WTTGTGAY |
| SEQ ID NO: 136 (Chothia) | HCDR1 | GYTFTTY |
| SEQ ID NO: 137 (Chothia) | HCDR2 | YPGTGG |
| SEQ ID NO: 138 (Chothia) | HCDR3 | WTTGTGAY |
| SEQ ID NO: 139 | VH | EVQLVQSGAEVKKPGESLRISCKGSGYTFTTYWMHWVRQATGQGLEWMGNIYPGTGGSN FDEKFKNRVTITADKSTSTAYMELSSLRSEDTAVYYCTRWTTGTGAYWGQGTTVTVSS |
| SEQ ID NO: 140 | DNA VH | Gaggtgcagctggtgcagtcaggcgccgaagtgaagaagcccggcgagtcactgagaat tagctgtaaaggttcaggctacaccttcactacctactggatgcactgggtccgccagg ctaccggtcaaggcctcgagtggatgggtaatatctaccccggcaccggcggctctaac ttcgacgagaagtttaagaatagagtgactatcaccgccgataagtctactagcaccgc ctatatggaactgtctagcctgagatcagaggacaccgccgtctactactgcactaggt ggactaccggcacaggcgcctactgggtcaaggcactaccgtgaccgtgtctagc |
| SEQ ID NO: 141 | HC | EVQLVQSGAEVKKPGESLRISCKGSGYTFTTYWMHWVRQATGQGLEWMGNIYPGTGGSN FDEKFKNRVTITADKSTSTAYMELSSLRSEDTAVYYCTRWTTGTGAYWGQGTTVTVSSA STKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPPCPAPEFLGGPS VFLFPPKPKDTLMISRTPEVTCVVVDVSQEDPEVQFNWYVDGVEVHNAKTKPREEQFNS TYRVVSVLTVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYSRLTVDKSR WQEGNVFSCSVMHEALHNHYTQKSLSLSLG |
| SEQ ID NO: 142 | DNA HC | gaggtgcagctggtgcagtcaggcgccgaagtgaagaagcccggcgagtcactgagaat tagctgtaaaggttcaggctacaccttcactacctactggatgcactgggtccgccagg ctaccggtcaaggcctcgagtggatgggtaatatctaccccggcaccggcggctctaac ttcgacgagaagtttaagaatagagtgactatcaccgccgataagtctactagcaccgc ctatatggaactgtctagcctgagatcagaggacaccgccgtctactactgcactaggt ggactaccggcacaggcgcctactgggtcaaggcacctaccgtgaccgtgtctagcgct agcactaagggcccgtccgtgttcccccctgcaccttgtagccggagcactagcgaatc caccgctgccctcggctgcctggtcaaggattacttcccggagcccgtgaccgtgtcct ggaacagcggagccctgacctccggagtgcacaccttccccgctgtgctgcagagctcc gggctgtactcgctgtcgtcggtggtcacggtgccttcatctagcctgggtaccaagac ctacacttgcaacgtggaccacaagccttccaacactaaggtggacaagcgcgtcgaat cgaagtacgggccccaccgtgcccgccttgtcccgtgccggagttcctcggcggtccctcg gtctttctgttcccaccgaagcccaaggacactttgatgatttcccgcaccctgaagt gacatgcgtggtcgtggacgtgtcacaggaagatccggaggtgcagttcaattggtacg tggatggcgtcgaggtgcacaacgccaaaaccaagccgagggaggagcagttcaactcc acttaccgcgtcgtgtccgtgctgacggtgctgcatcaggactggctgaacgggaagga gtacaagtgcaaagtgtccaacaagggacttcctagctcaatcgaaaagaccatctcga |

| | SEQUENCES/SEQUENCE TABLE | |
|---|---|---|
| | | aagccaagggacagccccgggaacccaagtgtataccctgccaccgagccaggaagaa<br>atgactaagaaccaagtctcattgactgccttgtgaagggcttctaccatcggatat<br>cgccgtggaatgggagtccaacggccagccggaaaacaactacaagaccaccctccgg<br>tgctggactcagacggatccttcttcctctactcgcggctgaccgtggataagagcaga<br>tggcaggagggaaatgtgttcagctgttctgtgatgcatgaagccctgcacaaccacta<br>cactcagaagtccctgtccctctccctggga |
| BAP049-Clone-B LC | | |
| SEQ ID NO: 143 (Kabat) | LCDR1 | KSSQSLLDSGNQKNFLT |
| SEQ ID NO: 144 (Kabat) | LCDR2 | WASTRES |
| SEQ ID NO: 145 (Kabat) | LCDR3 | QNDYSYPYT |
| SEQ ID NO: 146 (Chothia) | LCDR1 | SQSLLDSGNQKNF |
| SEQ ID NO: 147 (Chothia) | LCDR2 | WAS |
| SEQ ID NO: 148 (Chothia) | LCDR3 | DYSYPY |
| SEQ ID NO: 149 | VL | EIVLTQSPATLSLSPGERATLSCKSSQSLLDSGNQKNFLTWYQQKPGKAPKLLIYWAST<br>RESGVPSRFSGSGSGTDFTFTISSLQPEDIATYYCQNDYSYPYTFGQGTKVEIK |
| SEQ ID NO: 150 | DNA VL | Gagatcgtcctgactcagtcacccgctaccctgagcctgagccctggcgagcgggctac<br>actgagctgtaaatctagtcagtcactgctggatagcggtaatcagaagaacttcctga<br>cctggtatcagcagaagcccggtaaagcccctaagctgctgatctactgggcctctact<br>agagaatcaggcgtgccctctaggtttagcggtagcggtagtggcaccgacttcacctt<br>cactatctctagcctgcagcccgaggatatcgctacctactactgtcagaacgactata<br>gctaccctacaccttcggtcaaggcactaaggtcgagattaag |
| SEQ ID NO: 151 | LC | EIVLTQSPATLSLSPGERATLSCKSSQSLLDSGNQKNFLTWYQQKPGKAPKLLIYWAST<br>RESGVPSRFSGSGSGTDFTFTISSLQPEDIATYYCQNDYSYPYTFGQGTKVEIKRTVAA<br>PSVFIFPPSDEQLKSGTASVVCLLNNFYPREAKVQWKVDNALQSGNSQESVTEQDSKDS<br>TYSLSSTLTLSKADYEKHKVYACEVTHQGLSSPVTKSFNRGEC |
| SEQ ID NO: 152 | DNA LC | Gagatcgtcctgactcagtcacccgctaccctgagcctgagccctggcgagcgggctac<br>actgagctgtaaatctagtcagtcactgctggatagcggtaatcagaagaacttcctga<br>cctggtatcagcagaagcccggtaaagcccctaagctgctgatctactgggcctctact<br>agagaatcaggcgtgccctctaggtttagcggtagcggtagtggcaccgacttcacctt<br>cactatctctagcctgcagcccgaggatatcgctacctactactgtcagaacgactata<br>gctaccctacaccttcggtcaaggcactaaggtcgagattaagcgtacggtggccgct<br>cccagcgtgttcatcttcccccccagcgacgagcagctgaagagcggcaccgccagcgt<br>ggtgtgcctgctgaacaacttctaccccgggaggccaaggtgcagtggaaggtggaca<br>acgccctgcagagcggcaacagccaggagagcgtcaccgagcaggacagcaaggactcc<br>acctacagcctgagcagcaccctgaccctgagcaaggccgactacgagaagcataaggt<br>gtacgcctgcgaggtgacccaccagggcctgtccagccccgtgaccaagagcttcaaca<br>ggggcgagtgc |
| BAP049-Clone-E HC | | |
| SEQ ID NO: 153 (Kabat) | HCDR1 | TYIMH |
| SEQ ID NO: 154 (Kabat) | HCDR2 | NIYPGTGGSNFDEKFKN |
| SEQ ID NO: 155 (Kabat) | HCDR3 | WTTGTGAY |
| SEQ ID NO: 156 (Chothia) | HCDR1 | GYTFTTY |
| SEQ ID NO: 157 (Chothia) | HCDR2 | YPGTGG |
| SEQ ID NO: 158 (Chothia) | HCDR3 | WTTGTGAY |
| SEQ ID NO: 159 | VH | EVQLVQSGAEVKKPGESLRISCKGSGYTFTTYWMHWVRQATGQGLEWMGNIYPGTGGSN<br>FDEKFKNRVTITADKSTSTAYMELSSLRSEDTAVYYCTRWTTGTGAYWGQGTTVTVSS |
| SEQ ID NO: 160 | DNA VH | Gaggtgcagctggtgcagtcaggcgccgaagtgaagaagcccggcgagtcactgagaat<br>tagctgtaaaggttcaggctacaccttcactacctactggatgcactgggtccgccagg<br>ctaccggtcaaggcctcgagtggatgggtaatatctaccccggcaccggcggctctaac<br>ttcgacgagaagtttaagaatagagtgactatcaccgccgataagtctactagcaccgc<br>ctatatggaactgtctagcctgagatcagaggacaccgccgtctactactgcactaggt<br>ggactaccggcacaggcgcctactggggtcaaggcactaccgtgaccgtgtctagc |

-continued

| SEQUENCES/SEQUENCE TABLE | | |
|---|---|---|
| SEQ ID NO: 161 | HC | EVQLVQSGAEVKKPGESLRISCKGSGYTFTTYWMHWVRQATGQGLEWMGNIYPGTGGSN FDEKFKNRVTITADKSTSTAYMELSSLRSEDTAVYYCTRWTTGTGAYWGQGTTVTVSSA STKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPPCPAPEFLGGPS VFLFPPKPKDTLMISRTPEVTCVVVDVSQEDPEVQFNWYVDGVEVHNAKTKPREEQFNS TYRVVSVLTVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYSRLTVDKSR WQEGNVFSCSVMHEALHNHYTQKSLSLSLG |
| SEQ ID NO: 162 | DNA HC | gaggtgcagctggtgcagtcaggcgccgaagtgaagaagcccggcgagtcactgagaat tagctgtaaaggttcaggctacaccttcactacctactggatgcactgggtccgccagg ctaccggtcaaggcctcgagtggatgggtaatatctaccccggcaccggcggctctaac ttcgacgagaagtttaagaatagagtgactataccgccgataagtctactagcaccgc ctatatggaactgtctagcctgagatcagaggacaccgccgtctactactgcactaggt ggactaccggcacaggcgcctactgggtcaaggcactaccgtgaccgtgtctagcgct agcactaagggcccgtccgtgttcccctggcaccttgtagccggagcactagcgaatc caccgctgccctcggctgcctggtcaaggattacttcccggagcccgtgaccgtgtcct ggaacagcggagccctgacctccgagtgcacaccttccccgctgtgctgcagagctcc gggctgtactcgctgtcgtcggtggtcacggtgccttcatctagcctgggtaccaagac ctacacttgcaacgtggaccacaagccttccaacactaaggtggacaagcgcgtcgaat cgaagtacgggcccaccgtgcccgccttgtcccgcgccggagttcctcggcggtccctcg gtctttctgttcccaccgaagcccaaggacacttttgatgatttcccgcacccctgaagt gacatgcgtggtcgtggacgtgtcacaggaagatccggaggtgcagttcaattggtacg tggatggcgtcgaggtgcacaacgccaaaaccaagccgagggaggagcagttcaactcc acttaccgcgtcgtgtccgtgctgacggtgctgcatcaggactggctgaacgggaagga gtacaagtgcaaagtgtccaacaaaggacttcctagctcaatcgaaaagaccatctcga aagccaagggacagccccgggaacccaagtgtataccctgccaccgagccaggaagaa atgactaagaaccaagtctcattgacttgccttgtgaagggcttctaccatcggatat cgccgtggaatgggagtccaacggccagccggaaaacaactacaagaccacccctccgg tgctggactcagacggatccttcttcctctactcgcggctgaccgtggataagagcaga tggcaggagggaaatgtgttcagctgttctgtgatgcatgaagccctgcacaaccacta cactcagaagtccctgtccctctccctggga |
| BAP049-Clone-E LC | | |
| SEQ ID NO: 163 (Kabat) | LCDR1 | KSSQSLLDSGNQKNFLT |
| SEQ ID NO: 164 (Kabat) | LCDR2 | WASTRES |
| SEQ ID NO: 165 (Kabat) | LCDR3 | QNDYSYPYT |
| SEQ ID NO: 166 (Chothia) | LCDR1 | SQSLLDSGNQKNF |
| SEQ ID NO: 167 (Chothia) | LCDR2 | WAS |
| SEQ ID NO: 168 (Chothia) | LCDR3 | DYSYPY |
| SEQ ID NO: 169 | VL | EIVLTQSPATLSLSPGERATLSCKSSQSLLDSGNQKNFLTWYQQKPGQAPRLLIYWAST RESGVPSRFSGSGSGTDFTFTISSLEAEDAATYYCQNDYSYPYTFGQGTKVEIK |
| SEQ ID NO: 170 | DNA VL | Gagatcgtcctgactcagtcacccgctaccctgagcctgagcctggcgagcggctac actgagctgtaaatctagtcagtcactgctggatagcggtaatcagaagaacttcctga cctggtatcagcagaagcccggtcaagcccctagactgctgatctactgggcctctact agagaatcaggcgtgccctctaggtttagcggtagcggtagtggcaccgacttcacctt cactatctctagcctggaagccgaggacgccgctacctactactgtcagaacgactata gctaccctacaccttcggtcaaggcactaaggtcgagattaag |
| SEQ ID NO: 171 | LC | EIVLTQSPATLSLSPGERATLSCKSSQSLLDSGNQKNFLTWYQQKPGQAPRLLIYWAST RESGVPSRFSGSGSGTDFTFTISSLEAEDAATYYCQNDYSYPYTFGQGTKVEIKRTVAA PSVFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC |
| SEQ ID NO: 172 | DNA LC | Gagatcgtcctgactcagtcacccgctaccctgagcctgagcctggcgagcggctac actgagctgtaaatctagtcagtcactgctggatagcggtaatcagaagaacttcctga cctggtatcagcagaagcccggtcaagcccctagactgctgatctactgggcctctact agagaatcaggcgtgccctctaggtttagcggtagcggtagtggcaccgacttcacctt cactatctctagcctggaagccgaggacgccgctacctactactgtcagaacgactata gctaccctacaccttcggtcaaggcactaaggtcgagattaagcgtacggtggccgct cccagcgtgttcatcttccccccagcgacgagcagctgaagagcggcaccgccagcgt ggtgtgcctgctgaacaacttctaccccggggaggccaaggtgcagtggaaggtggaca acgccctgcagagcggcaacagccaggagagcgtcaccgagcaggacagcaaggactcc acctacagcctgagcagcaccctgaccctgagcaaggccgactacgagaagcataaggt gtacgcctgcgaggtgacccaccagggcctgtccagcccgtgaccaagagcttcaaca ggggcgagtgc |

| SEQUENCES/SEQUENCE TABLE | | | |
|---|---|---|---|
| BAP049-Clone-B HC | | | |
| SEQ ID NO: 173 (Kabat) | HCDR1 | ACCTACTGGATGCAC | |
| SEQ ID NO: 174 (Kabat) | HCDR2 | AATATCTACCCCGGCACCGGCGGCTCTAACTTCGACGAGAAGTTTAAGAAT | |
| SEQ ID NO: 175 (Kabat) | HCDR3 | TGGACTACCGGCACAGGCGCCTAC | |
| SEQ ID NO: 176 (Chothia) | HCDR1 | GGCTACACCTTCACTACCTAC | |
| SEQ ID NO: 177 (Chothia) | HCDR2 | TACCCCGGCACCGGCGGC | |
| SEQ ID NO: 178 (Chothia) | HCDR3 | TGGACTACCGGCACAGGCGCCTAC | |
| BAP049-Clone-B LC | | | |
| SEQ ID NO: 179 (Kabat) | LCDR1 | AAATCTAGTCAGTCACTGCTGGATAGCGGTAATCAGAAGAACTTCCTGACC | |
| SEQ ID NO: 180 (Kabat) | LCDR2 | TGGGCCTCTACTAGAGAATCA | |
| SEQ ID NO: 181 (Kabat) | LCDR3 | CAGAACGACTATAGCTACCCCTACACC | |
| SEQ ID NO: 182 (Chothia) | LCDR1 | AGTCAGTCACTGCTGGATAGCGGTAATCAGAAGAACTTC | |
| SEQ ID NO: 183 (Chothia) | LCDR2 | TGGGCCTCT | |
| SEQ ID NO: 184 (Chothia) | LCDR3 | GACTATAGCTACCCCTAC | |
| BAP049-Clone-E HC | | | |
| SEQ ID NO: 185 (Kabat) | HCDR1 | ACCTACTGGATGCAC | |
| SEQ ID NO: 186 (Kabat) | HCDR2 | AATATCTACCCCGGCACCGGCGGCTCTAACTTCGACGAGAAGTTTAAGAAT | |
| SEQ ID NO: 187 (Kabat) | HCDR3 | TGGACTACCGGCACAGGCGCCTAC | |
| SEQ ID NO: 188 (Chothia) | HCDR1 | GGCTACACCTTCACTACCTAC | |
| SEQ ID NO: 189 (Chothia) | HCDR2 | TACCCCGGCACCGGCGGC | |
| SEQ ID NO: 190 (Chothia) | HCDR3 | TGGACTACCGGCACAGGCGCCTAC | |
| BAP049-Clone-E LC | | | |
| SEQ ID NO: 191 (Kabat) | LCDR1 | AAATCTAGTCAGTCACTGCTGGATAGCGGTAATCAGAAGAACTTCCTGACC | |
| SEQ ID NO: 192 (Kabat) | LCDR2 | TGGGCCTCTACTAGAGAATCA | |
| SEQ ID NO: 193 (Kabat) | LCDR3 | CAGAACGACTATAGCTACCCCTACACC | |
| SEQ ID NO: 194 (Chothia) | LCDR1 | AGTCAGTCACTGCTGGATAGCGGTAATCAGAAGAACTTC | |
| SEQ ID NO: 195 (Chothia) | LCDR2 | TGGGCCTCT | |
| SEQ ID NO: 196 (Chothia) | LCDR3 | GACTATAGCTACCCCTAC | |
| Nivolumab | | | |
| SEQ ID NO: 197 | HC | QVQLVESGGGVVQPGRSLRLDCKASGITFSNSGMHWVRQAPGKGLEWVAVIWYDGSKRY YADSVKGRFTISRDNSKNTLFLQMNSLRAEDTAVYYCATNDDYWGQGTLVTVSSASTKG PSVFPLAPCSRSTSESTAALGCLVKDYFPEPVTVSWNSGALTSGVHTFPAVLQSSGLYS LSSVVTVPSSSLGTKTYTCNVDHKPSNTKVDKRVESKYGPPCPPCPAPEFLGGPSVFLF PPKPKDTLMISRTPEVTCVVVDVSQEDPEVQFNWYVDGVEVHNAKTKPREEQFNSTYRV VSVLTVLHQDWLNGKEYKCKVSNKGLPSSIEKTISKAKGQPREPQVYTLPPSQEEMTKN QVSLTCLVKGFYPSDIAVEWESNGQPENNYKTTPPVLDSDGSFFLYSRLTVDKSRWQEG NVFSCSVMHEALHNHYTQKSLSLSLGK | |

-continued

| SEQUENCES/SEQUENCE TABLE | | |
|---|---|---|
| SEQ ID NO: 198 | LC | EIVLTQSPATLSLSPGERATLSCRASQSVSSYLAWYQQKPGQAPRLLIYDASNRATGIP<br>ARFSGSGSGTDFTLTISSLEPEDFAVYYCQQSSNWPRTFGQGTKVEIKRTVAAPSVFIF<br>PPSDEQLKSGTASVVCLLNNFYPREAKVQWKVDNALQSGNSQESVTEQDSKDSTYSLSS<br>TLTLSKADYEKHKVYACEVTHQGLSSPVTKSFNRGEC |
| Pembrolizumab | | |
| SEQ ID NO: 199 | HC | QVQLVQSGVEVKKPGASVKVSCKASGYTFTNYYMYWVRQAPGQGLEWMGGINPSNGGTN<br>FNEKFKNRVTLTTDSSTTTAYMELKSLQFDDTAVYYCARRDYRFDMGFDYWGQGTTVTV<br>SSASTKGPSVFPLAPCSRSTSESTAALGCLVKDYFPEPVTVSWNSGALTSGVHTFPAVL<br>QSSGLYSLSSVVTVPSSSLGTKTYTCNVDHKPSNTKVDKRVESKYGPPCPPCPAPEFLG<br>GPSVFLFPPKPKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSRLTVD<br>KSRWQEGNVFSCSVMHEALHNHYTQKSLSLSLGK |
| SEQ ID NO: 200 | LC | EIVLTQSPATLSLSPGERATLSCRASKGVSTSGYSYLHWYQQKPGQAPRLLIYLASYLE<br>SGVPARFSGSGSGTDFTLTISSLEPEDFAVYYCQHSRDLPLTFGGGTKVEIKRTVAAPS<br>VFIFPPSDEQLKSGTASVVCLLNNFYPREAKVQWKVDNALQSGNSQESVTEQDSKDSTY<br>SLSSTLTLSKADYEKHKVYACEVTHQGLSSPVTKSFNRGEC |
| Pidilizumab | | |
| SEQ ID NO: 201 | HC | QVQLVQSGSELKKPGASVKISCKASGYTFTNYGMNWVRQAPGQGLQWMGWINTDSGEST<br>YAEEFKGRFVFSLDTSVNTAYLQITSLTAEDTGMYFCVRVGYDALDYWGQGTLVTVSSA<br>STKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKRVEPKSCDKTHTCPPCPAPELLG<br>GPSVFLFPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFFLYSKLTVD<br>KSRWQQGNVFSCSVMHEALHNHYTQKSLSLSPGK |
| SEQ ID NO: 202 | LC | EIVLTQSPSSLSASVGDRVTITCSARSSVSYMHWFQQKPGKAPKLWIYRTSNLASGVPS<br>RFSGSGSGTSYCLTINSLQPEDFATYYCQQRSSFPLTFGGGTKLEIKRTVAAPSVFIFP<br>PSDEQLKSGTASVVCLLNNFYPREAKVQWKVDNALQSGNSQESVTEQDSKDSTYSLSST<br>LTLSKADYEKHKVYACEVTHQGLSSPVTKSFNRGEC |
| SEQ ID NO: 203 | | GYTFTTYWMH |

MODES FOR CARRYING OUT THE INVENTION

HuCAL PLATINUM® Pannings

The phagemid library is based on the HuCAL® concept (Knappik et al., J Mol Biol 296, 57-86. 2000) and employs the CysDisplay® technology for displaying the Fab on the phage surface (WO 01/05950).

Bead-Based Panning Against TGF-β2

Prior to a bead-based panning, the antigen had to be immobilized to carboxy beads (Dynabeads® M-270 Carboxylic Acid, Invitrogen). Per phage pool, 1×10⁷ antigen coated beads were blocked with an equal volume of PBS/0.1% Tween20/5% milk powder. In parallel, for each panning HuCAL PLATINUM® phage-antibodies were blocked with an equal volume of PBS/0.05% Tween20/5% milk powder/5% BSA. For removal of bead-binding phage, pre-adsorption of blocked phage particles was performed twice using 0.5-1.0×10⁷ BSA coated beads each. Then, blocked antigen coated beads were added to the pre-adsorbed and blocked phage particles and incubated for 1-2 h at RT (room temperature) on a rotator. Phage particles bound to the antigen coated beads were collected with a magnetic separator. Unspecific bound phage were washed off by several washing steps using PBS/0.05% Tween20 and PBS and specifically bound phage were eluted from antigen coated beads using DDT. The DTT eluate was then transferred into E. coli TG1 and incubated for 45 min in a water bath at 37° C. for phage infection. The bacterial pellets were resuspended in 2×YT medium, plated on LB/Cam agar plates and incubated o/n. Colonies were scraped off the plates and were used for phage rescue, polyclonal amplification of selected clones, and phage production. With purified phage the next panning round was started. The second and third round of bead-based panning was performed according to the protocol of the first round except for more stringent washing conditions were applied.

Solution Panning Against TGF-β2

Prerequisite for a solution panning was biotinylation of the antigen and confirmation of retained activity of biotinylated antigen. During solution panning, the Fab displaying phage and the biotinylated antigen were incubated in solution which facilitated the accessibility of the antigen by the phage.

Solution Panning Protocol with Streptavidin-Coupled Magnetic Beads

Per phage pool, 4 mg Streptavidin beads (Dynabeads® M-280 Streptavidin, Invitrogen) were blocked in 1× Chemiblocker. In parallel, for each panning, HuCAL PLATINUM® phage-antibodies were blocked with Chemiblocker/0.1% Tween20. Subsequently, for removal of Streptavidin- or bead-binding phage, pre-adsorption of blocked phage particles was performed twice using Streptavidin beads each. Then, 100 nM biotinylated antigens TGF-β2 was added to the pre-adsorbed and blocked phage particles and incubated for 1-2 h at RT on a rotator. The phage-antigen complexes were captured using 2 mg blocked Streptavidin beads and phage particles bound to the Streptavidin beads were collected with a magnetic separator. Unspecific bound phage were washed off by several washing steps using PBS/0.05% Tween20 and PBS. Specifically bound phage were eluted from Streptavidin beads using DDT. The DTT eluate was then transferred into E. coli TG1 and the mix of TG1 and DTT eluate was incubated for phage infection. The bacterial pellets were resuspended in 2×YT medium, plated on LB/Cam agar plates and incubated o/n. Colonies were scraped off the plates and were used for phage rescue, polyclonal amplification of selected clones, and phage production. With purified phage the next panning round was started. The second and third round of the solution panning was performed according to the protocol of the first round except for decreased amounts of antigen and more stringent washing conditions.

RapMAT® Pannings

In order to obtain specific antibodies with increased affinities, RapMAT® pannings were performed (Prassler et al., Immunotherapy 1, 571-583. 2009). For this purpose, two rounds of Bead-based or Solution pannings were performed with antigen TGF-β2 as described above.

a) For LCDR3 RapMAT®: After the 2nd round of panning, Fab-encoding fragments of phage derived pMORPH30® vector DNA were enzymatically digested and TRIM™ LCDR3 maturation cassettes were inserted by enzymatic ligation (Virnekas et al., 1994) to diversify LCDR3s.

b) For HCDR2 RapMAT®: After the 2nd round of panning, Fab-encoding fragments of phage derived pMORPH®30 vector DNA were enzymatically digested and TRIM™ HCDR2 maturation cassettes (Virnekas et al., Nucleic Acids Res 22, 5600-5607. 1994) were inserted by enzymatic ligation to diversify HCDR2s.

Ligation mixtures were electroporated in $E.$ $coli$ TOP10F' cells yielding in >5×10$^6$ independent colonies. The generated libraries were amplified and subjected to two more rounds of panning with increased stringency using antigen concentrations of 5 nM and 0.5 nM for the 3rd and 4th round of solution pannings, respectively.

Subcloning and Screening Scale Expression of Selected Fab Fragments

To facilitate rapid expression of soluble Fab, the Fab encoding inserts of the selected HuCAL PLATINUM® phage were subcloned from pMORPH®30 display vector into pMORPH® x11 expression vector pMORPH® x11_Fab_FH. After transformation of $E.$ $coli$ TG1-F⁻ single clone expression and preparation of periplasmic extracts containing HuCAL®-Fab fragments were performed as described previously (Rauchenberger et al., J Biol Chem 278, 38194-38205. 2003).

Generation of Masterplates

Chloramphenicol resistant single clones were picked into the wells of a sterile 384-well microtiter plate pre-filled with 2×YT-CG (34 µg/ml chloramphenicol (Cam); 0.1% Glucose) medium and grown o/n at 37° C. Next morning, sterile 2×YT media containing glycerol was added into each well of the masterplates; plates were sealed with aluminum foil and stored at −80° C. The following two chapters describe the preparation of lysates from Fab-expressing $E.$ $coli$ in 384- and 96-well format, respectively. These expression plates are later used for screening approaches.

Preparation of Fab Containing Bacterial Lysates for ELISA and FMAT Screening

5 µl of each o/n culture were transferred to a sterile 384-well microtiter plate pre-filled with 40 µl 2×YT-CG medium (34 µg/ml chloramphenicol (Cam); 0.1% Glucose) per well. Plates were incubated at 37° C. until the cultures were slightly turbid and 2×YT medium containing Cam and IPTG was added per well. After overnight incubation BEL buffer (2.5 mg/ml lysozyme, 4 mM EDTA, 10 U/µl Benzonase) was added and plates were incubated for 1 hour.

Preparation of Fab Containing Bacterial Lysates for pSMAD3 SureFire® Assay

5 µl of each o/n culture were transferred to a sterile 96-well microtiter plate pre-filled with 100 µl 2×YT-CG medium (34 µg/ml Cam; 0.1% Glucose) per well. Plates were incubated at 22° C. until the cultures were slightly turbid and 2×YT medium containing CAM and IPTG was added per well. Next morning, bacteria were spun down by centrifugation, supernatant was discarded and BEL buffer (2.5 mg/ml lysozyme, Complete (w/o EDTA; Roche), 20 U/µml Benzonase) was added into each well. Plates were incubated for 2 hand BEL-lysates (lysates produced by using the BEL buffer) were centrifuged to spin down bacterial cell debris. Fab containing supernatants were used for screening purposes (e.g. pSMAD3 SureFire® Assay).

Screening of Fab-Containing Raw Bacterial Lysates

ELISA Screening

Using ELISA screening, single Fab clones are identified from panning output for binding to the target antigen human TGF-β2 protein. Fabs are tested using Fab containing crude $E.$ $coli$ lysates describe above.

ELISA Screening on Directly Coated Antigen

This approach was used for screening of some RapMAT® pannings prior to SET. Maxisorp™ 384-well plates were coated with mouse TGF-β2 at concentrations of 5 µg/ml or 1 µg/ml, respectively, in PBS. After blocking of plates with 5% skim milk powder in PBS, Fab-containing $E.$ $coli$ lysates were added. Binding of Fabs was detected by F(ab)$_2$ specific goat anti-human IgG conjugated to alkaline phosphatase (Jackson Immuno Research, #109-055-097) (diluted 1:5000) using Attophos fluorescence substrate (Roche, #11681982001). Fluorescence emission at 535 nm was recorded with excitation at 430 nm.

ELISA Screening of Biotinylated Antigen (Fab Capture ELISA)

The specificity of anti-TGF-β2 Fab antibodies to human TGF-β2 and mouse TGF-β2 and crossreactivity to rat TGF-β3, human TGF-β1 was evaluated in an ELISA setting. For this, if not stated otherwise, Maxisorp™ 384-well plates were coated with Fd fragment specific sheep anti-human IgG (The binding site, #PC075) diluted 1:1000 in PBS. After blocking with 5% skim milk powder in PBS, Fab-containing $E.$ $coli$ lysates were added. Subsequently the captured HuCAL® Fab fragments were allowed to bind to biotinylated antigens. The following concentrations of biotinylated antigens were used for screening:

1 µg/ml biotinylated human TGF-β2/biotinylated transferrin (for counter screening on irrelevant biotinylated protein) for Fab capture ELISA based screening of standard pannings;

0.01 µg/ml biotinylated human TGF-β2 for Fab capture ELISA based screening of some RapMAT® pannings prior to SET;

Anti-TGF-β2 Fab antibodies bound biotinylated antigens were detected by incubation with streptavidin conjugated to alkaline phosphatase (phosphatase (Invitrogen (Zymed), #43-4322)) followed by addition of AttoPhos fluorescence substrate (Roche, #11681982001). Fluorescence emission at 535 nm was recorded with excitation at 430 nm.

FMAT Screening

Using FMAT (Fluorometric Microvolume Assay Technology) screening, single Fab clones are identified from panning output for binding to the target antigen immobilized on beads (antigens or BSA were immobilized on Carboxy beads as described above). Fabs are tested using Fab containing crude $E.$ $coli$ lysates (prepared as described above).

Fab-containing lysates and beads were blocked in PBS/0.1% Tween20/3% BSA. Blocked lysates, blocked beads and Cy™5-conjugated AffiniPure F(ab')$_2$ fragment goat anti-human IgG (Jackson ImmunoResearch, #109-176-097) were transferred to the FMAT plates. Plates were incubated for ~3 hours at room temperature in the dark. FMAT readings were taken using the 8200 Cellular Detection System (Applied Biosystems) according to the manufacturer's instructions.

SET Screening

Affinity ranking was in principle performed as described above. For ranking of the matured binders by Solution Equilibrium Titration based on the principles described by (Haenel et al., Anal Biochem 339, 182-184 2005), a constant amount of diluted BEL extract (lysates produced by using the BEL buffer: 2.5 mg/ml lysozyme, 4 mM EDTA, 10 U/µl Benzonase) was equilibrated overnight with different concentrations of antigen.

Then the mixture was transferred to MSD plates which were previously coated with antigen, and after incubation and washing, a suitable MSD-Sulfo-Tag labeled detection antibody was added. Subsequently, the concentration of unbound Fab was quantified via ECL detection using the Sector Imager 6000 (Meso Scale Discovery, Gaithersburg, Md., USA). Results were processed using XLfit (IDBS) software, applying the corresponding fit model (see below) to estimate affinities and thus identify clones most improved by the maturation.

Expression and Purification of HuCAL® Fab Fragments

Micro-Expression and -Purification of His-Tagged HuCAL® Fab Fragments in E. coli Expression of Fab fragments encoded by pMORPH® x11_Fab_FH in E. coli TG1 F⁻ cells was carried out in 50 ml Falcons using 25 ml of 2×YT medium supplemented with 0.1% glucose, 34 µg/ml chloramphenicol and 0.1 mM IPTG (isopropyl-11-D-thiogalacto-pyranoside). Cultures were shaken at 30° C. for 18 h. Cells were harvested and disrupted using a combination of lysozyme and Bug Buster Protein Extraction Reagent (Novagen, Germany). $His_6$-tagged Fab fragments ("$His_6$" disclosed as SEQ ID NO: 204) were isolated via IMAC (Qiagen, Germany). Buffer exchange to 1× Dulbecco's PBS (pH 7.2) was performed using D-Tube96™-Dialyzer (MWCO 6-8 kDa, Novagen, Germany). Protein concentrations were determined by UV-spectrophotometry. The purity of representatively selected samples was analyzed in denaturing, reducing 15% SDS-PAGE.

Expression and Purification of His-tagged HuCAL® Fab Fragments in E. coli Expression of Fab fragments encoded by pMORPH® x11_Fab_FH in E. coli TG1 cells was carried out in shake flask cultures using 500 ml of 2×YT medium supplemented with 0.1% glucose and 34 µg/ml chloramphenicol. Cultures were shaken at 30° C. until the $OD_{600}$ reached a value of 0.5. Fab expression was induced by addition of IPTG (isopropyl-11-D-thiogalactopyranoside) at a final concentration of 0.75 mM and further cultivation for 20 h at 30° C. Cells were harvested and disrupted using lysozyme. $His_6$-tagged Fab fragments ("$His_6$" disclosed as SEQ ID NO: 204) were isolated via IMAC (Bio-Rad, Germany) and eluted using imidazole. Buffer exchange to 1× Dulbecco's PBS (pH 7.2) was performed using PD10 columns (GE Healthcare, Germany). Samples were sterile filtered (0.2 µm). Protein concentrations were determined by UV-spectrophotometry. The purity of the samples was analyzed in denaturing, reducing 15% SDS-PAGE. The homogeneity of Fab preparations was determined in native state by size exclusion chromatography (HP-SEC) with calibration standards.

Functional Bio-Assays
Reporter Gene Assay (RGA)
Cultivation of HEK293T/17 Cell Lines HEK293T/17 cells were maintained in DMEM (Dulbecco's Modified Eagle's Medium) containing 10% FBS (Fetal Bovine Serum), 2 mM L-glutamine, penicillin (50 IE/ml), and streptomycin (50 µg/ml). Cells were grown in an incubator at 37° C. and 5% $CO_2$ and subcultured every 3-4 days. Cells were detached using Accutase™ and then transferred into a new flask containing fresh medium. HEK293T/17 cells stably transfected with CAGA-12 luc were cultured as described above for parental HEK293T/17 cells but cell growth medium was supplemented with 4 mM L-glutamine and 3 µg/ml blasticidin in addition to FBS, penicillin and streptomycin.

TGF-β-Protein Induced Luciferase Reporter Gene Assay

To determine the capacity of anti-TGF-β2 antibodies to inhibit TGF-β2-induced signaling and specificity against other TGF-β1, TGF-β3, myostatin, Activins and GDF-11, a reporter gene assay using the stable reporter cell line HEK293T/17 CAGA-12 luc was performed. The CAGA-12 luciferase reporter construct carries the luciferase gene downstream of a minimal promoter and multiple CAGA boxes which are specific for phosphorylated Smad-2 and Smad-3. Addition of purified recombinant TGF-β2 (but also TGF-β3, TGF-β1, myostatin, GDF-11 and Activins) induce Smad-2 and Smad-3 phosphorylation and thus binding to the CAGA-12 reporter and leads to luciferase gene expression. At 90% confluency of HEK293T/17 CAGA-12 luc cells, cells were detached using accutase and diluted in assay medium (DMEM supplemented with 2% FBS and 2 mM L Glutamine) to a concentration of 2.5×105 cells/ml. Subsequently, 100 µl cells per well were seeded into white flat-bottomed 96-well plates (BD Falcon, #353296) and incubated at 37° C. and 5% $CO_2$ overnight. The next day, the TGF-β2 antibodies (Fab or IgG) at the desired concentrations and the TGF-β proteins were mixed in PBS. Final concentrations of antigens in the mixtures correspond to their respective $\sim EC_{80}$ concentrations in this assay and are as follows: TGF-β1/2/3 proteins—12 pM (active dimer), Activin A, GDF-8, GDF-11-1 nM (active dimer) and Activin B, Activin AB—100 pM (active dimer). Antigens and antibodies were incubated for 30 minutes at room temperature. Assay medium was removed from the cells and the mixtures were added to the seeded cells. After overnight incubation, assay medium was removed and 70 µl of PBS (with CaCl2 and MgCl2) was added to each well. After adaptation to room temperature, 50 µl of freshly prepared BriteLite Plus reagent (PerkinElmer, #6016761) was added to each well. After 5 min incubation time, the luminescence was read in a luminometer (GeniosPro, Tecan). The half maximal inhibitory concentration (1050 values) was calculated using Prism software (GraphPad Software) after full titration of the respective antibodies.

Receptor/Ligand Interaction Elisa

To assess whether the inhibitory Fabs act via blocking the TGF-β2 binding sites of human TGF-βRIII/Fc TGF-β receptor-TGF-β interaction ELISAs were performed.

TGF-β2-TGF-βRIII Interaction Assay

For this, Maxisorp™ 384-well plates were coated overnight at 4° C. with 2 µg/ml (~22 nM) TGF-βRIII (R&D Systems, #LF1309051). 1.25 µg/ml (~100 nM) biotinylated human TGF-β2 was incubated for 30 min with different Fab/IgG concentrations and then added to the coated wells blocked with Chemiblocker. Bound biotinylated human TGF-β2 was detected by incubation with streptavidin conjugated to alkaline phosphatase (Invitrogen (Zymed), #43-4322) followed by addition of AttoPhos fluorescence substrate (Roche, #11681982001). Fluorescence emission at 535 nm was recorded with excitation at 430 nm.

pSMAD3 SureFire® Assay

For this functional screening specially prepared Fab-containing bacterial lysates (BEL buffer) were used to determine TGF-β-induced Smad3 phosphorylation in HEK293T cells with the AlphaScreen® SureFire® for phospho-SMAD3 (Ser423/425) kit (PerkinElmer #TGRSM3S10K) and AlphaScreen® IgG(ProteinA) Detection Kit (#6760617C). To determine TGF-β2/3 neutralization capacity of BEL lysates (lysates produced by using the BEL buffer), 8.000 cells per well from the reporter cell line HEK293T (CAGA-12 luciferase) were seeded into a collagen coated Proxiplate™ in assay medium, (DMEM supplemented with 2% FBS and 2 mM L-Glutamine) and cultivated at 37° C. and 5% $CO_2$ overnight. The next day a master plate was prepared containing 25 µl of the BEL lysates and 75 µl of serum-free assay medium supplemented with 0.3 ng/ml TGF-β2 or 3, respectively. Assay medium was removed from the cells by flicking and tabbing the plates on paper towels. Then 15 µl from the master plate were transferred to the HEK293T cells and stimulated at 37° C. and 5% $CO_2$ for 1 h. Medium was removed and 4 µl 1× lysis buffer was added to each well. Plates were stored until analysis at −80° C. For analysis 5 µl "acceptor bead mix" were added for two hours, followed by the addition of 2 µl "donor bead mix" and incubated for further two hours. Plates were read on AlphaScreen plate reader using AlphaScreen settings.

Skeletal Muscle Cell Differentiation Assay (Creatine Kinase (CK) Assay)

Human skeletal muscle cells (HsKMCs; Lonza) were cultured in 96-well plates (7500 cells/well) using growth medium (GM) consisting of skeletal muscle basal medium (skBM; Lonza) supplemented with 20% FCS (PAA). Differentiation was initiated 24 to 48 hours after seeding by changing to serum-free differentiation medium (DM) consisting of skBM. Effects on HuSKMCs differentiation were assessed by adding either 0.3 ng/ml TGF-β2 and the respective IgG1s at 7 different concentrations (up to 3 µg/ml) at the onset of differentiation and cells were differentiated into myotubes for up to 120 h. Cells were washed three times with PBS and then lysed with Reporter lysis buffer (Promega) and stored till measurement at −80° C. CK activity was measured using the CK (IFCC) reagent (Thermo Electron). The CK reagent was prepared according to the manufacturer's instructions. To allow adjustment to room temperature (RT) the assay plate was taken out of the −80° C. freezer at least 90 minutes prior to measurement. After adding 75 µl CK reagent to each well (see plate design) the assay plate was immediately transferred to an ELISA reader and absorbance was read at 340 nm for 20 min, reading interval 1 min. To calculate CK activity a standard curve (0.02-40 µg/ml) was freshly prepared in Reporter lysis buffer using CK from rabbit muscle (#10127566001; Roche Diagnostics).

Protein content was determined using the bicinchoninic acid (BCA) reagent (#BCA-1; Sigma). BCA reagent was prepared according to manufacturer's instructions. After adding 200 µl BCA reagent to each well the assay plate was incubated for 30 min at 37° C. and absorbance was then read at 562 nm. To calculate protein content a protein standard curve (0.25-1 mg/ml in Reporter lysis buffer) was prepared. CK activity was calculated as follows (see also Florini et al. 1989). Absorbance values at each of the 21 time points recorded were averaged and plotted. From the linear part of these plots the maximal slope was determined by linear regression (using SigmaPlot software) and converted into CK activity (mUnits) with the help of the CK standard curve. Values were then normalized with the corresponding protein content and CK activity was expressed either as mUnits/mg protein or percentage of control (CK activity Concentration-response data were evaluated, if possible, by sigmoid curve fitting (using XLfit software) yielding $EC_{50}$ values (concentration causing half-maximal effects) and $E_{max}$ (maximal effects).

Affinity Determination

Affinity Determination Using Surface Plasmon Resonance (Biacore)

For direct antigen immobilisation standard EDC-NHS amine coupling chemistry was used. CM5 chips (Biacore, Sweden) were coated with appropriate resonance units (RU) of human- or mouse-TGFbeta-2/Fc (according to the activity of the antigens) in 10 mM acetate buffer, pH 4.5. For the reference flow cell, a respective amount of HSA was used. Regeneration was done with 5 µl 10 mM Glycine/HCl buffer pH1.5. Alternatively, the antigens were not immobilized directly, but captured on a CM5 chip, which was modified with an anti-human-Fc antibody (Fc capture kit, GE Healthcare/Biacore). On the reference flow cell, capture antibody was immobilized, but no antigen captured. Regeneration was achieved using 2 injections of 5 µL 3M $MgCl_2$. Kinetic measurements were done in Dulbecco's PBS at a flow rate of 20 µl/min using a serial dilution row of Fab samples. The Fab concentrations ranged from 15.6 to 500 nM. Injection time for each concentration was 1 min. The dissociation time was set to at least 2 min (or more, according to determined affinity). A blank injection of running buffer was used for double referencing. All sensorgrams were fitted globally using BIA evaluation software 3.2 (Biacore, Sweden).

Affinity Determination of Selected Anti-Human TGF-β2 Fabs and IgGs Using Solution Equilibrium Titration (SET) Method (Sector Imager 6000 (MSD)

For KD determinations, monomer fractions of antibody protein were used (at least 90% monomer content, analyzed by analytical SEC; Superdex75 (Amersham Pharmacia) for Fab, or Tosoh G3000SWXL (Tosoh Bioscience) for IgG, respectively). Affinity determination in solution was basically performed as described in the literature (Friquet et al., J Immnunol Meth 77, 305-319. 1985). In order to improve the sensitivity and accuracy of the SET method, it was transferred from classical ELISA to ECL based technology (Haenel et al., Anal Biochem 339, 182-184. 2005). 1 mg/ml goat-anti-human (Fab)2 fragment specific antibodies (Dianova) were labeled with MSD-Sulfo-TAGTM NHS-Ester (Meso Scale Discovery, Gaithersburg, Md., USA) according to the manufacturer's instructions. The experiments were carried out in polypropylene microtiter plates and PBS pH 7.4 containing 0.5% BSA and 0.02% Tween-20 as assay buffer. Unlabeled antigen was diluted in a 2n series, starting with a concentration at least 10 times higher than the expected KD. Wells without antigen were used to determine Bmax values; wells containing only assay buffer were used to determine background. After addition of appropriate amount of binder (antibody concentration similar to or below the expected KD, 60 µl final volume), the mixture was incubated overnight at RT. MSD plates were coated with antigen (30 µl per well). After washing the plate with PBS with 0.02% Tween-20, the equilibrated samples were transferred to those plates (30 µl per well) and incubated for 20 min. After washing, 30 µl per well of the MSD-Sulfo-Tag labeled detection antibody (anti-human (Fab)2, final dilution typically 1:2,000) was added to the MSD plate and incubated for 30 min at RT on an Eppendorf shaker (700 rpm). After washing the MSD plate and adding 30 µl/well MSD Read Buffer T with surfactant, electrochemiluminescence signals were detected using a Sector Imager 6000 (Meso Scale Discovery, Gaithersburg, Md., USA).

The data was evaluated with XLfit (IDBS) software applying customized fitting models. For KD determination of Fab molecules the following fit model was used (according to (Haenel et al., Anal Biochem 339, 182-184.2005), modified according to (Abraham et al., J Mol Recognit. 9, 456-461.1996):

$$y = B_{max} - \left( \frac{B_{max}}{2[Fab]_t} \left( [Fab]_t + x + K_D - \sqrt{([Fab]_t + x + K_D)^2 - 4x[Fab]_t} \right) \right)$$

[Fab]t: applied total Fab concentration
x: applied total soluble antigen concentration (binding sites)
Bmax: maximal signal of Fab without antigen
KD: affinity Affinity Determination of Fab KD determination of anti-TGF-β2 Fab was basically performed as follows: For all dilutions, human TGF-β2 was prediluted with 4 mM HCl to 100 µg/mL. For coating, the antigens were further diluted in PBS to 0.05 µg/ml (TGF-β2), and coated o/n at 4° C. on standard MSD plates. Subsequently MSD plates were blocked with 3% BSA in PBS for 1 h at RT.

Binding to TGF-β1/3 and Counter-Targets

For SET based analysis of binding to TGF-β1, TGF-β3 and counter-targets (Myostatin, GDF-11, Activin A, Activin B and Activin AB) the specific antigen, human TGF-β1 or TGF-β3 respectively, was coated as described. The proteins to be tested were used for titration and diluted in a 2ⁿ series. The starting concentration was 2 µM for TGF-β1, 0.05 µg/ml for TGF-β3 or 100 nM for all counter targets, respectively.

Epitope Binning

Maxisorp™ 384-well plates were coated overnight at 4° C. with 2.5 µg/ml of TGF-β2 specific Fabs diluted in PBS. Biotinylated TGF-β2 proteins were incubated for one hour at room temperature with Fabs in solution with a constant TGF-β2 concentration of 0.1 µg/ml (~8 nM) and a titration of Fabs starting with a 12.5 molar excess of Fabs (5 µg/ml (100 nM)) compared to TGF-β2 proteins. Fab-TGF-β2 complexes were then added to Fab coated wells blocked with BSA for 30 minutes. Bound biotinylated TGF-β2 were detected by incubation with streptavidin conjugated to alkaline phosphatase (Invitrogen (Zymed), #43-4322) followed by addition of AttoPhos fluorescence substrate (Roche, #11681982001). Fluorescence emission at 535 nm was recorded with excitation at 430 nm.

Conversion to IgG

In order to express full length IgG, variable domain fragments of heavy (VH) and light chains (VL) were subcloned from Fab expression vectors into pMorph®4_hIg1f_LALA_kappa or pMorph®4_hIg1f_LALA_lambda vector for human IgG1f_LALA.

Production of HuCAL® Immunoglobulins

Transient Exploratory Expression and Purification of Human IgG using pMORPH®4 vector system. Eukaryotic HKB11 cells were transfected with pMORPH®4 expression vector DNA encoding both heavy and light chains of IgGs. Cell culture supernatant was harvested on day 3 or 7 post transfection and subjected to standard Protein A affinity chromatography (MabSelect SURE, GE Healthcare). If not stated otherwise, buffer exchange was performed to 1× Dulbcecco's PBS (pH 7.2, Invitrogen) and samples were sterile filtered (0.2 µm pore size). Purity of IgG was analyzed under denaturing, reducing and non-reducing conditions using a Labchip System (Caliper Life Sciences, USA or Agilent, USA) or on SDS-PAGE. Protein concentrations were determined by UV-spectrophotometry and HP-SEC was performed to analyze IgG preparations in native state.

Pannings, Antibody Identification and Characterization

Therapeutic antibodies which neutralize the biological activities of the antigens TGF-β2 protein were generated by selection of clones having high binding affinities, using as the source of antibody variant proteins a commercially available phage display library, the MorphoSys HuCAL PLATINUM® library. The HuCAL PLATINUM® phagemid library is based on the HuCAL® concept (Knappik et al., J Mol Biol 296, 57-86, 2000) and employs the CysDisplay® technology for displaying the Fab on the phage surface (WO 01/05950).

Five panning strategies were performed, three bead-based and two solution pannings. RapMAT® pannings were performed using the outputs of the second rounds of standard pannings. To increase the probability of selecting highly diverse HuCAL® antibodies the library pools were kept mainly separate. To increase the probability of generating high affinity antibodies, the second round outputs of the standard pannings were used to perform RapMAT®. H-CDR2 and L-CDR3 were diversified separately. Standard panning output was screened for binding to human TGF-β2. Screening method was chosen based on the panning strategy: bead pannings were screened using FMAT approach and solution pannings were screened using Fab capture ELISA approach. Counter screening against TGF-β1 was performed using FMAT. pSmad3 SureFire® based screening was performed for pannings against rh TGF-β2. RapMAT® panning output was screened mainly for the most affine hits using SET approach. pSmad3 SureFire® based screening was performed for pannings against rh TGF-β2 as part of standard vs. RapMAT® pannings. Using these methods, inhibition of hTGF-β2 was analyzed. Stringent ELISA screening to select for hTGF-β2 and TGF-β3 negative clones was applied. Additionally, SET screening included counter-screening against TGF-β1 to exclude high affine ($K_D$ on TGF-β1<25 nM) TGF-β1 binders. Out of the primary hits identified in primary screening of standard pannings 27 monoclonal TGF-β2 inhibitory antibodies identified in pSmad3 SureFire® based screening consolidated. Subsequently, 10/27 unique consolidated clones were expressed and purified in exploratory scale. These purified Fab proteins were then also analyzed in the RGA. Primary hits identified in primary screening of RapMAT® pannings were micro-expressed and -purified in Fab-FH format and subsequently analysed for inhibition of hTGF-β2, mTGF-β2, TGF-β3 and TGF-β1 in the RGA. Combined with mTGF-β2 inhibitory hits identified in pSmad3 SureFire® screening approach 38 unique consolidated antibodies were then expressed in exploratory scale in Fab-FH format and also analysed in the RGA. The most potent secondary hits were selected for the consolidation step which included the analysis of binding to different TGF-β isoforms in ELISA and sequencing. In total 190 unique Fabs could be consolidated from all panning and screening strategies. Sequence analysis of 190 unique consolidated antibodies showed:

90 HCDR3 families;
89 kappa and 101 lambda antibodies.

The 190 consolidated Fabs were expressed in *E. coli* and purified. 169/190 expressed Fabs passed quality control and were characterised in the RGA for inhibition of human TGF-β2, mouse TGF-β2, human TGF-β3 and human TGF- β1. Based on the results of this characterisation, the most promising 116 antibodies were selected for conversion into hIgG1f_LALA format via RapCLONE®

IgG Characterisation Including Selection-Developability Assessement (s-DAS)

116 IgGs were expressed in eukaryotic HKB11 cells and purified. 90/116 expressed IgGs passed the quality control and were characterised in the RGA for inhibition of human TGF-β2, mouse TGF-β2, human TGF-β3 and human TGF-β1. A high proportion of antibodies were found to have high or moderate developability risk due to aggregation propensity. Within extended s-DAS analysis, hydrophobicity analysis was also performed. The results revealed high proportion of very hydrophobic antibodies. High hydrophobicity was found to correlate with aggregation tendency of antibodies: higher proportion of antibodies with high/moderate hydrophobicity was found among antibodies stated to have high or moderate developability risk in comparison with antibodies stated to have low developability risk.

Characterisation of Candidates (Before Germlining and PTM Removal)

56 antibodies that passed s-DAS showed affinity and potency in the RGA. Based on activities in the RGA and CK assay and extended s-DAS data (s-DAS+hydrophobicity assessment). Six anti TGF-β2 antibodies were selected for in vivo characterisation and PTM removal/germlining. These 6 selected antibodies (MOR12773, MOR13436, MOR13438, MOR12413, MOR13416, MOR13426) were characterized in various assays summarized below.

Affinity Determination $K_D$ values of antibody antigen interactions were determined using SET according to the principles and conditions described above. TGF-β2 specific Ab MOR13436) and $K_D$ values for selected TGF-β2 antibodies are summarized in Table 1. The $K_D$ success criterion for this project was set to be below 200 pM for human TGF-β2. All selected TGF-β2 specific antibody candidates fulfilled this criterion. TGF-β2 specific should preferably bind to mouse TGF-β2 with 5-fold relaxed criteria. 4 out of the 6 selected TGF-β2 specific antibodies fulfilled the criteria.

TABLE 1

$K_D$ determination by SET measurement (before germlining/PTM removal)

| Number | hTGF-b2 KD [pM] | mTGF-b2 KD [pM] | hTGF-b3 KD [pM] |
|---|---|---|---|
| MOR12773 | 23 | 2700 | No signal |
| MOR13436 | 4 | 18 | n.a. |
| MOR13438 | 2 | 110 | n.a. |
| MOR12413 | 8 | 2000 | n.a. |
| MOR13416 | 2 | 130 | n.a. |
| MOR13426 | 8 | 4 | n.a. | n.a. no affinity up to 2 μM

Cross-Reactivity to Counter Targets

Binding of final antibodies (before PTM removal and germlining) to TGF-β1 and five counter targets (Myostatin, GDF-11, Activin A, Activin B and Activin AB) was analyzed using SET according to the principles and conditions described above. All selected TGF-β2-specific Abs fulfilled the success criteria.

Activity in RGA

Activities of final antibodies (before PTM removal and germlining) were analyzed for inhibition of hTGF-β2, mTGF-β2, TGF-β3 and TGF-β1 in the RGA using conditions described above. An example of the RGA activity data for MOR13436 is given in FIG. 3. The $IC_{50}$ in RGA success criterion for this project was set to be below 200 pM for human TGF-β2. All selected TGF-β2 specific antibodies candidates fulfilled this criterion.

Activity in CK Assay

Activities of final antibodies (before PTM removal and germlining) were analyzed in the CK assay using conditions described above. The CK assay data correlated well with the RGA data with generally lower potencies in the CK assay. The $IC_{50}$ in CK assay success criterion for this project was set to be below 1000 pM for human TGF-β2 and TGF-β3 antibodies, respectively. Example for concentrations-response curves of MOR13436 are presented in FIG. 5

Receptor-Ligand Interaction Assay

Ability of final antibodies (before PTM removal and germlining) to inhibit TGF-β2-TGF-βRIII binding was analyzed in receptor-ligand interaction assay using conditions described above.

Germlining/Engineering of Final Candidates

TABLE 2

Sequences of TGF-β2 specific antibodies were analysed for necessary PTM removal and germlining.

| Number | VH | VL | PTMs to remove | | | | | | Germlining to be done |
|---|---|---|---|---|---|---|---|---|---|
| | | | HCDR1 | HCDR2 | HCDR3 | LCDR1 | LCDR2 | LCDR3 | VH-FR1 |
| MOR12773 | VH2 | κ1 | — | — | — | — | — | — | 2 |
| MOR13436 | VH5 | λ3 | — | NS | — | — | NS | — | — |
| MOR13438 | VH5 | λ3 | — | NS | — | — | — | — | — |
| MOR12413 | VH1A | κ1 | — | — | DG | — | — | — | — |

| Number | Germlining to be done | | | | | | |
|---|---|---|---|---|---|---|---|
| | VH-FR2 | VH-FR3 | VH-FR4 | VL-FR1 | VL-FR2 | VL-FR3 | VL-FR4 |
| MOR12773 | — | — | — | — | — | — | — |
| MOR13436 | — | — | — | 6 | — | 3 | — |
| MOR13438 | — | — | — | 6 | — | 3 | — |
| MOR12413 | — | — | — | — | — | — | — |

In total 23 derivatives were generated in pM4_hIgG1f_LALA_kappa or pM4_hIgG1f_LALA_lambda after PTM removal and germlining. Table provides an overview of antibody derivatives after PTM removal and germlining.

TABLE 3

Antibody derivatives after PTM removal/germlining

| Parental Antibody | Derivative Antibody | PTM removal/germlining detail |
|---|---|---|
| MOR12773 | 14797 | VH2 germlining: aa positions according to Chothia |
| MOR13436 | 14799 | N54Q (HCDR2) + λ3 germlining to VL3_3j + N51K (LCDR2) |
|  | 14800 | N54Q (HCDR2) + λ3 germlining to VL3_3j + N51T (LCDR2) |
|  | 14805 | N54T (HCDR2) + λ3 germlining to VL3_3j + N51K (LCDR2) |
| MOR13438 | 14809 | N54T (HCDR2) + λ3 germlining to VL3_3j |
| MOR12413 | 14787 | D95E (HCDR3) |

Activity in RGA

Activities of final antibodies (after PTM removal and germlining) were analyzed for inhibition of hTGF-β2, mTGF-β2, TGF-β3 and TGF-β1 in the RGA using conditions described above. Data are summarized in Table 4

Activity in CK Assay

Activities of final antibodies (after PTM removal and germlining) were analyzed in the CK assay using conditions described above. The CK assay data are summarized in table 4.

TGF-β2 antibodies MOR14797, MOR14799, MOR14800, MOR14805, MOR14809 and MOR14787 were tested for difference to control antibody) and differences were considered to be significant when the probability value was <0.05: *: P<0.05, **: P<0.01, NS: no significance versus IgG control. Statistical analyses were performed by GraphPad Prism version 5.0 (GraphPad Software, Inc). Body weight were calculated by subtracting body weight at day 0, and muscle weight was normalized by body weight at day 0 (initial body weight).

Ex Vivo Testing of Anti-TGF-β2 Antibodies in Tissues Form Patients Suffering from the Dupuytren's Disease The TGF-β2-specific Ab MOR14797 was tested and compared to the pan-TGF-β Ab 1D11 in a recently described 3-D ex vivo culturing system of Dupuytren's contracture disease (Karkampouna et al. 2014, Molecular Therapy—Nucleic Acids, (2014) 3, e142) to determine its anti-fibrotic activity measuring fibrosis markers by immunohistochemistry and mRNA. Results are shown in FIGS. 7 and 8. The ex vivo model was done as described in Karkampouna et al. 2014. Patient tissue was sliced and cultured on nitrocellular membranes in the presence of antibodies at 3 μg/ml for seven days. At day 7 tissue slices were collected for mRNA isolation or fixed and processed for cryoembeding if used for immunohistochemistry analysis.

For immunohistochemistry 5 μm sections were cut at and stained with antibodies against Collagen1 and a-smooth muscle actin. Nuclei were assessed using the nuclear dye DAPI. 3 images per section were acquired with a confocal

TABLE 4

Binding and biologic activity of TGF-b2-specific Ab

| | RGA (CAGA-12 luc/Smad-2/3 RGA; IC 50 [pM]) | | | | BiaCORE (surface plasmon resonance; KD [M]) | | | CK (IC 50 [pM]) | |
|---|---|---|---|---|---|---|---|---|---|
| Ab | Human TGF-β2 | Mouse TGF-β2 | Human TGF-β3 | Human TGF-β1 | Human TGF-β2 | Mouse TGF-β2 | Human TGF-β3 | Human TGF-β2 | Mouse TGF-β2 |
| MOR 14797 | 8.4 | 329 | n.e. | n.e | 4.46E-15 | 6.33E-13 | 2.74E-08 | 105 | 1504 |
| MOR 14799 | 78 | 138 | n.e. | n.e | 1.08E-15 | 2.77E-15 | 1.99E-11 | 1050 | 909 |
| MOR 14800 | 29 | 123 | n.e. | n.e | 4.34E-16 | 1.09E-15 | >1E-06 | 491 | 1200 |
| MOR 14805 | 106 | 248 | n.e. | n.e. | 9.70E-13 | 1.31E-16 | 7.05E-11 | 315 | 629 |
| MOR 14809 | 94 | 598 | n.e. | n.e. | 5.24E-14 | 2.36E-15 | >1E-06 | 220 | 800 |
| MOR 14787 | 2.8 | n.e. | n.e. | n.e. | 7.38E-16 | 1.89E-12 | >1E-06 | 366 | 3000 |
| CAT-152 | 26 | 298 | 1234 | n.e. | 7.3E-11 | | 1.175E-09 | | |
| 1D11 | 4370 | n.e. | 32 | 108 | 1.17E-10 | | 2.0E-11 | | |

CK: Skeletal Muscle Cell Differentiation Assay (Creatine Kinase);
n.e. no effect up to 100 nM Cross-Reactivity to Counter Targets (RGA)

Cross-reactivity of final antibodies (after PTM removal and germlining) to TGF-β3 and five counter targets (Myostatin, GDF-11, Activin A, Activin B and Activin AB) was analyzed in the RGA using conditions described above and are shown in FIG. 4.

In summary, no concentration dependent inhibition of TGF-β3 and five counter targets could be detected for any of the antibodies tested. Final antibodies were also tested for inhibition of TGF-131. None of the antibodies showed concentration dependent inhibition of TGF-β1 up to 100 nM IgG.

Statistical Analysis

Results are expressed as mean+/−SEM. Statistical analysis was carried out using Dunnett's multiple comparison test following one-way analysis of variance. Treatment (antimicroscope of labelled specimens and quantified by imaging analysis. For RNA analysis total RNA was isolation and quantitative PCR (qPCR) was performed. Results are expressed as mRNA expression normalized to expression of house-keeping genes. In cultures from three different patients, MOR14797 3 μg/ml effectively reduced the fibrosis marker collagen 1 and a-smooth muscle actin (SMA; see FIG. 7) as measured by immunohistochemistry; MOR14797 was more efficacious than the pan-TGF-β AB 1D11. In cultures from two additional patients, a dose-dependent (0.03-3 μg/ml) reduction of the fibrosis markers collagen 1 and a-smooth muscle actin were shown. Examples of collagen 1 immunostaining inhibition of the TGF-β2-specific Ab MOR14797 is shown in FIG. 8. MOR14797 also reduced expression of various fibrosis markers on mRNA level.

In Vivo Testing in the Unilateral Ureteral Obstruction (UUO) Mouse Kidney Fibrosis Model The TGF-β2-specific Ab MOR13436 in a mouse kidney fibrosis model, unilateral ureteral obstruction (UUO) to determine its anti-fibrotic activity measuring fibrosis markers by mRNA. Results are shown in FIG. 9. The ex vivo model was done as described in Kitamoto et al. 2009 (J Pharmacol Sci, 111, 285-292). Briefly, UUO was performed by complete ligation of the left ureter and treated for 14 days with the TGF-β2-specific AB MOR14346 at 5 mg/kg. Kidneys were collected for mRNA isolation. For RNA analysis total RNA was isolation and quantitative PCR (qPCR) was performed. Results are expressed as mRNA expression normalized to expression of house-keeping genes.

X-Ray Crystal Structure of the Human TGFβ-2/MOR14797 Fab Complex

The crystal structure of a human TGFβ-2 (residues 303-414, SEQ ID NO: 122) bound to the Fab fragment of MOR14797 (SEQ ID NO: 69 (partial sequence) and 79, Table 5) was determined. As detailed below, the individual components of the complex were produced using separate expression systems and were combined to generate the purified complex. X-ray crystallography was then employed to generate diffraction data for TGFβ-2 bound to the MOR14797 Fab, elucidating the antigen-binding site.

complex was neutralized with 1:5 (v/v) of 1 M Tris-HCl (pH 8.5) and was then concentrated before being loaded onto a HiLoad 16/600 Superdex 200 column (GE Healthcare Life Sciences) equilibrated with 20 mM HEPES (pH 7.5), 150 mM NaCl. Peak fractions underwent analysis by SDS-PAGE and selected fractions were combined for crystallization trials.

Crystallization and Structure Determination

The TGFβ-2-MOR14797 complex was concentrated to 20 mg/ml, followed by centrifugation at 20,000×g for 10 min prior to dispensing crystallization screens. Crystals were grown at 20° C. using a sitting drop vapor diffusion setup. 0.1 µl of the TGFβ-2-MOR14797 complex was mixed with 0.1 µl of a reservoir solution containing 0.1 M HEPES (pH 7.5) and 70% (v/v) MPD, and the drop was equilibrated against 45 µl of the reservoir solution. Crystals were flash-cooled directly in liquid nitrogen and were sent to the Advanced Photon Source (Argonne National Laboratory, USA) for collection of diffraction data at beamline 17-ID. Datasets were processed using autoPROC (version 1.1.6, Global Phasing Ltd.) to a resolution of 2.4 Å in space group $P2_12_12_1$ with cell dimensions a=77.2 Å, b=122.1 Å, c=130.1 Å, α=90°, β=90°, and γ=90°. The structure of the complex was solved by molecular replacement using Phaser (version 2.5.5, McCoy et al., J. Appl. Cryst. 40, 658-674, 2007), with

TABLE 5

Proteins used for crystal structure determination

| Construct | Amino acid sequence in one letter code | SEQ ID NO |
|---|---|---|
| MOR14797 Fab heavy chain | QVTLRESGPALVKPTQTLTLTCTFSGFSLSTSGMGVGWIRQPPGKALEWLAHIYWNDDK SYSTSLKTRLTISKDTSKNQVVLTMTNMDPVDTATYYCARDFYYSGYFDSWGQGTLVTV SSASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKRVEPKSCDKTHTC | 69 (partial sequence; residues 1-229 of SEQ ID NO: 69) |
| MOR14797 Fab light chain | DIQMTQSPSSLSASVGDRVTITCRASQDISNYLNWYQQKPGKAPKLLIFGASSLQSGVP SRFSGSGSGTDFTLTISSLQPEDFATYYCQQTNTMNTFGQGTKVEIKRTVAAPSVFIFP PSDEQLKSGTASVVCLLNNFYPREAKVQWKVDNALQSGNSQESVTEQDSKDSTYSLSST LTLSKADYEKHKVYACEVTHQGLSSPVTKSFNRGEC | 79 |

Protein Production

Fab Production from Papain Cleavage of IgG:

MOR14797 Fab was produced by cleavage of full-length MOR14797 IgG with immobilized papain (Thermo Scientific Pierce). MOR14797 IgG at 20 mg/ml in 20 mM sodium phosphate (pH 7.0), 10 mM EDTA was mixed with immobilized papain at a weight ratio of 80:1, and the mixture was incubated on a rotating platform overnight at 37° C. The Fab and Fc fragments were then separated from the immobilized papain using a gravity flow column. The collected flow through was then loaded onto a HiTrap MabSelect SURE column (GE Healthcare Life Sciences) to remove any Fc fragments. The Fab-containing flow through was then concentrated and loaded onto a HiLoad 16/600 Superdex 200 column (GE Healthcare Life Sciences) equilibrated with 20 mM HEPES (pH 7.5), 150 mM NaCl. Peak fractions underwent analysis by SDS-PAGE, and the combined fractions were then used to form a complex with TGFβ-2.

In Vitro Reconstitution of the TGFβ-2-MOR14797 Fab Complex:

The Fab at a concentration of 1 mg/ml was acidified by adding 1:10 (v/v) of 1 M trisodium citrate (pH 3.5). Purified TGFβ-2 was then mixed with MOR14797 Fab at a molar ratio of 1:1.5 (concentration measured by OD A280). The the final model being built in COOT (version 0.8.7, Emsley et al., Acta Cryst. D 66, 486-501, 2010) and refined using Phenix (version 1.11.1, Afonine et al., Acta Cryst. D 66, 213-221, 2010). The $R_{work}$ and $R_{free}$ values are 17.5% and 23.0%, respectively. The RMSD values for the bond lengths and angles were 0.008 Å and 1.054°.

The epitope is defined as the residues of TGFβ-2 that contain atoms within 5 Å of any atom of the MOR14797 Fab, identified using PyMOL (Version 1.8, Schrödinger, LLC.) and listed in Table 6. There are two copies of the TGFβ-2/MOR14797 Fab complex in the asymmetric unit (the smallest unique unit in the crystal), and only those antibody-contacting residues that are common in both copies are listed as epitope residues.

Epitope and Paratope of MOR14797 Binding to TGFβ-2

The crystal structure of the TGFβ-2-MOR14797 Fab complex was used to identify the epitope and paratope of MOR14797 binding to TGFβ-2. The surface on TGFβ-2 interacting with MOR14797 Fab is formed by several non-contiguous sequences as detailed in Table 6. These residues form the three-dimensional conformational epitope that is recognized by the MOR14797 Fab (FIG. 1). The surface on MOR14797 interacting with TGFβ-2 is formed by several noncontiguous sequences as detailed in Table 6. These residues form the three-dimensional paratope of MOR14797 binding to TGFβ-2 (FIG. 11).

TABLE 6

Interactions between human TGFβ-2 and the MOR14797 Fab. TGFβ-2 residues were numbered based upon UniProt entry P61812 (SEQ ID NO: 122) and the two chain of the TGFβ-2 dimer are labeled as A and B. Fab residues are numbered based upon their linear amino acid sequence (SEQ ID NO: 69 (partial sequence) and 79) and corresponding chains are labeled ("H" for heavy chain, "L" for light chain). TGFβ-2 residues shown have at least one atom within 5 Å of an atom in the MOR14797 Fab, to account for potential water mediated interactions.

| TGFβ-2 | | | MOR14797 | | |
|---|---|---|---|---|---|
| Amino acid | Number | Chain | Amino acid | Number | Chain |
| LEU | 304 | A | GLN | 1 | H |
| ASN | 316 | A | SER | 56 | L |
| LYS | 327 | B | TYR | 32 | L |
| GLY | 331 | B | TYR | 32 | L |
| TRP | 332 | B | TYR | 32 | L |
|  |  |  | PHE | 101 | H |
|  |  |  | TYR | 102 | H |
| LYS | 333 | B | TYR | 32 | L |
|  |  |  | THR | 91 | L |
|  |  |  | ASN | 92 | L |
|  |  |  | THR | 93 | L |
| TRP | 334 | B | TRP | 55 | H |
|  |  |  | TYR | 102 | H |
|  |  |  | TYR | 103 | H |
| PRO | 351 | A | SER | 56 | L |
| TYR | 352 | A | GLN | 55 | L |
|  |  |  | PHE | 101 | H |
|  |  |  | SER | 104 | H |
|  |  |  | TYR | 106 | H |
|  |  |  | ASP | 108 | H |
| LEU | 353 | A | GLN | 1 | H |
|  |  |  | MET | 34 | H |
|  |  |  | ARG | 99 | H |
|  |  |  | PHE | 101 | H |
|  |  |  | ASP | 108 | H |
| TRP | 354 | A | GLN | 1 | H |
| SER | 355 | A | GLN | 1 | H |
| SER | 356 | A | GLN | 1 | H |
| GLN | 359 | A | SER | 32 | H |
|  |  |  | TYR | 102 | H |
| ARG | 362 | A | THR | 31 | H |
|  |  |  | SER | 32 | B |
|  |  |  | MET | 34 | H |
|  |  |  | PHE | 101 | H |
| VAL | 363 | A | PHE | 101 | H |
|  |  |  | TYR | 102 | H |
| LEU | 366 | A | PHE | 49 | L |
|  |  |  | PHE | 101 | H |
|  |  |  | TYR | 102 | H |
| THR | 369 | A | PHE | 49 | L |
|  |  |  | SER | 53 | L |
|  |  |  | LEU | 54 | L |
|  |  |  | GLN | 55 | L |
| ILE | 370 | A | PHE | 49 | L |
|  |  |  | SER | 53 | L |
| TYR | 392 | B | TRP | 55 | H |
|  |  |  | ASN | 56 | H |
|  |  |  | TYR | 103 | H |
| ILE | 394 | B | ASN | 56 | H |
|  |  |  | ASP | 58 | H |
|  |  |  | TYR | 103 | H |

TABLE 6-continued

Interactions between human TGFβ-2 and the MOR14797 Fab. TGFβ-2 residues were numbered based upon UniProt entry P61812 (SEQ ID NO: 122) and the two chain of the TGFβ-2 dimer are labeled as A and B. Fab residues are numbered based upon their linear amino acid sequence (SEQ ID NO: 69 (partial sequence) and 79) and corresponding chains are labeled ("H" for heavy chain, "L" for light chain). TGFβ-2 residues shown have at least one atom within 5 Å of an atom in the MOR14797 Fab, to account for potential water mediated interactions.

| TGFβ-2 | | | MOR14797 | | |
|---|---|---|---|---|---|
| Amino acid | Number | Chain | Amino acid | Number | Chain |
| LYS | 399 | B | ASN | 56 | H |
| GLU | 401 | B | SER | 32 | H |
|  |  |  | TRP | 55 | H |
|  |  |  | ASN | 56 | H |
| LEU | 403 | B | SER | 32 | H |
|  |  |  | TYR | 102 | H |

Epitope of MOR14800 Binding to TGFβ-2

TABLE 7

Interactions between human TGFβ-2 and the MOR14800 Fab. TGFβ-2 residues were numbered based upon UniProt entry P61812 (SEQ ID NO: 122) and the two chain of the TGFβ-2 dimer are labeled as A and B. TGFβ-2 residues shown have at least one atom within 5 Å of an atom in the MOR14797 Fab, to account for potential water mediated interactions.

| Protein | Amino acid | Sequence position |
|---|---|---|
| TGF_B2_chain B | 1 (ALA). | 1 |
| TGF_B2_chain B | 2 (LEU). | 2 |
| TGF_B2_chain B | 3 (ASP). | 3 |
| TGF_B2_chain B | 5 (ALA). | 5 |
| TGF_B2_chain B | 6 (TYR). | 6 |
| TGF_B2_chain B | 10 (ASN). | 10 |
| TGF_B2_chain B | 14 (ASN). | 14 |
| TGF_B2_chain A | 29 (GLY). | 29 |
| TGF_B2_chain A | 30 (TRP). | 30 |
| TGF_B2_chain A | 31 (LYS). | 31 |
| TGF_B2_chain A | 32 (TRP). | 32 |
| TGF_B2_chain B | 49 (PRO). | 49 |
| TGF_B2_chain B | 50 (TYR). | 50 |
| TGF_B2_chain B | 51 (LEU). | 51 |
| TGF_B2_chain B | 52 (TRP). | 52 |
| TGF_B2_chain B | 53 (SER). | 53 |
| TGF_B2_chain B | 54 (SER). | 54 |
| TGF_B2_chain B | 55 (ASP). | 55 |
| TGF_B2_chain B | 57 (GLN). | 57 |
| TGF_B2_chain B | 60 (ARG). | 60 |
| TGF_B2_chain B | 61 (VAL). | 61 |
| TGF_B2_chain B | 64 (LEU). | 64 |
| TGF_B2_chain B | 81 (GLN). | 81 |
| TGF_B2_chain A | 90 (TYR). | 90 |
| TGF_B2_chain A | 91 (TYR). | 91 |
| TGF_B2_chain A | 92 (ILE). | 92 |
| TGF_B2_chain A | 99 (GLU). | 99 |
| TGF_B2_chain A | 101 (LEU). | 101 |
| TGF_B2_chain A | 104 (MET). | 104 |
| TGF_B2_chain B | 110 (LYS) | 110 |

The invention claimed is:

1. A human monoclonal anti-transforming growth factor beta 2 (TGF-β2) TGF-β02 antibody or a functional fragment thereof that neutralizes the human TGF-β isoform TGF-β02 and does not neutralize human isoform TGF-β3, wherein neutralization is determined by a Smad dependent reporter gene assay, and wherein said antibody or functional fragment thereof comprises:
   (a) a heavy chain variable region CDR1 of SEQ ID NO: 1; a heavy chain variable region CDR2 of SEQ ID NO: 2; a heavy chain variable region CDR3 of SEQ ID NO: 3; a light chain variable region CDR1 of SEQ ID NO: 11; a light chain variable region CDR2 of SEQ ID NO: 12; and a light chain variable region CDR3 of SEQ ID NO: 13,
   (b) a heavy chain variable region CDR1 of SEQ ID NO: 21 a heavy chain variable region CDR2 of SEQ ID NO: 22; a heavy chain variable region CDR3 of SEQ ID NO: 23; a light chain variable region CDR1 of SEQ ID NO: 31; a light chain variable region CDR2 of SEQ ID NO: 32; and a light chain variable region CDR3 of SEQ ID NO: 33,
   (c) a heavy chain variable region CDR1 of SEQ ID NO: 41; a heavy chain variable region CDR2 of SEQ ID NO: 42; a heavy chain variable region CDR3 of SEQ ID NO: 43; a light chain variable region CDR1 of SEQ ID NO: 51; a light chain variable region CDR2 of SEQ ID NO: 52; and a light chain variable region CDR3 of SEQ ID NO: 53,
   (d) a heavy chain variable region CDR1 of SEQ ID NO: 61; a heavy chain variable region CDR2 of SEQ ID NO: 62; a heavy chain variable region CDR3 of SEQ ID NO: 63; a light chain variable region CDR1 of SEQ ID NO: 71; a light chain variable region CDR2 of SEQ ID NO: 72; and a light chain variable region CDR3 of SEQ ID NO: 73,
   (e) a heavy chain variable region CDR1 of SEQ ID NO: 81; a heavy chain variable region CDR2 of SEQ ID NO: 82; a heavy chain variable region CDR3 of SEQ ID NO: 83; a light chain variable region CDR1 of SEQ ID NO: 91; a light chain variable region CDR2 of SEQ ID NO: 92; and a light chain variable region CDR3 of SEQ ID NO: 93, or
   (f) a heavy chain variable region CDR1 of SEQ ID NO: 101; a heavy chain variable region CDR2 of SEQ ID NO: 102; a heavy chain variable region CDR3 of SEQ ID NO: 103; a light chain variable region CDR1 of SEQ ID NO: 111; a light chain variable region CDR2 of SEQ ID NO: 112; and a light chain variable region CDR3 of SEQ ID NO: 113.

2. The antibody or functional fragment according to claim 1, wherein said antibody or functional fragment thereof comprises a VH polypeptide sequence having at least 95% sequence identity to at least one of SEQ ID NOs: 7, 27, 47, 67, 87, or 107 and a VL polypeptide sequence having at least 95% sequence identity to at least one of SEQ ID NOs: 17, 37, 57, 77, 97, or 117.

3. The antibody or functional fragment according to claim 1, wherein said antibody or functional fragment thereof comprises a full length heavy chain amino acid sequence having at least 95% sequence identity to at least one sequence selected from the group consisting of SEQ ID NOs: 9, 29, 49, 69, 89, 109 and a full length light chain amino acid sequence having at least 95% sequence identity to at least one sequence selected from the group consisting of SEQ ID NOs: 19, 39, 59, 79, 99, 119.

4. The antibody or functional fragment according to claim 1, which is a human monoclonal anti-TGF-β2 antibody, and which comprises:
   (a) the variable heavy chain sequence of SEQ ID NO: 7 and variable light chain sequence of SEQ ID NO: 17;
   (b) the variable heavy chain sequence of SEQ ID NO: 27 and variable light chain sequence of SEQ ID NO: 37;
   (c) the variable heavy chain sequence of SEQ ID NO: 47 and variable light chain sequence of SEQ ID NO: 57;
   (d) the variable heavy chain sequence of SEQ ID NO: 67 and variable light chain sequence of SEQ ID NO: 77;
   (e) the variable heavy chain sequence of SEQ ID NO: 87 and variable light chain sequence of SEQ ID NO: 97; or
   (f) the variable heavy chain sequence of SEQ ID NO: 107 and variable light chain sequence of SEQ ID NO: 117.

5. The antibody or functional fragment according to claim 1, which is a human monoclonal anti-TGF-β2 antibody, and which comprises:
   (a) the heavy chain sequence of SEQ ID NO: 9 and light chain sequence of SEQ ID NO: 19;
   (b) the heavy chain sequence of SEQ ID NO: 29 and light chain sequence of SEQ ID NO: 39;
   (c) the heavy chain sequence of SEQ ID NO: 49 and light chain sequence of SEQ ID NO: 59;
   (d) the heavy chain sequence of SEQ ID NO: 69 and light chain sequence of SEQ ID NO: 79;
   (e) the heavy chain sequence of SEQ ID NO: 89 and light chain sequence of SEQ ID NO: 99; or
   (f) the heavy chain sequence of SEQ ID NO: 109 and light chain sequence of SEQ ID NO: 119.

6. An isolated polynucleotide sequence encoding an antibody or functional fragment according to claim 1.

7. The isolated polynucleotide sequence according to claim 6, comprising one or more of SEQ ID NOs: 8, 10, 18, 20, 28, 30, 38, 40, 48, 50, 58, 60, 68, 70, 78, 80, 88, 90, 98, 100, 108, 110, 118, or 120.

8. A cloning or expression vector comprising one or more isolated polynucleotide sequences according to claim 7.

9. The vector according to claim 8, wherein said vector comprises one or more of SEQ ID NOs: 8, 10, 18, 20, 28, 30, 38, 40, 48, 50, 58, 60, 68, 70, 78, 80, 88, 90, 98, 100, 108, 110, 118, or 120, or fragment thereof encoding at least one CDR region.

10. A host cell comprising one or more vectors according to claim 8.

11. A process for the production of an anti-TGF-β2 antibody or functional fragment thereof, comprising culturing the host cell of claim 10 and isolating said antibody or functional fragment.

12. A pharmaceutical composition comprising an antibody or functional fragment thereof according to claim 1.

13. The pharmaceutical composition according to claim 12, further comprising a pharmaceutically acceptable diluent or carrier.

* * * * *